(12) United States Patent
Lakdawalla et al.

(10) Patent No.: US 12,378,593 B2
(45) Date of Patent: Aug. 5, 2025

(54) NUCLEIC ACID CLONAL AMPLIFICATION AND SEQUENCING METHODS, SYSTEMS, AND KITS

(71) Applicant: Ultima Genomics, Inc., Newark, CA (US)

(72) Inventors: Abizar Lakdawalla, Los Altos Hills, CA (US); Florian Oberstrass, Menlo Park, CA (US); Chandan Shee, Newark, CA (US)

(73) Assignee: Ultima Genomics, Inc., Fremont, CA (US)

( * ) Notice: Subject to any disclaimer, the term of this patent is extended or adjusted under 35 U.S.C. 154(b) by 1209 days.

(21) Appl. No.: 17/150,659

(22) Filed: Jan. 15, 2021

(65) Prior Publication Data

US 2021/0230669 A1    Jul. 29, 2021

Related U.S. Application Data

(63) Continuation of application No. PCT/US2019/042451, filed on Jul. 18, 2019.

(60) Provisional application No. 62/700,686, filed on Jul. 19, 2018, provisional application No. 62/801,420, filed on Feb. 5, 2019.

(51) Int. Cl.
*C12Q 1/6806*    (2018.01)
*C12Q 1/6855*    (2018.01)

(52) U.S. Cl.
CPC ......... *C12Q 1/6806* (2013.01); *C12Q 1/6855* (2013.01)

(58) Field of Classification Search
CPC ................................ C12Q 1/68; C07H 21/00
See application file for complete search history.

(56) References Cited

U.S. PATENT DOCUMENTS

| | | | |
|---|---|---|---|
| 7,270,981 B2 | 9/2007 | Armes et al. | |
| 7,972,820 B2 | 7/2011 | Mayer | |
| 9,309,566 B2 | 4/2016 | Li et al. | |
| 2005/0266418 A1 | 12/2005 | Chen et al. | |
| 2007/0219367 A1 | 9/2007 | Shchepinov et al. | |
| 2012/0156728 A1 | 6/2012 | Li et al. | |
| 2012/0157322 A1 | 6/2012 | Myllykangas et al. | |
| 2015/0111256 A1 | 4/2015 | Church et al. | |
| 2017/0067098 A1* | 3/2017 | Li ........................... | C12Q 1/46 |

FOREIGN PATENT DOCUMENTS

| | | |
|---|---|---|
| CN | 101200759 A | 6/2008 |
| EP | 3205730 A1 | 8/2017 |
| WO | WO-2007041201 A2 | 4/2007 |
| WO | WO-2009097626 A2 | 8/2009 |
| WO | WO-2020018824 A1 | 1/2020 |

OTHER PUBLICATIONS

Broude, et al. DNA microarrays with stem-loop DNA probes: preparation and applications. Nucleic acids research 29.19 (2001): e92-e92.
Broude, et al. Stem-loop oligonucleotides: a robust tool for molecular biology and biotechnology. Trends in Biotechnology 20.6 (2002): 249-256.
Broude, Natalia E. (2005) Molecular beacons and other hairpin probes. Encyclopedia of Diagnostic Genomics and Proteomics: 846-850.
Fei, et al. Watching DNA breath one molecule at a time. Proceedings of the National Academy of Sciences 110.43 (2013): 17173-17174.
Gautam, et al. An Efficient LCM-Based Method for Tissue Specific Expression Analysis of Genes and miRNAs. Scientific reports vol. 6 21577, FIG.4. Feb. 10, 2016.
Jung, et al. A universal TaqMan-based RT-PCR protocol forcost-efficient detection of small noncoding RNA. RNA (New York, N.Y.) vol. 19,12 (2013): 1864-73, FIG. 1.
Ma, et al. Isothermal amplification method for next-generation sequencing. Proceedings of the National Academy of Sciences 110.35 (2013): 14320-14323.
Marcial-Quino, et al. Stem-loop RT-qPCR as an efficient tool for the detection and quantification of small RNAs in giardia lamblia. Genes 7.12 (2016): 131.
PCT/US2019/042451 International Search Report dated Dec. 6, 2019.
Rieloff, et al. Structural Characterization of Bubbles Formed in DNA Melting: A Monte Carlo Simulation Study. ACS omega 2.5 (2017): 1915-1921.
Shi, et al. Triggered isothermal PCR by denaturation bubble-mediated strand exchange amplification. Chemical Communications 52.77 (2016): 11551-11554.
Shigemori, et al. Multiplex PCR: use of heat-stable Thermus thermophilus RecA protein to minimize non-specific PCR products. Nucleic Acids Research 33.14 (2005): e126-e126.

* cited by examiner

*Primary Examiner* — Ethan C Whisenant
(74) *Attorney, Agent, or Firm* — Wilson Sonsini Goodrich & Rosati

(57) ABSTRACT

The present disclosure provides methods and systems for processing nucleic acid samples. Methods for processing a nucleic acid sample may comprise providing a double-stranded nucleic acid molecule comprising a partially denaturable region; partially denaturing the partially denaturable region of the double-stranded nucleic acid molecule, thereby generating a region comprising two single strands; and hybridizing a priming sequence to a sequence of one of the single strands. The methods described herein may facilitate amplification without the need for a multitude of complex steps or numerous reagents.

20 Claims, 24 Drawing Sheets

Specification includes a Sequence Listing.

TTTTTTTTT..AATGATACGGCGACCACCGAGAUCTA..TTTTTTTTTTTTTTTTTTTT..CACTCTTTCCCTACACGACGCTCTTCCGATCT

AAAAAAAAA..TTACTATGCCGCTGGTGGCTCTAGAT..AAAAAAAAAAAAAAAAAAAA..GTGAGAAAGGGATGTGCTGCGAGAAGGCTAGA 12.9°C      61.7°C      43.5°C      65.4°C      69.5°C

FIG. 8

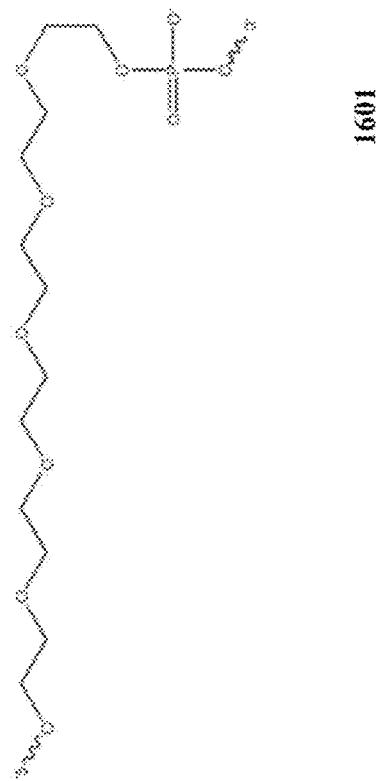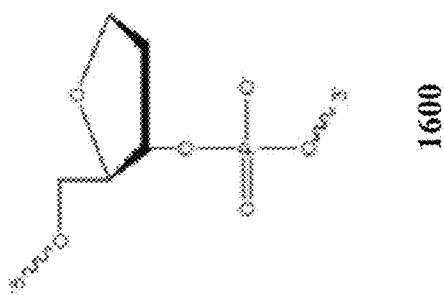
FIG. 16

SEQUENCE LISTING

```
<160> NUMBER OF SEQ ID NOS: 15

<210> SEQ ID NO 1
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccatctcatc cctgcgtgtc tccgactcag aaaaaaaaaa aaaaaaaaaa aaaaaactga      60
gactgccaag gcacacaggg gatagg                                          86

<210> SEQ ID NO 2
<211> LENGTH: 86
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 2
cctatcccct gtgtgccttg gcagtctcag tttttttttt tttttttttt tttctgagtc    60
gtcggagaca cgcagggatg agatgg                                        86

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttttttttt ttttttt                                                  17

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccatctcatc cctgcgtgtc t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctatcccct gtgtgccttg g                                             21

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccatctcatc cctgcgtgtc tccgactcag                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggtagagtag ggacgcacag aggctgagtc                                    30

<210> SEQ ID NO 8
<211> LENGTH: 26
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 8
aaaaaaaaaa aaaaaaaaaa aaaaaa                                             26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt tttttttttt tttttt                                             26

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgagactgc caaggcacac aggggatagg                                         30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gactctgacg gttccgtgtg tcccctatcc                                         30

<210> SEQ ID NO 12
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caagcagaag acggcatacg agatatatat atatatatat atgtgactgg agttcagacg        60
tgtgctcttc cgatctcagt acgagcgtgt agacgtgtcg tacgtgcgac gtagtgagta      120
tacatgctct gacactatgt acgctgtagg catacgagat cggaagagcg tcgtgtaggg      180
aaagagtgta tatatatata tatatatata tatatatgtg tagatctcgg tggtcgccgt      240
atcatt                                                                 246

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caagcagaag acggcatacg ag                                                 22
```

```
<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aatgatacgg cgaccaccga gatctacaca                                    30

<210> SEQ ID NO 15
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
tttttttttt aatgatacgg cgaccaccga gauctatttt tttttttttt tttttttttt   60
tcactctttc cctacacgac gctcttccga tct                                93
```

NUCLEIC ACID CLONAL AMPLIFICATION AND SEQUENCING METHODS, SYSTEMS, AND KITS

CROSS-REFERENCE

This application is a continuation of International Application No. PCT/US2019/042451, filed Jul. 18, 2019, which claims the benefit of U.S. Provisional Application No. 62/700,686, filed Jul. 19, 2018, and U.S. Provisional Application No. 62/801,420, filed Feb. 5, 2019, each of which applications is entirely incorporated herein by reference.

SEQUENCE LISTING

The instant application contains a Sequence Listing which has been submitted electronically in ASCII format and is hereby incorporated by reference in its entirety. Said ASCII copy, created on Apr. 2, 2021, is named 51024-711_301_SL.txt and is 4,503 bytes in size.

BACKGROUND

Samples may be analyzed for various purposes, including detecting the presence or amount of a target such as a nucleic acid molecule in a sample. Analysis of a sample comprising one or more nucleic acid molecules may involve amplification of the nucleic acid molecules to process the nucleic acid molecules and/or increase their concentration for subsequent analysis. For example, nucleic acid molecules in a sample may be amplified in preparation for sequencing.

Sequencing can be performed by a sequencing by synthesis (SBS) reaction in which a nucleic acid molecule is sequenced by detecting the incorporation of nucleotides into an elongating strand that is complimentary to the nucleic acid molecule to be sequenced. Amplification of many nucleic acid molecules (e.g., clones) in parallel may result in a loss of molecular integrity (e.g., clonal integrity) in solution. Accordingly, amplification of large numbers of nucleic acid molecules may be carried out in a controlled fashion to preserve clonal integrity.

One approach to controlled amplification involves carrying out amplification reactions in individual reactors, such as compartmentalized plates, microreactors, or droplets. For example, emulsion polymerase chain reaction (PCR) may be used to amplify multiple clones in individual droplets, in some cases by attachment of the amplified molecules onto beads coated with oligonucleotides. Each emulsion PCR droplet may contain an oligonucleotide-coated bead to which a single nucleic acid template may be attached. When PCR is performed in the droplets separated by an immiscible barrier, the amplification products will remain isolated and bound to the bead in the droplets. Though emulsion PCR may preserve molecular integrity during amplification, emulsion PCR has significant limitations. Emulsion PCR is a complex process requiring multiple, time-consuming steps, including generation of an emulsion of oligonucleotide-coated beads captured in aqueous droplets with deoxyribonucleic acid (DNA) polymerase, nucleotides, and other reagents, with each aqueous droplet being separated from other droplets via oil; thermocycling of a large volume of the emulsified mix; disruption of the emulsion; and enrichment of beads that have amplified DNA from beads that do not have amplified DNA. This method may be difficult to scale to genome scale sequencing as substantial volumes of reagents and a large number of beads are required. For example, for the approximately 100 gigabases (Gb) of sequence data required to sequence a human genome, about 1 billion beads with monoclonal amplified templates are needed. To get a billion monoclonal beads as output, emulsion PCR may be performed with an excess of beads to decrease the number of polyclonal beads (that is, beads that contain two or more different templates). Emulsion PCR of the large excess of beads may require reaction volumes of up to ~100 milliliters (mL) per human whole genome sample and the process may take up to 12 hours.

Another approach to preserving clonal integrity involves attaching individual molecules and amplified products to a substrate to constrain the migration of amplified products to other clones by diffusion. Solid-phase nucleic acid clonal amplification methods that generate bound or localized amplicons have been instrumental for the development and adoption of genomic methods such as next generation sequencing in which millions or billions of clones are amplified in parallel and then subjected to highly parallel sequencing.

Methods based on spatial separation of amplified nucleic acid templates by binding of the templates to a planar substrate coated with oligonucleotides include Bridge Amplification, Wildfire Amplification, and Recombinase Polymerase Amplification (RPA). Bridge Amplification generates DNA colonies on an oligonucleotide coated substrate and uses multiple reagents flowing over the oligonucleotide substrate for multiple cycles to produce amplified colonies on the substrate. The method requires greater reagent volumes and is relatively inefficient at amplification, producing just a few thousand molecules per colony after 30 cycles of amplification instead of the expected ~1 billion molecules. Instrumentation associated with bridge amplification has greater complexity due to the need to repeatedly pump different reagents in a defined order. Methods of amplification such as Wildfire and RPA that produce colonies on solid substrates (planar or spherical) are simpler to implement but require expensive enzymes or produce uneven colonies. Wildfire methods are limited to using Poly A-base sequences in critical areas of oligonucleotide adapter sequences, making it difficult to optimize sequences to minimize hybridization to naturally occurring Poly-A base sequences in genomic DNA and in complementary DNA created from messenger ribonucleic acid (mRNA) molecules. During amplification, the Poly-A base sequences are affected by slippage between the primer and the template and may affect the efficiency of amplification. Thus, while each of these amplification methods may amplify nucleic acid molecules without a loss of clonal integrity, they also suffer from significant limitations.

SUMMARY

Recognized herein is a need for improved methods, systems, and kits for processing nucleic acid samples. The present disclosure provides methods for clonal amplification that may use only a single reagent mixture and obviate the need for multiple reagent exchanges. Methods provided herein may be performed directly on a sequencing instrument without the need for separate automation and fluidic systems. The methods provided herein may also be performed in a short period of time (e.g., less than an hour). Methods of the present disclosure may amplify a nucleic acid sample (e.g., prior to or during sequencing) while advantageously preserving clonal integrity. Such methods may be useful for, for example, sample preparation for sequencing to identify genetic aberrations for, e.g., cancer detection.

In an aspect, the present disclosure provides a method for processing a nucleic acid sample, comprising: (a) providing the nucleic acid sample comprising a double-stranded nucleic acid molecule comprising a first strand and a second strand having sequence complementarity with the first strand, wherein the first strand comprises a template region that is attached to an adapter comprising a first sequence and a second sequence adjacent to the first sequence, wherein the first sequence and the second sequence are respectively hybridized to a third sequence and a fourth sequence of the second strand, wherein the first sequence hybridized to the third sequence has a first melting point and the second sequence hybridized to the fourth sequence has a second melting point higher than the first melting point; (b) subjecting the double-stranded nucleic acid molecule to conditions sufficient to partially denature the double-stranded nucleic acid molecule, thereby separating the first sequence of the first strand from the third sequence of the second strand; (c) bringing a primer molecule having sequence complementarity with the third sequence of the second strand in contact with the second strand under conditions sufficient to permit the primer molecule to hybridize to the third sequence of the second strand; and (d) subjecting the second strand comprising the primer molecule hybridized to the third sequence of the second strand to a primer extension reaction under conditions sufficient to generate a third strand hybridized to at least a portion of the second strand.

In some embodiments, (b) comprises exposing the double-stranded nucleic acid molecule or a portion thereof to a chemical denaturant. In some embodiments, the chemical denaturant is selected from the group consisting of a salt, formamide, urea, guanidine hydrochloride, and an organic solvent. In some embodiments, (b) is performed under isothermal conditions.

In some embodiments, the first melting point is at least 1° C. lower than the second melting point. In some embodiments, the first melting point is at least 5° C. lower than the second melting point.

In some embodiments, (b) comprises heating the double-stranded nucleic acid molecule to a temperature higher than the first melting point and lower than the second melting point. In some embodiments, (b) comprises heating the double-stranded nucleic acid molecule to partially denature the double-stranded nucleic acid molecule. In some embodiments, the heating includes optical heating. In some embodiments, the heating includes resistive heating. In some embodiments, the heating includes convective heating. In some embodiments, the heating includes inductive heating.

In some embodiments, in (b), at most a portion of the first strand separates from the second strand.

In some embodiments, the adapter is ligated to the template region of the first strand. In some embodiments, the method further comprises, prior to (a), ligating the adapter to the template region of the first strand. In some embodiments, the first strand is provided as a single-stranded molecule, and further comprising, prior to (a), subjecting the first strand to a nucleic acid amplification reaction under conditions sufficient to generate the second strand hybridized to the first strand, thereby generating the double-stranded nucleic acid molecule.

In some embodiments, the second sequence is at an end of the adapter. In some embodiments, the fourth sequence is at an end of the second strand.

In some embodiments, the method further comprises (e) bringing an additional primer molecule having sequence complementarity with the first strand in contact with the first strand under conditions sufficient to permit the additional primer molecule to hybridize to the first strand. In some embodiments, the additional primer molecule hybridizes to the second sequence. In some embodiments, the method further comprises (f) subjecting the first strand comprising the additional primer molecule hybridized thereto to a primer extension reaction under conditions sufficient to generate a fourth strand hybridized to at least a portion of the first strand, thereby generating a double-stranded nucleic acid molecule comprising the first strand and the fourth strand. In some embodiments, the additional primer molecule is immobilized to a support. In some embodiments, the support comprises a plurality of additional primer molecules immobilized thereto. In some embodiments, the plurality of additional primer molecules are immobilized to the support in a predetermined pattern. In some embodiments, the plurality of additional primer molecules are uniformly distributed on the support. In some embodiments, the plurality of additional primer molecules are immobilized to the support at a density of at least 10,000 primer molecules per $mm^2$. In some embodiments, the method further comprises repeating (b)-(f) with the double-stranded nucleic acid molecule comprising the first strand and the fourth strand, thereby generating a copy of the double-stranded nucleic acid molecule comprising the first strand and the fourth strand. In some embodiments, the method further comprises repeating (b)-(f) with at least the copy of the double-stranded nucleic acid molecule comprising the first strand and the fourth strand to generate at least 10 copies of the double-stranded nucleic acid molecule comprising the first strand and the fourth strand. In some embodiments, the method further comprises sequencing all or a portion of the first strand, the fourth strand, or a copy or derivative thereof.

In some embodiments, the adapter is immobilized to a support. In some embodiments, the support is a planar array. In some embodiments, the support is a bead. In some embodiments, the support is a well.

In some embodiments, the second sequence is part of an additional adapter attached to the second strand, wherein the additional adapter is immobilized to a support. In some embodiments, the support is a planar array. In some embodiments, the support is a bead.

In some embodiments, subsequent to subjecting the double-stranded nucleic acid molecule to the conditions in (b), the first sequence is separated from the third sequence and the second sequence is hybridized to the fourth sequence. In some embodiments, the primer extension reaction in (d) separates the second sequence from the fourth sequence.

In some embodiments, the first sequence and the third sequence comprise one or more bases selected from the group consisting of adenosine, thymidine, uridine, and inosine. In some embodiments, the first sequence and the third sequence only comprise bases selected from the group consisting of adenosine, thymidine, uridine, and inosine.

In some embodiments, the first sequence and the third sequence each comprise at least 5 bases. In some embodiments, the first sequence and the third sequence each comprise at least 10 bases.

In some embodiments, the nucleic acid sample comprises a plurality of double-stranded nucleic acid molecules, wherein each double-stranded nucleic acid molecule of the plurality of double-stranded nucleic acid molecules comprises a first strand and a second strand having sequence complementarity with the first strand, wherein the first strand comprises a template region that is attached to an adapter comprising a first sequence and a second sequence adjacent to the first sequence, wherein the first sequence and the second sequence are respectively hybridized to a third sequence and a fourth sequence of the second strand, wherein the first sequence hybridized to the third sequence has a first melting point and the second sequence hybridized to the fourth sequence has a second melting point higher than the first melting point; and further comprising: (g) repeating (b)-(d) for each double-stranded nucleic acid molecule of the plurality of double-stranded nucleic acid molecules of the nucleic acid sample. In some embodiments, the plurality of double-stranded nucleic acid molecules comprises at least 100 double-stranded nucleic acid molecules. In some embodiments, the plurality of double-stranded nucleic acid molecules comprises at least 1,000 double-stranded nucleic acid molecules. In some embodiments, the plurality of double-stranded nucleic acid molecules comprises at least 10,000 double-stranded nucleic acid molecules. In some embodiments, the plurality of double-stranded nucleic acid molecules comprises one or more different template regions. In some embodiments, (g) is performed simultaneously with (b)-(d).

In some embodiments, the adapter further comprises a fifth sequence, wherein the second sequence and the fifth sequence flank the first sequence. In some embodiments, the second strand of the double-stranded nucleic acid molecule further comprises a sixth sequence hybridized to the fifth sequence, wherein the fourth sequence and the sixth sequence flank the third sequence.

In another aspect, the present disclosure provides a system for processing a nucleic acid sample, comprising: a support configured to retain the nucleic acid sample comprising a double-stranded nucleic acid molecule comprising a first strand and a second strand having sequence complementarity with the first strand, wherein the first strand comprises a template region that is attached to an adapter comprising a first sequence and a second sequence adjacent to the first sequence, wherein the first sequence and the second sequence are respectively hybridized to a third sequence and a fourth sequence of the second strand, wherein the first sequence hybridized to the third sequence has a first melting point and the second sequence hybridized to the fourth sequence has a second melting point higher than the first melting point; and a controller operatively coupled to the support, wherein the controller is programmed to: (i) subject the double-stranded nucleic acid molecule to conditions sufficient to partially denature the double-stranded nucleic acid molecule, thereby separating the first sequence from the third sequence; (ii) bring a primer molecule having sequence complementarity with the third sequence in contact with the second strand under conditions sufficient to permit the primer molecule to hybridize to the third sequence; and (iii) subject the second strand comprising the primer molecule hybridized to the third sequence to a primer extension reaction under conditions sufficient to generate a third strand hybridized to at least a portion of the second strand.

In some embodiments, (i) comprises exposing the double-stranded nucleic acid molecule or a portion thereof to a chemical denaturant. In some embodiments, the chemical denaturant is selected from the group consisting of a salt, formamide, urea, guanidine hydrochloride, and an organic solvent. In some embodiments, the controller is programmed to heat the double-stranded nucleic acid molecule to a temperature higher than the first melting point and lower than the second melting point. In some embodiments, the first melting point is at least 1° C. lower than the second melting point. In some embodiments, the first melting point is at least 5° C. lower than the second melting point.

In some embodiments, the controller is programmed to provide thermal energy to the double-stranded nucleic acid molecule to partially denature the double-stranded nucleic acid molecule. In some embodiments, the controller is programmed to provide thermal energy by optical heating. In some embodiments, the controller is programmed to provide thermal energy by resistive heating. In some embodiments, the controller is programmed to provide thermal energy by convective heating. In some embodiments, the controller is programmed to provide thermal energy by inductive heating. In some embodiments, the controller is programmed to provide thermal energy by microwave heating.

In some embodiments, in (i), at most a portion of the first strand separates from the second strand. In some embodiments, the adapter is ligated to the first strand. In some embodiments, the second sequence is at an end of the adapter. In some embodiments, the fourth sequence is at an end of the second strand. In some embodiments, the controller is further programmed to (iv) bring an additional primer molecule having sequence complementarity with the first strand in contact with the first strand under conditions sufficient to permit the additional primer molecule to hybridize to the first strand. In some embodiments, the additional primer molecule hybridizes to the second sequence. In some embodiments, the controller is further programmed to (v) subject the first strand comprising the additional primer molecule hybridized thereto to a primer extension reaction under conditions sufficient to generate a fourth strand hybridized to at least a portion of the first strand, thereby generating a double-stranded nucleic acid molecule comprising the first strand and the fourth strand. In some embodiments, the additional primer molecule is immobilized to a support. In some embodiments, the support comprises a plurality of additional primer molecules immobilized thereto. In some embodiments, the plurality of additional primer molecules are immobilized to the support in a predetermined pattern. In some embodiments, the plurality of additional primer molecules are immobilized to the support at a density of at least 10,000 primer molecules per $mm^2$. In some embodiments, the controller is further programmed to repeat (i)-(v) with the double-stranded nucleic acid molecule comprising the first strand and the fourth strand, thereby generating a copy of the double-stranded nucleic acid molecule comprising the first strand and the fourth strand. In some embodiments, the controller is further programmed to repeat (i)-(v) with at least the copy of the double-stranded nucleic acid molecule comprising the first strand and the fourth strand to generate at least 10 copies of the double-stranded nucleic acid molecule comprising the first strand and the fourth strand. In some embodiments, the controller is further programmed to sequence all or a portion of the first strand, the fourth strand, or a copy or derivative thereof.

In some embodiments, the adapter is immobilized to a support. In some embodiments, the support is a planar array. In some embodiments, the support is a bead.

In some embodiments, the second sequence is part of an additional adapter attached to the second strand, wherein the additional adapter is immobilized to a support. In some embodiments, the support is a planar array. In some embodiments, the support is a bead.

In some embodiments, the controller is programmed provide sufficient thermal energy to separate the first sequence from the third sequence but not the second sequence from the fourth sequence. In some embodiments, the controller is programmed to subject the second strand comprising the primer molecule hybridized to the third sequence to a primer extension reaction under conditions sufficient to separate the second sequence from the fourth sequence.

In some embodiments, the first sequence and the third sequence comprise one or more bases selected from the group consisting of adenosine, thymidine, uridine, and inosine. In some embodiments, the first sequence and the third sequence only comprise bases selected from the group consisting of adenosine, thymidine, uridine, and inosine.

In some embodiments, the first sequence and the third sequence each comprise at least 5 bases. In some embodiments, the first sequence and the third sequence each comprise at least 10 bases.

In some embodiments, the adapter further comprises a fifth sequence, wherein the second sequence and the fifth sequence flank the first sequence. In some embodiments, the second strand of the double-stranded nucleic acid molecule further comprises a sixth sequence hybridized to the fifth sequence, wherein the fourth sequence and the sixth sequence flank the third sequence.

In a further aspect, the present disclosure provides a method for processing a nucleic acid sample, comprising: (a) providing the nucleic acid sample comprising a first nucleic acid molecule comprising a single strand; (b) attaching an adapter to an end of the first nucleic acid molecule, wherein the adapter comprises a first sequence and a second sequence; and (c) using the adapter to generate a double-stranded nucleic acid molecule comprising a second nucleic acid molecule that is complementary to the first nucleic acid molecule, wherein the double-stranded nucleic acid molecule comprises a third sequence hybridized to the first sequence and a fourth sequence hybridized to the second sequence, wherein the first sequence hybridized to the third sequence has a first melting point and the second sequence hybridized to the fourth sequence has a second melting point higher than the first melting point.

In some embodiments, prior to (c), the adapter is immobilized to a support. In some embodiments, the support is a planar array. In some embodiments, the support is a bead.

In some embodiments, subsequent to (c), the adapter is immobilized to a support. In some embodiments, the support is a planar array. In some embodiments, the support is a bead.

In some embodiments, the method further comprises attaching an additional adapter to another end of the first nucleic acid molecule. In some embodiments, the additional adapter comprises a fifth sequence and a sixth sequence.

In some embodiments, (b) comprises ligating the adapter to the first nucleic acid molecule. In some embodiments, (c) comprises hybridizing a primer to the adapter and using the primer to perform a primer extension reaction to yield the second nucleic acid molecule hybridized to the first nucleic acid molecule.

In some embodiments, (b) comprises hybridizing the adapter to the first nucleic acid molecule, and wherein in (c) comprises using the adapter as a primer to conduct a primer extension reaction to yield the second nucleic acid molecule hybridized to the first nucleic acid molecule.

In some embodiments, the first sequence and the third sequence comprise one or more bases selected from the group consisting of adenosine, thymidine, uridine, and inosine. In some embodiments, the first sequence and the third sequence only comprise bases selected from the group consisting of adenosine, thymidine, uridine, and inosine.

In some embodiments, the first sequence and the third sequence each comprise at least 5 bases. In some embodiments, the first sequence and the third sequence each comprise at least 10 bases.

In another aspect, the present disclosure provides a method for processing a nucleic acid sample, comprising: (a) providing the nucleic acid sample comprising a double-stranded nucleic acid molecule immobilized to a support, wherein the double-stranded nucleic acid molecule comprises a first strand and a second strand having sequence complementarity with the first strand, wherein: (i) the first strand comprises a template region that is attached to a first adapter comprising a first sequence and a second sequence adjacent to the first sequence, and (ii) the second strand comprises a sequence complementary to the template region that is attached to a second adapter comprising a third sequence and a fourth sequence adjacent to the third sequence, wherein the first sequence and the second sequence are respectively hybridized to the third sequence and the fourth sequence, wherein the first sequence hybridized to the third sequence has a first melting point and the second sequence hybridized to the fourth sequence has a second melting point higher than the first melting point, and wherein the support comprises a plurality of primer molecules immobilized thereto; and (b) performing an amplification reaction using a primer molecule of the plurality of primer molecules by subjecting the nucleic acid sample to conditions sufficient to (i) partially denature the double-stranded nucleic acid molecule, thereby separating the first sequence of the first adapter of the first strand from the third sequence of the second adapter of the second strand; (ii) hybridize the first primer molecule to the second sequence of the first strand; and (iii) generate a copy of the second strand.

In some embodiments, the method further comprises repeating (b) for at least the copy of the double-stranded nucleic acid molecule in the nucleic acid sample to generate at least 10 copies of the double-stranded nucleic acid molecule. In some embodiments, the method further comprises sequencing the all or a portion of the first strand, the second strand, or a copy or derivative thereof.

In some embodiments, (b) comprises exposing the double-stranded nucleic acid molecule or a portion thereof to a chemical denaturant. In some embodiments, the chemical denaturant is selected from the group consisting of a salt, formamide, urea, guanidine hydrochloride, and an organic solvent.

In some embodiments, (b) is performed under isothermal conditions.

In some embodiments, the first melting point is at least 1° C. lower than the second melting point. In some embodiments, the first melting point is at least 5° C. lower than the second melting point.

In some embodiments, (b) comprises heating the double-stranded nucleic acid molecule to a temperature higher than the first melting point and lower than the second melting point. In some embodiments, (b) comprises heating the double-stranded nucleic acid molecule to partially denature the double-stranded nucleic acid molecule. In some embodiments, the heating includes optical heating. In some embodiments, the heating includes resistive heating. In some embodiments, the heating includes convective heating. In some embodiments, the heating includes inductive heating.

In some embodiments, in (b), at most a portion of the first strand separates from the second strand.

In some embodiments, the adapter is ligated to the template region of the first strand. In some embodiments, the method further comprises, prior to (a), ligating the adapter to the template region of the first strand. In some embodiments, the first strand is provided as a single-stranded molecule, and further comprising, prior to (a), subjecting the first strand to a nucleic acid amplification reaction under conditions sufficient to generate the second strand hybridized to the first strand, thereby generating the double-stranded nucleic acid molecule.

In some embodiments, the second sequence is at an end of the first adapter of the first strand. In some embodiments, the fourth sequence is at an end of the second adapter of the second strand.

In some embodiments, the plurality of primer molecules are immobilized to the support in a predetermined pattern. In some embodiments, the plurality of primer molecules are uniformly distributed on the support.

In some embodiments, the plurality of primer molecules are immobilized to the support at a density of at least 10,000 primer molecules per $mm^2$. In some embodiments, the support is a planar array. In some embodiments, the support is a bead. In some embodiments, the support is a well.

In some embodiments, in (b), generating the copy of the second strand comprises performing a primer extension reaction.

In some embodiments, the first sequence and the third sequence comprise one or more bases selected from the group consisting of adenosine, thymidine, uridine, and inosine. In some embodiments, the first sequence and the third sequence only comprise bases selected from the group consisting of adenosine, thymidine, uridine, and inosine.

In some embodiments, the first sequence and the third sequence each comprise at least 5 bases. In some embodiments, the first sequence and the third sequence each comprise at least 10 bases.

In some embodiments, the nucleic acid sample comprises a plurality of double-stranded nucleic acid molecules immobilized to the support, wherein each double-stranded nucleic acid molecule of the plurality of double-stranded nucleic acid molecules comprises a first strand and a second strand having sequence complementarity with the first strand, wherein the first strand comprises a template region that is attached to a first adapter comprising a first sequence and a second sequence adjacent to the first sequence, and the second strand comprises a sequence complementary to the template region that is attached to a second adapter comprising a third sequence and a fourth sequence adjacent to the third sequence, wherein the first sequence and the second sequence are respectively hybridized to the third sequence and the fourth sequence, wherein the first sequence hybridized to the third sequence has a first melting point and the second sequence hybridized to the fourth sequence has a second melting point higher than the first melting point; and further comprising: (c) repeating (b) for each double-stranded nucleic acid molecule of the plurality of double-stranded nucleic acid molecules of the nucleic acid sample. In some embodiments, the plurality of double-stranded nucleic acid molecules comprises at least 100 double-stranded nucleic acid molecules. In some embodiments, the plurality of double-stranded nucleic acid molecules comprises at least 1,000 double-stranded nucleic acid molecules. In some embodiments, the plurality of double-stranded nucleic acid molecules comprises at least 10,000 double-stranded nucleic acid molecules. In some embodiments, the plurality of double-stranded nucleic acid molecules comprises one or more different template regions.

In yet another aspect, the present disclosure provides a method for processing a nucleic acid sample, comprising: (a) providing the nucleic acid sample comprising a single-stranded nucleic acid molecule immobilized to a support at a first end of the single-stranded nucleic acid molecule, wherein the single-stranded nucleic acid molecule comprises a template region that is attached to an adapter comprising a first sequence and a second sequence adjacent to the first sequence, wherein the adapter is disposed at a second end of the single-stranded nucleic acid molecule, and wherein the support comprises a plurality of primer molecules immobilized thereto, wherein each primer molecule of the plurality of primer molecules comprises a third sequence and a fourth sequence; (b) subjecting the single-stranded nucleic acid molecule to conditions sufficient to hybridize the first sequence of the adapter to the third sequence of a primer molecule of the plurality of primer molecules and the second sequence of the adapter to the fourth sequence of the primer molecule, thereby generating a double-stranded region comprising the adapter and the primer molecule, wherein the first sequence hybridized to the third sequence has a first melting point and the second sequence hybridized to the fourth sequence has a second melting point higher than the first melting point; (c) subjecting the double-stranded region to conditions sufficient to extend the primer molecule to provide a second strand that is partially complementary to the single-stranded nucleic acid molecule; and (d) subjecting the double-stranded region to conditions sufficient to partially denature the double-stranded region, thereby separating the first sequence of the adapter from the third sequence of the primer molecule, wherein (d) comprises exposing the double-stranded region to a chemical denaturant or heating the double-stranded region to a temperature higher than the first melting point and lower than the second melting point.

In some embodiments, (d) comprises exposing the double-stranded region to a chemical denaturant, wherein the chemical denaturant is selected from the group consisting of a salt, formamide, urea, guanidine hydrochloride, and an organic solvent.

In some embodiments, (b) is performed under isothermal conditions.

In some embodiments, the first melting point is at least 1° C. lower than the second melting point. In some embodiments, the first melting point is at least 5° C. lower than the second melting point.

In some embodiments, (d) comprises heating the double-stranded region to a temperature higher than the first melting point and lower than the second melting point. In some embodiments, the heating includes optical heating. In some embodiments, the heating includes resistive heating. In some embodiments, the heating includes convective heating. In some embodiments, the heating includes inductive heating.

In some embodiments, the adapter is ligated to the template region of the first strand. In some embodiments, the method further comprises, prior to (a), ligating the adapter to the template region of the first strand.

In some embodiments, the plurality of primer molecules are immobilized to the support in a predetermined pattern. In some embodiments, the plurality of primer molecules are uniformly distributed on the support. In some embodiments, the plurality of primer molecules are immobilized to the support at a density of at least 10,000 primer molecules per $mm^2$.

In some embodiments, the method further comprises, subsequent to (d), hybridizing the adapter to a second primer molecule of the plurality of primer molecules. In some embodiments, the method further comprises separating the first strand and the second strand. In some embodiments, the method further comprises repeating (c) and (d) to provide a third strand that is partially complementary to the single-stranded nucleic acid molecule.

In some embodiments, the support is a planar array. In some embodiments, the support is a bead. In some embodiments, the support is a well.

In some embodiments, the first sequence and the third sequence comprise one or more bases selected from the group consisting of adenosine, thymidine, uridine, and inosine. In some embodiments, the first sequence and the third sequence only comprise bases selected from the group consisting of adenosine, thymidine, uridine, and inosine.

In some embodiments, the first sequence and the third sequence each comprise at least 5 bases. In some embodiments, the first sequence and the third sequence each comprise at least 10 bases.

In a further aspect, the present disclosure provides a method for processing a double-stranded nucleic acid molecule, comprising: (a) providing the double-stranded nucleic acid molecule immobilized to a support, wherein the double-stranded nucleic acid molecule comprises a first strand and a second strand, wherein the first strand comprises a first sequence and a second sequence hybridized to a respective third sequence and fourth sequence of the second strand, and wherein the second sequence is disposed closer to the support than the first sequence; and (b) subjecting the double-stranded nucleic acid molecule to conditions sufficient to (i) separate the first sequence from the third sequence while keeping the second sequence hybridized to the fourth sequence, to partially denature the double-stranded nucleic acid molecule, and (ii) hybridize a primer molecule immobilized to the support to the first sequence.

In some embodiments, the first sequence hybridized to the third sequence has a first melting point and the second sequence hybridized to the fourth sequence has a second melting point different from the first melting point. In some embodiments, the first melting point is at least 1° C. lower than the second melting point. In some embodiments, the first melting point is at least 5° C. lower than the second melting point.

In some embodiments, (b) comprises heating the double-stranded nucleic acid molecule to a temperature higher than the first melting point and lower than the second melting point.

In some embodiments, the method further comprises using the primer molecule to separate the first strand and the second strand and generate a copy of the second strand hybridized to the first strand to generate a first copy of the double-stranded nucleic acid molecule. In some embodiments, the method further comprises hybridizing another primer molecule to the separated second strand to generate a copy of the first strand hybridized to the second strand to generate a second copy of the double-stranded nucleic acid molecule. In some embodiments, the method further comprises repeating (b) for at least a copy of the double-stranded nucleic acid molecule to generate at least 10 copies of the double-stranded nucleic acid molecule.

In some embodiments, the method further comprises sequencing the all or a portion of the first strand, the second strand, or a copy or derivative thereof.

In some embodiments, (b) comprises exposing the double-stranded nucleic acid molecule or a portion thereof to a chemical denaturant. In some embodiments, the chemical denaturant is selected from the group consisting of a salt, formamide, urea, guanidine hydrochloride, and an organic solvent.

In some embodiments, (b) is performed under isothermal conditions. In some embodiments, (b) comprises heating the double-stranded nucleic acid molecule to partially denature the double-stranded nucleic acid molecule. In some embodiments, the heating includes optical heating. In some embodiments, the heating includes resistive heating. In some embodiments, the heating includes convective heating. In some embodiments, the heating includes inductive heating.

In some embodiments, in (b), at most a portion of the first strand separates from the second strand.

In some embodiments, the first sequence is ligated to a template region of the first strand. In some embodiments, the method further comprises, prior to (a), ligating the first sequence to the template region of the first strand. In some embodiments, the first strand is provided as a single-stranded molecule, and further comprising, prior to (a), subjecting the first strand to a nucleic acid amplification reaction under conditions sufficient to generate the second strand hybridized to the first strand, thereby generating the double-stranded nucleic acid molecule.

In some embodiments, the second sequence is at an end of the first strand. In some embodiments, the fourth sequence is at an end of the second strand. In some embodiments, the support comprises a plurality of primer molecules, including the primer molecule, immobilized thereto. In some embodiments, the plurality of primer molecules are disposed in a predetermined pattern on the support. In some embodiments, the plurality of primer molecules are immobilized to the support at a density of at least 10,000 primer molecules per $mm^2$.

In some embodiments, the support is a planar array. In some embodiments, the support is a bead. In some embodiments, the support is a well.

In some embodiments, the method further comprises performing a primer extension reaction to generate a copy of the second strand.

In some embodiments, the first sequence and the third sequence comprise one or more bases selected from the group consisting of adenosine, thymidine, uridine, and inosine. In some embodiments, the first sequence and the third sequence only comprise bases selected from the group consisting of adenosine, thymidine, uridine, and inosine.

In some embodiments, the first sequence and the third sequence each comprise at least 5 bases. In some embodiments, the first sequence and the third sequence each comprise at least 10 bases.

In some embodiments, the nucleic acid sample comprises a plurality of double-stranded nucleic acid molecules immobilized to the support, wherein each double-stranded nucleic acid molecule of the plurality of double-stranded nucleic acid molecules comprises a first strand hybridized to a second strand, wherein the first strand comprises a first sequence and a second sequence hybridized to a respective third sequence and fourth sequence, and wherein the second sequence is disposed closer to the support than the first sequence; and further comprising: (c) repeating (b) for each double-stranded nucleic acid molecule of the plurality of double-stranded nucleic acid molecules of the nucleic acid sample. In some embodiments, the plurality of double-stranded nucleic acid molecules comprises at least 100 double-stranded nucleic acid molecules. In some embodiments, the plurality of double-stranded nucleic acid molecules comprises at least 1,000 double-stranded nucleic acid molecules. In some embodiments, the plurality of double-stranded nucleic acid molecules comprises at least 10,000 double-stranded nucleic acid molecules. In some embodiments, the plurality of double-stranded nucleic acid molecules comprises one or more different template regions.

The present disclosure additionally provides compositions and methods for use in nucleic acid processing. The methods provided herein may comprise the use of a nucleic acid molecule in a J-shaped configuration, which nucleic acid molecule may facilitate the amplification and/or sequencing of target nucleic acid molecules of a biological sample. The nucleic acid molecule may be immobilized to a substrate or may be provided in solution (e.g., to an immobilized target nucleic acid molecule). Target nucleic acid molecules may be functionalized with one or more adapters configured to interact with the nucleic acid molecule (e.g., having sequence complementarity to a sequence of the nucleic acid molecule). The nucleic acid molecule may be used to perform paired-end sequencing analyses of a target nucleic acid molecule, permitting collection of sequence information from both ends of the target nucleic acid molecule. Accordingly, the methods provided herein may allow for a doubling of the sequencing output from a fixed number of template nucleic acid molecules; reduction in errors by reading template molecules twice, once as a reverse complement; improved alignment of sequencing reads to a genome as two linked reads separated by a distance provide better alignment to a genome as compared to a single read; and simplified detection of structural variants if sequencing reads are far apart.

In an aspect, the present disclosure provides a method for paired-end sequencing, comprising (a) bringing a first end of a first nucleic acid strand comprising a first template sequence in contact with a sequencing primer, and subjecting the first nucleic acid strand to sequencing to yield a first sequencing read in a first direction away from the first end, which sequencing generates a second nucleic acid strand comprising a second template sequence complementary to the first template sequence and a first capture sequence, wherein the first nucleic acid strand is immobilized to a support via an immobilized nucleic acid molecule comprising a second capture sequence complementary to the first capture sequence, a first binding sequence, and a second binding sequence hybridized to the first binding sequence, wherein the second capture sequence of the immobilized nucleic acid molecule is adjacent to a second end of the first nucleic acid strand opposite the first end and hybridized to the first capture sequence of the second nucleic acid strand; (b) removing the first nucleic acid strand from the immobilized nucleic acid molecule to provide the second nucleic acid strand immobilized to the support via the immobilized nucleic acid molecule; and (c) using the second capture sequence of the immobilized nucleic acid molecule as a sequencing primer, subjecting the second nucleic acid strand to sequencing to generate a second sequencing read in a second direction opposite the first direction.

In some embodiments, the method for paired-end sequencing further comprises processing the first sequencing read and/or the second sequencing read to identify the first template sequence or the second template sequence. The first sequencing read may be processed to identify the second template sequence within the first sequencing read. The second sequencing read may be processed to identify the first template sequence within the second sequencing read. In some embodiments, sequencing comprises sequencing by synthesis. In some embodiments, sequencing comprises sequencing by hybridization. In some embodiments, sequencing comprises sequencing by ligation. In some embodiments, (a) comprises subjecting the first nucleic acid strand to conditions sufficient to hybridize the sequencing primer to the first nucleic acid strand. In some embodiments, (a) comprises subjecting the sequencing primer to a primer extension reaction. The primer extension reaction may comprise use of a polymerase. In some embodiments, subsequent to (a), the second nucleic acid strand is ligated to the second binding sequence of the immobilized nucleic acid molecule.

In some embodiments, (c) comprises generating a third nucleic acid strand comprising a third template sequence complementary to the second template sequence. In some embodiments, the method for paired-end sequencing further comprises removing the second nucleic acid strand from the immobilized nucleic acid molecule. In some embodiments, removing the second nucleic acid strand further comprises bringing the third nucleic acid strand in contact with an additional sequencing primer and sequencing the third nucleic acid strand to generate a third sequencing read. In some embodiments, prior to (a), the method for paired-end sequencing further comprises (d) providing the immobilized nucleic acid molecule and a template nucleic acid molecule comprising a template sequence complementary to the first template sequence, a first end comprising a third capture sequence complementary to the second capture sequence of the immobilized nucleic acid molecule, and a second end; (e) subjecting the template nucleic acid molecule to conditions sufficient to hybridize the third capture sequence of the template nucleic acid molecule to the second capture sequence, and (f) subjecting the immobilized nucleic acid molecule to conditions sufficient to extend the second capture sequence to the second end of the template nucleic acid molecule, thereby generating the first nucleic acid strand immobilized to the support.

In some embodiments, (f) comprises generating a third sequencing read. In some embodiments, sequencing the third nucleic acid strand comprises sequencing by synthesis. In some embodiments, sequencing the third nucleic acid strand comprises sequencing by hybridization. In some embodiments, sequencing the third nucleic acid strand comprises sequencing by ligation. In some embodiments, prior to (a), the method for paired-end sequencing further comprises (g) subjecting the template nucleic acid molecule attached to the immobilized nucleic acid molecule to conditions sufficient to remove the template nucleic acid molecule. In some embodiments, the template nucleic acid molecule is a deoxyribonucleic acid (DNA) molecule. In some embodiments, the template nucleic acid molecule is a ribonucleic acid (RNA) molecule. In some embodiments, (f) comprises subjecting the second capture sequence of the immobilized nucleic acid molecule to an extension reaction. In some embodiments, the extension reaction comprises use of a polymerase. In some embodiments, the support is a bead. In some embodiments, the support is a planar surface. In some embodiments, the immobilized nucleic acid molecule is attached to the support via a chemical linker. In some embodiments, the chemical linker comprises an amine group. In some embodiments, the second capture sequence resides in a capture region of the immobilized nucleic acid molecule that comprises a cleavable base. In some embodiments, the cleavable base is a uridine base or an 8-oxoguanine base. In some embodiments, (b) comprises cleaving the cleavable base. In some embodiments, (b) comprises use of a cleaving enzyme. In some embodiments, the first sequencing read and the second sequencing read do not overlap. In some embodiments, the first sequencing read and the second sequencing read overlap. In some embodiments, overlap between the first sequencing read and the second sequencing read comprises 5 or more bases. In some embodiments, the first sequencing read and the second sequencing read completely overlap. In some embodiments, the immobilized nucleic acid molecule comprises a replication block. In some embodiments, the second binding sequence of the immobilized nucleic acid molecule comprises the replication block.

In another aspect, the present disclosure provides a method for sequencing a template nucleic acid molecule, comprising (a) bringing an immobilized nucleic acid molecule in contact with a first nucleic acid strand derived from the template nucleic acid molecule to hybridize a first capture sequence of the immobilized nucleic acid molecule to a second capture sequence of the first nucleic acid strand, wherein (i) the immobilized nucleic acid molecule comprises the first capture sequence, a first binding sequence, and a second binding sequence hybridized to the first binding sequence, and (ii) the first nucleic acid strand comprises the second capture sequence that is complementary to the first capture sequence, a first template sequence, and a third capture sequence; (b) using the first capture sequence of the immobilized nucleic acid molecule as a primer to subject the first nucleic acid strand to a reaction under conditions sufficient to generate a second nucleic acid strand complementary to the first nucleic acid strand, which second nucleic acid strand comprises a second template sequence complementary to the first template sequence and a fourth capture sequence complementary to the third capture sequence; (c) removing the first nucleic acid strand from the immobilized nucleic acid molecule to provide the second nucleic acid strand immobilized to the support via the immobilized nucleic acid molecule; (d) subjecting the second nucleic acid strand to sequencing to yield a sequencing read corresponding to the second nucleic acid strand, which sequencing generates a third nucleic acid strand complementary to the second nucleic acid strand, which third nucleic acid strand comprises (i) a third template sequence complementary to the second template sequence and (ii) a fifth capture sequence complementary to the fourth capture sequence; and (e) using the sequencing read to identify the first template sequence of the first nucleic acid strand, thereby sequencing the template nucleic acid molecule.

In some embodiments, generating the sequencing read comprises sequencing by synthesis. In some embodiments, generating the sequencing read comprises sequencing by hybridization. In some embodiments, generating the sequencing read comprises sequencing by ligation. In some embodiments, (b) comprises subjecting the first nucleic acid strand to conditions sufficient to hybridize the first capture sequence to the first nucleic acid strand. In some embodiments, (b) comprises subjecting the first capture sequence to a primer extension reaction. In some embodiments, the primer extension reaction comprises use of a polymerase. In some embodiments, subsequent to (d), the third nucleic acid strand is ligated to the second binding sequence of the immobilized nucleic acid molecule. In some embodiments, method for sequencing a template nucleic acid molecule further comprises removing the second nucleic acid strand from the immobilized nucleic acid molecule. In some embodiments, removing the second nucleic acid strand further comprises using the first capture sequence of the immobilized nucleic acid molecule as a primer to subject the third nucleic acid strand to a reaction under conditions sufficient to generate a second sequencing read corresponding to the third nucleic acid strand. In some embodiments, the sequencing comprises sequencing by synthesis. In some embodiments, the sequencing comprises sequencing by hybridization. In some embodiments, the sequencing comprises sequencing by ligation.

In some embodiments, the sequencing read and the second sequencing read do not overlap. In some embodiments, the sequencing read and the second sequencing read overlap. In some embodiments, the overlap between the first sequencing read and the second sequencing read comprises 5 or more bases. In some embodiments, the first sequencing read and the second sequencing read completely overlap. In some embodiments, the template nucleic acid molecule is a deoxyribonucleic acid (DNA) molecule. In some embodiments, the template nucleic acid molecule is a ribonucleic acid (RNA) molecule. In some embodiments, the support comprises a bead. In some embodiments, the support comprises a planar surface. In some embodiments, the immobilized nucleic acid molecule is attached to the support via a chemical group. In some embodiments, the chemical group comprises an amine. In some embodiments, the first capture sequence resides in a region of the immobilized nucleic acid molecule that comprises a cleavable base. In some embodiments, the cleavable base is selected from a uridine base and an 8-oxoguanine base. In some embodiments, the immobilized nucleic acid molecule comprises a replication block.

In another aspect, the present disclosure provides a method for sequencing a template nucleic acid molecule, comprising (a) providing (i) the template nucleic acid molecule comprising a first nucleic acid strand comprising a first template nucleic acid sequence and (ii) an immobilized nucleic acid molecule comprising a first capture sequence, a first binding sequence, and a second binding sequence hybridized to the first binding sequence, and wherein the immobilized nucleic acid molecule is immobilized to a support; (b) using the first capture sequence of the immobilized nucleic acid molecule as a sequencing primer to sequence the immobilized nucleic acid molecule to yield a first sequencing read corresponding to the first template nucleic acid sequence, which sequencing comprises generating a second nucleic acid strand attached to the immobilized nucleic acid molecule, wherein the second nucleic acid strand comprises a second template nucleic acid sequence complementary to the first template nucleic acid sequence; and (c) sequencing the second nucleic acid strand attached to the immobilized nucleic acid molecule to yield a second sequencing read corresponding to the second template nucleic acid sequence.

In some embodiments, the sequencing comprises sequencing by synthesis. In some embodiments, the sequencing comprises sequencing by hybridization. In some embodiments, the sequencing comprises sequencing by ligation. In some embodiments, (b) comprises subjecting the first nucleic acid strand to conditions sufficient to hybridize the first capture sequence of the immobilized nucleic acid molecule to the first nucleic acid strand. In some embodiments, (b) comprises subjecting the first capture sequence to a primer extension reaction. In some embodiments, the primer extension reaction comprises use of a polymerase. In some embodiments, prior to (c), the first nucleic acid strand is removed from the immobilized nucleic acid molecule to provide the second nucleic acid strand immobilized to the support via the immobilized nucleic acid molecule. In some embodiments, the sequencing comprises bringing the second nucleic acid strand in contact with a sequencing primer, hybridizing the sequencing primer to the second nucleic acid strand, and subjecting the sequencing primer to a primer extension reaction. In some embodiments, (c) comprises generating a third nucleic acid strand comprising a third template nucleic acid sequence complementary to the second template nucleic acid sequence.

In some embodiments, the first sequencing read and the second sequencing read do not overlap. In some embodiments, the first sequencing read and the second sequencing read overlap. In some embodiments, the overlap between the first sequencing read and the second sequencing read comprises 5 or more bases. In some embodiments, the first sequencing read and the second sequencing read completely overlap. In some embodiments, the template nucleic acid molecule is a deoxyribonucleic acid (DNA) molecule. In some embodiments, the template nucleic acid molecule is a ribonucleic acid (RNA) molecule. In some embodiments, the support comprises a bead. In some embodiments, the support comprises a planar surface. In some embodiments, the immobilized nucleic acid molecule is attached to the support via a chemical group. In some embodiments, the chemical group comprises an amine. In some embodiments, the first capture sequence resides in a region of the immobilized nucleic acid molecule that comprises a cleavable base. In some embodiments, the cleavable base is selected from a uridine base and an 8-oxoguanine base. In some embodiments, the immobilized nucleic acid molecule comprises a replication block. In some embodiments, the second binding sequence of the immobilized nucleic acid molecule comprises the replication block.

In another aspect, the present disclosure provides a method for sequencing, comprising (a) providing a support comprising (i) a first nucleic acid strand comprising a first template sequence and a first capture sequence at a first end, which first nucleic acid strand is immobilized to the support via a first immobilized nucleic acid molecule that comprises a first binding sequence, a second binding sequence hybridized to the first binding sequence, and a second capture sequence, wherein the second capture sequence of the immobilized nucleic acid molecule is adjacent to a second end of the first nucleic acid strand opposite the first end; and (ii) a second immobilized nucleic acid molecule, which second immobilized nucleic acid molecule comprises a third binding sequence, a fourth binding sequence hybridized to the third binding sequence, and a third capture sequence; and (b) subjecting the first nucleic acid strand to sequencing to yield a sequencing read in a first direction away from the first end, which sequencing comprises (i) hybridizing the first capture sequence of the first nucleic acid strand to the third capture sequence of the second immobilized nucleic acid molecule, and (ii) generating a second nucleic acid strand comprising a second template sequence complementary to the first template sequence.

In some embodiments, the method for sequencing further comprises (c) subjecting the first nucleic acid strand and the second nucleic acid strand to conditions sufficient to separate the first nucleic acid strand and the second nucleic acid strand, thereby providing the first nucleic acid strand immobilized to the support via the first immobilized nucleic acid molecule and the second nucleic acid strand immobilized to the support via the second immobilized nucleic acid molecule. In some embodiments, the third binding sequence and the first binding sequence are the same, and wherein the fourth binding sequence and the second binding sequence are the same. In some embodiments, the second capture sequence of the first immobilized nucleic acid molecule is the same as the third capture sequence of the second immobilized nucleic acid molecule. In some embodiments, the first capture sequence of the first nucleic acid strand is complementary to the third capture sequence of the second immobilized nucleic acid molecule. In some embodiments, separating the first nucleic acid strand and the second nucleic acid strand further comprises repeating (b) and (c) with a third immobilized nucleic acid molecule, which third immobilized nucleic acid molecule comprises a fifth binding sequence, a sixth binding sequence hybridized to the fifth binding sequence, and a fourth capture sequence. In some embodiments, the method for sequencing further comprises processing the sequencing read to identify the first template sequence. In some embodiments, the sequencing comprises sequencing by synthesis. In some embodiments, the sequencing comprises sequencing by hybridization. In some embodiments, the sequencing comprises sequencing by ligation. In some embodiments, (b) comprises the use of a polymerase.

In some embodiments, in the method for sequencing, prior to (a), (d) providing the first immobilized nucleic acid molecule and a template nucleic acid molecule comprising a template sequence complementary to the first template sequence, a first end comprising a fourth capture sequence complementary to the second capture sequence of the first immobilized nucleic acid molecule, and a second end; (e) subjecting the template nucleic acid molecule to conditions sufficient to hybridize the fourth capture sequence of the template nucleic acid molecule to the second capture sequence, and (f) subjecting the first immobilized nucleic acid molecule to conditions sufficient to extend the second capture sequence to the second end of the template nucleic acid molecule, thereby generating the first nucleic acid strand immobilized to the support. In some embodiments, (f) comprises sequencing to yield a second sequencing read. In some embodiments, the sequencing comprises sequencing by synthesis. In some embodiments, the sequencing comprises sequencing by hybridization. In some embodiments, the sequencing comprises sequencing by ligation. In some embodiments, in the method for sequencing, prior to providing the support further comprises (g) subjecting the template nucleic acid molecule attached to the first immobilized nucleic acid molecule to conditions sufficient to remove the template nucleic acid molecule. In some embodiments, the template nucleic acid molecule is a deoxyribonucleic acid (DNA) molecule. In some embodiments, the template nucleic acid molecule is a ribonucleic acid (RNA) molecule. In some embodiments, (f) comprises subjecting the second capture sequence of the first immobilized nucleic acid molecule to an extension reaction.

In some embodiments, the extension reaction comprises use of a polymerase. In some embodiments, the support comprises a bead. In some embodiments, the support comprises a planar surface. In some embodiments, the first and second immobilized nucleic acid molecules are attached to the support via one or more chemical groups. In some embodiments, the one or more chemical groups comprise an amine. In some embodiments, the second capture sequence resides in a capture region of the first immobilized nucleic acid molecule that comprises a cleavable base. In some embodiments, the cleavable base is selected from a uridine base and an 8-oxoguanine base. In some embodiments, the first immobilized nucleic acid molecule comprises a replication block. In some embodiments, the second binding sequence of the first immobilized nucleic acid molecule comprises the replication block.

In another aspect, the present disclosure provides a method for sequencing a template nucleic acid molecule, comprising (a) providing a support comprising (i) a first immobilized nucleic acid molecule that comprises a first binding sequence, a second binding sequence hybridized to the first binding sequence, and a first capture sequence; and (ii) a second immobilized nucleic acid molecule that comprises a third binding sequence, a fourth binding sequence hybridized to the third binding sequence, and a second capture sequence; (b) bringing the first immobilized nucleic acid molecule in contact with a first nucleic acid strand derived from the template nucleic acid molecule to hybridize the first capture sequence of the first immobilized nucleic acid molecule to a third capture sequence of the first nucleic acid strand, wherein the first nucleic acid strand comprises the third capture sequence that is complementary to the first capture sequence and a first template sequence; (c) using the first capture sequence of the immobilized nucleic acid molecule as a primer to subject the first nucleic acid strand to a reaction under conditions sufficient to generate a second nucleic acid strand complementary to the first nucleic acid strand, which second nucleic acid strand comprises a second template sequence complementary to the first template sequence; and (d) subjecting the first nucleic acid strand immobilized to the support via the first immobilized nucleic acid molecule to conditions sufficient to (i) separate the third capture sequence from the first capture sequence of the first immobilized nucleic acid molecule and (ii) hybridize the third capture sequence to the second capture sequence of the second immobilized nucleic acid molecule.

In some embodiments, the method for sequencing a template nucleic acid molecule further comprises (e) subjecting the third capture sequence of the first nucleic acid strand hybridized to the second capture sequence of the second immobilized nucleic acid molecule to sequencing to yield a sequencing read corresponding to the first nucleic acid strand, which sequencing comprises generating a third nucleic acid strand comprising a second template sequence complementary to the first template sequence. In some embodiments, the first nucleic acid strand comprises a fourth capture sequence and the second nucleic acid strand comprises a fifth capture sequence complementary to the fourth capture sequence, and the method further comprises (f) bringing the fifth capture sequence of the second nucleic acid strand in contact with a sequencing primer and subjecting the second nucleic acid strand to sequencing to yield a second sequencing read corresponding to the second nucleic acid strand, which sequencing comprises generating a fourth nucleic acid strand comprising a third template sequence complementary to the second template sequence of the second nucleic acid strand. In some embodiments, the sequencing of the first nucleic acid strand comprises sequencing by synthesis. In some embodiments, the sequencing of the first nucleic acid strand comprises sequencing by hybridization. In some embodiments, the sequencing of the first nucleic acid strand comprises sequencing by ligation. In some embodiments, the sequencing of the second nucleic acid strand comprises sequencing by synthesis. In some embodiments, the sequencing of the second nucleic acid strand comprises sequencing by hybridization. In some embodiments, the sequencing of the second nucleic acid strand comprises sequencing by ligation. In some embodiments, (c) comprises subjecting the first capture sequence to a primer extension reaction. In some embodiments, the primer extension reaction comprises use of a polymerase. In some embodiments, (e) comprises subjecting the second capture sequence to a primer extension reaction. In some embodiments, the primer extension reaction comprises use of a polymerase. In some embodiments, the template nucleic acid molecule is a deoxyribonucleic acid (DNA) molecule. In some embodiments, the template nucleic acid molecule is a ribonucleic acid (RNA) molecule. In some embodiments, the support comprises a bead. In some embodiments, the support comprises a planar surface. In some embodiments, the first immobilized nucleic acid molecule and the second immobilized nucleic acid molecule are attached to the support via one or more chemical groups. In some embodiments, the one or more chemical groups comprise an amine. In some embodiments, the first capture sequence resides in a region of the first immobilized nucleic acid molecule that comprises a cleavable base. In some embodiments, the cleavable base is selected from a uridine base and an 8-oxoguanine base. In some embodiments, the first immobilized nucleic acid molecule comprises a replication block.

In another aspect, the present disclosure provides a method for sequencing a template nucleic acid molecule, comprising (a) providing a support comprising (i) a first immobilized nucleic acid molecule that comprises a first binding sequence, a second binding sequence hybridized to the first binding sequence, and a first capture sequence; and (ii) a second immobilized nucleic acid molecule that comprises a third binding sequence, a fourth binding sequence hybridized to the third binding sequence, and a second capture sequence; (b) bringing the first immobilized nucleic acid molecule in contact with a first nucleic acid strand derived from the template nucleic acid molecule to hybridize the first capture sequence of the first immobilized nucleic acid molecule to a third capture sequence of the first nucleic acid strand, wherein the first nucleic acid strand comprises the third capture sequence that is complementary to the first capture sequence and a first template sequence; (c) using the first capture sequence of the first immobilized nucleic acid molecule as a primer to subject the first nucleic acid strand to a reaction under conditions sufficient to generate a second nucleic acid strand complementary to the first nucleic acid strand, which second nucleic acid strand comprises a second template sequence complementary to the first template sequence, and which second nucleic acid is hybridized to a first portion of the first nucleic acid strand comprising the third capture sequence and a second portion of the first nucleic acid strand that does not comprise the third capture sequence; and (d) subjecting the first capture sequence of the first immobilized nucleic acid molecule hybridized to the third capture sequence of the first nucleic acid strand to conditions sufficient to at least partially separate the first capture sequence from the third capture sequence.

In some embodiments, all or a portion of the first capture sequence hybridized to the third capture sequence has a first melting point and the second nucleic acid strand hybridized to the second portion of the first nucleic acid strand has a second melting point that is higher than the first melting point. In some embodiments, (d) comprises exposing the first capture sequence hybridized to the third capture sequence to a chemical denaturant. In some embodiments, the chemical denaturant is selected from the group consisting of a salt, formamide, urea, guanidine hydrochloride, and an organic solvent. In some embodiments, (d) is performed under isothermal conditions.

In some embodiments, the first melting point is at least 1° C. lower than the second melting point. In some embodiments, the first melting point is at least 5° C. lower than the second melting point. In some embodiments, (d) comprises heating the double-stranded nucleic acid molecule to a temperature higher than the first melting point and lower than the second melting point. In some embodiments, (d) comprises heating the double-stranded nucleic acid molecule to partially denature the double-stranded nucleic acid molecule. In some embodiments, the heating includes optical heating. In some embodiments, the heating includes resistive heating. In some embodiments, the heating includes convective heating. In some embodiments, the heating includes inductive heating. In some embodiments, sequencing a template nucleic acid molecule further comprises bringing the first capture sequence, or a portion thereof, in contact with a primer molecule such that the first capture sequence, or a portion thereof, hybridizes to the primer molecule. In some embodiments, bringing the first capture sequence, or a portion thereof, in contact with a primer molecule further comprises subjecting the primer molecule hybridized to the first capture sequence, or a portion thereof, to a primer extension reaction. In some embodiments, the primer extension reaction comprises the use of a polymerase. In some embodiments, the primer extension reaction separates the first capture sequence and the third capture sequence of the first nucleic acid strand. In some embodiments, sequencing a template nucleic acid molecule, further comprises (e) separating the first capture sequence and the third capture sequence. In some embodiments, subsequent to (e), the third capture sequence of the first nucleic acid strand hybridizes to the second capture sequence of the second immobilized nucleic acid molecule. In some embodiments, hybridizing the third capture sequence of the first nucleic acid strand to the second capture sequence of the second immobilized nucleic acid molecule further comprises subjecting the second capture sequence to sequencing to yield a sequencing read corresponding to the first nucleic acid strand, which sequencing comprises generating a third nucleic acid strand comprising a third template sequence, which third template sequence is complementary to the first template sequence of the first nucleic acid strand. In some embodiments, generating the sequencing read and the third nucleic acid strand comprises a primer extension reaction. In some embodiments, the primer extension reaction comprises the use of a polymerase. In some embodiments, the sequencing comprises sequencing by synthesis. In some embodiments, the sequencing comprises sequencing by hybridization. In some embodiments, the sequencing comprises sequencing by ligation. In some embodiments, the first nucleic acid strand comprises a fourth capture sequence and the second nucleic acid strand comprises a fifth capture sequence complementary to the fourth capture sequence, and the method further comprises (f) bringing the fifth capture sequence of the second nucleic acid strand in contact with a sequencing primer and subjecting the second nucleic acid strand to sequencing to yield a second sequencing read corresponding to the second nucleic acid strand, which sequencing comprises generating a fourth nucleic acid strand comprising a third template sequence complementary to the second template sequence of the second nucleic acid strand. In some embodiments, subjecting the second capture sequence to sequencing further comprises using the sequencing read to identify the first template sequence of the first nucleic acid strand, thereby sequencing the template nucleic acid molecule. In some embodiments, the template nucleic acid molecule is a deoxyribonucleic acid (DNA) molecule. In some embodiments, the template nucleic acid molecule is a ribonucleic acid (RNA) molecule. In some embodiments, the support comprises a bead. In some embodiments, the support comprises a planar surface. In some embodiments, the first immobilized nucleic acid molecule and the second immobilized nucleic acid molecule are attached to the support via one or more chemical groups. In some embodiments, the one or more chemical groups comprises an amine. In some embodiments, the first capture sequence resides in a region of the first immobilized nucleic acid molecule that comprises a cleavable base. In some embodiments, the cleavable base is selected from a uridine base and an 8-oxoguanine base. In some embodiments, the immobilized nucleic acid molecule comprises a replication block.

In another aspect, the present disclosure provides a method for sequencing a template nucleic acid molecule, comprising (a) providing an immobilized nucleic acid strand that is immobilized to a support, which immobilized nucleic acid strand comprises (i) a first nucleic acid strand derived from the template nucleic acid molecule, the first nucleic acid strand comprising a first capture sequence and a first template sequence, and (ii) a second capture sequence hybridized to the first capture sequence of the first nucleic acid strand, wherein the first capture sequence and the second capture sequence are separated by a single-stranded region; (b) subjecting the immobilized nucleic acid strand to sequencing to yield a sequencing read corresponding to the first nucleic acid strand of the immobilized nucleic acid strand, which sequencing comprises generating a second nucleic acid strand complementary to the first nucleic acid strand, which second nucleic acid strand comprises a second template sequence complementary to the first template sequence; (c) bringing the single-stranded region of the immobilized nucleic acid strand into contact with a primer molecule and subjecting the immobilized nucleic acid strand to conditions sufficient to extend the primer molecule, thereby separating the first nucleic acid strand and the second nucleic acid strand.

In some embodiments, the method for sequencing a template nucleic acid molecule further comprises using the sequencing read to identify the first template sequence of the first nucleic acid strand, thereby sequencing the template nucleic acid molecule. In some embodiments, the method for sequencing a template nucleic acid molecule, prior to (a), further comprises (d) bringing the first nucleic acid strand immobilized to the support in contact with a capture nucleic acid molecule to hybridize the second capture sequence of the capture nucleic acid molecule to the first capture sequence of the first nucleic acid strand, wherein the capture nucleic acid molecules comprises the second capture sequence, a first binding sequence, and a second binding sequence hybridized to the first binding sequence; (e) using the second capture sequence of the capture nucleic acid molecule as a primer to subject the first nucleic acid strand to sequencing to yield a second sequencing read corresponding to the first nucleic acid strand, which sequencing comprises generating a third nucleic acid strand complementary to the first nucleic acid strand, which third nucleic acid strand comprises a third template sequence complementary to the first template sequence; and (f) removing the third nucleic acid strand from the first nucleic acid strand and separating the first capture sequence hybridized to the second capture sequence, thereby providing the immobilized nucleic strand.

In some embodiments, the sequencing the first nucleic acid strand comprises sequencing by synthesis. In some embodiments, the sequencing the first nucleic acid strand comprises sequencing by hybridization. In some embodiments, the sequencing the first nucleic acid strand comprises sequencing by ligation. In some embodiments, the sequencing the first nucleic acid strand comprises sequencing by synthesis. In some embodiments, the sequencing the first nucleic acid strand comprises sequencing by hybridization. In some embodiments, the sequencing the first nucleic acid strand comprises sequencing by ligation. In some embodiments, (b) comprises subjecting the immobilized nucleic acid strand to a primer extension reaction. In some embodiments, the primer extension reaction comprises use of a polymerase. In some embodiments, (e) comprises subjecting the first nucleic acid strand to a primer extension reaction. In some embodiments, the primer extension reaction comprises use of a polymerase. In some embodiments, the template nucleic acid molecule is a deoxyribonucleic acid (DNA) molecule. In some embodiments, the template nucleic acid molecule is a ribonucleic acid (RNA) molecule. In some embodiments, the support comprises a bead. In some embodiments, support comprises a planar surface. In some embodiments, the immobilized nucleic acid molecule is attached to the support via a chemical group. In some embodiments, the chemical group comprises an amine. In some embodiments, the second capture sequence resides in a region of the capture nucleic acid molecule that comprises a cleavable base. In some embodiments, the cleavable base is selected from a uridine base and an 8-oxoguanine base. In some embodiments, the capture nucleic acid molecule comprises a replication block. In some embodiments, sequencing a template nucleic acid molecule further comprises bringing a sequencing primer in contact with the second nucleic acid strand and subjecting the second nucleic acid strand to sequencing to yield a third sequencing read corresponding to the second nucleic acid strand, which sequencing comprises generating a fourth nucleic acid strand, which fourth nucleic acid strand comprises a fourth template sequence that is complementary to the second template sequence of the second nucleic acid strand. In some embodiments, (b) and (c) occur simultaneously. In some embodiments, (b) occurs before (c).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 8 shows construction of an adapter with regions of high and low melting temperatures (SEQ ID NO: 15);

FIG. 16 illustrates example chemical structures of replication blocks.

DETAILED DESCRIPTION

Figure 1:
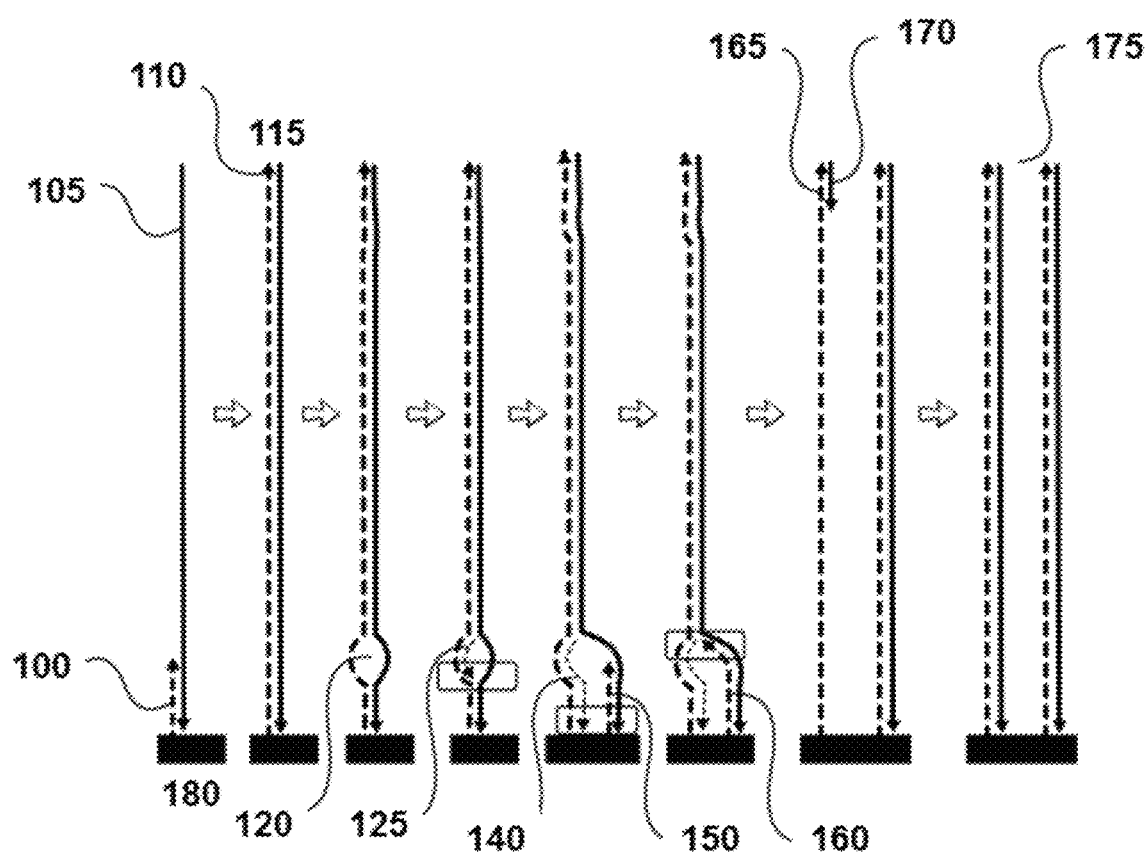
FIG. 1 schematically illustrates a clonal amplification method.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "amplification," as used herein, generally refers to the production of copies of a nucleic acid molecule. An amplicon is a single-stranded or double-stranded nucleic acid molecule that is generated by an amplification procedure from a starting template nucleic acid molecule. The amplicon may comprise a nucleic acid strand, of which at least a portion may be substantially identical or substantially complementary to at least a portion of the starting template. Where the starting template is a double-stranded nucleic acid molecule, an amplicon may comprise a nucleic acid strand that is substantially identical to at least a portion of one strand and is substantially complementary to at least a portion of either strand. The amplicon can be single-stranded or double-stranded irrespective of whether the initial template is single-stranded or double-stranded.

The term "denaturation," as used herein, generally refers to separation of a double-stranded molecule (e.g., DNA) into single-stranded molecules. Denaturation may be complete or partial denaturation. In partial denaturation, a single-stranded region may form in a double-stranded molecule by denaturation of the two deoxyribonucleic acid (DNA) strands flanked by double-stranded regions in DNA. Partial denaturation may also be referred to herein as "bubble formation."

The term "clonal," as used herein, generally refers to a population of nucleic acids for which a substantial portion (e.g., greater than 50%, 60%, 70%, 80%, 90%, 95%, or 99%) of its members have substantially identical sequences. Members of a clonal population of nucleic acid molecules may have sequence homology to one another. Such members may have sequence homology to a template nucleic acid molecule. The members of the clonal population may be double stranded or single stranded. Members of a population may not be 100% identical or complementary, e.g., "errors" may occur during the course of synthesis such that a minority of a given population may not have sequence homology with a majority of the population. For example, at least 50% of the members of a population may be substantially identical to each other or to a reference nucleic acid molecule (i.e., a molecule of defined sequence used as a basis for a sequence comparison). At least 60%, at least 70%, at least 80%, at least 90%, at least 95%, at least 99%, or more of the members of a population may be substantially identical to the reference nucleic acid molecule. Two molecules may be considered substantially identical (or homologous) if the percent identity between the two molecules is at least 60%, 70%, 75%, 80%, 85%, 90%, 95%, 98%, 99%, 99.9% or greater. Two molecules may be considered substantially complementary if the percent complementarity between the two molecules is at least 60%, 70%, 75%, 80%, 85%, 90%, 95%, 98%, 99%, 99.9% or greater. A low or insubstantial level of mixing of non-homologous nucleic acids may occur, and thus a clonal population may contain a minority of diverse nucleic acids (e.g., less than 30%, e.g., less than 10%).

The term "complementary sequence," as used herein, generally refers to a sequence that hybridizes to another sequence. Hybridization between two single-stranded nucleic acid molecules may involve the formation of a double-stranded structure that is stable under certain conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "polymerizing enzyme," as used herein, generally refers to a substance catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending 3' end of an existing nucleotide chain, adding new nucleotides matched to the template strand one at a time via the creation of phosphodiester bonds. A polymerizing enzyme may be a polymerase such as a nucleic acid polymerase. A polymerase may be naturally occurring or synthesized. A polymerase may have relatively high processivity, namely the capability of the polymerase to consecutively incorporate nucleotides into a nucleic acid template without releasing the nucleic acid template. A polymerizing enzyme may be a transcriptase. Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase, 029 (phi29) DNA polymerase, Taq polymerase, Tth polymerase, Tli polymerase, Pfu polymerase, Pwo polymerase, VENT polymerase, DEEPVENT polymerase, EXTaq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. A polymerase may be a single subunit polymerase.

The term "melting temperature" or "melting point," as used herein, generally refers to the temperature at which at least a portion of a strand of a nucleic acid molecule in a sample has separated from at least a portion of a complementary strand. The melting temperature may be the temperature at which a double-stranded nucleic acid molecule has partially or completely denatured. The melting temperature may refer to a temperature of a sequence among a plurality of sequences of a given nucleic acid molecule, or a temperature of the plurality of sequences. Different regions of a double-stranded nucleic acid molecule may have different melting temperatures. For example, a double-stranded nucleic acid molecule may include a first region having a first melting point and a second region having a second melting point that is higher than the first melting point. Accordingly, different regions of a double-stranded nucleic acid molecule may melt (e.g., partially denature) at different temperatures. The melting point of a nucleic acid molecule or a region thereof (e.g., a nucleic acid sequence) may be determined experimentally (e.g., via a melt analysis or other procedure) or may be estimated based upon the sequence and length of the nucleic acid molecule. For example, a software program such as MELTING may be used to estimate a melting temperature for a nucleic acid sequence (Dumousseau M, Rodriguez N, Juty N, Le Novère N, MELTING, a flexible platform to predict the melting temperatures of nucleic acids. BMC Bioinformatics. 2012 May 16; 13:101. doi: 10.1186/1471-2105-13-101). Accordingly, a melting point as described herein may be an estimated melting point. A true melting point of a nucleic acid sequence may vary based upon the sequences or lack thereof adjacent to the nucleic acid sequence of interest as well as other factors.

The term "nucleotide," as used herein, generally refers to a substance including a base (e.g., a nucleobase), sugar moiety, and phosphate moiety. A nucleotide may comprise a free base with attached phosphate groups. A substance including a base with three attached phosphate groups may be referred to as a nucleoside triphosphate. When a nucleotide is being added to a growing nucleic acid molecule strand, the formation of a phosphodiester bond between the proximal phosphate of the nucleotide to the growing chain may be accompanied by hydrolysis of a high-energy phosphate bond with release of the two distal phosphates as a pyrophosphate. The nucleotide may be naturally occurring or non-naturally occurring (e.g., a modified or engineered nucleotide).

The term "nucleotide analog," as used herein, may include, but is not limited to, a nucleotide that may or may not be a naturally occurring nucleotide. For example, a nucleotide analog may be derived from and/or include structural similarities to a canonical nucleotide such as adenine-(A), thymine-(T), cytosine-(C), uracil-(U), or guanine-(G) including nucleotide. A nucleotide analog may comprise one or more differences or modifications relative to a natural nucleotide. Examples of nucleotide analogs include inosine, diaminopurine, 5-fluorouracil, 5-bromouracil, 5-chlorouracil, 5-iodouracil, hypoxanthine, xanthine, deazaxanthine, deazaguanine, isocytosine, isoguanine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, 2,6-diaminopurine, ethynyl nucleotide bases, 1-propynyl nucleotide bases, azido nucleotide bases, phosphoroselenoate nucleic acids, and modified versions thereof (e.g., by oxidation, reduction, and/or addition of a substituent such as an alkyl, hydroxyalkyl, hydroxyl, or halogen moiety). Nucleic acid molecules (e.g., polynucleotides, double-stranded nucleic acid molecules, single-stranded nucleic acid molecules, primers, adapters, etc.) may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety, or phosphate backbone. In some cases, a nucleotide may include a modification in its phosphate moiety, including a modification to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates), and modifications with selenium moieties (e.g., phosphoroselenoate nucleic acids). A nucleotide or nucleotide analog may comprise a sugar selected from the group consisting of ribose, deoxyribose, and modified versions thereof (e.g., by oxidation, reduction, and/or addition of a substituent such as an alkyl, hydroxyalkyl, hydroxyl, or halogen moiety). A nucleotide analog may also comprise a modified linker moiety (e.g., in lieu of a phosphate moiety). Nucleotide analogs may also contain amine-modified groups, such as aminoallyl-dUTP (aa-dUTP) and aminohexylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure may provide, for example, higher density in bits per cubic mm, higher safety (resistant to accidental or purposeful synthesis of natural toxins), easier discrimination in photo-programmed polymerases, and/or lower secondary structure. Nucleotide analogs may be capable of reacting or bonding with detectable moieties for nucleotide detection.

The term "support" or "substrate," as used herein, generally refers to any solid or semi-solid article on which reagents such as nucleic acid molecules may be immobilized. Nucleic acid molecules may be synthesized, attached, ligated, or otherwise immobilized. Nucleic acid molecules may be immobilized on a substrate by any method including, but not limited to, physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous, and may have swelling or non-swelling characteristics. A substrate may be shaped to comprise one or more wells, depressions, or other containers, vessels, features, or locations. A plurality of substrates may be configured in an array at various locations. A substrate may be addressable (e.g., for robotic delivery of reagents), or by detection approaches, such as scanning by laser illumination and confocal or deflective light gathering. For example, a substrate may be in optical and/or physical communication with a detector. Alternatively, a substrate may be physically separated from a detector by a distance. An amplification substrate (e.g., a bead) can be placed within or on another substrate (e.g., within a well of a second support).

The term "primer," as used herein, generally refers to a polynucleotide which is complementary to a portion of a template nucleic acid molecule. For example, a primer may be complementary to a portion of a strand of a template nucleic acid molecule. A primer may exhibit sequence identity or homology or complementarity to a template nucleic acid molecule. The complementarity or homology or sequence identity between the primer and the template nucleic acid molecule may be limited. The homology or sequence identity or complementarity between the primer and a template nucleic acid molecule may be based on the length of the primer. For example, if the primer length is about 20 nucleotide bases, it may contain 10 or more contiguous nucleotide bases complementary to the template nucleic acid molecule. The length of the primer may be, for example, between 8 and 50 nucleotide bases. In some cases, the length of a primer may be more than 2 nucleotide bases, such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, or more nucleotide bases. In some cases, the length of a primer may be less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or fewer nucleotide bases.

The term "primer extension reaction," as used herein, generally refers to binding of a primer to a strand of a template nucleic acid molecule, followed by elongation of the primer. It may also include denaturing of a double-stranded nucleic acid molecule and the binding of a primer to either one or both denatured strands of the double-stranded nucleic acid molecule, followed by elongation of one or more primers. Primer extension reactions may be used to incorporate nucleotides or nucleotide analogs to a primer in template-directed fashion by using enzymes (e.g., polymerizing enzymes).

The term "label," as used herein, generally refers to a moiety that is capable of coupling with a species, such as, for example a nucleotide analog. A label may include an affinity moiety. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after a primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris (2-carboxyethyl) phosphine (TCEP), tris (hydroxypropyl) phosphine (THP) or enzymatically cleavable (e.g., via an esterase, lipase, peptidase or protease). In some cases, the label may be luminescent; that is, fluorescent or phosphorescent. Labels may be quencher molecules. The term "quencher," as used herein refers to a molecule that can reduce an emitted signal. For example, a template nucleic acid molecule may be designed to emit a detectable signal. Incorporation of a nucleotide or nucleotide analog comprising a quencher can reduce or eliminate the signal, which reduction or elimination is then detected. In some cases, as described elsewhere herein, labelling with a quencher can occur after nucleotide or nucleotide analog incorporation. Non-limiting examples of dyes include SYBR green, SYBR blue, DAPI, propidium iodine, Hoechst, SYBR gold, ethidium bromide, acridine, proflavine, acridine orange, acriflavine, fluorcoumarin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5-(or 6-) iodoacetamidofluorescein, 5-{[2 (and 3)-5-(Acetylmercapto)-succinyl] amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxy-pyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be a type that does not self-quench or exhibit proximity quenching. Non-limiting examples of a label type that does not self-quench or exhibit proximity quenching include Bimane derivatives such as Monobromobimane. The term "proximity quenching," as used herein, generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nm to 50 nm of each other.

The term "detector," as used herein, generally refers to a device that is capable of detecting a signal, such as a signal indicative of the presence or absence of an incorporated nucleotide or nucleotide analog. A detector may include optical and/or electronic components that may detect signals. Non-limiting examples of detection methods involving a detector include optical detection, spectroscopic detection, electrostatic detection, and electrochemical detection. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "sequencing," as used herein, generally refers to a process for generating or identifying a sequence of a biological molecule, such as a nucleic acid molecule. Such a sequence may be a nucleic acid sequence, which may include a sequence of nucleic acid bases (e.g., nucleobases). Sequencing may be, for example, single molecule sequencing, sequencing by synthesis, sequencing by hybridization, or sequencing by ligation. Sequencing may be performed using template nucleic acid molecules immobilized on a support, such as a flow cell or one or more beads (e.g., as described herein).

The term "mesoscopic," as used herein, generally refers to materials of an intermediate length. The scale of these materials can be described as being between the size of a quantity of atoms (such as a molecule) and of materials measuring micrometers. The lower limit of mesoscopic materials can also be defined as being the size of individual atoms. A mesoscopic object, by contrast, is affected by fluctuations around the average, and is subject to quantum mechanics.

The term "read," as used herein, generally refers to a nucleic acid sequence, such as a sequencing read. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

The term "subject," as used herein, generally refers to an individual or entity from which a biological sample (e.g., a biological sample that is undergoing or will undergo processing or analysis) may be derived. A subject may be an animal (e.g., mammal or non-mammal) or plant. The subject may be a human, dog, cat, horse, pig, bird, non-human primate, simian, farm animal, companion animal, sport animal, or rodent. A subject may be a patient. The subject may have or be suspected of having a disease or disorder, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. Alternatively or in addition, a subject may be known to have previously had a disease or disorder. The subject may have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, *porphyria*, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease. A subject may be undergoing treatment for a disease or disorder. A subject may be symptomatic or asymptomatic of a given disease or disorder. A subject may be healthy (e.g., not suspected of having disease or disorder). A subject may have one or more risk factors for a given disease. A subject may have a given weight, height, body mass index, or other physical characteristic. A subject may have a given ethnic or racial heritage, place of birth or residence, nationality, disease or remission state, family medical history, or other characteristic.

As used herein, the term "biological sample" generally refers to a sample obtained from a subject. The biological sample may be obtained directly or indirectly from the subject. A sample may be obtained from a subject via any suitable method, including, but not limited to, spitting, swabbing, blood draw, biopsy, obtaining excretions (e.g., urine, stool, sputum, vomit, or saliva), excision, scraping, and puncture. A sample may be obtained from a subject by, for example, intravenously or intraarterially accessing the circulatory system, collecting a secreted biological sample (e.g., stool, urine, saliva, sputum, etc.), breathing, or surgically extracting a tissue (e.g., biopsy). The sample may be obtained by non-invasive methods including but not limited to: scraping of the skin or cervix, swabbing of the cheek, or collection of saliva, urine, feces, menses, tears, or semen. Alternatively, the sample may be obtained by an invasive procedure such as biopsy, needle aspiration, or phlebotomy. A sample may comprise a bodily fluid such as, but not limited to, blood (e.g., whole blood, red blood cells, leukocytes or white blood cells, platelets), plasma, serum, sweat, tears, saliva, sputum, urine, semen, mucus, synovial fluid, breast milk, colostrum, amniotic fluid, bile, bone marrow, interstitial or extracellular fluid, or cerebrospinal fluid. For example, a sample may be obtained by a puncture method to obtain a bodily fluid comprising blood and/or plasma. Such a sample may comprise both cells and cell-free nucleic acid material. Alternatively, the sample may be obtained from any other source including but not limited to blood, sweat, hair follicle, buccal tissue, tears, menses, feces, or saliva. The biological sample may be a tissue sample, such as a tumor biopsy. The sample may be obtained from any of the tissues provided herein including, but not limited to, skin, heart, lung, kidney, breast, pancreas, liver, intestine, brain, prostate, esophagus, muscle, smooth muscle, bladder, gall bladder, colon, or thyroid. The methods of obtaining provided herein include methods of biopsy including fine needle aspiration, core needle biopsy, vacuum assisted biopsy, large core biopsy, incisional biopsy, excisional biopsy, punch biopsy, shave biopsy or skin biopsy. The biological sample may comprise one or more cells. A biological sample may comprise one or more nucleic acid molecules such as one or more deoxyribonucleic acid (DNA) and/or ribonucleic acid (RNA) molecules (e.g., included within cells or not included within cells). Nucleic acid molecules may be included within cells. Alternatively or in addition, nucleic acid molecules may not be included within cells (e.g., cell-free nucleic acid molecules). The biological sample may be a cell-free sample.

The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition, cell-free nucleic acid molecules may be released into bodily fluids from healthy cells.

A biological sample obtained directly from a subject may not have been further processed following being obtained from the subject. For example, a blood sample may be obtained directly from a subject by accessing the subject's circulatory system, removing the blood from the subject (e.g., via a needle), and transferring the removed blood into a receptacle. The receptacle may comprise reagents (e.g., anti-coagulants) such that the blood sample is useful for further analysis. In another example, a swab may be used to access epithelial cells on an oropharyngeal surface of the subject. Following obtaining the biological sample from the subject, the swab containing the biological sample may be contacted with a fluid (e.g., a buffer) to collect the biological fluid from the swab.

Any suitable biological sample that comprises one or more nucleic acid molecules may be obtained from a subject. A sample (e.g., a biological sample or cell-free biological sample) suitable for use according to the methods provided herein may be any material comprising tissues, cells, degraded cells, nucleic acids, genes, gene fragments, expression products, gene expression products, and/or gene expression product fragments of an individual to be tested. A biological sample may be solid matter (e.g., biological tissue) or may be a fluid (e.g., a biological fluid). In general, a biological fluid may include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. Methods for determining sample suitability and/or adequacy are provided. A sample may include, but is not limited to, blood, plasma, tissue, cells, degraded cells, cell-free nucleic acid molecules, and/or biological material from cells or derived from cells of an individual such as cell-free nucleic acid molecules. The sample may be a heterogeneous or homogeneous population of cells, tissues, or cell-free biological material. The biological sample may be obtained using any method that can provide a sample suitable for the analytical methods described herein.

A sample (e.g., a biological sample or cell-free biological sample) may undergo one or more processes in preparation for analysis, including, but not limited to, filtration, centrifugation, selective precipitation, permeabilization, isolation, agitation, heating, purification, and/or other processes. For example, a sample may be filtered to remove contaminants or other materials. In an example, a sample comprising cells may be processed to separate the cells from other material in the sample. Such a process may be used to prepare a sample comprising only cell-free nucleic acid molecules. Such a process may consist of a multi-step centrifugation process. Multiple samples, such as multiple samples from the same subject (e.g., obtained in the same or different manners from the same or different bodily locations, and/or obtained at the same or different times (e.g., seconds, minutes, hours, days, weeks, months, or years apart)) or multiple samples from different subjects may be obtained for analysis as described herein. In an example, the first sample is obtained from a subject before the subject undergoes a treatment regimen or procedure and the second sample is obtained from the subject after the subject undergoes the treatment regimen or procedure. Alternatively or in addition, multiple samples may be obtained from the same subject at the same or approximately the same time. Different samples obtained from the same subject may be obtained in the same or different manner. For example, a first sample may be obtained via a biopsy and a second sample may be obtained via a blood draw. Samples obtained in different manners may be obtained by different medical professionals, using different techniques, at different times, and/or at different locations. Different samples obtained from the same subject may be obtained from different areas of a body. For example, a first sample may be obtained from a first area of a body (e.g., a first tissue) and a second sample may be obtained from a second area of the body (e.g., a second tissue).

A biological sample as used herein (e.g., a biological sample comprising one or more nucleic acid molecules) may not be purified when provided in a reaction vessel. Furthermore, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) molecules of a biological sample may not be extracted from the biological sample when providing the biological sample to a reaction vessel. Moreover, a target nucleic acid (e.g., a target RNA or target DNA molecules) present in a biological sample may not be concentrated when providing the biological sample to a reaction vessel. Alternatively, a biological sample may be purified and/or nucleic acid molecules may be isolated from other materials in the biological sample.

A biological sample as described herein may contain a target nucleic acid. As used herein, the terms "template nucleic acid", "target nucleic acid", "nucleic acid molecule," "nucleic acid sequence," "nucleic acid fragment," "oligonucleotide," "polynucleotide," and "nucleic acid" generally refer to polymeric forms of nucleotides of any length, such as deoxyribonucleotides (dNTPs) or ribonucleotides (rNTPs), or analogs thereof, and may be used interchangeably. Nucleic acids may have any three dimensional structure, and may perform any function, known or unknown. A nucleic acid molecule may have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Non-limiting examples of nucleic acids include DNA, RNA, genomic DNA (e.g., gDNA such as sheared gDNA), cell-free DNA (e.g., cfDNA), synthetic DNA/RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or following assembly of the nucleic acid. The sequence of nucleotides of a nucleic acid may be interrupted by non-nucleotide components. A nucleic acid may be further modified following polymerization, such as by conjugation or binding with a reporter agent.

A target nucleic acid or sample nucleic acid as described herein may be amplified to generate an amplified product. A target nucleic acid may be a target RNA or a target DNA. When the target nucleic acid is a target RNA, the target RNA may be any type of RNA, including types of RNA described elsewhere herein. The target RNA may be viral RNA and/or tumor RNA. A viral RNA may be pathogenic to a subject. Non-limiting examples of pathogenic viral RNA include human immunodeficiency virus I (HIV I), human immunodeficiency virus n (HIV 11), orthomyxoviruses, Ebola virus. Dengue virus, influenza viruses (e.g., H1N1, H3N2, H7N9, or H5N1), hepesvirus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

A biological sample may comprise a plurality of target nucleic acid molecules. For example, a biological sample may comprise a plurality of target nucleic acid molecules from a single subject. In another example, a biological sample may comprise a first target nucleic acid molecule from a first subject and a second target nucleic acid molecule from a second subject.

The present disclosure provides a method for processing a nucleic acid sample, comprising: (a) providing the nucleic acid sample comprising a double-stranded nucleic acid molecule comprising a first strand and a second strand having sequence complementarity with the first strand, wherein the first strand comprises a template region that is attached to an adapter comprising a first sequence and a second sequence adjacent to the first sequence, wherein the first sequence and the second sequence are respectively hybridized to a third sequence and a fourth sequence of the second strand, wherein the first sequence hybridized to the third sequence has a first melting point and the second sequence hybridized to the fourth sequence has a second melting point higher than the first melting point; (b) subjecting the double-stranded nucleic acid molecule to conditions sufficient to partially denature the double-stranded nucleic acid molecule, thereby separating the first sequence of the first strand from the third sequence of the second strand; (c) bringing a primer molecule having sequence complementarity with the third sequence of the second strand in contact with the second strand under conditions sufficient to permit the primer molecule to hybridize to the third sequence of the second strand; and (d) subjecting the second strand comprising the primer molecule hybridized to the third sequence of the second strand to a primer extension reaction under conditions sufficient to generate a third strand hybridized to at least a portion of the second strand.

In some cases, (b) comprises exposing the double-stranded nucleic acid molecule or a portion thereof to a chemical denaturant. In some instances, the chemical denaturant is selected from the group consisting of a salt, formamide, urea, guanidine hydrochloride, and an organic solvent. In some instances, (b) is performed under isothermal conditions.

In some cases, the first melting point is at least 1° C. lower than the second melting point. In some cases, the first melting point is at least 5° C. lower than the second melting point.

In some cases, (b) comprises heating the double-stranded nucleic acid molecule to a temperature higher than the first melting point and lower than the second melting point. In some cases, (b) comprises heating the double-stranded nucleic acid molecule to partially denature the double-stranded nucleic acid molecule. In some instances, the heating includes optical heating. In some cases, the heating includes resistive heating. In some instances, the heating includes convective heating. In some cases, the heating includes inductive heating.

In some cases, in (b), at most a portion of the first strand separates from the second strand.

In some cases, the adapter is ligated to the template region of the first strand. In some instances, the method further comprises, prior to (a), ligating the adapter to the template region of the first strand. In some instances, the first strand is provided as a single-stranded molecule, and further comprising, prior to (a), subjecting the first strand to a nucleic acid amplification reaction under conditions sufficient to generate the second strand hybridized to the first strand, thereby generating the double-stranded nucleic acid molecule.

In some cases, the second sequence is at an end of the adapter. In some cases, the fourth sequence is at an end of the second strand.

In some cases, the method further comprises (e) bringing an additional primer molecule having sequence complementarity with the first strand in contact with the first strand under conditions sufficient to permit the additional primer molecule to hybridize to the first strand. In some instances, the additional primer molecule hybridizes to the second sequence. In some instances, the method further comprises (f) subjecting the first strand comprising the additional primer molecule hybridized thereto to a primer extension reaction under conditions sufficient to generate a fourth strand hybridized to at least a portion of the first strand, thereby generating a double-stranded nucleic acid molecule comprising the first strand and the fourth strand. In some instances, the additional primer molecule is immobilized to a support. In some instances, the support comprises a plurality of additional primer molecules immobilized thereto. In some instances, the plurality of additional primer molecules are immobilized to the support in a predetermined pattern. In some instances, the plurality of additional primer molecules are uniformly distributed on the support. In some instances, the plurality of additional primer molecules are immobilized to the support at a density of at least 10,000 primer molecules per mm$^2$. In some instances, the method further comprises repeating (b)-(f) with the double-stranded nucleic acid molecule comprising the first strand and the fourth strand, thereby generating a copy of the double-stranded nucleic acid molecule comprising the first strand and the fourth strand. In some instances, the method further comprises repeating (b)-(f) with at least the copy of the double-stranded nucleic acid molecule comprising the first strand and the fourth strand to generate at least 10 copies of the double-stranded nucleic acid molecule comprising the first strand and the fourth strand. In some instances, the method further comprises sequencing all or a portion of the first strand, the fourth strand, or a copy or derivative thereof.

In some cases, the adapter is immobilized to a support. In some instances, the support is a bead, well, or planar support.

In some cases, the second sequence is part of an additional adapter attached to the second strand, wherein the additional adapter is immobilized to a support. In some instancers, the support is a planar array or a bead.

In some cases, subsequent to subjecting the double-stranded nucleic acid molecule to the conditions in (b), the first sequence is separated from the third sequence and the second sequence is hybridized to the fourth sequence. In some cases, the primer extension reaction in (d) separates the second sequence from the fourth sequence.

In some cases, the first sequence and the third sequence comprise one or more bases selected from the group consisting of adenosine, thymidine, uridine, and inosine. In some instances, the first sequence and the third sequence only comprise bases selected from the group consisting of adenosine, thymidine, uridine, and inosine.

In some cases, the first sequence and the third sequence each comprise at least 5 bases. In some cases, the first sequence and the third sequence each comprise at least 10 bases.

In some cases, the nucleic acid sample comprises a plurality of double-stranded nucleic acid molecules, wherein each double-stranded nucleic acid molecule of the plurality of double-stranded nucleic acid molecules comprises a first strand and a second strand having sequence complementarity with the first strand, wherein the first strand comprises a template region that is attached to an adapter comprising a first sequence and a second sequence adjacent to the first sequence, wherein the first sequence and the second sequence are respectively hybridized to a third sequence and a fourth sequence of the second strand, wherein the first sequence hybridized to the third sequence has a first melting point and the second sequence hybridized to the fourth sequence has a second melting point higher than the first melting point; and further comprising: (g) repeating (b)-(d) for each double-stranded nucleic acid molecule of the plurality of double-stranded nucleic acid molecules of the nucleic acid sample. In some instances, the plurality of double-stranded nucleic acid molecules comprises at least 100 double-stranded nucleic acid molecules. In some instances, the plurality of double-stranded nucleic acid molecules comprises at least 1,000 double-stranded nucleic acid molecules. In some instances, the plurality of double-stranded nucleic acid molecules comprises at least 10,000 double-stranded nucleic acid molecules. In some instances, the plurality of double-stranded nucleic acid molecules comprises one or more different template regions. In some instances, (g) is performed simultaneously with (b)-(d).

In some cases, the adapter further comprises a fifth sequence, wherein the second sequence and the fifth sequence flank the first sequence. In some instances, the second strand of the double-stranded nucleic acid molecule further comprises a sixth sequence hybridized to the fifth sequence, wherein the fourth sequence and the sixth sequence flank the third sequence.

The present disclosure further provides a system for processing a nucleic acid sample, comprising: a support configured to retain the nucleic acid sample comprising a double-stranded nucleic acid molecule comprising a first strand and a second strand having sequence complementarity with the first strand, wherein the first strand comprises a template region that is attached to an adapter comprising a first sequence and a second sequence adjacent to the first sequence, wherein the first sequence and the second sequence are respectively hybridized to a third sequence and a fourth sequence of the second strand, wherein the first sequence hybridized to the third sequence has a first melting point and the second sequence hybridized to the fourth sequence has a second melting point higher than the first melting point; and a controller operatively coupled to the support, wherein the controller is programmed to: (i) subject the double-stranded nucleic acid molecule to conditions sufficient to partially denature the double-stranded nucleic acid molecule, thereby separating the first sequence from the third sequence; (ii) bring a primer molecule having sequence complementarity with the third sequence in contact with the second strand under conditions sufficient to permit the primer molecule to hybridize to the third sequence; and (iii) subject the second strand comprising the primer molecule hybridized to the third sequence to a primer extension reaction under conditions sufficient to generate a third strand hybridized to at least a portion of the second strand.

In some cases, (i) comprises exposing the double-stranded nucleic acid molecule or a portion thereof to a chemical denaturant. In some instances, the chemical denaturant is selected from the group consisting of a salt, formamide, urea, guanidine hydrochloride, and an organic solvent. In some instances, the controller is programmed to heat the double-stranded nucleic acid molecule to a temperature higher than the first melting point and lower than the second melting point. In some instances, the first melting point is at least 1° C. lower than the second melting point. In some instances, the first melting point is at least 5° C. lower than the second melting point.

In some cases, the controller is programmed to provide thermal energy to the double-stranded nucleic acid molecule to partially denature the double-stranded nucleic acid molecule. In some instances, the controller is programmed to provide thermal energy by optical heating. In some instances, the controller is programmed to provide thermal energy by resistive heating. In some instances, the controller is programmed to provide thermal energy by convective heating. In some instances, the controller is programmed to provide thermal energy by inductive heating. In some instances, the controller is programmed to provide thermal energy by microwave heating.

In some cases, in (i), at most a portion of the first strand separates from the second strand. In some instances, the adapter is ligated to the first strand. In some instances, the second sequence is at an end of the adapter. In some instances, the fourth sequence is at an end of the second strand. In some instances, the controller is further programmed to (iv) bring an additional primer molecule having sequence complementarity with the first strand in contact with the first strand under conditions sufficient to permit the additional primer molecule to hybridize to the first strand. In some instances, the additional primer molecule hybridizes to the second sequence. In some instances, the controller is further programmed to (v) subject the first strand comprising the additional primer molecule hybridized thereto to a primer extension reaction under conditions sufficient to generate a fourth strand hybridized to at least a portion of the first strand, thereby generating a double-stranded nucleic acid molecule comprising the first strand and the fourth strand. In some instances, the additional primer molecule is immobilized to a support. In some instances, the support comprises a plurality of additional primer molecules immobilized thereto. In some instances, the plurality of additional primer molecules are immobilized to the support in a predetermined pattern. In some instances, the plurality of additional primer molecules are immobilized to the support at a density of at least 10,000 primer molecules per $mm^2$. In some instances, the controller is further programmed to repeat (i)-(v) with the double-stranded nucleic acid molecule comprising the first strand and the fourth strand, thereby generating a copy of the double-stranded nucleic acid molecule comprising the first strand and the fourth strand. In some instances, the controller is further programmed to repeat (i)-(v) with at least the copy of the double-stranded nucleic acid molecule comprising the first strand and the fourth strand to generate at least 10 copies of the double-stranded nucleic acid molecule comprising the first strand and the fourth strand. In some instances, the controller is further programmed to sequence all or a portion of the first strand, the fourth strand, or a copy or derivative thereof.

In some cases, the adapter is immobilized to a support. In some instances, the support is a planar array. In some instances, the support is a bead.

In some cases, the second sequence is part of an additional adapter attached to the second strand, wherein the additional adapter is immobilized to a support. In some instances, the support is a planar array. In some instances, the support is a bead.

In some cases, the controller is programmed provide sufficient thermal energy to separate the first sequence from the third sequence but not the second sequence from the fourth sequence. In some instances, the controller is programmed to subject the second strand comprising the primer molecule hybridized to the third sequence to a primer extension reaction under conditions sufficient to separate the second sequence from the fourth sequence.

In some cases, the first sequence and the third sequence comprise one or more bases selected from the group consisting of adenosine, thymidine, uridine, and inosine. In some instances, the first sequence and the third sequence only comprise bases selected from the group consisting of adenosine, thymidine, uridine, and inosine.

In some cases, the first sequence and the third sequence each comprise at least 5 bases. In some cases, the first sequence and the third sequence each comprise at least 10 bases.

In some cases, the adapter further comprises a fifth sequence, wherein the second sequence and the fifth sequence flank the first sequence. In some instances, the second strand of the double-stranded nucleic acid molecule further comprises a sixth sequence hybridized to the fifth sequence, wherein the fourth sequence and the sixth sequence flank the third sequence.

In a further aspect, the present disclosure provides a method for processing a nucleic acid sample, comprising: (a) providing the nucleic acid sample comprising a first nucleic acid molecule comprising a single strand; (b) attaching an adapter to an end of the first nucleic acid molecule, wherein the adapter comprises a first sequence and a second sequence; and (c) using the adapter to generate a double-stranded nucleic acid molecule comprising a second nucleic acid molecule that is complementary to the first nucleic acid molecule, wherein the double-stranded nucleic acid molecule comprises a third sequence hybridized to the first sequence and a fourth sequence hybridized to the second sequence, wherein the first sequence hybridized to the third sequence has a first melting point and the second sequence hybridized to the fourth sequence has a second melting point higher than the first melting point.

In some cases, prior to (c), the adapter is immobilized to a support. In some instances, the support is a planar array. In some instances, the support is a bead.

In some cases, subsequent to (c), the adapter is immobilized to a support. In some instances, the support is a planar array. In some cases, the support is a bead.

In some cases, the method further comprises attaching an additional adapter to another end of the first nucleic acid molecule. In some instances, the additional adapter comprises a fifth sequence and a sixth sequence.

In some cases, (b) comprises ligating the adapter to the first nucleic acid molecule. In some cases, (c) comprises hybridizing a primer to the adapter and using the primer to perform a primer extension reaction to yield the second nucleic acid molecule hybridized to the first nucleic acid molecule.

In some cases, (b) comprises hybridizing the adapter to the first nucleic acid molecule, and wherein in (c) comprises using the adapter as a primer to conduct a primer extension reaction to yield the second nucleic acid molecule hybridized to the first nucleic acid molecule.

In some cases, the first sequence and the third sequence comprise one or more bases selected from the group consisting of adenosine, thymidine, uridine, and inosine. In some instances, the first sequence and the third sequence only comprise bases selected from the group consisting of adenosine, thymidine, uridine, and inosine.

In some cases, the first sequence and the third sequence each comprise at least 5 bases. In some cases, the first sequence and the third sequence each comprise at least 10 bases.

In another aspect, the present disclosure provides a method for processing a nucleic acid sample, comprising: (a) providing the nucleic acid sample comprising a double-stranded nucleic acid molecule immobilized to a support, wherein the double-stranded nucleic acid molecule comprises a first strand and a second strand having sequence complementarity with the first strand, wherein: (i) the first strand comprises a template region that is attached to a first adapter comprising a first sequence and a second sequence adjacent to the first sequence, and (ii) the second strand comprises a sequence complementary to the template region that is attached to a second adapter comprising a third sequence and a fourth sequence adjacent to the third sequence, wherein the first sequence and the second sequence are respectively hybridized to the third sequence and the fourth sequence, wherein the first sequence hybridized to the third sequence has a first melting point and the second sequence hybridized to the fourth sequence has a second melting point higher than the first melting point, and wherein the support comprises a plurality of primer molecules immobilized thereto; and (b) performing an amplification reaction using a primer molecule of the plurality of primer molecules by subjecting the nucleic acid sample to conditions sufficient to (i) partially denature the double-stranded nucleic acid molecule, thereby separating the first sequence of the first adapter of the first strand from the third sequence of the second adapter of the second strand; (ii) hybridize the first primer molecule to the second sequence of the first strand; and (iii) generate a copy of the second strand.

In some cases, the method further comprises repeating (b) for at least the copy of the double-stranded nucleic acid molecule in the nucleic acid sample to generate at least 10 copies of the double-stranded nucleic acid molecule. In some instances, the method further comprises sequencing the all or a portion of the first strand, the second strand, or a copy or derivative thereof.

In some cases, (b) comprises exposing the double-stranded nucleic acid molecule or a portion thereof to a chemical denaturant. In some instances, the chemical denaturant is selected from the group consisting of a salt, formamide, urea, guanidine hydrochloride, and an organic solvent.

In some cases, (b) is performed under isothermal conditions.

In some cases, the first melting point is at least 1° C. lower than the second melting point. In some cases, the first melting point is at least 5° C. lower than the second melting point.

In some cases, (b) comprises heating the double-stranded nucleic acid molecule to a temperature higher than the first melting point and lower than the second melting point. In some cases, (b) comprises heating the double-stranded nucleic acid molecule to partially denature the double-stranded nucleic acid molecule. In some instances, the heating includes optical heating. In some instances, the heating includes resistive heating. In some instances, the heating includes convective heating. In some instances, the heating includes inductive heating.

In some cases, in (b), at most a portion of the first strand separates from the second strand.

In some cases, the adapter is ligated to the template region of the first strand. In some instances, the method further comprises, prior to (a), ligating the adapter to the template region of the first strand. In some instances, the first strand is provided as a single-stranded molecule, and further comprising, prior to (a), subjecting the first strand to a nucleic acid amplification reaction under conditions sufficient to generate the second strand hybridized to the first strand, thereby generating the double-stranded nucleic acid molecule.

In some cases, the second sequence is at an end of the first adapter of the first strand. In some cases, the fourth sequence is at an end of the second adapter of the second strand.

In some cases, the plurality of primer molecules are immobilized to the support in a predetermined pattern. In some instances, the plurality of primer molecules are uniformly distributed on the support.

In some cases, the plurality of primer molecules are immobilized to the support at a density of at least 10,000 primer molecules per mm$^2$. In some instances, the support is a planar array. In some instances, the support is a bead. In some instances, the support is a well.

In some cases, in (b), generating the copy of the second strand comprises performing a primer extension reaction.

In some cases, the first sequence and the third sequence comprise one or more bases selected from the group consisting of adenosine, thymidine, uridine, and inosine. In some instances, the first sequence and the third sequence only comprise bases selected from the group consisting of adenosine, thymidine, uridine, and inosine.

In some cases, the first sequence and the third sequence each comprise at least 5 bases. In some cases, the first sequence and the third sequence each comprise at least 10 bases.

In some cases, the nucleic acid sample comprises a plurality of double-stranded nucleic acid molecules immobilized to the support, wherein each double-stranded nucleic acid molecule of the plurality of double-stranded nucleic acid molecules comprises a first strand and a second strand having sequence complementarity with the first strand, wherein the first strand comprises a template region that is attached to a first adapter comprising a first sequence and a second sequence adjacent to the first sequence, and the second strand comprises a sequence complementary to the template region that is attached to a second adapter comprising a third sequence and a fourth sequence adjacent to the third sequence, wherein the first sequence and the second sequence are respectively hybridized to the third sequence and the fourth sequence, wherein the first sequence hybridized to the third sequence has a first melting point and the second sequence hybridized to the fourth sequence has a second melting point higher than the first melting point; and further comprising: (c) repeating (b) for each double-stranded nucleic acid molecule of the plurality of double-stranded nucleic acid molecules of the nucleic acid sample. In some instances, the plurality of double-stranded nucleic acid molecules comprises at least 100 double-stranded nucleic acid molecules. In some cases, the plurality of double-stranded nucleic acid molecules comprises at least 1,000 double-stranded nucleic acid molecules. In some cases, the plurality of double-stranded nucleic acid molecules comprises at least 10,000 double-stranded nucleic acid molecules. In some cases, the plurality of double-stranded nucleic acid molecules comprises one or more different template regions.

In yet another aspect, the present disclosure provides a method for processing a nucleic acid sample, comprising: (a) providing the nucleic acid sample comprising a single-stranded nucleic acid molecule immobilized to a support at a first end of the single-stranded nucleic acid molecule, wherein the single-stranded nucleic acid molecule comprises a template region that is attached to an adapter comprising a first sequence and a second sequence adjacent to the first sequence, wherein the adapter is disposed at a second end of the single-stranded nucleic acid molecule, and wherein the support comprises a plurality of primer molecules immobilized thereto, wherein each primer molecule of the plurality of primer molecules comprises a third sequence and a fourth sequence; (b) subjecting the single-stranded nucleic acid molecule to conditions sufficient to hybridize the first sequence of the adapter to the third sequence of a primer molecule of the plurality of primer molecules and the second sequence of the adapter to the fourth sequence of the primer molecule, thereby generating a double-stranded region comprising the adapter and the primer molecule, wherein the first sequence hybridized to the third sequence has a first melting point and the second sequence hybridized to the fourth sequence has a second melting point higher than the first melting point; (c) subjecting the double-stranded region to conditions sufficient to extend the primer molecule to provide a second strand that is partially complementary to the single-stranded nucleic acid molecule; and (d) subjecting the double-stranded region to conditions sufficient to partially denature the double-stranded region, thereby separating the first sequence of the adapter from the third sequence of the primer molecule, wherein (d) comprises exposing the double-stranded region to a chemical denaturant or heating the double-stranded region to a temperature higher than the first melting point and lower than the second melting point.

In some cases, (d) comprises exposing the double-stranded region to a chemical denaturant, wherein the chemical denaturant is selected from the group consisting of a salt, formamide, urea, guanidine hydrochloride, and an organic solvent.

In some cases, (b) is performed under isothermal conditions.

In some cases, the first melting point is at least 1° C. lower than the second melting point. In some cases, the first melting point is at least 5° C. lower than the second melting point.

In some cases, (d) comprises heating the double-stranded region to a temperature higher than the first melting point and lower than the second melting point. In some instances, the heating includes optical heating. In some instances, the heating includes resistive heating. In some instances, the heating includes convective heating. In some instances, the heating includes inductive heating.

In some cases, the adapter is ligated to the template region of the first strand. In some instances, the method further comprises, prior to (a), ligating the adapter to the template region of the first strand.

In some cases, the plurality of primer molecules are immobilized to the support in a predetermined pattern. In some instances, the plurality of primer molecules are uniformly distributed on the support. In some instances, the plurality of primer molecules are immobilized to the support at a density of at least 10,000 primer molecules per $mm^2$.

In some cases, the method further comprises, subsequent to (d), hybridizing the adapter to a second primer molecule of the plurality of primer molecules. In some instances, the method further comprises separating the first strand and the second strand. In some instances, the method further comprises repeating (c) and (d) to provide a third strand that is partially complementary to the single-stranded nucleic acid molecule.

In some cases, the support is a planar array. In some instances, the support is a bead. In some instances, the support is a well.

In some cases, the first sequence and the third sequence comprise one or more bases selected from the group consisting of adenosine, thymidine, uridine, and inosine. In some instances, the first sequence and the third sequence only comprise bases selected from the group consisting of adenosine, thymidine, uridine, and inosine.

In some cases, the first sequence and the third sequence each comprise at least 5 bases. In some cases, the first sequence and the third sequence each comprise at least 10 bases.

In a further aspect, the present disclosure provides a method for processing a double-stranded nucleic acid molecule, comprising: (a) providing the double-stranded nucleic acid molecule immobilized to a support, wherein the double-stranded nucleic acid molecule comprises a first strand and a second strand, wherein the first strand comprises a first sequence and a second sequence hybridized to a respective third sequence and fourth sequence of the second strand, and wherein the second sequence is disposed closer to the support than the first sequence; and (b) subjecting the double-stranded nucleic acid molecule to conditions sufficient to (i) separate the first sequence from the third sequence while keeping the second sequence hybridized to the fourth sequence, to partially denature the double-stranded nucleic acid molecule, and (ii) hybridize a primer molecule immobilized to the support to the first sequence.

In some cases, the first sequence hybridized to the third sequence has a first melting point and the second sequence hybridized to the fourth sequence has a second melting point different from the first melting point. In some instances, the first melting point is at least 1° C. lower than the second melting point. In some instances, the first melting point is at least 5° C. lower than the second melting point.

In some cases, (b) comprises heating the double-stranded nucleic acid molecule to a temperature higher than the first melting point and lower than the second melting point.

In some cases, the method further comprises using the primer molecule to separate the first strand and the second strand and generate a copy of the second strand hybridized to the first strand to generate a first copy of the double-stranded nucleic acid molecule. In some instances, the method further comprises hybridizing another primer molecule to the separated second strand to generate a copy of the first strand hybridized to the second strand to generate a second copy of the double-stranded nucleic acid molecule. In some instances, the method further comprises repeating (b) for at least a copy of the double-stranded nucleic acid molecule to generate at least 10 copies of the double-stranded nucleic acid molecule.

In some cases, the method further comprises sequencing the all or a portion of the first strand, the second strand, or a copy or derivative thereof.

In some cases, (b) comprises exposing the double-stranded nucleic acid molecule or a portion thereof to a chemical denaturant. In some instances, the chemical denaturant is selected from the group consisting of a salt, formamide, urea, guanidine hydrochloride, and an organic solvent.

In some instances, (b) is performed under isothermal conditions. In some instances, (b) comprises heating the double-stranded nucleic acid molecule to partially denature the double-stranded nucleic acid molecule. In some instances, the heating includes optical heating. In some instances, the heating includes resistive heating. In some instances, the heating includes convective heating. In some instances, the heating includes inductive heating.

In some cases, in (b), at most a portion of the first strand separates from the second strand.

In some cases, the first sequence is ligated to a template region of the first strand. In some instances, the method further comprises, prior to (a), ligating the first sequence to the template region of the first strand. In some instances, the first strand is provided as a single-stranded molecule, and further comprising, prior to (a), subjecting the first strand to a nucleic acid amplification reaction under conditions sufficient to generate the second strand hybridized to the first strand, thereby generating the double-stranded nucleic acid molecule.

In some cases, the second sequence is at an end of the first strand. In some cases, the fourth sequence is at an end of the second strand. In some cases, the support comprises a plurality of primer molecules, including the primer molecule, immobilized thereto. In some instances, the plurality of primer molecules are disposed in a predetermined pattern on the support. In some instances, the plurality of primer molecules are immobilized to the support at a density of at least 10,000 primer molecules per $mm^2$.

In some cases, the support is a planar array. In some instances, the support is a bead. In some instances, the support is a well.

In some cases, the method further comprises performing a primer extension reaction to generate a copy of the second strand.

In some cases, the first sequence and the third sequence comprise one or more bases selected from the group consisting of adenosine, thymidine, uridine, and inosine. In some instances, the first sequence and the third sequence only comprise bases selected from the group consisting of adenosine, thymidine, uridine, and inosine.

In some cases, the first sequence and the third sequence each comprise at least 5 bases. In some cases, the first sequence and the third sequence each comprise at least 10 bases.

In some cases, the nucleic acid sample comprises a plurality of double-stranded nucleic acid molecules immobilized to the support, wherein each double-stranded nucleic acid molecule of the plurality of double-stranded nucleic acid molecules comprises a first strand hybridized to a second strand, wherein the first strand comprises a first sequence and a second sequence hybridized to a respective third sequence and fourth sequence, and wherein the second sequence is disposed closer to the support than the first sequence; and further comprising: (c) repeating (b) for each double-stranded nucleic acid molecule of the plurality of double-stranded nucleic acid molecules of the nucleic acid sample. In some instances, the plurality of double-stranded nucleic acid molecules comprises at least 100 double-stranded nucleic acid molecules. In some instances, the plurality of double-stranded nucleic acid molecules comprises at least 1,000 double-stranded nucleic acid molecules. In some instances, the plurality of double-stranded nucleic acid molecules comprises at least 10,000 double-stranded nucleic acid molecules. In some cases, the plurality of double-stranded nucleic acid molecules comprises one or more different template regions.

The present disclosure additionally provides compositions and methods for use in nucleic acid processing. The methods provided herein may comprise the use of a nucleic acid molecule in a J-shaped configuration, which nucleic acid molecule may facilitate the amplification and/or sequencing of target nucleic acid molecules of a biological sample. The nucleic acid molecule may be immobilized to a substrate or may be provided in solution (e.g., to an immobilized target nucleic acid molecule). Target nucleic acid molecules may be functionalized with one or more adapters configured to interact with the nucleic acid molecule (e.g., having sequence complementarity to a sequence of the nucleic acid molecule). The nucleic acid molecule may be used to perform paired-end sequencing analyses of a target nucleic acid molecule, permitting collection of sequence information from both ends of the target nucleic acid molecule. Accordingly, the methods provided herein may allow for a doubling of the sequencing output from a fixed number of template nucleic acid molecules; reduction in errors by reading template molecules twice, once as a reverse complement; improved alignment of sequencing reads to a genome as two linked reads separated by a distance provide better alignment to a genome as compared to a single read; and simplified detection of structural variants if sequencing reads are far apart.

In an aspect, the present disclosure provides a method for paired-end sequencing, comprising (a) bringing a first end of a first nucleic acid strand comprising a first template sequence in contact with a sequencing primer, and subjecting the first nucleic acid strand to sequencing to yield a first sequencing read in a first direction away from the first end, which sequencing generates a second nucleic acid strand comprising a second template sequence complementary to the first template sequence and a first capture sequence, wherein the first nucleic acid strand is immobilized to a support via an immobilized nucleic acid molecule comprising a second capture sequence complementary to the first capture sequence, a first binding sequence, and a second binding sequence hybridized to the first binding sequence, wherein the second capture sequence of the immobilized nucleic acid molecule is adjacent to a second end of the first nucleic acid strand opposite the first end and hybridized to the first capture sequence of the second nucleic acid strand; (b) removing the first nucleic acid strand from the immobilized nucleic acid molecule to provide the second nucleic acid strand immobilized to the support via the immobilized nucleic acid molecule; and (c) using the second capture sequence of the immobilized nucleic acid molecule as a sequencing primer, subjecting the second nucleic acid strand to sequencing to generate a second sequencing read in a second direction opposite the first direction.

In some cases, the method for paired-end sequencing further comprises processing the first sequencing read and/or the second sequencing read to identify the first template sequence or the second template sequence. The first sequencing read may be processed to identify the second template sequence within the first sequencing read. The second sequencing read may be processed to identify the first template sequence within the second sequencing read. In some instances, sequencing comprises sequencing by synthesis. In some cases, sequencing comprises sequencing by hybridization. In some instances, sequencing comprises sequencing by ligation. In some instances, (a) comprises subjecting the first nucleic acid strand to conditions sufficient to hybridize the sequencing primer to the first nucleic acid strand. In some cases, (a) comprises subjecting the sequencing primer to a primer extension reaction. The primer extension reaction may comprise use of a polymerase. In some cases, subsequent to (a), the second nucleic acid strand is ligated to the second binding sequence of the immobilized nucleic acid molecule.

In some cases, (c) comprises generating a third nucleic acid strand comprising a third template sequence complementary to the second template sequence. In some cases, the method for paired-end sequencing further comprises removing the second nucleic acid strand from the immobilized nucleic acid molecule. In some cases, removing the second nucleic acid strand further comprises bringing the third nucleic acid strand in contact with an additional sequencing primer and sequencing the third nucleic acid strand to generate a third sequencing read. In some cases, prior to (a), the method for paired-end sequencing further comprises (d) providing the immobilized nucleic acid molecule and a template nucleic acid molecule comprising a template sequence complementary to the first template sequence, a first end comprising a third capture sequence complementary to the second capture sequence of the immobilized nucleic acid molecule, and a second end; (e) subjecting the template nucleic acid molecule to conditions sufficient to hybridize the third capture sequence of the template nucleic acid molecule to the second capture sequence, and (f) subjecting the immobilized nucleic acid molecule to conditions sufficient to extend the second capture sequence to the second end of the template nucleic acid molecule, thereby generating the first nucleic acid strand immobilized to the support.

In some cases, (f) comprises generating a third sequencing read. In some instances, sequencing the third nucleic acid strand comprises sequencing by synthesis. In some instances, sequencing the third nucleic acid strand comprises sequencing by hybridization. In some instances, sequencing the third nucleic acid strand comprises sequencing by ligation. In some cases, prior to (a), the method for paired-end sequencing further comprises (g) subjecting the template nucleic acid molecule attached to the immobilized nucleic acid molecule to conditions sufficient to remove the template nucleic acid molecule. In some cases, the template nucleic acid molecule is a deoxyribonucleic acid (DNA) molecule. In some cases, the template nucleic acid molecule is a ribonucleic acid (RNA) molecule. In some cases, (f) comprises subjecting the second capture sequence of the immobilized nucleic acid molecule to an extension reaction. In some cases, the extension reaction comprises use of a polymerase. In some instances, the support is a bead. In some instances, the support is a planar surface. In some cases, the immobilized nucleic acid molecule is attached to the support via a chemical linker. In some instances, the chemical linker comprises an amine group. In some cases, the second capture sequence resides in a capture region of the immobilized nucleic acid molecule that comprises a cleavable base. In some cases, the cleavable base is a uridine base or an 8-oxoguanine base. In some cases, (b) comprises cleaving the cleavable base. In some cases, (b) comprises use of a cleaving enzyme. In some cases, the first sequencing read and the second sequencing read do not overlap. In some cases, the first sequencing read and the second sequencing read overlap. In some cases, overlap between the first sequencing read and the second sequencing read comprises 5 or more bases. In some cases, the first sequencing read and the second sequencing read completely overlap. In some cases, the immobilized nucleic acid molecule comprises a replication block. In some cases, the second binding sequence of the immobilized nucleic acid molecule comprises the replication block.

In another aspect, the present disclosure provides a method for sequencing a template nucleic acid molecule, comprising (a) bringing an immobilized nucleic acid molecule in contact with a first nucleic acid strand derived from the template nucleic acid molecule to hybridize a first capture sequence of the immobilized nucleic acid molecule to a second capture sequence of the first nucleic acid strand, wherein (i) the immobilized nucleic acid molecule comprises the first capture sequence, a first binding sequence, and a second binding sequence hybridized to the first binding sequence, and (ii) the first nucleic acid strand comprises the second capture sequence that is complementary to the first capture sequence, a first template sequence, and a third capture sequence; (b) using the first capture sequence of the immobilized nucleic acid molecule as a primer to subject the first nucleic acid strand to a reaction under conditions sufficient to generate a second nucleic acid strand complementary to the first nucleic acid strand, which second nucleic acid strand comprises a second template sequence complementary to the first template sequence and a fourth capture sequence complementary to the third capture sequence; (c) removing the first nucleic acid strand from the immobilized nucleic acid molecule to provide the second nucleic acid strand immobilized to the support via the immobilized nucleic acid molecule; (d) subjecting the second nucleic acid strand to sequencing to yield a sequencing read corresponding to the second nucleic acid strand, which sequencing generates a third nucleic acid strand complementary to the second nucleic acid strand, which third nucleic acid strand comprises (i) a third template sequence complementary to the second template sequence and (ii) a fifth capture sequence complementary to the fourth capture sequence; and (e) using the sequencing read to identify the first template sequence of the first nucleic acid strand, thereby sequencing the template nucleic acid molecule.

In some cases, generating the sequencing read comprises sequencing by synthesis. In some cases, generating the sequencing read comprises sequencing by hybridization. In some instances, generating the sequencing read comprises sequencing by ligation. In some cases, (b) comprises subjecting the first nucleic acid strand to conditions sufficient to hybridize the first capture sequence to the first nucleic acid strand. In some cases, (b) comprises subjecting the first capture sequence to a primer extension reaction. In some cases, the primer extension reaction comprises use of a polymerase. In some cases, subsequent to (d), the third nucleic acid strand is ligated to the second binding sequence of the immobilized nucleic acid molecule. In some cases, method for sequencing a template nucleic acid molecule further comprises removing the second nucleic acid strand from the immobilized nucleic acid molecule. In some cases, removing the second nucleic acid strand further comprises using the first capture sequence of the immobilized nucleic acid molecule as a primer to subject the third nucleic acid strand to a reaction under conditions sufficient to generate a second sequencing read corresponding to the third nucleic acid strand. In some instances, the sequencing comprises sequencing by synthesis. In some instances, the sequencing comprises sequencing by hybridization. In some instances, the sequencing comprises sequencing by ligation.

In some cases, the sequencing read and the second sequencing read do not overlap. In some instances, the sequencing read and the second sequencing read overlap. In some instances, the overlap between the first sequencing read and the second sequencing read comprises 5 or more bases. In some instances, the first sequencing read and the second sequencing read completely overlap. In some cases, the template nucleic acid molecule is a deoxyribonucleic acid (DNA) molecule. In some cases, the template nucleic acid molecule is a ribonucleic acid (RNA) molecule. In some instances, the support comprises a bead. In some instances, the support comprises a planar surface. In some instances, the immobilized nucleic acid molecule is attached to the support via a chemical group. In some instances, the chemical group comprises an amine. In some cases, the first capture sequence resides in a region of the immobilized nucleic acid molecule that comprises a cleavable base. In some instances, the cleavable base is selected from a uridine base and an 8-oxoguanine base. In some instances, the immobilized nucleic acid molecule comprises a replication block.

In another aspect, the present disclosure provides a method for sequencing a template nucleic acid molecule, comprising (a) providing (i) the template nucleic acid molecule comprising a first nucleic acid strand comprising a first template nucleic acid sequence and (ii) an immobilized nucleic acid molecule comprising a first capture sequence, a first binding sequence, and a second binding sequence hybridized to the first binding sequence, and wherein the immobilized nucleic acid molecule is immobilized to a support; (b) using the first capture sequence of the immobilized nucleic acid molecule as a sequencing primer to sequence the immobilized nucleic acid molecule to yield a first sequencing read corresponding to the first template nucleic acid sequence, which sequencing comprises generating a second nucleic acid strand attached to the immobilized nucleic acid molecule, wherein the second nucleic acid strand comprises a second template nucleic acid sequence complementary to the first template nucleic acid sequence; and (c) sequencing the second nucleic acid strand attached to the immobilized nucleic acid molecule to yield a second sequencing read corresponding to the second template nucleic acid sequence.

In some instances, the sequencing comprises sequencing by synthesis. In some instances, the sequencing comprises sequencing by hybridization. In some instances, the sequencing comprises sequencing by ligation. In some cases, (b) comprises subjecting the first nucleic acid strand to conditions sufficient to hybridize the first capture sequence of the immobilized nucleic acid molecule to the first nucleic acid strand. In some cases, (b) comprises subjecting the first capture sequence to a primer extension reaction. In some cases, the primer extension reaction comprises use of a polymerase. In some cases, prior to (c), the first nucleic acid strand is removed from the immobilized nucleic acid molecule to provide the second nucleic acid strand immobilized to the support via the immobilized nucleic acid molecule. In some cases, the sequencing comprises bringing the second nucleic acid strand in contact with a sequencing primer, hybridizing the sequencing primer to the second nucleic acid strand, and subjecting the sequencing primer to a primer extension reaction. In some cases, (c) comprises generating a third nucleic acid strand comprising a third template nucleic acid sequence complementary to the second template nucleic acid sequence.

In some cases, the first sequencing read and the second sequencing read do not overlap. In some instances, the first sequencing read and the second sequencing read overlap. In some instances, the overlap between the first sequencing read and the second sequencing read comprises 5 or more bases. In some instances, the first sequencing read and the second sequencing read completely overlap. In some cases, the template nucleic acid molecule is a deoxyribonucleic acid (DNA) molecule. In some cases, the template nucleic acid molecule is a ribonucleic acid (RNA) molecule. In some instances, the support comprises a bead. In some instances, the support comprises a planar surface. In some instances, the immobilized nucleic acid molecule is attached to the support via a chemical group. In some instances, the chemical group comprises an amine. In some instances, the first capture sequence resides in a region of the immobilized nucleic acid molecule that comprises a cleavable base. In some instances, the cleavable base is selected from a uridine base and an 8-oxoguanine base. In some cases, the immobilized nucleic acid molecule comprises a replication block. In some cases, the second binding sequence of the immobilized nucleic acid molecule comprises the replication block.

In another aspect, the present disclosure provides a method for sequencing, comprising (a) providing a support comprising (i) a first nucleic acid strand comprising a first template sequence and a first capture sequence at a first end, which first nucleic acid strand is immobilized to the support via a first immobilized nucleic acid molecule that comprises a first binding sequence, a second binding sequence hybridized to the first binding sequence, and a second capture sequence, wherein the second capture sequence of the immobilized nucleic acid molecule is adjacent to a second end of the first nucleic acid strand opposite the first end; and (ii) a second immobilized nucleic acid molecule, which second immobilized nucleic acid molecule comprises a third binding sequence, a fourth binding sequence hybridized to the third binding sequence, and a third capture sequence; and (b) subjecting the first nucleic acid strand to sequencing to yield a sequencing read in a first direction away from the first end, which sequencing comprises (i) hybridizing the first capture sequence of the first nucleic acid strand to the third capture sequence of the second immobilized nucleic acid molecule, and (ii) generating a second nucleic acid strand comprising a second template sequence complementary to the first template sequence.

In some cases, the method for sequencing further comprises (c) subjecting the first nucleic acid strand and the second nucleic acid strand to conditions sufficient to separate the first nucleic acid strand and the second nucleic acid strand, thereby providing the first nucleic acid strand immobilized to the support via the first immobilized nucleic acid molecule and the second nucleic acid strand immobilized to the support via the second immobilized nucleic acid molecule. In some instances, the third binding sequence and the first binding sequence are the same, and wherein the fourth binding sequence and the second binding sequence are the same. In some instances, the second capture sequence of the first immobilized nucleic acid molecule is the same as the third capture sequence of the second immobilized nucleic acid molecule. In some instances, the first capture sequence of the first nucleic acid strand is complementary to the third capture sequence of the second immobilized nucleic acid molecule. In some cases, separating the first nucleic acid strand and the second nucleic acid strand further comprises repeating (b) and (c) with a third immobilized nucleic acid molecule, which third immobilized nucleic acid molecule comprises a fifth binding sequence, a sixth binding sequence hybridized to the fifth binding sequence, and a fourth capture sequence. In some cases, the method for sequencing further comprises processing the sequencing read to identify the first template sequence. In some instances, the sequencing comprises sequencing by synthesis. In some instances, the sequencing comprises sequencing by hybridization. In some instances, the sequencing comprises sequencing by ligation. In some cases, (b) comprises the use of a polymerase.

In some cases, in the method for sequencing, prior to (a), (d) providing the first immobilized nucleic acid molecule and a template nucleic acid molecule comprising a template sequence complementary to the first template sequence, a first end comprising a fourth capture sequence complementary to the second capture sequence of the first immobilized nucleic acid molecule, and a second end; (e) subjecting the template nucleic acid molecule to conditions sufficient to hybridize the fourth capture sequence of the template nucleic acid molecule to the second capture sequence, and (f) subjecting the first immobilized nucleic acid molecule to conditions sufficient to extend the second capture sequence to the second end of the template nucleic acid molecule, thereby generating the first nucleic acid strand immobilized to the support. In some cases, (f) comprises sequencing to yield a second sequencing read. In some instances, the sequencing comprises sequencing by synthesis. In some instances, the sequencing comprises sequencing by hybridization. In some instances, the sequencing comprises sequencing by ligation. In some cases, in the method for sequencing, prior to providing the support further comprises (g) subjecting the template nucleic acid molecule attached to the first immobilized nucleic acid molecule to conditions sufficient to remove the template nucleic acid molecule. In some cases, the template nucleic acid molecule is a deoxyribonucleic acid (DNA) molecule. In some cases, the template nucleic acid molecule is a ribonucleic acid (RNA) molecule. In some cases, (f) comprises subjecting the second capture sequence of the first immobilized nucleic acid molecule to an extension reaction.

In some cases, the extension reaction comprises use of a polymerase. In some instances, the support comprises a bead. In some instances, the support comprises a planar surface. In some cases, the first and second immobilized nucleic acid molecules are attached to the support via one or more chemical groups. In some cases, the one or more chemical groups comprise an amine. In some instances, the second capture sequence resides in a capture region of the first immobilized nucleic acid molecule that comprises a cleavable base. In some instances, the cleavable base is selected from a uridine base and an 8-oxoguanine base. In some instances, the first immobilized nucleic acid molecule comprises a replication block. In some cases, the second binding sequence of the first immobilized nucleic acid molecule comprises the replication block.

In another aspect, the present disclosure provides a method for sequencing a template nucleic acid molecule, comprising (a) providing a support comprising (i) a first immobilized nucleic acid molecule that comprises a first binding sequence, a second binding sequence hybridized to the first binding sequence, and a first capture sequence; and (ii) a second immobilized nucleic acid molecule that comprises a third binding sequence, a fourth binding sequence hybridized to the third binding sequence, and a second capture sequence; (b) bringing the first immobilized nucleic acid molecule in contact with a first nucleic acid strand derived from the template nucleic acid molecule to hybridize the first capture sequence of the first immobilized nucleic acid molecule to a third capture sequence of the first nucleic acid strand, wherein the first nucleic acid strand comprises the third capture sequence that is complementary to the first capture sequence and a first template sequence; (c) using the first capture sequence of the immobilized nucleic acid molecule as a primer to subject the first nucleic acid strand to a reaction under conditions sufficient to generate a second nucleic acid strand complementary to the first nucleic acid strand, which second nucleic acid strand comprises a second template sequence complementary to the first template sequence; and (d) subjecting the first nucleic acid strand immobilized to the support via the first immobilized nucleic acid molecule to conditions sufficient to (i) separate the third capture sequence from the first capture sequence of the first immobilized nucleic acid molecule and (ii) hybridize the third capture sequence to the second capture sequence of the second immobilized nucleic acid molecule.

In some cases, the method for sequencing a template nucleic acid molecule further comprises (e) subjecting the third capture sequence of the first nucleic acid strand hybridized to the second capture sequence of the second immobilized nucleic acid molecule to sequencing to yield a sequencing read corresponding to the first nucleic acid strand, which sequencing comprises generating a third nucleic acid strand comprising a second template sequence complementary to the first template sequence. In some cases, the first nucleic acid strand comprises a fourth capture sequence and the second nucleic acid strand comprises a fifth capture sequence complementary to the fourth capture sequence, and the method further comprises (f) bringing the fifth capture sequence of the second nucleic acid strand in contact with a sequencing primer and subjecting the second nucleic acid strand to sequencing to yield a second sequencing read corresponding to the second nucleic acid strand, which sequencing comprises generating a fourth nucleic acid strand comprising a third template sequence complementary to the second template sequence of the second nucleic acid strand. In some instances, the sequencing of the first nucleic acid strand comprises sequencing by synthesis. In some instances, the sequencing of the first nucleic acid strand comprises sequencing by hybridization. In some instances, the sequencing of the first nucleic acid strand comprises sequencing by ligation. In some instances, the sequencing of the second nucleic acid strand comprises sequencing by synthesis. In some instances, the sequencing of the second nucleic acid strand comprises sequencing by hybridization. In some cases, the sequencing of the second nucleic acid strand comprises sequencing by ligation. In some cases, (c) comprises subjecting the first capture sequence to a primer extension reaction. In some cases, the primer extension reaction comprises use of a polymerase. In some cases, (e) comprises subjecting the second capture sequence to a primer extension reaction. In some cases, the primer extension reaction comprises use of a polymerase. In some cases, the template nucleic acid molecule is a deoxyribonucleic acid (DNA) molecule. In some cases, the template nucleic acid molecule is a ribonucleic acid (RNA) molecule. In some instances, the support comprises a bead. In some instances, the support comprises a planar surface. In some cases, the first immobilized nucleic acid molecule and the second immobilized nucleic acid molecule are attached to the support via one or more chemical groups. In some instances, the one or more chemical groups comprise an amine. In some cases, the first capture sequence resides in a region of the first immobilized nucleic acid molecule that comprises a cleavable base. In some instances, the cleavable base is selected from a uridine base and an 8-oxoguanine base. In some instances, the first immobilized nucleic acid molecule comprises a replication block.

In another aspect, the present disclosure provides a method for sequencing a template nucleic acid molecule, comprising (a) providing a support comprising (i) a first immobilized nucleic acid molecule that comprises a first binding sequence, a second binding sequence hybridized to the first binding sequence, and a first capture sequence; and (ii) a second immobilized nucleic acid molecule that comprises a third binding sequence, a fourth binding sequence hybridized to the third binding sequence, and a second capture sequence; (b) bringing the first immobilized nucleic acid molecule in contact with a first nucleic acid strand derived from the template nucleic acid molecule to hybridize the first capture sequence of the first immobilized nucleic acid molecule to a third capture sequence of the first nucleic acid strand, wherein the first nucleic acid strand comprises the third capture sequence that is complementary to the first capture sequence and a first template sequence; (c) using the first capture sequence of the first immobilized nucleic acid molecule as a primer to subject the first nucleic acid strand to a reaction under conditions sufficient to generate a second nucleic acid strand complementary to the first nucleic acid strand, which second nucleic acid strand comprises a second template sequence complementary to the first template sequence, and which second nucleic acid is hybridized to a first portion of the first nucleic acid strand comprising the third capture sequence and a second portion of the first nucleic acid strand that does not comprise the third capture sequence; and (d) subjecting the first capture sequence of the first immobilized nucleic acid molecule hybridized to the third capture sequence of the first nucleic acid strand to conditions sufficient to at least partially separate the first capture sequence from the third capture sequence.

In some cases, all or a portion of the first capture sequence hybridized to the third capture sequence has a first melting point and the second nucleic acid strand hybridized to the second portion of the first nucleic acid strand has a second melting point that is higher than the first melting point. In some cases, (d) comprises exposing the first capture sequence hybridized to the third capture sequence to a chemical denaturant. In some instances, the chemical denaturant is selected from the group consisting of a salt, formamide, urea, guanidine hydrochloride, and an organic solvent. In some instances, (d) is performed under isothermal conditions.

In some cases, the first melting point is at least 1° C. lower than the second melting point. In some cases, the first melting point is at least 5° C. lower than the second melting point. In some cases, (d) comprises heating the double-stranded nucleic acid molecule to a temperature higher than the first melting point and lower than the second melting point. In some cases, (d) comprises heating the double-stranded nucleic acid molecule to partially denature the double-stranded nucleic acid molecule. In some instances, the heating includes optical heating. In some instances, the heating includes resistive heating. In some instances, the heating includes convective heating. In some instances, the heating includes inductive heating. In some cases, sequencing a template nucleic acid molecule further comprises bringing the first capture sequence, or a portion thereof, in contact with a primer molecule such that the first capture sequence, or a portion thereof, hybridizes to the primer molecule. In some cases, bringing the first capture sequence, or a portion thereof, in contact with a primer molecule further comprises subjecting the primer molecule hybridized to the first capture sequence, or a portion thereof, to a primer extension reaction. In some cases, the primer extension reaction comprises the use of a polymerase. In some cases, the primer extension reaction separates the first capture sequence and the third capture sequence of the first nucleic acid strand. In some cases, sequencing a template nucleic acid molecule, further comprises (e) separating the first capture sequence and the third capture sequence. In some cases, subsequent to (e), the third capture sequence of the first nucleic acid strand hybridizes to the second capture sequence of the second immobilized nucleic acid molecule. In some cases, hybridizing the third capture sequence of the first nucleic acid strand to the second capture sequence of the second immobilized nucleic acid molecule further comprises subjecting the second capture sequence to sequencing to yield a sequencing read corresponding to the first nucleic acid strand, which sequencing comprises generating a third nucleic acid strand comprising a third template sequence, which third template sequence is complementary to the first template sequence of the first nucleic acid strand. In some cases, generating the sequencing read and the third nucleic acid strand comprises a primer extension reaction. In some cases, the primer extension reaction comprises the use of a polymerase. In some instances, the sequencing comprises sequencing by synthesis. In some instances, the sequencing comprises sequencing by hybridization. In some instances, the sequencing comprises sequencing by ligation. In some cases, the first nucleic acid strand comprises a fourth capture sequence and the second nucleic acid strand comprises a fifth capture sequence complementary to the fourth capture sequence, and the method further comprises (f) bringing the fifth capture sequence of the second nucleic acid strand in contact with a sequencing primer and subjecting the second nucleic acid strand to sequencing to yield a second sequencing read corresponding to the second nucleic acid strand, which sequencing comprises generating a fourth nucleic acid strand comprising a third template sequence complementary to the second template sequence of the second nucleic acid strand. In some cases, subjecting the second capture sequence to sequencing further comprises using the sequencing read to identify the first template sequence of the first nucleic acid strand, thereby sequencing the template nucleic acid molecule. In some cases, the template nucleic acid molecule is a deoxyribonucleic acid (DNA) molecule. In some cases, the template nucleic acid molecule is a ribonucleic acid (RNA) molecule. In some instances, the support comprises a bead. In some instances, the support comprises a planar surface. In some cases, the first immobilized nucleic acid molecule and the second immobilized nucleic acid molecule are attached to the support via one or more chemical groups. In some cases, the one or more chemical groups comprises an amine. In some cases, the first capture sequence resides in a region of the first immobilized nucleic acid molecule that comprises a cleavable base. In some instances, the cleavable base is selected from a uridine base and an 8-oxoguanine base. In some cases, the immobilized nucleic acid molecule comprises a replication block.

In another aspect, the present disclosure provides a method for sequencing a template nucleic acid molecule, comprising (a) providing an immobilized nucleic acid strand that is immobilized to a support, which immobilized nucleic acid strand comprises (i) a first nucleic acid strand derived from the template nucleic acid molecule, the first nucleic acid strand comprising a first capture sequence and a first template sequence, and (ii) a second capture sequence hybridized to the first capture sequence of the first nucleic acid strand, wherein the first capture sequence and the second capture sequence are separated by a single-stranded region; (b) subjecting the immobilized nucleic acid strand to sequencing to yield a sequencing read corresponding to the first nucleic acid strand of the immobilized nucleic acid strand, which sequencing comprises generating a second nucleic acid strand complementary to the first nucleic acid strand, which second nucleic acid strand comprises a second template sequence complementary to the first template sequence; (c) bringing the single-stranded region of the immobilized nucleic acid strand into contact with a primer molecule and subjecting the immobilized nucleic acid strand to conditions sufficient to extend the primer molecule, thereby separating the first nucleic acid strand and the second nucleic acid strand.

In some cases, the method for sequencing a template nucleic acid molecule further comprises using the sequencing read to identify the first template sequence of the first nucleic acid strand, thereby sequencing the template nucleic acid molecule. In some cases, the method for sequencing a template nucleic acid molecule, prior to (a), further comprises (d) bringing the first nucleic acid strand immobilized to the support in contact with a capture nucleic acid molecule to hybridize the second capture sequence of the capture nucleic acid molecule to the first capture sequence of the first nucleic acid strand, wherein the capture nucleic acid molecules comprises the second capture sequence, a first binding sequence, and a second binding sequence hybridized to the first binding sequence; (e) using the second capture sequence of the capture nucleic acid molecule as a primer to subject the first nucleic acid strand to sequencing to yield a second sequencing read corresponding to the first nucleic acid strand, which sequencing comprises generating a third nucleic acid strand complementary to the first nucleic acid strand, which third nucleic acid strand comprises a third template sequence complementary to the first template sequence; and (f) removing the third nucleic acid strand from the first nucleic acid strand and separating the first capture sequence hybridized to the second capture sequence, thereby providing the immobilized nucleic strand.

In some instances, the sequencing the first nucleic acid strand comprises sequencing by synthesis. In some instances, the sequencing the first nucleic acid strand comprises sequencing by hybridization. In some instances, the sequencing the first nucleic acid strand comprises sequencing by ligation. In some instances, the sequencing the first nucleic acid strand comprises sequencing by synthesis. In some instances, the sequencing the first nucleic acid strand comprises sequencing by hybridization. In some instances, the sequencing the first nucleic acid strand comprises sequencing by ligation. In some cases, (b) comprises subjecting the immobilized nucleic acid strand to a primer extension reaction. In some cases, the primer extension reaction comprises use of a polymerase. In some cases, (e) comprises subjecting the first nucleic acid strand to a primer extension reaction. In some cases, the primer extension reaction comprises use of a polymerase. In some cases, the template nucleic acid molecule is a deoxyribonucleic acid (DNA) molecule. In some cases, the template nucleic acid molecule is a ribonucleic acid (RNA) molecule. In some instances, the support comprises a bead. In some instances, support comprises a planar surface. In some cases, the immobilized nucleic acid molecule is attached to the support via a chemical group. In some instances, the chemical group comprises an amine. In some cases, the second capture sequence resides in a region of the capture nucleic acid molecule that comprises a cleavable base. In some instances, the cleavable base is selected from a uridine base and an 8-oxoguanine base. In some cases, the capture nucleic acid molecule comprises a replication block. In some cases, sequencing a template nucleic acid molecule further comprises bringing a sequencing primer in contact with the second nucleic acid strand and subjecting the second nucleic acid strand to sequencing to yield a third sequencing read corresponding to the second nucleic acid strand, which sequencing comprises generating a fourth nucleic acid strand, which fourth nucleic acid strand comprises a fourth template sequence that is complementary to the second template sequence of the second nucleic acid strand. In some cases, (b) and (c) occur simultaneously. In some cases, (b) occurs before (c).

Additional aspects and advantages of the present disclosure will become readily apparent to those skilled in this art from the following detailed description, wherein only illustrative cases of the present disclosure are shown and described. As will be realized, the present disclosure is capable of other and different cases, and its several details are capable of modifications in various obvious respects, all without departing from the disclosure.

Methods of Processing a Nucleic Acid Molecule

The methods described herein may be useful for processing a nucleic acid molecule. For example, the methods described herein may be used to amplify one or more nucleic acid molecules of a nucleic acid sample before or during sequencing. The methods of the present disclosure may be useful for, for example, sample preparation for sequencing to identify genetic aberrations for, e.g., cancer detection.

The methods may comprise partially denaturing a double-stranded nucleic acid molecule to provide a region comprising two single strands. Such a region may be referred to as a "bubble." In some cases, a single-stranded portion of a partially denatured region may provide a site for hybridization of a primer. Partial denaturation of a nucleic acid molecule may occur without denaturing reagents or high temperatures, significantly simplifying analysis and processing. For example, partial denaturation of a nucleic acid template may occur after heating the template to a first temperature that is lower than a second temperature that would be needed for full denaturation of the template. In some cases, partial denaturation may involve exposing a nucleic acid template to a chemical denaturant, changing a pH or salt concentration, or heating the nucleic acid template. Following formation of a single-stranded region in the nucleic acid molecule, yielding a first strand and a second strand in the single-stranded region (e.g., bubble region), the single-stranded region may be expanded to further separate the two strands of the double-stranded nucleic acid molecule. In some cases, a bubble region may expand in size on its own or as a result of application of a partially denaturing condition, such as a condition used to generate the bubble (e.g., heating, chemical denaturant, or changing a pH or salt concentration). Expansion of a bubble region may result in separation of the ends of the double-stranded nucleic acid molecule. In other cases, a primer molecule may hybridize to a complementary sequence in the first strand of the single-stranded region and be extended (e.g., by a polymerase) to further separate the two single strands of the double-stranded nucleic acid molecule, thereby effectively expanding the bubble region. Upon separation of the ends of the double-stranded nucleic acid molecule, a primer molecule may hybridize to a complementary sequence in the second strand of the single-stranded region and be extended (e.g., by a polymerase) to an end of the second strand, thereby generating a copy of the nucleic acid template (or its complement). The process may be repeated to further amplify the original nucleic acid template. In some cases, this process may occur at more than one end of the double-stranded nucleic acid molecule. For example, a first bubble may form near a first end of a double-stranded nucleic acid molecule and be expanded to the first end and a second bubble may form near a second end of the double-stranded nucleic acid molecule and be expanded to the second end.

Accordingly, the methods described herein may facilitate amplification of nucleic acid molecules without the need for a multitude of complex steps or numerous reagents. The present methods may be useful in, for example, sequencing, screening, diagnosis, nucleic acid synthesis, and gene expression applications.

The methods described herein utilize the weak interaction of base pairs in double-stranded nucleic acid molecules to generate regions comprising two single strands (e.g., "bubbles"). A double-stranded nucleic acid molecule may dynamically dissociate in certain region(s) at a melting temperature by allowing local opening of base pairs to generate a bubble. DNA melting is driven by entropy overruling the attraction of hydrogen bonds between the nucleic acid bases. The spontaneous and induced localized melting behavior may be determined by statistical models such as the Poland and Sheraga model and by thermodynamic nearest-neighbor models. The mesoscopic Peyrard-Bishop-Dauxious model also reflects bubble formation and stability seen experimentally.

Accordingly, the present disclosure provides methods, systems, and kits for processing nucleic acid samples. A method for processing a nucleic acid sample may comprise providing a sample including a double-stranded nucleic acid molecule having a first strand and a second strand having sequence complementarity with the first strand. The first strand may comprise an adapter, comprising a first sequence and a second sequence adjacent to the first sequence, where the first sequence and the second sequence are hybridized to a third sequence and a fourth sequence, respectively, of the second strand. The first sequence hybridized to the third sequence has a first melting point and the second sequence hybridized to the fourth sequence has a second melting point higher than the first melting point. The region of the double-stranded nucleic acid molecule comprising the first sequence of the first strand and the third sequence of the second strand may be referred to herein as an insert region. The method may further comprise subjecting the double-stranded nucleic acid molecule to conditions sufficient to partially denature the double-stranded nucleic acid molecule, thereby separating the first sequence from the third sequence, and expanding the resultant single-stranded region to an end of the double-stranded nucleic acid molecule. Expanding the single-stranded region may comprise bringing a primer molecule having sequence complementarity with the third sequence in contact with the second strand under conditions sufficient to permit the primer molecule to hybridize to the third sequence; and subjecting the second strand comprising the primer molecule hybridized to the third sequence to a primer extension reaction under conditions sufficient to generate a third strand hybridized to at least a portion of the second strand.

The double-stranded nucleic acid molecule for analysis and processing according to the methods described herein may be provided as a component in a sample or may be generated from another nucleic acid molecule of interest included within a sample. An adapter (e.g., an adapter free in solution or immobilized to a substrate) may be used to generate the double-stranded nucleic acid molecule from a single-stranded nucleic acid molecule. Accordingly, the present disclosure also provides methods for generating the double-stranded nucleic acid molecule as well as systems and kits for carrying out the amplification and generation methods.

A method for processing a nucleic acid sample may comprise providing a nucleic acid sample comprising a first nucleic acid molecule comprising a single strand; attaching an adapter to an end of the first nucleic acid molecule, where the adapter comprises a first sequence and a second sequence; and using the adapter to generate a double-stranded nucleic acid molecule comprising a second nucleic acid molecule that is complementary to the first nucleic acid molecule, where the second nucleic acid molecule comprises a third sequence hybridized to the first sequence and a fourth sequence hybridized to the second sequence. The first sequence hybridized to the third sequence has a first melting point and the second sequence hybridized to the fourth sequence has a second melting point higher than the first melting point. In some cases, the adapter may further comprise a fifth sequence, where the second sequence and the fifth sequence flank the first sequence. The second nucleic acid molecule may further comprise a sixth sequence hybridized to the fifth sequence, where the sixth sequence and the fourth sequence flank the third sequence. Upon partial denaturation of the adapter, a single-stranded region comprising the first and third sequences may form, where the single-stranded region may be contained within the adapter and a complement thereof (e.g., a region comprising the third, fourth, and, in some cases, sixth sequences). The adapter may be immobilized to a support (e.g., a planar array or bead) prior to or subsequent to the generation of the double-stranded nucleic acid molecule. In some cases, an additional adapter may be attached to another end (e.g., opposite the (first) end) of the first nucleic acid molecule. For example, the double-stranded nucleic acid molecule may comprise a first adapter at a first end and a second adapter at a second end, where the first and second adapter may be the same or different. This additional adapter may include one or more additional sequences. In some cases, the one or more sequences of the additional adapter may be the same as, or similar to, the sequences of the adapter.

An adapter may be used to immobilize a nucleic acid molecule to a support (e.g., a substrate). Immobilization, as used herein, may generally refer to substantially stable attachment of a first object (e.g., the nucleic acid molecule) to a second object (e.g., the support) under defined conditions, either directly or through a linking moiety. The attachment can be by any mechanism, including, but not limited to, non-covalent bonding, ionic interactions, and covalent linkage. If a first nucleic acid molecule is hybridized to a second nucleic acid molecule immobilized on a support, then the first nucleic acid molecule may also be considered to be immobilized to the support during amplification, if amplification conditions are such that substantial amounts of the first and second nucleic acid molecules are associated or connected with each other at any or all times during amplification. For example, first and second nucleic acid molecules may be associated together by hybridization involving Watson-Crick base pairing or hydrogen bonding. In an example, amplification conditions may allow at least 50%, 80%, 90%, 95% or 99% of a first nucleic acid molecule to remain hybridized with a second nucleic acid molecule, or vice versa, during amplification. A nucleic acid molecule may be considered un-immobilized or non-immobilized if it is not directly or indirectly attached to or associated with a support.

An adapter may attach to a nucleic acid molecule via hybridization or ligation (e.g., as described herein). For example, an adapter (e.g., an adapter immobilized to a substrate) may hybridize to a complementary sequence of a single-stranded nucleic acid molecule. The complementary sequence of the nucleic acid molecule may be introduced into the nucleic acid molecule via ligation of another adapter comprising the complementary sequence. As described elsewhere herein, an adapter may include two or more regions having different characteristics. For example, an adapter may include a first region comprising a first sequence and a second region comprising a second sequence. In some cases, the first region may comprise at least 5 bases, such as 10, 15, 20, 25, 30, 35, 40, 45 or more bases. The first region may comprise one or more adenine, thymine, uridine, and inosine bases, and may in some cases comprise only adenine, thymine, uridine, and inosine bases. The second region may comprise the same or a different number of bases. Sequences of an adapter may be selected for maximal hybridization with a target sequence and very low hybridization to any other sequence. For an adapter immobilized to a substrate, the first region comprising the first sequence may be disposed closer to the substrate than the second region comprising the second sequence, or vice versa (e.g., the second region comprising the second sequence may be disposed closer to the substrate than the first region comprising the first sequence). A first adapter attached to a first end of a nucleic acid molecule may be the same or different adapter from a second adapter attached to a second end (opposite the first end) of the nucleic acid molecule.

A single-stranded nucleic acid molecule (e.g., template nucleic acid molecule) hybridized to an adapter may be subjected to conditions sufficient to promote extension of the adapter to generate a sequence complementary to the single-stranded nucleic acid molecule, thereby providing a double-stranded nucleic acid molecule. The double-stranded nucleic acid molecule may comprise a first strand including the first adapter and a sequence complementary to the single-stranded nucleic acid molecule, and a second strand including the single-stranded nucleic acid molecule and a sequence complementary to the first adapter which may be considered a second adapter. The second adapter of the second strand may comprise a third sequence hybridized to the first sequence of the first adapter and a fourth sequence hybridized to the second sequence of the first adapter, where the first sequence hybridized to the third sequence may have a first melting point and the second sequence hybridized to the fourth sequence may have a second melting point that is higher than the first melting point (e.g., as described herein). The first melting point may be at least about 1 degree Celsius (° C.) lower than the second melting point. For example, the first melting point may be at least 5° C. lower than the second melting point. In some cases, the first strand of the double-stranded nucleic acid molecule may comprise a third adapter at a second end, and the second strand may comprise a sequence complementary to the third adapter which may be considered a fourth adapter. The third and fourth adapters together may comprise regions comprising different melting points or may not include regions comprising different melting points. For example, the third and fourth adapters together may comprise a region that may be partially denatured, e.g., as described herein. In another example, the third and fourth adapters together may not comprise a region that may be partially denatured.

Extension may involve a polymerizing enzyme such as a DNA polymerase or an RNA polymerase. The polymerase may be a non-processive DNA-dependent DNA polymerase. Alternatively, the polymerase may be a processive DNA-dependent DNA polymerase, such as Bst, Bst2, Bst3, or Phi29. The polymerase may also be an RNA-dependent DNA polymerase or an RNA-dependent RNA polymerase. Extension may take place in the presence of nucleoside triphosphate molecules (e.g., natural or non-natural nucleotides, and/or nucleotides labeled with a detectable moiety) or other nucleotide precursors such as modified nucleoside triphosphate molecules.

Upon generating or otherwise providing a double-stranded nucleic acid molecule, the double-stranded nucleic acid molecule may be subjected to conditions sufficient to partially denature the double-stranded nucleic acid molecule. Partially denaturing the double-stranded nucleic acid molecule may comprise exposing the molecule or a portion thereof to a chemical denaturant, such as a salt, formamide, urea, guanidine hydrochloride, or an organic solvent. Alternatively or in addition, partial denaturation may be achieved by lowering a salt concentration and/or increasing a pH of a solution including the double-stranded nucleic acid molecule. Alternatively or in addition, partially denaturing the double-stranded nucleic acid molecule may comprise heating the molecule. For example, the molecule may be heated to a temperature higher than the first melting point of the first sequence of the first adapter hybridized to the third sequence of the second adapter and lower than the second melting point of the second sequence of the first adapter hybridized to the fourth sequence of the second adapter. Heating the double-stranded nucleic acid molecule may include optical heating, resistive heating, convective heating, inductive heating, and/or microwave heating. Partial denaturation may result in at most a portion of the first strand of the double-stranded nucleic acid molecule separating from the second strand of the double-stranded nucleic acid molecule. At the end of partial denaturation of the double-stranded nucleic acid molecule, at least a portion of the double-stranded nucleic acid molecule may remain double-stranded. For example, partial denaturation may result in the formation of a bubble in the double-stranded nucleic acid molecule. Partial denaturation may result in the separation of the first sequence of the first adapter of the first strand from the third sequence of the second adapter of the second strand. In some cases, a bubble formed as a result of partial denaturation may expand to an end of the double-stranded nucleic acid molecule.

Upon separation of the first and third sequences of the double-stranded nucleic acid molecule, the resultant single-stranded region may be expanded to an end of the double-stranded nucleic acid molecule. In some cases, the bubble may expand in size under the conditions applied to partially denature the double-stranded nucleic acid molecule, thereby separating the second and fourth sequences of the double-stranded nucleic acid molecule. In some cases, a primer molecule having sequence complementarity with the third sequence of the second strand may be brought into contact with the second strand under conditions sufficient to permit the primer molecule to hybridize to the third sequence. A polymerase (e.g., as described herein) may then bind to and extend the primer molecule (e.g., as described herein), further separating the first and second strands and resulting in an increase in the size of the bubble. Extension of the primer molecule may result in separation of two ends of the double-stranded nucleic acid molecule, such that the molecule is open ("unzipped") at an end. The further separation of the first and second strands may facilitate hybridization of a primer molecule to, for example, the second sequence of the first strand. In some cases, this primer molecule may be immobilized to a substrate. This substrate may be the same substrate to which an adapter of the double-stranded nucleic acid molecule may be attached. The primer molecule may be complementary to the first adapter or a portion thereof. For example, the primer molecule may have the same sequence as the second adapter. A polymerase may bind to and extend the primer molecule toward another end of the double-stranded nucleic acid molecule (e.g., as described herein), thereby separating the first and second strands to result in the generation of a double-stranded nucleic acid molecule comprising the first strand and a third strand complementary to the first strand and a free second strand. In some cases, an additional primer molecule (e.g., a primer molecule in solution that is not immobilized to a substrate) may hybridize to an end of the second strand (e.g., an end that is not attached to a substrate), and a polymerase molecule may bind to and extend the additional primer molecule (e.g., as described herein) to generate a fourth strand that is complementary to the second strand. In some cases, the additional primer molecule may be immobilized to a support. By repeating the processes described herein, multiple copies of the initial single-stranded nucleic acid molecule (e.g., the first strand), as well as its complement, may be generated. In some cases, 1 or more copies of an initial single-stranded nucleic acid molecule, and/or a complement thereof, may be generated. For example, 2, 3, 4, 5, 6, 7, 8, 9, 10, 20, 30, 40 50, 60, 70, 80, 90, 100, 150, 200, 250, 500, 750, 1,000, 1,500, 2,000, 2,500, 5,000, 7,500, 10,000, 15,000, 20,000, 50,000, 75,000, 100,000, 500,000, 1,000,000 or more copies may be generated. In some cases, a partially denatured region may also form near another end of the double-stranded nucleic acid molecule. For example, the double-stranded nucleic acid molecule may include a third adapter at a second end of the first strand of the double-stranded nucleic acid molecule and a fourth adapter having sequence complementarity to the third adapter at a second end of the second strand of the double-stranded nucleic acid molecule. The third adapter may not include specified regions of low or high melting points. Alternatively, the third adapter hybridized to the fourth adapter may include one or more low melting point regions and one or more high melting point regions. The one or more low melting point regions may be susceptible to partial denaturation (e.g., as described herein). In some cases, the third adapter may be the same as, or similar to, the first adapter. For example, both the first adapter and the third adapter may include a single low melting point region that may be flanked by two high melting point regions. Additional exemplary configurations are shown in FIGS. 7A-7D. In cases, where the third adapter hybridized to the fourth adapter is susceptible to partial denaturation, a bubble region formed upon partial separation of the first and second strands in the third and fourth adapters may be expanded to the second end of the double-stranded nucleic acid molecule. In some cases, expanding the bubble may comprise hybridizing a primer molecule to a sequence of the single-stranded region of the bubble and extending the primer molecule to the end of the double-stranded nucleic acid molecule. Upon expansion of the bubble and separation of the ends of the double-stranded nucleic acid molecule, a primer molecule may hybridize to the third or fourth adapter and then be extended to generate a strand having sequence complementarity to the first or second strand of the double-stranded nucleic acid molecule. The primer molecule may be free in solution or immobilized to a support. This process may also be repeated to facilitate the generation of multiple copies of first and second strands of the double-stranded nucleic acid molecule.

Accordingly, the methods described herein may be used to amplify a template nucleic acid molecule without the need for high temperatures or complex reaction schemes. The amplification processes may be repeated one or more times to generate additional copies of a template nucleic acid molecule and/or its complement. The template nucleic acid molecule and copies thereof, and/or its complement and copies thereof, may subsequently undergo additional processing and/or analysis including sequencing (e.g., as described herein).

FIG. 1 schematically illustrates a method of amplifying a template nucleic acid molecule. In the first panel, a single-stranded template nucleic acid molecule 105 having a sequence complementary to an adapter 100 that is immobilized to a substrate 180 may hybridize to adapter 100. A polymerase (e.g., a DNA polymerase) may then attach to the 3' terminus of adapter 100 (indicated with an arrow head) and extend adapter 100 to the end of the nucleic acid template 105, thereby generating complementary strand 110. Together, strands 105 and 110 form a double-stranded nucleic acid molecule 115. Strands 105 and 110 of double-stranded nucleic acid molecule 115 may then be partially denatured to generate a single-stranded region or "bubble" 120. As described herein, the temperature may be elevated to increase the likelihood of localized denaturation or bubble formation in double-stranded nucleic acid molecule 115. The regions of denaturation may be controlled by placing sequences in the nucleic acid template that are likely to denature at lower temperatures (e.g., as described herein). For example, double-stranded nucleic acid molecule 115 may comprise a region including a sequence of adapter 100 hybridized to a complementary sequence of strand 110 that has a low melting point. The low melting point region may be localized close to an end of double-stranded nucleic acid molecule 115. For example, the low melting point region may be localized close to substrate 180. Primer molecule 125 may then hybridize to the single-stranded region of strand 110 in bubble 120. A polymerase may be used to extend primer molecule 125 to an end of strand 110 (e.g., towards the substrate) to generate a partial complementary strand 140, and separate the end of strand 110 from an end of strand 105. The end of strand 105 may then hybridize to an additional primer molecule 150 that may be immobilized to substrate 180. A polymerase may then be used to generate a strand 160 that is complementary to strand 105. Generation of strand 160 results in the regeneration of free strand 165. A third primer molecule 170 may then hybridize to strand 165. A polymerase may then be used to generate a strand 175 that is complementary to strand 165. The net effect of this process is the formation of two double-stranded nucleic acid molecules from an original single-stranded template nucleic acid molecule. The process may be repeated to further amplify the template nucleic acid molecule and its complement.

In some cases, a nucleic acid molecule may be amplified from both ends of a double-stranded nucleic acid molecule. A single-stranded nucleic acid molecule may comprise a first adapter at a first end of the molecule and a second adapter at a second end (opposite the first end) of the molecule. Each adapter may include two or more different sequences. For example, the first adapter may include a first sequence and a second sequence, and the second adapter may include a third sequence and a fourth sequence. The first end of the single-stranded nucleic acid molecule may hybridize to an adapter that may be attached to a substrate, and a polymerase may be used to extend the adapter to the second end of the single-stranded nucleic acid molecule, thereby generating a second strand that is complementary to the template single-stranded nucleic acid molecule. The first sequence and the third sequence may, upon hybridization to complementary sequences in the second strand, form regions having low melting points, while the second and fourth sequence may form regions having high melting points. The double-stranded nucleic acid molecule comprising the first and second strands may then be partially denatured (e.g., as described herein). In some cases, a bubble may form at the site of the first sequence, and no bubble may form at the site of the third sequence. In some cases, a bubble may form at the site of the third sequence, and no bubble may form at the site of the first sequence. In certain cases, a first bubble may form at the site of the first sequence and a second bubble may form at the site of the third sequence. A first primer molecule may attach to a single strand in the first bubble, and a second primer molecule may attach to a single strand in the second bubble. Polymerases may be used to extend the first and second primers to, for example, (different) ends of the double-stranded nucleic acid molecule. Third and fourth primer molecules may then hybridize to single-stranded portions of the double-stranded nucleic acid molecule and be extended using polymerases to generate two double-stranded nucleic acid molecules.

Figure 2:
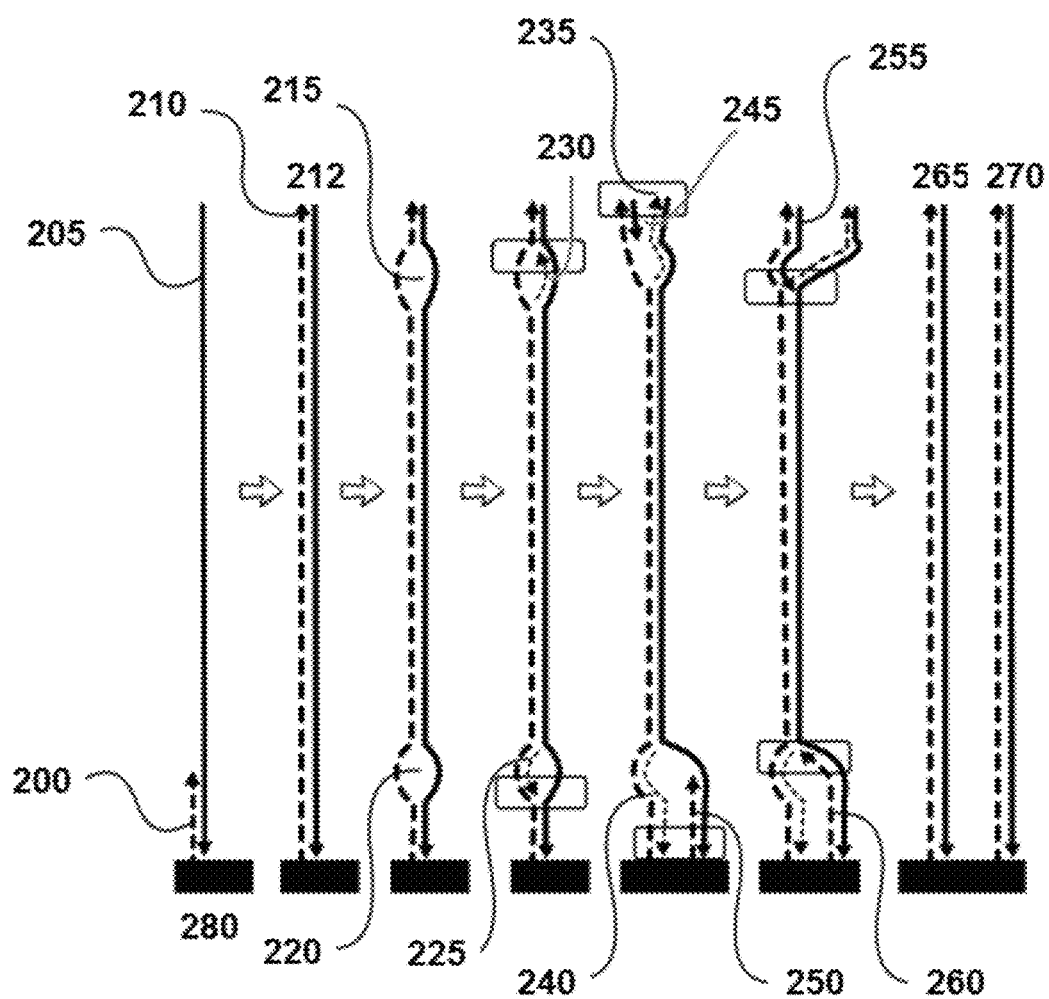
FIG. 2 schematically illustrates a clonal amplification method involving primer hybridization to two ends of a nucleic acid molecule.

FIG. 2 schematically illustrates an amplification method involving partial denaturation of multiple regions of a double-stranded nucleic acid molecule. In the first panel, a single-stranded template nucleic acid molecule 205 having a sequence complementary to an adapter 200 that is immobilized to a substrate 280 may hybridize to adapter 200. A polymerase (e.g., a DNA polymerase) may then attach to the 3' terminus of adapter 200 (indicated with an arrow head) and extend adapter 200 to the end of the nucleic acid template 205, thereby generating complementary strand 210. Together, strands 205 and 210 form a double-stranded nucleic acid molecule 212. Strands 205 and 210 may then be partially denatured to generate bubble 215 near a first end of double-stranded nucleic acid molecule 212 and bubble 220 near a second end of double-stranded nucleic acid molecule 212 that is in proximity to the substrate 280 to which double-stranded nucleic acid molecule 212 is attached. The first end may be opposite the second end. Partial denaturation of double-stranded nucleic acid molecule 212 may be achieved by, for example, exposing double-stranded nucleic acid molecule 212 to a chemical denaturant (e.g., as described herein) or heating double-stranded nucleic acid molecule 212 to separate sequences comprising low melting points. Primer molecule 225 may then hybridize to the single-stranded region of strand 210 in bubble 220, and primer molecule 230 may hybridize to the single-stranded region of strand 205 in bubble 215. A polymerase may be used to extend primer molecule 225 to an end of strand 210 (the second end of double-stranded nucleic acid molecule 212) to generate a partial complementary strand 240. The same or a different polymerase may be used to extend primer molecule 230 to an end of strand 205 (the first end of double-stranded nucleic acid molecule 212) to generate a partial complementary strand 235. The effect of these extensions may be the denaturation of the termini of the nucleic acid template. Strand 205 may then hybridize to an additional primer molecule 250 that is immobilized to the substrate at one end and to an additional primer molecule at another end 245 that is free in solution. A polymerase may then be used to generate a strand 260 that is complementary to strand 205 and a strand 255 that is complementary to strand 210. Generation of strands 255 and 260 results in the generation two double-stranded nucleic acid molecules 265 and 270. This process may be repeated with bubbles being formed, primers attaching to single-stranded regions of the bubbles and being extended to effect the denaturation of ends of nucleic acid templates, hybridization to additional primers complementary to terminal sequences, and extension of terminal primers to generate additional copies of the original nucleic acid template, and/or complements thereof, at every cycle. Multiple adapter types may be immobilized to a substrate such that the amplification process may occur in both directions.

Figure 4:
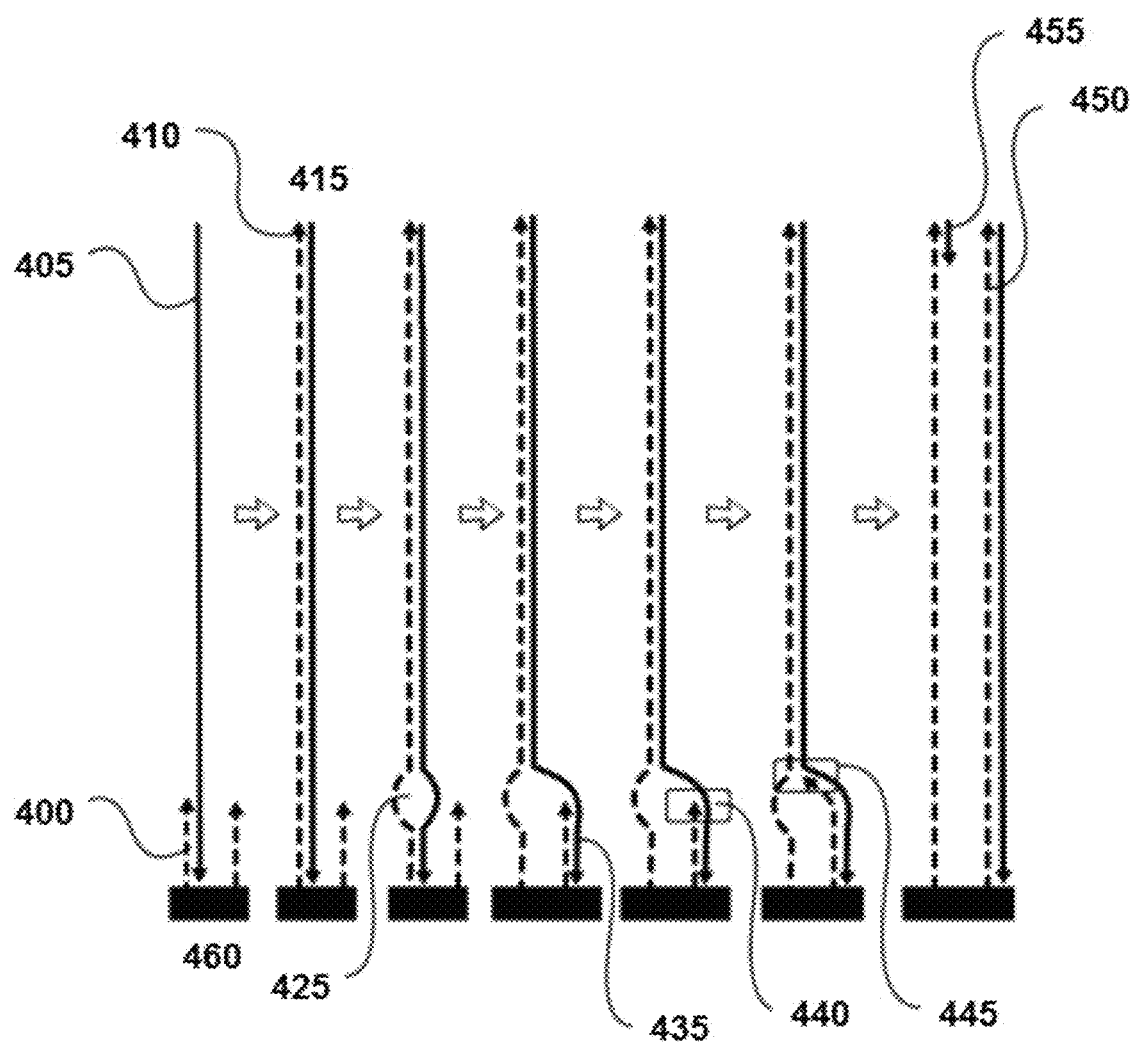
FIG. 4 schematically illustrates another clonal amplification method.

FIG. 4 schematically illustrates an alternative amplification method involving partial denaturation of a region of a double-stranded nucleic acid molecule. In the first panel, a single-stranded template nucleic acid molecule 405 having a sequence complementary to an adapter 400 that is immobilized to a substrate 460 may hybridize to adapter 400. A polymerase (e.g., a DNA polymerase) may then attach to the 3' terminus of adapter 400 (indicated with an arrow head) and extend adapter 400 to the end of the nucleic acid template 405, thereby generating complementary strand 410. Together, strands 405 and 410 form a double-stranded nucleic acid molecule 415. Strands 405 and 410 may then be partially denatured to generate bubble 425 near an end of double-stranded nucleic acid molecule 415 that is in proximity to the substrate 460 to which double-stranded nucleic acid molecule 415 is attached. Partial denaturation of double-stranded nucleic acid molecule 415 may be achieved by, for example, exposing double-stranded nucleic acid molecule 415 to a chemical denaturant (e.g., as described herein) or heating double-stranded nucleic acid molecule 415 to separate sequences comprising low melting points. From bubble 425, the double-stranded nucleic acid molecule 415 may further partially denature such that the two strands 405 and 410 are completely separated at the end to 'un-zip.' Such separation may be achieved without use of a primer to hybridize to a single stranded region in the bubble 425 to facilitate the separation (as illustrated in FIGS. 1-2). Primer molecule 435 that is immobilized to substrate 460 may then hybridize to strand 405. A polymerase 440 may be used to extend primer molecule 435 to an end of strand 405 to generate a partial complementary strand 445. Strand 445 may be extended to provide double-stranded nucleic acid molecule 450. A primer molecule 455 may then be hybridized to an end of strand 410 and extended to generate another double-stranded nucleic acid molecule. This double-stranded nucleic acid molecule may then be subjected to the same amplification process. These processes may be repeated with bubbles being formed, primers attaching to single-stranded regions of double-stranded nucleic acid molecules, and extension of primers to generate additional copies of the original nucleic acid template, and/or complements thereof, at every cycle.

Figure 3:
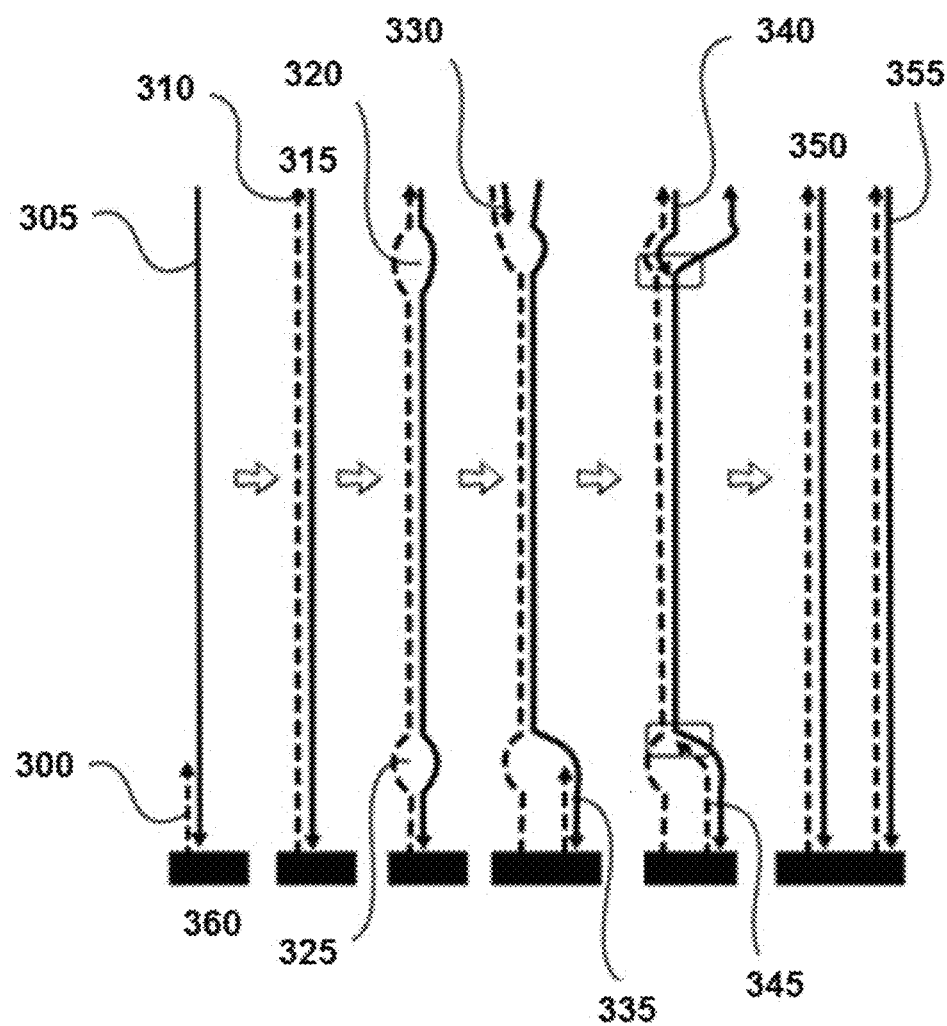
FIG. 3 schematically illustrates another clonal amplification method involving primer hybridization to two ends of a nucleic acid molecule.

FIG. 3 schematically illustrates an amplification method involving partial denaturation of multiple regions of a double-stranded nucleic acid molecule. In the first panel, a single-stranded template nucleic acid molecule 305 having a sequence complementary to an adapter 300 that is immobilized to a substrate 360 may hybridize to adapter 300. A polymerase (e.g., a DNA polymerase) may then attach to the 3' terminus of adapter 300 (indicated with an arrow head) and extend adapter 300 to the end of the nucleic acid template 305, thereby generating complementary strand 310. Together, strands 305 and 310 form a double-stranded nucleic acid molecule 315. Strands 305 and 310 may then be partially denatured to generate bubble 320 near a first end of double-stranded nucleic acid molecule 315 and bubble 325 near a second end of double-stranded nucleic acid molecule 315 that is in proximity to the substrate 360 to which double-stranded nucleic acid molecule 315 is attached. The first end may be opposite the second end. Partial denaturation of double-stranded nucleic acid molecule 315 may be achieved by, for example, exposing double-stranded nucleic acid molecule 315 to a chemical denaturant (e.g., as described herein) or heating double-stranded nucleic acid molecule 315 to separate sequences comprising low melting points. From bubble 320, the double-stranded nucleic acid molecule 315 may further partially denature such that the two strands 305 and 310 are completely separated at the first end to 'un-zip.' Such separation may be achieved without use of a primer to hybridize to a single stranded region in the bubble 320 to facilitate the separation (as illustrated in FIGS. 1-2). Similarly, from bubble 325, the double-stranded nucleic acid molecule 315 may further partially denature such that the two strands 305 and 310 are completely separated at the second end to 'un-zip.' Such separation may be achieved without use of a primer to hybridize to a single stranded region in the bubble 325 to facilitate the separation (as illustrated in FIGS. 1-2).

Primer molecule 335 that is immobilized to substrate 360 may then hybridize to strand 305, and primer molecule 330 may hybridize to strand 310. A polymerase may be used to extend primer molecule 335 to an end of strand 305 to generate a partial complementary strand 345. The same or a different polymerase may be used to extend primer molecule 330 to an end of strand 310 (the first end of double-stranded nucleic acid molecule 315) to generate a partial complementary strand 340. Strands 340 and 345 may be extended to provide double-stranded nucleic acid molecules 350 and 355. This process may be repeated with bubbles being formed, primers attaching to single-stranded regions of double-stranded nucleic acid molecules, and extension of primers to generate additional copies of the original nucleic acid template, and/or complements thereof, at every cycle. Multiple adapter and primer types may be immobilized to a substrate such that the amplification process may occur in both directions.

Figure 5:
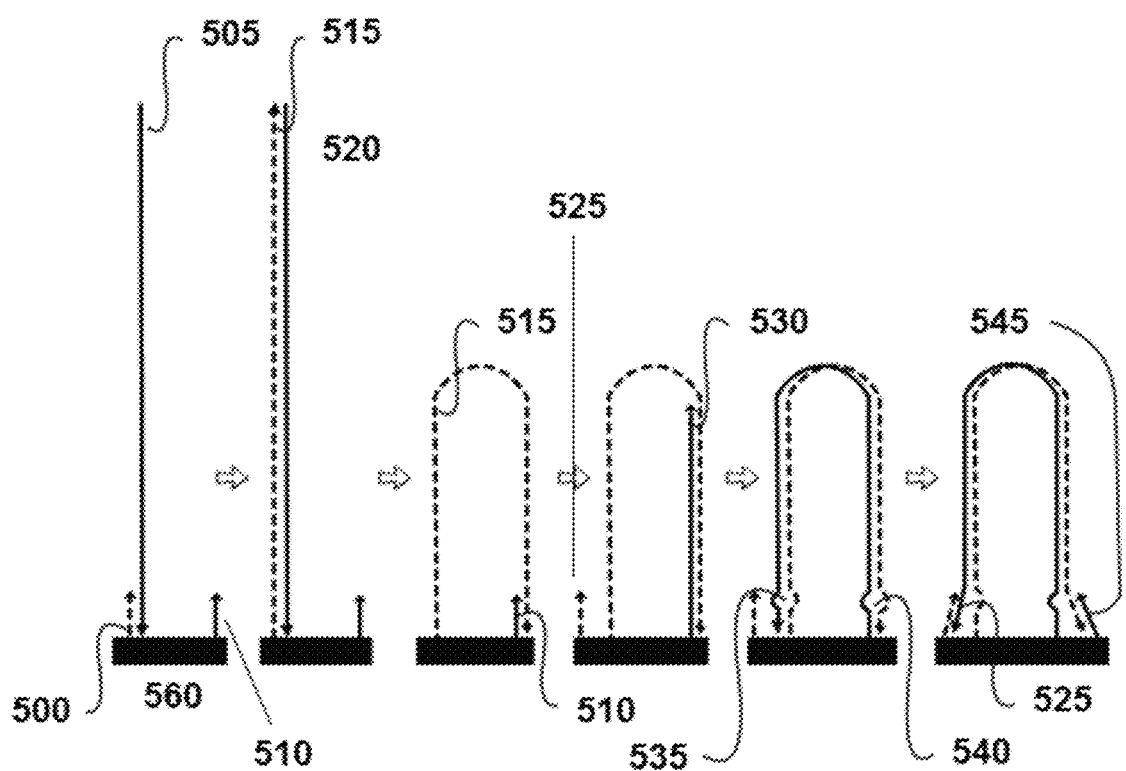
FIG. 5 schematically illustrates a looped or bridged clonal amplification method.

FIG. 5 schematically illustrates an alternative amplification method comprising a bridging or looping process. In the first panel, a single-stranded template nucleic acid molecule 505 having a sequence complementary to an adapter 500 that is immobilized to a substrate 560 may hybridize to adapter 500. Single-stranded template nucleic acid molecule 505 may comprise a template nucleic acid sequence. Substrate 560 may also comprise additional adapters including adapter 510 immobilized thereto. Adapter 510 may be the same as adapter 500. Alternatively, adapter 510 may be a different adapter from adapter 500. A polymerase (e.g., a DNA polymerase) may then attach to the 3' terminus of adapter 500 (indicated with an arrow head) and extend adapter 500 to the end of the nucleic acid template 505, thereby generating complementary strand 515. Together, strands 505 and 515 form a double-stranded nucleic acid molecule 520. Strand 505 may then be denatured to provide single strand 515 immobilized to substrate 560 at a first end. A second end of single strand 515, opposite the first end, may then hybridize to adapter 510 that is immobilized to substrate 560 to form a double-stranded region. Adapter 510 may act as a primer, and a polymerase may be used to extend adapter 510 to the other end of strand 515 to generate a partial complementary strand 530. The resultant double-stranded nucleic acid molecule comprising strands 515 and 530 may then be partially denatured at both ends to generate bubbles 535 and 540. In some cases, the double-stranded nucleic acid molecule may only be partially denatured at one end. Bubbles 535 and 540 may expand in size (e.g., independently or by hybridization of primers to single-stranded regions of the bubbles and subsequent extension to ends of the double-stranded nucleic acid molecules), thereby separating (e.g., un-zipping) the ends of the double-stranded nucleic acid molecule. Primers 525 and 545 that are immobilized to substrate 560 may hybridize to ends of strands 530 and 515, respectively. Hybridized primers 525 and 545 may then be extended to provide two double-stranded nucleic acid molecules immobilized to substrate 560. These double-stranded nucleic acid molecules may be used to repeat the processes described above. For example, a double-stranded nucleic acid molecule comprising strand 515 and a strand complementary to strand 515 may be denatured to provide single strand 515 immobilized to substrate 560. An end of strand 515 may then hybridize to a primer immobilize to substrate 560 and the primer may be extended to generate a double-stranded nucleic acid molecule that is immobilized to substrate 560 at both ends. One or both ends of the double-stranded nucleic acid molecule may be partially denatured, the resultant bubbles may be expanded, and additional primers may be used to generate additional copies of strands 505 and 515. Substrate 560 may comprise a plurality of adapters immobilized thereto. In some cases, substrate 560 may comprise a plurality of adapter populations immobilized thereto. For example, substrate 560 may comprise a first adapter population comprising a plurality of first adapters comprising adapter 510, and a second adapter population comprising a plurality of second adapters. Alternatively, a plurality of first adapters may be immobilized to substrate 560 and a plurality of second adapters may be free in solution (e.g., not immobilized to substrate 560). The plurality of first adapters and the plurality of second adapters may have different sequences. For example, the plurality of first adapters may comprise a region that, when hybridized to a complementary sequence, may be partially denatured for example, by heating, while the plurality of second adapters may not include such a sequence.

Figure 6:
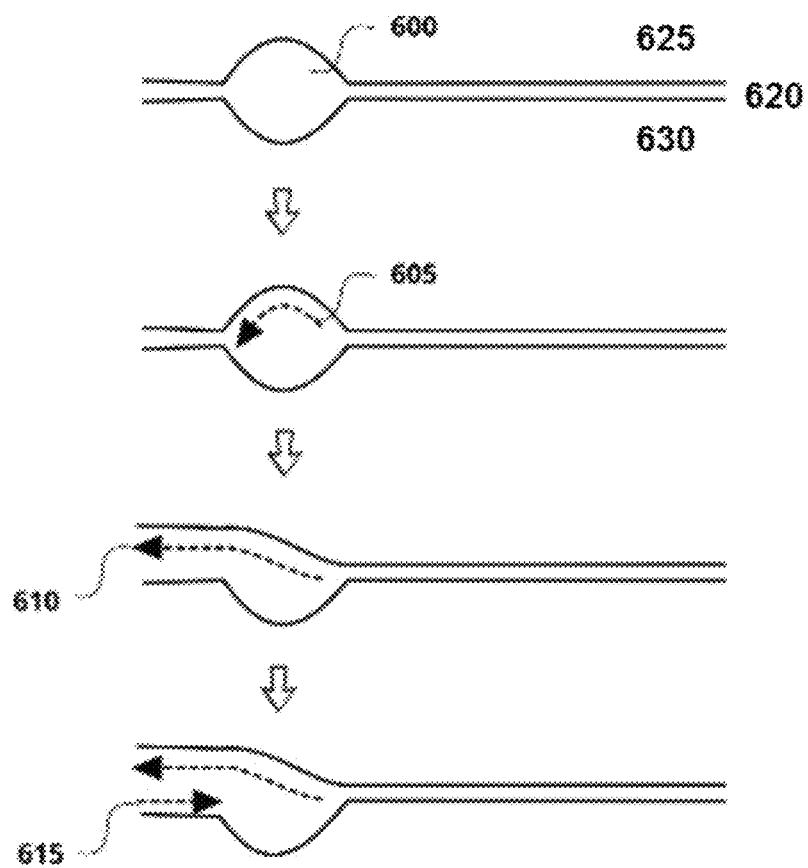
FIG. 6 schematically illustrates a bubble expansion process.

FIG. 6 schematically illustrates a bubble expansion process. A bubble 600 may be formed via partial denaturation of double-stranded nucleic acid molecule 620 to provide single-stranded regions including portions of both strands 625 and 630 of double-stranded nucleic acid molecule 620. Primer molecule 605 may hybridize to a single-stranded region of double-stranded nucleic acid molecule 620 comprising a portion of strand 625. Primer molecule 605 may then be extended to generate a strand 610 that is partially complementary to strand 625. In extending primer molecule 605, the ends of strands 625 and 630 may be separated. A primer molecule 615 may then hybridize to the available end of strand 630. Primer molecule 615 may subsequently be extended to generate a strand complementary to strand 630 (e.g., as described herein). In some cases, the bubble may be expanded without the use of a primer molecule (e.g., under partially denaturing conditions).

One or more processes of the methods described herein may be performed isothermally. For example, hybridization of an adapter or primer to a nucleic acid molecule, as well as binding of a polymerase and extension of an adapter or primer, may occur isothermally. Partial denaturation may also occur at a constant temperature (e.g., if partial denaturation is initiated by adjustment of pH or a salt concentration or by exposure to a chemical denaturant). Where multiple processes of the present methods are performed isothermally, amplification may be considered continuous. In some cases, partial denaturation may be initiated by heating a nucleic acid molecule to a given temperature (e.g., as described herein), and the temperature may remain elevated throughout multiple amplification cycles. In some cases, partial denaturation may not be performed isothermally but hybridization, polymerase binding, and extension processes may be performed isothermally. For example, thermal cycling may be used to promote multiple amplification cycles. A temperature (e.g., of a solution, substrate, or container) may be elevated to promote partial denaturation of a low melting point region of a double-stranded nucleic acid molecule and then lowered while hybridization, polymerase binding, and extension processes occur. In this manner, the amount of amplification products produced by the methods described herein may be controlled. A temperature may be elevated for any useful amount of time. In some cases, a temperature may be elevated for at least 1 second, such as for at least about 2 seconds, 3 seconds, 4 seconds, 5 seconds, 6 seconds, 7 seconds, 8 seconds, 9 seconds, 10 seconds, 15 seconds, 30 seconds, 45 seconds, 60 seconds, 90 seconds, 120 seconds, or more. Alternatively or in addition, the temperature may be elevated for at most 120 seconds, such as for at most about 90 seconds, 60 seconds, 45 seconds, 30 seconds, 15 seconds, 10 seconds, 9 seconds, 8 seconds, 7 seconds, 6 seconds, 5 seconds, 4 seconds, 3 seconds, 2 seconds, 1 second or less. A temperature may be elevated by transferring thermal energy via, for example, inductive heating, convective heating, microwave heating, optical heating, or resistive heating. A temperature for performing one or more processes of the methods described herein (e.g., a binding and extension process) may be a temperature at or near a temperature in which a selected polymerase exhibits optimal activity. For example, the temperature may be between about 55° C. and 85° C., such as between 60° C. and 70° C. The temperature at which a polymerase exhibits optimal activity may also be a temperature at which partial denaturation of one or more regions of a nucleic acid molecule may occur (e.g., as described herein). Non-specific primer-template hybridization events may also be reduced at such a temperature.

The methods described herein may be used to amplify one or more nucleic acid templates. For example, different nucleic acid templates having the same adapters attached thereto may be amplified simultaneously. Alternatively, different nucleic acid templates may have different adapters attached thereto and may be amplified simultaneously or sequentially. Different adapters may be immobilized to a substrate to facilitate amplification of different nucleic templates having different adapters attached thereto. The different adapters attached to different nucleic acid templates may comprise one or more common sequences. For example, a first adapter attached to a first nucleic acid template may comprise first and second sequences, and a second adapter attached to a second nucleic acid template that is different from the first nucleic acid template may comprise third and fourth sequences, where the third and first sequences are the same. This may simplify the amplification scheme, as the same or similar conditions (e.g., common melting temperatures for the regions having the third and first sequences) may be used to partially denature nucleic acid molecules including the different nucleic acid templates, and the same primers may hybridize to single-stranded regions of nucleic acid molecules including the different nucleic acid templates. In some cases, a plurality of different nucleic acid molecules comprising more than 103 molecules, 105 molecules, 107 molecules, 109 molecules, 1011 molecules, 1014 molecules, 1020 molecules, or more molecules may be amplified simultaneously or sequentially.

In some cases, the concentration of a nucleic acid template subjected to amplification using the methods described herein may be in the sub-nanomolar range. A template nucleic acid molecule may undergo one or more amplification processes prior to instigation of the methods described herein to, for example, increase a starting concentration of a template nucleic acid molecule to facilitate amplification by present methods. For example, a template nucleic acid may be inserted into an expression vector and amplified in a suitable biological host, or a polymerase chain reaction (PCR) may be performed.

In some cases, the concentration of primers (e.g., substrate-immobilized primers) in a reaction vessel may be at least 50 times greater than the concentration of a nucleic acid template (e.g., in a solution, flow cell, or container in which the present methods are performed). For example, the concentration of primers may be at least 60, 70 80, 90, 100, 200, 300, 400, 500, 1,000, 5,000, 10,000, 50,000, or 100,000 times greater than the concentration of a nucleic acid template.

In some cases, a double-stranded nucleic acid template that is not attached to a substrate-immobilized primer may partially denature (e.g., form a bubble) upon being subjected to, for example, a sufficient temperature, pH, salt, or other chemical condition. A bubble may expand, e.g., to separate ends of the double-stranded nucleic acid template. A separated end may then hybridize to a substrate-immobilized primer and undergo additional hybridization and extension processes, as described herein. In some cases, a single-stranded region of a bubble of such a molecule may hybridize to a primer that hybridizes to the bubble region and may subsequently displace a strand of the molecule. The displaced strand may then hybridize to a substrate-immobilized primer and undergo additional hybridization and extension processes, as described herein.

In some cases, while performing the methods described herein, additional sequences may be introduced into nucleic acid molecules, such as additional sequences for restriction enzyme sites, nucleic acid tags enabling the identification and/or isolation of amplification products (e.g., barcode sequences or unique molecular identifiers), DNA sequences that form hairpin loops or other secondary structures when rendered single-stranded, 'control' DNA sequences which direct protein/DNA interactions, such as a promoter, an enhancer, a replication origin, or an operator DNA sequence which are recognized by specific DNA-binding proteins.

In some cases, non-natural nucleotides (e.g., nucleotide analogs) may be used while performing the methods described herein. For example, non-natural nucleotides may be incorporated into nucleic acid strands during extension reactions. A non-natural nucleotide incorporated into a nucleic acid molecule may include, for example, an affinity moiety or a detectable label (e.g., as described herein).

The presently described methods may be performed over short timescales. For example, the present methods may be performed in less than an hour, such as less than 50 minutes, 45 minutes, 40 minutes, 35 minutes, 30 minutes, 25 minutes, 20 minutes, or 15 minutes.

Samples

A sample for processing by the methods described herein may derive from an environmental or a biological source. A biological source may be, for example, from a subject. The subject may be an individual having or providing a biological sample for processing or analysis. The subject may be a human, a plant, or an animal such as a primate, rodent, cat, dog, rabbit, horse, pig, or other mammal. The subject may have or be suspected of having a disease, such as cancer (e.g., breast cancer, colorectal cancer, brain cancer, leukemia, lung cancer, skin cancer, liver cancer, pancreatic cancer, lymphoma, esophageal cancer, or cervical cancer) or an infectious disease. The subject may have or be suspected of having a genetic disorder such as achondroplasia, alpha-1 antitrypsin deficiency, antiphospholipid syndrome, autism, autosomal dominant polycystic kidney disease, Charcot- Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, *porphyria*, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease. A subject may be symptomatic or asymptomatic of a given disease or disorder. A subject may be healthy (e.g., not suspected of having disease or disorder). A subject may have one or more risk factors for a given disease. A subject may have a given weight, height, body mass index, or other physical characteristic. A subject may have a given ethnic or racial heritage, place of birth or residence, nationality, disease or remission state, family medical history, or other characteristic.

A biological sample may be obtained invasively (e.g., tissue biopsy) or non-invasively (e.g., venipuncture or swab). A sample may comprise a tissue or fluid sample from a subject such as saliva, semen, blood (e.g., whole blood), serum, synovial fluid, tear, urine, milk, colostrum, amniotic fluid, bile, or plasma. A tissue sample may comprise, for example, a portion of an organ or tumor of a subject.

Alternatively, a sample may be an environmental sample. An environmental sample may be collected from a surface or reservoir. For example, an environmental sample may be collected from a surface that is handled by or interacts with a human or animal. An environmental sample may comprise solid or fluid material. For example, an environmental sample may comprise water derived from a body of water or a plumbed system.

A sample may have any suitable volume or quantity. For example, a sample may comprise at least about 1 nanoliter (nl), 2 nl, 5 nl, 10 nl, 20 nl, 30 nl, 40 nl, 50 nl, 60 nl, 70 nl, 80 nl, 90 nl, 100 nl, 200 nl, 500 nl, 1 microliter ($\mu$l), 2 $\mu$l, 5 $\mu$l, 10 $\mu$l, 20 $\mu$l, 30 $\mu$l, 40 $\mu$l, 50 $\mu$l, 60 $\mu$l, 70 $\mu$l, 80 $\mu$l, 90 $\mu$l, 100 $\mu$l, 200 $\mu$l, 500 $\mu$l, 1 milliliter (ml), 2 ml, 5 ml, 10 ml, 20 ml, 50 ml, 100 ml, or more than about 100 ml of a material. In some cases, a sample may be divided into aliquots prior to processing.

A sample may include one or more amino acids, polypeptides proteins, carbohydrates, fats, viruses, and/or nucleic acid molecules. Materials such as nucleic acid molecules contained within a sample may derive from one or more different sources. For example, an environmental sample may comprise nucleic acid molecules associated with multiple organisms, such as multiple humans who have interacted with the same surface from which a sample may derive.

A sample may undergo one or more pre-processing operations in preparation for processing or analysis. For example, a sample may be processed to lyse or permeabilize cells (e.g., as described herein), remove solid or other materials, denature proteins and/or nucleic acid molecules, dilute the sample, buffer the sample to a particular pH, or any combination thereof. Phase separation to separate one or more liquid and solid phases may also be performed. For example, a precipitation, extraction, clarification, crystallization, sedimentation, centrifugation, fluid flow, mechanical agitation (e.g., bead beating), or filtration process may be performed. Pre-processing of a sample may comprise heating a sample (e.g., as described herein) and/or combining a sample with one or more reagents such as buffers and washes.

Nucleic acid molecules included within a sample may derive from cells. Nucleic acid molecules may be cell-free nucleic acid molecules. Nucleic acid molecules may be extracellular or may be contained within one or more cells. Nucleic acid molecules included within cells may be accessed by lysing or permeabilizing the cells. For example, a mechanical method (e.g., mechanical agitation such as vortexing, stirring, bead beating, shaking, centrifuging, or a combination thereof) and/or a chemical agent (e.g., addition of one or more reagents such as lysis buffers or solvents) may be used to lyse or permeabilize a cell to provide access to one or more nucleic acid molecules contained therein.

Non-limiting examples of nucleic acid molecules include, but are not limited to, deoxyribonucleic acid (DNA), genomic DNA, plasmid DNA, complementary DNA (cDNA), ribonucleic acid (RNA), messenger RNA (mRNA), transfer RNA (tRNA), ribosomal RNA (rRNA), short interfering RNA (siRNA), short hairpin RNA (shRNA), micro RNA (miRNA), synthetic DNA or RNA, coding or non-coding regions of a gene or gene fragment, exons, introns, ribozymes, recombinant nucleic acid molecules, branched nucleic acid molecules, plasmids, vectors, isolated DNA of any sequence, isolated RNA of any sequence, artificial nucleic acid analogs (e.g., peptide nucleic acids, morpholino oligomers, locked nucleic acids, glycol nucleic acids, and threose nucleic acids), and chromatin. A nucleic acid molecule may be double-stranded or single-stranded.

Nucleic acid molecules may have any useful characteristics. For example, a nucleic acid molecule may have any useful size (e.g., length). For example, a single-stranded nucleic acid molecule may comprise at least 10 bases (e.g., nucleobases), 20 bases, 30 bases, 40 bases, 50 bases, 60 bases, 70 bases, 80 bases, 90 bases, 100 bases, 200 bases, 300 bases, 400 bases, 500 bases, 600 bases, 700 bases, 800 bases, 900 bases, 1 kilobase (kb), 2 kb, 3 kb, 4 kb, 5 kb, 6 kb, 7 kb, 8 kb, 9 kb, 10 kb, or more bases. Similarly, a double-stranded nucleic acid molecule may comprise at least 10 base pairs (bp), 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1,000 bp, 2,000 bp, 3,000 bp, 4,000 bp, 5,000 bp, 6,000 bp, 7,000 bp, 8,000 bp, 9,000 bp, 10,000 bp, or more base pairs.

A nucleic acid molecule may include naturally occurring and/or non-naturally occurring nucleotides (e.g., modified nucleotides or nucleotide analogs, as described herein).

A nucleic acid molecule may include a label such as a detectable moiety. For example, a nucleic acid molecule may include a fluorescent tag (e.g., in or attached to a nucleotide). Nucleic acid molecules may also include one or more features such as introns, exons, coding regions, untranslated regions, priming sequences, and barcode sequences.

Adapters

A nucleic acid molecule processed according to the methods described herein may include or be attached to one or more adapters (e.g., adapter oligonucleotides or J-shaped adapter moieties). An adapter may have any useful characteristics, including any useful length, base content, melting point, or other characteristic. For example, an adapter may comprise at least about 10 bases, such as at least 10 bases, 15 bases, 20 bases, 25 bases, 30 bases, 35 bases, 40 bases, 45 bases, 50 bases, 60 bases, 65 bases, 70 bases, 75 bases, 80 bases, 85 bases, 90 bases, 95 bases, 100 bases, 110 bases, 120 bases, 130 bases, 140 bases, 150 bases, 160 bases, 170 bases, 180 bases, 190 bases, 200 bases, 250 bases, 300 bases, 350 bases, 400 bases, 450 bases, 500 bases, or more bases.

An adapter may comprise one or more regions (e.g., 1 region, 2 regions, 3 regions, 4 regions, 5 regions, or more regions). The one or more regions may have similar or different characteristics. For example, a first region of an adapter may have the same or different base content, length, sequence, melting point, or other characteristic as a second region of the adapter. In some cases, an adapter may include two or more regions having one or more substantially similar characteristics and one or more additional regions having one or more substantially different characteristics. For example, an adapter may include a first region and a second region having the same or similar characteristics (e.g., the same sequence, melting point, length, and/or base content) and a third region having one or more different characteristics. Regions having similar or different characteristics may be arranged in any order. For example, a first region and a second region having the same or substantially similar characteristics may flank (e.g., each be adjacent on either side of) a third region having different characteristics, or a first region and a second region having the same or substantially similar characteristics may be adjacent to one another and a third region having different characteristics may be adjacent to the second region. As used herein with respect to two entities, "adjacent," may generally refer to the two entities being directly next to one other (e.g., contiguous) or in proximity to one another. For example, a first region that is adjacent to a second region may be directly next to a second region (e.g., having no other entity disposed between the first and second regions) or in proximity to a second region (e.g., having an intervening sequence or molecule between the first and second regions).

One or more regions of an adapter may comprise a nucleic acid sequence. Different regions of an adapter may include the same or substantially similar or different nucleic acid sequences (e.g., having the same, substantially similar, or different sequences, lengths, base contents, and/or melting points). For example, an adapter may include repeated sequences (e.g., degenerate primer sequences). Different sequences of an adapter may serve different functions. For example, an adapter may include a sequence that facilitates attachment of the adapter to a substrate (e.g., as described herein) and/or a sequence capable of hybridizing to a particular region of a nucleic acid template or complement thereof. A nucleic acid sequence of a region of an adapter may include any useful number of bases. For example, a nucleic acid sequence of a region of an adapter may include at least about 5 bases, 10 bases, 15 bases, 20 bases, 25 bases, 30 bases, 35 bases, 40 bases, 45 bases, 50 bases, 55 bases, 60 bases, or more bases. In some cases, a nucleic acid sequence of a region of an adapter may include at least 5 bases. In some cases, a nucleic acid sequence of a region of an adapter may include at least 10 bases. In certain cases, a nucleic acid sequence of a region of an adapter may include at least 20 bases.

An adapter or region thereof may include any combination of bases. An adapter may include both natural and non-natural nucleotides (e.g., nucleotide analogs, as described herein). In some cases, an adapter may include only natural bases (e.g., adenine, thymine, cytosine, guanine, and uracil). An adapter may include a base such as inosine that may hybridize to more than one different DNA base type. In some cases, an adapter may include a nucleotide that is cleavable. Bases of an adapter may be arranged in any useful sequence or combination of sequences. One or more regions of an adapter may include one or more different sequences having one or more different base contents and/or combinations of bases. For example, different sequences of an adapter may have different adenine, thymine, cytosine, guanine, and uracil content (e.g., % A, % T, % C, % G, and % U). A first sequence of an adapter may have a higher adenine and/or thymine content (e.g., a higher % A and/or % T) than a second sequence of an adapter. Similarly, a second sequence of an adapter may have a higher guanine and/or cytosine content (e.g., a higher % G and/or % C) than a first sequence of an adapter. In some cases, a sequence of an adapter may comprise one or more bases selected from the group consisting of adenine, thymine, uridine, inosine, and derivatives or modified versions thereof. In certain cases, a sequence may comprise only bases selected from the group consisting of adenine, thymine, uridine, and inosine. In one example, an adapter includes a first sequence and a second sequence that flank a third sequence, where the third sequence comprises only bases selected from the group consisting of adenine, thymine, uridine, and inosine and the flanking first and second sequences comprise bases selected from the group consisting of adenine, thymine, uridine, inosine, and other bases (e.g., cytosine, guanine, and/or non-natural bases). The first and second sequences may be the same or substantially similar or different and may have the same or substantially similar or different content and number of bases.

An adapter may have one or more melting points. For example, an adapter may comprise a single melting point. In another example, an adapter may comprise regions having different melting points. Alternatively, some regions may have the same or substantially the same melting points. A melting point of a region of an adapter may be at least about 10° C., 11° C., 12° C., 13° C., 14° C., 15° C., 16° C., 17° C., 18° C., 19° C., 20° C., 25° C., 30° C., 35° C., 40° C., 45° C., 50° C., 55° C., 60° C., 65° C., 70° C., 75° C., 80° C., 85° C., 90° C., 95° C., or higher. For example, a melting point of a region of an adapter may be at least about 10° C. A melting point of a region of an adapter may be between about 35° C. and 55° C., such as between about 40° C. and 45° C. A melting point of a region of an adapter may be between about 55° C. and 75° C., such as between about 60° C. and 70° C. In some cases, an adapter may include at least one region having a melting point between about 35° C. and 55° C. and at least one region having a melting point between about 55° C. and 75° C. For example, an adapter may include at least one region having a melting point between about 40° C. and 45° C. and at least one region having a melting point between about 60° C. and 70° C. The melting point of a region of an adapter may depend upon the base composition and/or sequence of the region.

For an adapter including two or more regions having two or more different melting points, the difference between the melting points of a first region of an adapter and a second region of an adapter may be at least about 1° C., 2° C., 3° C., 4° C., 5° C., 6° C., 7° C., 8° C., 9° C., 10° C., 11° C., 12° C., 13° C., 14° C., 15° C., or higher. For example, a first melting point for a first region of an adapter may be at least 1° C., 2° C., 3° C., 4° C., 5° C., 6° C., 7° C., 8° C., 9° C., 10° C., 11° C., 12° C., 13° C., 14° C., or 15° C. lower than a second melting point for a second region (e.g., a second region adjacent to the first region) of the adapter. In one example, the first melting point may be at least 1° C. lower than the second melting point. For example, the first melting point may be at least 5° C. lower than the second melting point. For an adapter including first and second regions having the same characteristics that flank a third region having different characteristics, the first and second regions may have first and second melting points and the third region may have a third melting point that differs from the first and second melting points. In some cases, the first and second melting points may be the same or approximately the same. In some cases, the third melting point may be higher than the first and second melting points, while in other cases the third melting point may be lower than the first and second melting points.

A nucleic acid molecule may comprise one or more adapters that are the same, substantially similar, or different. For example, a nucleic acid molecule may comprise a first adapter at a first end of the molecule and a second adapter at a second end of the molecule. The second adapter may be, in whole or in part, the reverse (e.g., the reverse sequence) of the first adapter. In one example, an adapter may be capable of ligating or hybridizing to two ends of a nucleic acid molecule, resulting in the circularization of the nucleic acid molecule.

Figures 7A, 7B, 7C, 7D:
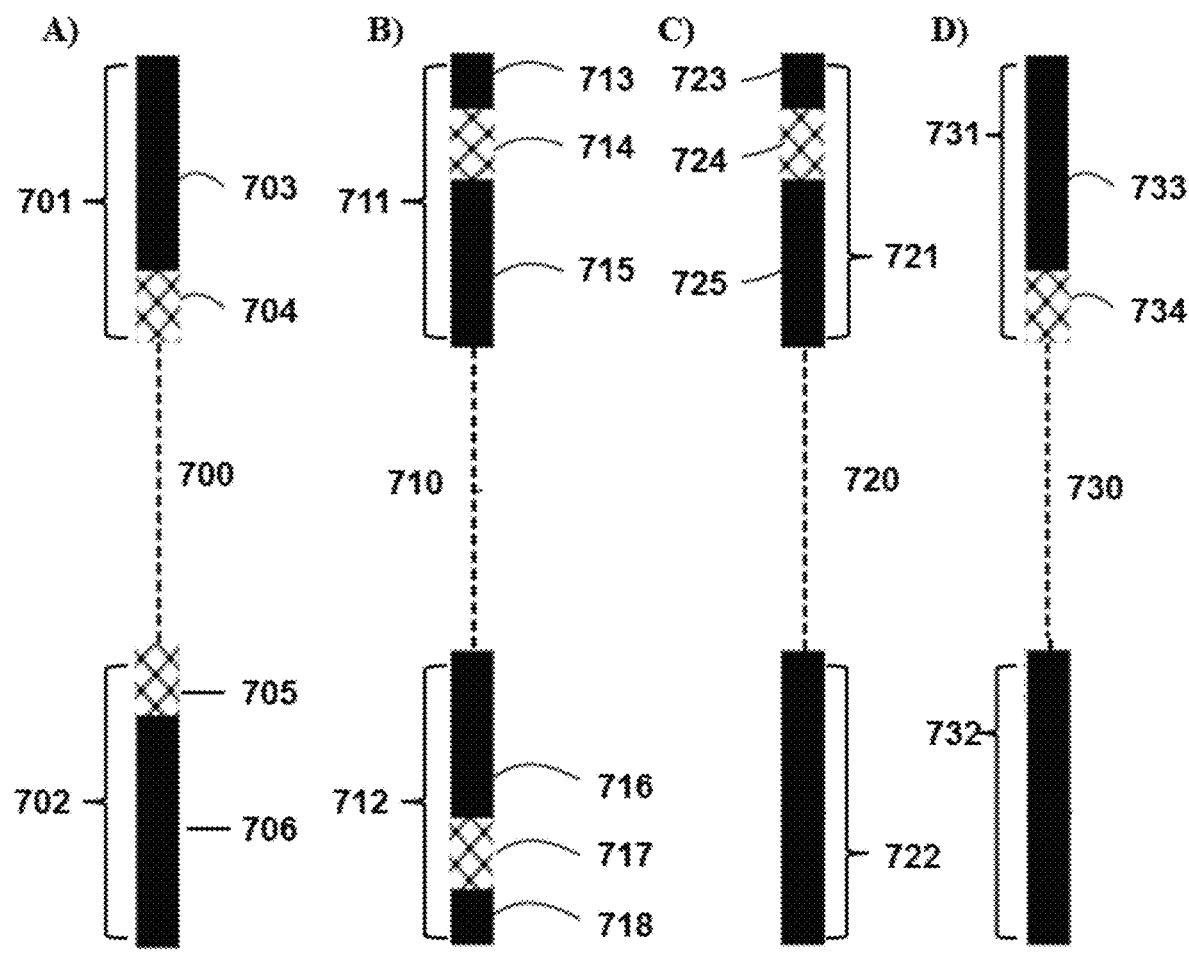
FIG. 7A-7D schematically illustrate templates including symmetrical adapters (FIGS. 7A and 7B) and asymmetrical adapters (FIGS. 7C and 7D)

FIGS. 7A-7D show schematics illustrating several adapter-template-adapter configurations. FIGS. 7A and 7B illustrate exemplary templates having symmetrical adapters. FIG. 7A shows a schematic illustrating a template 700 having attached thereto two adapters 701 and 702. Adapter 701 includes regions 703 and 704 and a lower adapter 702 including regions 705 and 706. Terminal regions 703 and 706 may contain sequences of bases that have a higher melting temperature, while regions 704 and 705 may contain sequences of bases that have a lower melting temperature. The melting points of regions 703 and 706 may be the same, substantially similar, or different. Similarly, the melting points of regions 704 and 705 may be the same, substantially similar, or different. FIG. 7B shows a schematic illustrating a template 710 having attached thereto two adapters 713 and 712. Adapter 713 includes regions 713, 714, and 715 and a lower adapter 712 including regions 716, 717, and 718. Terminal region 713 and inner region 715 may contain sequences of bases that have a higher melting temperature, while region 714 flanked by regions 713 and 715 may contain a sequence of bases that has a lower melting temperature. Similarly, terminal region 718 and inner region 716 may contain sequences of bases that have a higher melting temperature, while region 717 flanked by regions 716 and 718 may contain a sequence of bases that has a lower melting temperature. The melting points of regions 713, 715, 716, and 718 may be the same, substantially similar, or different. Similarly, the melting points of regions 714 and 717 may be the same, substantially similar, or different. FIGS. 7C and 7D illustrate exemplary templates having asymmetrical adapters. FIG. 7C shows a schematic illustrating a template 720 having attached thereto two adapters 721 and 722. Adapter 721 includes regions 723, 724, and 725. Terminal region 723 and inner region 725 may contain sequences of bases that have a higher melting temperature, while region 724 flanked by regions 723 and 725 may contain a sequence of bases that has a lower melting temperature. The melting points of regions 723 and 725 may be the same, substantially similar, or different. Adapter 722 may not have specified regions of low or high melting points. FIG. 7D shows a schematic illustrating a template 730 having attached thereto two adapters 731 and 732. Adapter 731 includes regions 733 and 734. Terminal region 733 may contain a sequence of bases that has a higher melting temperature, while region 734 may contain a sequence of bases that has a lower melting temperature. Adapter 732 may not have specified regions of low or high melting points. The sequences of regions 704, 705, 714, 717, 724, and 734 may be at least 10 nucleotides in length, such as between 11 and 100 nucleotides in length. For example, the nucleic acid sequences of regions 704, 705, 714, 717, 724, and 734 may be about 20 nucleotides in length. The sequences of regions 703, 706, 713, 715, 716, 718, 722, 723, 725, 732, and 733 may be at least 5 nucleotides in length, such as between 13 and 100 nucleotides in length. The nucleic acid sequences of different regions of the same adapter may be of the same, similar, or different lengths and base compositions. Similarly, nucleic acid sequences of different regions of different adapters attached to the same template may be of the same, similar, or different length and base composition.

FIG. 8 shows construction of paired adapter oligonucleotide sequences with regions of high and low melting temperatures such as those in FIGS. 7A-7C. The paired adapters include a central low melting temperature domain with Poly (A) sequences on one strand and Poly (T) sequences on the opposite strand. High melting temperature domains flank the low melting temperature domain. The high melting temperature domains comprise sequences having higher G and C ratios. An additional small A-T rich region is present for additional functionality. The melting temperature for each domain is shown below that domain. The left flanking high temperature domain has a melting temperature "Tm" of 61.7° C. The low melting temperature domain has a melting temperature of 43.5° C. and the right flanking high temperature domain has a melting temperature of 65.4° C. At a reaction temperature between 50° C. and 60° C., the domains including Poly (A) and Poly (T) sequences for a majority of such adapter pairs may be melted and thus denatured, while the domains including sequences with higher ratios of G and C may not be melted. Accordingly, the paired adapters may be "partially denatured." Between 50° C. and 60° C., the two strands of the central domain with the low melting temperature sequence may be separated, thereby forming a "bubble." In some cases, the adapter region is not the template region. In some cases, the adapter region is not derived from the template region. In some cases, the adapter region is not synthesized from the template nucleic acid molecules. In some cases, the adapter region is not derived from nucleic acid molecules taken from a sample.

Localized bubble formation in a double-stranded nucleic acid molecule may form a site for hybridization of a primer to one or more of the resultant single-stranded regions, as described elsewhere herein. In some cases, a chemical denaturant such as a salt, urea, guanidine hydrochloride, or an organic solvent may be used to partially denature sequences in a defined region of a nucleic acid molecule to generate a bubble. In some cases, the formation of a bubble in a defined region of a nucleic acid molecule may occur without denaturing reagents or high temperatures, as described herein. A region of a double-stranded nucleic acid molecule may dynamically dissociate at a reaction temperature (e.g., a temperature higher than the melting point of a low melting point region and lower than the melting points of adjacent higher melting point regions) by allowing local opening of base pairs to create a single-stranded denaturation bubble. Melting is driven by entropy overruling the attraction of hydrogen bonds between the nucleic acid bases. The spontaneous and induced localized melting behavior may be determined by statistical models such as the Poland and Sheraga model and by thermodynamic nearest-neighbor model. The Mesoscopic Peyrard-Bishop-Dauxious model may also reflect bubble formation and stability seen experimentally. The rate of bubble formation may be affected by, for example, the A-T base sequence content and the temperature. It has been demonstrated that A-T rich regions of at least 12-20 bp of double-stranded nucleic acid molecules may form stable bubbles.

In addition to regions of low and high melting temperature, an adapter may comprise one or more additional sequences having different functionalities. For example, an adapter may comprise a priming sequence or a barcode sequence. An adapter may also comprise a region to facilitate immobilization of an adapter to a support (e.g., as described herein).

In some cases, a sample may include a double-stranded nucleic acid molecule of interest, and one or both strands of the nucleic acid molecule may be processed and/or analyzed. In other cases, a sample may include a single-stranded nucleic acid molecule of interest. Localized bubble formation in a nucleic acid molecule depends upon the nucleic acid molecule comprising two strands. Accordingly, two complementary strands are prepared for processing and analysis. In some cases, a double-stranded adapter may be attached to a double-stranded nucleic acid molecule. For example, a double-stranded adapter may be ligated to an end of a double-stranded nucleic acid molecule using an enzyme such as DNA ligase that may facilitate the formation of a covalent bond between nucleotides of adjacent nucleotides to join adjacent strands of DNA. The double-stranded adapter may include a first strand comprising first and second sequences and a second strand comprising third and fourth sequences, where the first sequence is hybridized to the third sequence and the second sequence is hybridized to the fourth sequence. The first sequence hybridized to the third sequence may have a first melting point that is lower than the melting point of the second sequence hybridized to the fourth sequence.

In some cases, rather than attaching a double-stranded adapter, two single-stranded adapters, each corresponding to a strand of a double-stranded nucleic acid molecule (e.g., a 3' adapter and a 5' adapter), may be ligated to the double-stranded nucleic acid molecule simultaneously or sequentially. For example, a first single-stranded adapter may be attached to a first strand of the double-stranded nucleic acid molecule and then a second single-stranded adapter may be attached to the second strand of the double-stranded nucleic acid molecule. Attachment of the second single-stranded adapter may involve partial degradation of the first single-stranded adapter and annealing of the second single-stranded adapter to the second strand. As in the preceding example, the first adapter may include first and second sequences and the second adapter may include third and fourth sequences, where the first sequence is hybridized to the third sequence and has a melting point that is lower than the melting point of the second sequence hybridized to the fourth sequence. In some cases, an adapter may be associated with or bound to a protein or other factor to increase its ability to interpolate and/or hybridize to a nucleic acid template. For example, an adapter may comprise a RecA protein that facilitates entrance into a double-stranded nucleic acid molecule and hybridization to a complementary sequence without denaturation of the double-stranded nucleic acid molecule by other agents.

In some cases, a single-stranded adapter may be hybridized to a strand of a nucleic acid molecule. For example, an adapter comprising a first sequence and a second sequence may hybridize to a single-stranded nucleic acid molecule. The nucleic acid molecule may then undergo an extension reaction to generate a nucleic acid sequence that is complementary to the initial strand and includes the adapter. The newly formed strand including the complementary sequence and the adapter may then be denatured from the initial strand. Hybridization of a primer sequence to an end of the newly formed strand and subsequent extension may generate a double-stranded nucleic acid molecule in which the first strand includes the adapter and the sequence complementary to the template nucleic acid molecule, and the second strand is complementary to the first strand and includes a third sequence that is complementary to the first sequence of the adapter and a fourth sequence that is complementary to the second sequence of the adapter. The first sequence hybridized to the third sequence may have a melting point lower than the second sequence hybridized to the fourth sequence.

A nucleic acid molecule may comprise multiple adapters (e.g., attached thereto). For example, a single-stranded nucleic acid molecule may comprise a first adapter attached to a first end of the molecule and a second adapter attached to a second end of the molecule. As illustrated schematically in FIGS. 7A-7C, the first and second adapters may be the same or different. For example, both the first adapter and the second adapter may comprise at least first and second sequences, where the first and second sequences have different melting points (see, e.g., template 710 and adapters 713 and 712 of FIG. 7B). Alternatively, the first adapter may comprise at least first and second sequences, where the first and second sequences have different melting points, and the second adapter may not include specified regions of low or high melting points (see, e.g., template 720 and adapters 721 and 722 of FIG. 7C). Adapters may be attached to ends of a nucleic acid molecule in different ways. For example, a first adapter may be ligated to an end of a nucleic acid molecule and a second adapter may be hybridized to an end of a nucleic acid molecule. In some cases, a strand comprising an adapter may be generated via an extension reaction (e.g., as described herein).

An adapter attached to a nucleic acid molecule may be included in a solution or may immobilized to a substrate (e.g., as described herein). A substrate may comprise a plurality of adapters immobilized thereto. Adapters may be uniformly or non-uniformly distributed on a substrate. In some cases, adapters may be uniformly distributed on all exposed areas of a substrate. Adapters may be immobilized to a substrate in a predetermined pattern. In some cases, one or more exposed areas of a substrate may not include adapters immobilized thereto. Adapters may be immobilized to a support at a density of at least 1,000 molecules per $mm^2$, such as at least 10,000 molecules per $mm^2$, 50,000 molecules per $mm^2$, 100,000 molecules per $mm^2$, 500,000 molecules per $mm^2$, 1,000,000 molecules per $mm^2$, 5,000,000 molecules per $mm^2$, 10,000,000 molecules per $mm^2$, or more molecules per $mm^2$. For example, adapters may be immobilized to a support at a density of least 10,000 molecules per $mm^2$.

An adapter immobilized to a substrate may be inactivated. For example, adapters immobilized to a given area of a substrate may be inactivated. An adapter may be removable from the substrate, e.g., upon application of sufficient conditions to detach an adapter from the substrate. For example, a chemical reagent, temperature condition, pH condition, and/or other condition may be applied to remove an adapter from a substrate. In some cases, a substrate may comprise a plurality of first adapters and a plurality of second adapters. The plurality of first adapters and the plurality of second adapters may be dispersed on the substrate such that a given exposed area of the substrate includes both first adapters and second adapters immobilized thereto. Alternatively, different subsets or types of adapters may be immobilized to different areas of the substrate. An adapter may be immobilized to a substrate at an end of the adapter. For example, an end (e.g., 5' end) of an adapter may comprise approaches to immobilize the end of the adapter onto a substrate. An adapter may be immobilized to a substrate via a covalent bond formed directly or indirectly between the adapter and the substrate or by interaction between molecules such as avidin and biotin. In some cases, an end of an adapter may comprise a thiol, hydroxyl, dimethoxyl-trityl (DMT), amino, or phosphate group to facilitate attachment of the adapter to a substrate. In certain cases, an end of an adapter may comprise a carboxylic or aldehyde moiety and a "click" chemistry reaction may be used to immobilize an adapter to a substrate. Like adapters, primers may also be immobilized to a substrate, as described above.

0Systems for Processing a Nucleic Acid Molecule

In addition to the methods described herein, the present disclosure provides systems for performing amplification reactions. A system may comprise a support configured to retain a double-stranded nucleic acid molecule comprising a first strand and a second strand having sequence complementarity to the first strand, where the first strand comprises a template region that is attached to an adapter comprising a first sequence and a second sequence adjacent to the first sequence. The first and second sequence may be hybridized to third and fourth sequences, respectively, of the second strand, where the first sequence hybridized to the third sequence has a first melting point and the second sequence hybridized to the fourth sequence has a second melting point that is higher than the first melting point. The second sequence may be disposed nearer to an end of the first strand than the first sequence. The system may further comprise a controller operatively coupled to the container, where the controller is programmed to subject the double-stranded nucleic acid molecule to conditions sufficient to partially denature the double-stranded nucleic acid molecule, thereby separating the first sequence from the third sequence. The controller may further be programmed to subject the double-stranded nucleic acid molecule to conditions sufficient to subsequently separate the second sequence from the fourth sequence. For example, the controller may be programmed to bring a primer molecule having sequence complementarity with the third sequence in contact with the second strand under conditions sufficient to permit the primer molecule to hybridize to the third sequence; and subject the second strand comprising the primer molecule hybridized to the third sequence to a primer extension reaction under conditions sufficient to generate a third strand hybridized to at least a portion of the second strand.

A system may be useful for processing a single-stranded nucleic acid molecule or a double-stranded nucleic acid molecule. For example, a system may include a support having immobilized thereto an adapter capable of hybridizing to a sequence of a region of a single-stranded nucleic acid molecule. The system may be configured to provide a polymerase capable of binding to and extending the adapter to generate a strand that is complementary to all or a portion of the template nucleic acid molecule. The resultant double-stranded nucleic acid molecule may then be processed using the controller (e.g., as described herein). Alternatively, a double-stranded nucleic acid molecule may be provided immobilized to a support or may be attached to two adapters having complementary sequences that are immobilized to the support. In such an instance, the support may include multiple different adapters immobilized thereto.

An adapter attached to a double-stranded nucleic acid molecule may be ligated to the first strand of the double-stranded nucleic acid molecule. The adapter may be ligated to an end of the molecule such that the second sequence of the adapter is at the end of the adapter distal to the point of attachment between the nucleic acid template and the adapter. The fourth sequence that is complementary to the second sequence of the first strand may be disposed at an end of the second strand. The first and third sequences of the double-stranded nucleic acid molecule may comprise one or more bases selected from the group consisting of adenosine, thymidine, uridine, and inosine. In some cases, the first sequence and the third sequence may only comprise bases selected from adenosine, thymidine, uridine, and inosine. In some cases, the first and third sequences may each comprise at least 5 bases. For example the first and third sequences may each comprise at least 10 bases.

A controller of a system for processing a nucleic acid sample may be programmed to denature at most a portion of a double-stranded nucleic acid molecule such that at most a portion of the first strand separates from the second strand. For example, the first sequence and third sequence of the double-stranded nucleic acid molecule may separate, but the second sequence may remain hybridized to the fourth sequence. In some cases, the controller may be programmed to provide sufficient thermal energy to separate the first sequence from the third sequence but not the second sequence from the fourth sequence. In some cases, the controller may be programmed to subject the double-stranded nucleic acid molecule to conditions sufficient to, subsequent to separating the first sequence from the third sequence, separate the second sequence from the fourth sequence. For example, the controller may further be programmed to subject the second strand to conditions sufficient to hybridize a primer molecule to the third sequence and to subject the second strand comprising a primer molecule hybridized to the third sequence to a primer extension reaction under conditions sufficient to separate the second sequence from the fourth sequence.

The controller may be programmed to bring a primer molecule having sequence complementarity with the first strand in contact with the first strand under conditions sufficient to permit the additional primer molecule to hybridize to the first strand. The primer molecule may hybridize to the second sequence of the first strand. The controller may be further programmed to subject the first strand comprising the primer molecule hybridized thereto to a primer extension reaction under conditions sufficient to generate a fourth strand hybridized to at least a portion of the first strand. In some cases, the primer molecule may be immobilized to a support. For example, the primer molecule may be an adapter immobilized to a support (e.g., as described herein). The support may comprise a plurality of such primer molecules (e.g., adapters) immobilized thereto. The primer molecules may be immobilized to the support in a predetermined pattern, and may be immobilized at a density of at least 10,000 primer molecules per $mm^2$.

A support (e.g., as described herein) of a system may be included within or as a component of a container. For example, a support may be an element of a flow cell in which one or more processes such as partial denaturation, hybridization, binding of a polymerase, or extension of a primer or adapter may be performed (e.g., as described herein). A container may have any useful size and geometry and may comprise any useful material. The support may be, for example, a planar array. In other cases, a support may be a bead. In some cases, a system may include a plurality of beads. A support may a component of a sequencing instrument.

A controller of a system for processing a nucleic acid sample may be a component of a computer or processing system (e.g., as described herein). A controller may be operable by a user. A controller may include or be coupled to a display device and/or a user interface (e.g., as described herein). In some cases, a controller may be a component of a sequencing instrument. A controller may be used to initiate, increase the rate of, pause, suspend, and/or cancel one or more processes. For example, a controller may be used to control a partial denaturation (e.g., bubble formation) process, hybridization of a primer to a template nucleic acid, extension of a primer to a template nucleic acid, and/or another process. A controller may control one or more processes by regulating a temperature. For example, a controller may initiate, increase the rate of, pause, suspend, and/or terminate heating by, for example, interfacing with a device capable of providing thermal energy by resistive, convective, inductive, optical, or microwave heating. The controller may therefore be programmed to provide thermal energy to a double-stranded nucleic acid molecule to partially denature the double-stranded nucleic acid molecule. In some cases, the controller may be programmed to heat a double-stranded nucleic acid molecule to a temperature higher than a first melting point of a first region of the molecule and lower than a second melting point of a second region of the molecule (e.g., as described herein). The first melting point may be at least 1° C. lower than the second melting point. For example, the first melting point may be at least 5° C. lower than the second melting point.

A system for processing a nucleic acid sample may be configured to control exposure of a double-stranded nucleic acid molecule or a portion thereof to a chemical denaturant. For example, a controller of a system may be programmed to expose a double-stranded nucleic acid molecule or a portion thereof to a chemical denaturant selected from the group consisting of a salt, formamide, urea, guanidine hydrochloride, and an organic solvent. The controller may be configured to release a chemical denaturant or a solution including a chemical denaturant from a reservoir by, for example, opening a valve or removing a cap, lid, or stopper retaining the denaturant in the reservoir.

A system or component thereof may be configured for viewing and/or interrogation by a detector. For example, a component of a system may include an open area or a transparent region such as a window that may be viewable directly by a user, using a camera, or using an optical detector. A viewable or optically interrogable region may provide visual and/or optical access to a support. In some cases, fluorescence spectroscopy or imaging may be performed to monitor the progress of an amplification process being performed using the system.

A system may include one or more elements capable of monitoring and/or controlling conditions such as temperature, pressure, air quality, air flow, fluid flow, pH, and concentrations of various reagents. For example, a system may include a temperature monitoring device.

A system described herein may facilitate amplification of a nucleic acid template without requiring multiple reagent exchanges. Accordingly, a system may not require extensive automated and fluidic systems. In some cases, fluidic systems may be useful for providing one or more reagents (e.g., polymerases, primers, nucleotides, chemical denaturants, etc.) to a nucleic acid molecule for analysis. Automation may be employed to control the transfer of fluids and other materials between components of a system.

Kits for Processing Nucleic Acid Molecules

In addition to the methods and systems described herein, the present disclosure provides kits for processing nucleic acid molecules. A kit may comprise one or more reagents and materials. For example, a kit may comprise instructions for implementing the methods of the present disclosure.

A kit may comprise one or more adapters (e.g. adapters, as described herein). For example, a kit may comprise at least 1, 10, 100, 1,000, 10,000, 50,000, 100,000, 500,000, 1,000,000, or more adapters. Adapters included in a kit may be the same or different. For example, a kit may include a first adapter type and a second adapter type. Different adapters may be included in the same or different numbers. For example, approximately the same number of first adapters and second adapters may be included in a kit. Alternatively, a greater number of first adapters and a smaller number of second adapters may be included in the kit. One or more adapters of a kit may be provided immobilized to a substrate (e.g., as described herein).

An of a kit may comprise at least a first sequence and a second sequence, where the second sequence may be the same as, substantially similar to, or different from the first sequence in length, base composition, and/or other characteristics (e.g. as described herein). In some cases, an adapter of a kit may comprise two nucleic acid strands, where the first strand comprises a first sequence and a second sequence adjacent to the first sequence that are respectively hybridized to a third sequence and a fourth sequence of the second strand. The first sequence hybridized to the third sequence may have a first melting point and the second sequence hybridized to the fourth sequence may have a second melting point that is higher than the first melting point. A sequence of an adapter may be of any useful length or base composition. In some cases, a sequence of an adapter may comprise one or more thymine, adenine, uridine, and/or inosine bases. An adapter sequence may include only thymine, adenine, uridine, and/or inosine bases. Such a sequence may be, for example, at least 5 nucleotides in length, such as at least 10 nucleotides in length. In some cases, an adapter may include a first sequence and a second sequence adjacent to the first sequence, where the first sequence comprises only thymine, adenine, uridine, and/or inosine bases and the second sequence comprises one or more bases other than thymine, adenine, uridine, and inosine bases. Such an adapter may be a single-stranded adapter or a double-stranded adapter. Adapters may also comprise sequences to facilitate attachment to a substrate and/or a nucleic acid molecule, such as a template nucleic acid molecule.

A kit may comprise one or more primers (e.g., as described herein). For example, a kit may comprise at least 1, 10, 100, 1,000, 10,000, 50,000, 100,000, 500,000, 1,000,000, or more primers. Primers included in a kit may be the same or different. For example, a kit may include a first primer type and a second primer type. Different primers may be included in the same or different numbers. For example, approximately the same number of first primers and second primers may be included in a kit. Alternatively, a greater number of first primers and a smaller number of second primers may be included in the kit. One or more primers of a kit may be provided immobilized to a substrate (e.g., as described herein).

A primer of a kit may comprise a nucleic acid sequence that is capable of attaching (e.g., hybridizing) to a sequence of an adapter. For example, a primer may comprise a nucleic acid sequence that is complementary to all or a portion of a sequence of an adapter (e.g., an adapter included in a kit). A kit may include a primer that is capable of hybridizing to a sequence comprising only thymine, adenine, uridine, and/or inosine bases. A primer may be of any useful length and base composition. In some cases, the length of a primer may be the same as or shorter than the length of a sequence of an adapter. A kit may further comprise one or more polymerases capable of extending a primer molecule attached to a nucleic acid molecule. For example, a kit may comprise a first polymerase capable of extending a first primer or primer type and a second polymerase capable of extending a second primer or primer type. Different polymerases may, for example, be capable of extending nucleic acid molecule in different directions (e.g., 5' to 3' or 3' to 5) or interacting with particular types of nucleic acid molecules.

A kit may further comprise one or more reagents for immobilizing one or more adapters to a substrate, attaching adapters to nucleic acid molecules, extending primer molecules attached to nucleic acid molecules, and/or amplifying nucleic acid molecules. For example, a kit may further comprise one or more enzymes, nucleotides, nucleotide analogs, biotins, avidins, reagents for "click" chemistry, labels, or other reagents useful for implementing methods of the present disclosure.

In an example, a kit may comprise a plurality of adapters, where each adapter is a double-stranded adapter comprising a first strand and a second strand. The first strand may comprise a first sequence and a second sequence adjacent to the first sequence, where the first sequence and the second sequence are respectively hybridized to a third sequence and a fourth sequence of the second strand. The first sequence hybridized to the third sequence may have a first melting point and the second sequence hybridized to the fourth sequence may have a second melting point higher than the first melting point. In some cases, the kit may further comprise a plurality of second adapters that may be the same or different from the plurality of adapters. The kit may further comprise one or more reagents for attaching adapters to nucleic acid molecules.

In another example, a kit may comprise a plurality of adapters, a plurality of first primers, and a plurality of second primers. The plurality of adapters may be single-stranded adapters, where each adapter includes at least a first sequence and a second sequence adjacent to the first sequence. The first sequence may comprise only thymine, adenine, uridine, and/or inosine bases and may be at least 5 nucleotides in length. Alternatively, the plurality of adapters may be double-stranded adapters, where each adapter comprises a first strand and a second strand. The first strand may comprise a first sequence and a second sequence adjacent to the first sequence, where the first sequence and the second sequence are respectively hybridized to a third sequence and a fourth sequence of the second strand. The first sequence hybridized to the third sequence may have a first melting point and the second sequence hybridized to the fourth sequence may have a second melting point higher than the first melting point. The plurality of first primers may each comprise a sequence that is complementary to a sequence of the plurality of adapters, such as the first sequence of the plurality of adapters. The plurality of second primers may each comprise a sequence that is complementary to a sequence of the plurality of adapters or a complement thereof. For example, the plurality of second primers may each comprise a sequence that is complementary to a sequence of a fourth sequence of the second strand of a double-stranded adapter. Alternatively, the plurality of second primers may each comprise a sequence that is complementary to a complement of a sequence of a single-stranded adapter. A kit may further comprise one or more reagents for attaching adapters of the plurality of adapters to nucleic acid molecules, attaching primers to adapter sequences, and/or amplifying nucleic acid molecules (e.g., as described herein).

Computer Systems

Figure 13:
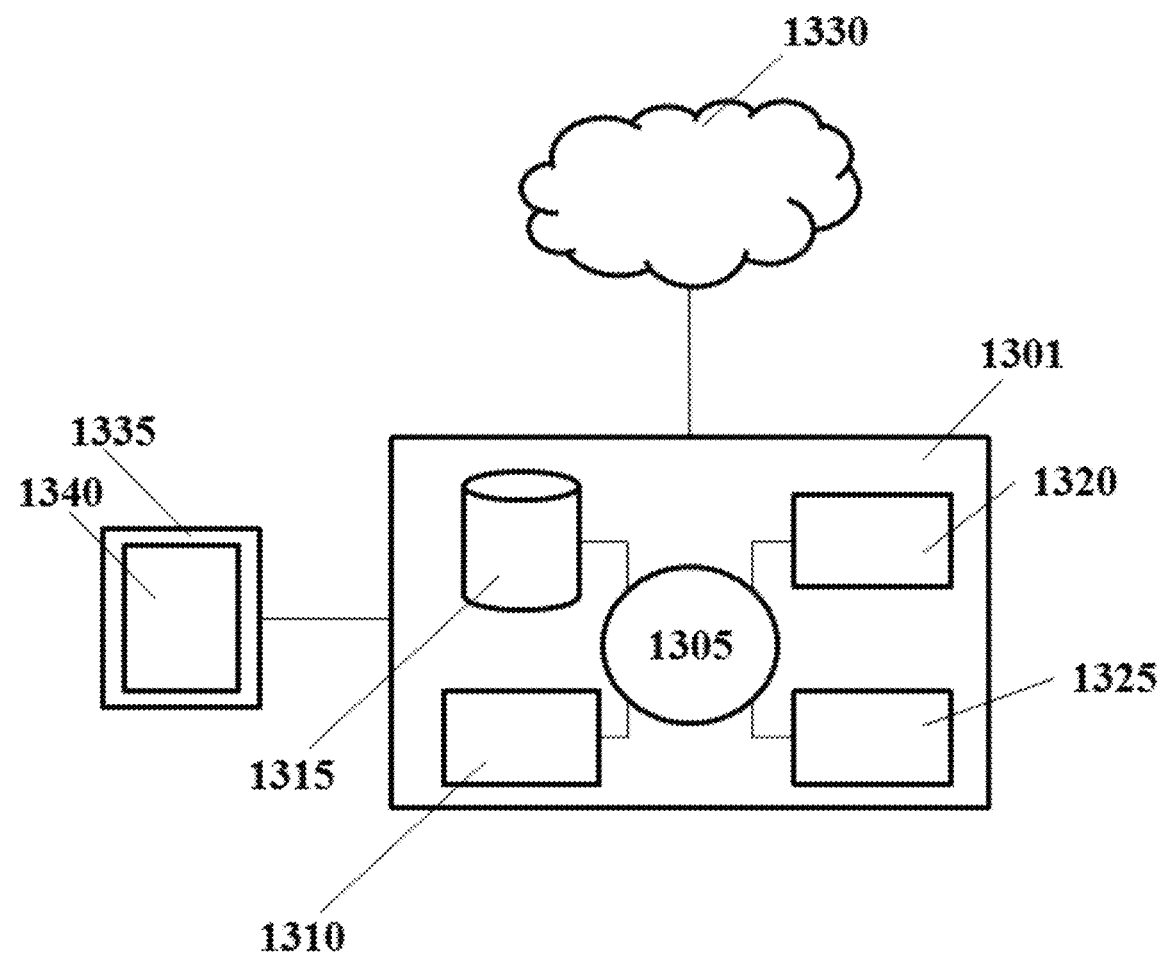
FIG. 13 shows a computer system that is programmed or otherwise configured to implement methods of the present disclosure herein.

The present disclosure provides computer systems that are programmed to implement methods of the disclosure. FIG. 13 shows a computer system 1301 that is programmed or otherwise configured to process and/or assay a sample. The computer system 1301 may regulate various aspects of sample processing and assaying of the present disclosure, such as, for example, activation of a valve or pump to transfer a reagent or sample from one chamber to another or application of heat to a sample (e.g., during an amplification reaction). The computer system 1301 may be an electronic device of a user or a computer system that is remotely located with respect to the electronic device. The electronic device may be a mobile electronic device.

The computer system 1301 includes a central processing unit (CPU, also "processor" and "computer processor" herein) 1305, which may be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 may be a data storage unit (or data repository) for storing data. The computer system 1301 may be operatively coupled to a computer network ("network") 1330 with the aid of the communication interface 1320. The network 1330 may be the Internet, an internet and/or extranet, or an intranet and/or extranet that is in communication with the Internet. The network 1330 in some cases is a telecommunication and/or data network. The network 1330 may include one or more computer servers, which may enable distributed computing, such as cloud computing. The network 1330, in some cases with the aid of the computer system 1301, may implement a peer-to-peer network, which may enable devices coupled to the computer system 1301 to behave as a client or a server.

The CPU 1305 may execute a sequence of machine-readable instructions, which may be embodied in a program or software. The instructions may be stored in a memory location, such as the memory 1310. The instructions may be directed to the CPU 1305, which may subsequently program or otherwise configure the CPU 1305 to implement methods of the present disclosure. Examples of operations performed by the CPU 1305 may include fetch, decode, execute, and writeback.

The CPU 1305 may be part of a circuit, such as an integrated circuit. One or more other components of the system 1301 may be included in the circuit. In some cases, the circuit is an application specific integrated circuit (ASIC).

The storage unit 1315 may store files, such as drivers, libraries and saved programs. The storage unit 1315 may store user data, e.g., user preferences and user programs. The computer system 1301 in some cases may include one or more additional data storage units that are external to the computer system 1301, such as located on a remote server that is in communication with the computer system 1301 through an intranet or the Internet.

The computer system 1301 may communicate with one or more remote computer systems through the network 1330. For instance, the computer system 1301 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user may access the computer system 1301 via the network 1330.

Methods as described herein may be implemented by way of machine (e.g., computer processor) executable code stored on an electronic storage location of the computer system 1301, such as, for example, on the memory 1310 or electronic storage unit 1315. The machine executable or machine readable code may be provided in the form of software. During use, the code may be executed by the processor 1305. In some cases, the code may be retrieved from the storage unit 1315 and stored on the memory 1310 for ready access by the processor 1305. In some situations, the electronic storage unit 1315 may be precluded, and machine-executable instructions are stored on memory 1310.

The code may be pre-compiled and configured for use with a machine having a processer adapted to execute the code, or may be compiled during runtime. The code may be supplied in a programming language that may be selected to enable the code to execute in a pre-compiled or as-compiled fashion.

Aspects of the systems and methods provided herein, such as the computer system 1301, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 may include or be in communication with an electronic display 1335 that comprises a user interface (UI) 1340 for providing, for example, a current stage of processing or assaying of a sample (e.g., a particular operation, such as a lysis operation, that is being performed). Examples of UI's include, without limitation, a graphical user interface (GUI) and web-based user interface.

Methods and systems of the present disclosure may be implemented by way of one or more algorithms. An algorithm may be implemented by way of software upon execution by the central processing unit 1305.

Amplification

The nucleic acid molecule that is to be sequenced can be amplified prior to performing a sequencing reaction (e.g., sequencing by synthesis (SBS)).

Amplification of many nucleic acid molecules (e.g., clones) in parallel may result in a loss of molecular integrity (e.g., clonal integrity) in solution. Accordingly, amplification of large numbers of nucleic acid molecules may be carried out in a controlled fashion to preserve clonal integrity.

One approach to controlled amplification involves carrying out amplification reactions in individual reactors, such as compartmentalized plates, microreactors, or droplets. For example, emulsion polymerase chain reaction (PCR) may be used to amplify multiple clones in individual droplets, in some cases by attachment of the amplified molecules onto beads coated with oligonucleotides. Each emulsion PCR droplet may contain an oligonucleotide-coated bead to which a single nucleic acid template may be attached. When PCR is performed in the droplets separated by an immiscible barrier, the amplification products may remain isolated and bound to the bead in the droplets. Emulsion PCR may involve generation of an emulsion of oligonucleotide-coated beads captured in aqueous droplets with deoxyribonucleic acid (DNA) polymerase, nucleotides, and other reagents, with each aqueous droplet being separated from other droplets via oil; thermocycling of the emulsified mix; disruption of the emulsion; and enrichment of beads that have amplified DNA from beads that do not have amplified DNA. To get a billion monoclonal beads as output, emulsion PCR may be performed with an excess of beads to decrease the number of polyclonal beads (that is, beads that contain two or more different templates).

Another approach to preserving clonal integrity may involve attaching individual molecules and amplified products to a substrate to constrain the migration of amplified products to other clones by diffusion. Solid-phase nucleic acid clonal amplification methods that generate bound or localized amplicons may be instrumental for the development and adoption of genomic methods such as next generation sequencing in which millions or billions of clones are amplified in parallel and then subjected to highly parallel sequencing.

Methods based on spatial separation of amplified nucleic acid templates by binding of the templates to a planar substrate coated with oligonucleotides may include Bridge Amplification, Wildfire Amplification (e.g., where sequencing libraries are isothermally amplified in-situ directly on a surface of a flow cell), and Recombinase Polymerase Amplification (RPA). Bridge Amplification may comprise generation of DNA colonies on an oligonucleotide coated substrate and use of multiple reagents flowing over the oligonucleotide substrate for multiple cycles to produce amplified colonies on the substrate. Wildfire methods may comprise use of Poly A-base sequences in critical areas of oligonucleotide adapter sequences.

J-shaped Adapters

The methods described herein may comprise the use of one or more adapters (e.g., in a particular implementation, J-shaped adapter moieties). The adapters may comprise one or more nucleic acid sequences. The adapter may comprise one or more regions (e.g., 1 region, 2 regions, 3 regions, 4 regions, 5 regions, or more regions). For example, the one or more regions may comprise one or more capture sequences configured to capture nucleic acid molecules (e.g., template nucleic acid molecules), one or more binding sequences (e.g., one or more binding sequences that are complementary to one another), one or more chemical groups that facilitates attachment to a substrate, one or more cleavable nucleotides, and/or a replication block. For example, the adapter may comprise a capture sequence linked to a first binding sequence, which first binding sequence is hybridized to a second binding sequence that is complementary to the first binding sequence. The first binding sequence may be linked to the second binding sequence. A short sequence may separate the first and second binding sequences, which short sequence may comprise a chemical group (e.g., amines or N-Hydroxysuccinimide esters) that facilitates attachment to a substrate. Such a chemical group may be positioned adjacent to the first or second binding sequence.

The adapter may have any useful characteristics, including any useful length, base content, melting point, or other characteristic. For example, the adapter may comprise at least about 10 bases, such as at least 10 bases, 15 bases, 20 bases, 25 bases, 30 bases, 35 bases, 40 bases, 45 bases, 50 bases, 60 bases, 65 bases, 70 bases, 75 bases, 80 bases, 85 bases, 90 bases, 95 bases, 100 bases, 110 bases, 120 bases, 130 bases, 140 bases, 150 bases, 160 bases, 170 bases, 180 bases, 190 bases, 200 bases, 250 bases, 300 bases, 350 bases, 400 bases, 450 bases, 500 bases, or more bases. Similarly, a sequence of an adapter (e.g., a capture sequence or binding sequence, as described herein) may comprise any useful number of bases. For example, a sequence of an adapter may comprise at least about 4 bases, 5 bases, 10 bases, 20 bases, 25 bases, 30 bases, 35 bases, 40 bases, 45 bases, 50 bases, 60 bases, 65 bases, 70 bases, 75 bases, 80 bases, 85 bases, 90 bases, 95 bases, 100 bases, or more.

The one or more regions of the adapter may have similar or different characteristics. For example, a first region of the adapter may have the same or different base content, length, sequence, melting point, or other characteristic as a second region of the adapter. In some cases, the adapter may include two or more regions having one or more substantially similar characteristics and one or more additional regions having one or more substantially different characteristics. For example, the adapter may include a first region and a second region having the same or similar characteristics (e.g., the same sequence, melting point, length, and/or base content) and a third region having one or more different characteristics. Regions having similar or different characteristics may be arranged in any order. For example, a first region and a second region having the same or substantially similar characteristics may flank (e.g., each be adjacent on either side of) a third region having different characteristics, or a first region and a second region having the same or substantially similar characteristics may be adjacent to one another and a third region having different characteristics may be adjacent to the second region. As used herein with respect to two entities, "adjacent," may generally refer to the two entities being directly next to one other (e.g., contiguous) or in proximity to one another. For example, a first region that is adjacent to a second region may be directly next to a second region (e.g., having no other entity disposed between the first and second regions) or in proximity to a second region (e.g., having an intervening sequence or molecule between the first and second regions).

The different sequence regions of the adapter may include the same or substantially similar or different nucleic acid sequences (e.g., having the same, substantially similar, or different sequences, lengths, base contents, and/or melting points). For example, the adapter may include repeated sequences (e.g., degenerate primer sequences). One of more sequences of an adapter may be complements or reverse complements of one another. For example, an adapter may comprise a first binding sequence having a first nucleic acid sequence and a second binding sequence having a second nucleic acid sequence, which first nucleic acid sequence may bind to the second nucleic acid sequence. The first and second binding sequences may be separated by a short sequence. Binding between the first and second binding sequences may result in formation of a fold or loop in the adapter, which may provide a hairpin, stem-loop, Y-shaped, or J-shaped adapter (e.g., as described herein).

The adapter may comprise a capture sequence. The capture sequence may comprise a random sequence or a defined sequence (e.g., a targeted capture sequence). For example, the capture sequence may hybridize to a complementary capture sequence (e.g., an adapter sequence) in a template nucleic acid strand, thereby attaching the template nucleic acid strand to the adapter. For an adapter (e.g., J-shaped adapter) that is immobilized to a substrate, hybridization of the adapter to a sequence of the template nucleic acid strand may immobilize the template nucleic acid strand to the substrate. Similarly, for a template nucleic acid strand immobilized to a substrate, hybridization of the adapter to a sequence of the template nucleic acid strand may immobilize the adapter to the substrate. The capture sequence may facilitate amplification or sequencing (e.g., paired-end sequencing) of the template nucleic acid strand or a sequence thereof (e.g., a template nucleic acid sequence). In some cases, the capture sequence comprises one or more cleavable groups, such as a cleavable base (e.g., a uridine base or an 8-oxoguanine base), that facilitate release of a nucleic acid strand (e.g., template nucleic acid strand) from the support. The cleavage group may be positioned near the terminus of adapter, such as a 3' end of the capture sequence of the adapter. During a cleavage reaction, a linkage (e.g., a covalent linkage) between a base moiety and a sugar moiety of a nucleotide may be severed. Alternatively or in addition, a linkage (e.g., a covalent linkage) between a sugar moiety and a phosphate moiety of a nucleotide may be severed. The capture sequence may comprise any useful characteristics, including any useful length, base content (e.g., canonical nucleotides and nucleotide analogs), melting point, or other characteristic. For example, the capture sequence may comprise at least about 5 bases, 10 bases, 15 bases, 20 bases, 25 bases, 30 bases, 35 bases, 40 bases, 45 bases, 50 bases, 55 bases, 60 bases, or more bases. In some cases, the capture sequence may include at least 5 bases. In some cases, the capture sequence may include at least 10 bases. In certain cases, the capture sequence may include at least 20 bases.

The adapter may also comprise one or more binding sequences, such as a first binding sequence and a second binding sequence. The first binding sequence may be positioned adjacent to a capture sequence. In some cases, a spacer sequence may separate a capture sequence and a first binding sequence. In some cases, the first binding sequence may comprise a replication block (e.g., hexa ethylene glycol, uridine, abasic site, or internal spacers) that blocks replication with a polymerase. Alternatively, a replication block may be positioned along any region of an adapter (e.g., a J-shaped adapter). For an adapter comprising a first binding sequence and a second binding sequence, the second binding sequence may be capable of hybridizing to the first binding sequence, thereby forming a double-stranded region. The resultant double-stranded region may be a stable double-stranded region (e.g., resistant to denaturation under mild denaturing conditions). In some cases, the first binding sequence and the second binding sequence may have a percent sequence complementarity of at least about 50%, 55%, 60%, 65%, 70%, 75%, 80%, 85%, 90%, 95%, 98%, 99%, 99.9%, or greater. In some cases, the first binding sequence and the second binding sequence may have a percent sequence complementarity of at most about 100%, 99%, 98%, 95%, 90%, 85%, 80%, 75%, 70%, 65%, 60%, 55%, or less. In some cases, the first binding sequence and the second binding sequence may be separated by a short linking sequence (e.g., a single-stranded region). The one or more binding sequences may comprise any useful characteristics, including any useful length, base content (e.g., canonical nucleotides and nucleotide analogs), melting point, or other characteristic. For example, the one or more binding sequences may comprise at least about 5 bases, 10 bases, 15 bases, 20 bases, 25 bases, 30 bases, 35 bases, 40 bases, 45 bases, 50 bases, 55 bases, 60 bases, or more bases. In some cases, the one or more binding sequences may include at least 5 bases. In some cases, the one or more binding sequences may include at least 10 bases. In certain cases, the one or more binding sequences may include at least 20 bases. An adapter may comprise multiple pairs of binding sequences that are capable of hybridizing to one another. In an example, an adapter comprises first, second, third, and fourth binding sequences. The adapter may be configured such that the first binding sequence and second binding sequence are separated by a first linking sequence, the second binding sequence and the third binding sequence are separated by a second linking sequence, and the third binding sequence and the fourth binding sequence are separated by a third linking sequence. The first binding sequence may be capable of hybridizing to the fourth binding sequence and the second binding sequence may be capable of binding to the third binding sequence. The various binding sequences may have the same or different lengths and compositions (e.g., as described herein). In some cases, one of the pairs of binding sequences may have a lower melting point than another pair of binding sequences, such that the binding sequences of the former pair may separate upon heating (e.g., a bubble may form). In some cases, the first and third linking sequences may be absent.

The adapter or region thereof may include any combination of bases. The adapter may include both natural and non-natural nucleotides (e.g., nucleotide analogs, as described herein). In some cases, the adapter may include only natural bases (e.g., adenine, thymine, cytosine, guanine, and uracil). The adapter may include a base such as inosine that may hybridize to more than one different DNA base type. Bases of an adapter may be arranged in any useful sequence or combination of sequences. One or more regions of the adapter may include one or more different sequences having one or more different base contents and/or combinations of bases. For example, different sequences of the adapter may have different adenine, thymine, cytosine, guanine, and uracil content (e.g., % A, % T, % C, % G, and % U). A first sequence of the adapter may have a higher adenine and/or thymine content (e.g., a higher % A and/or % T) than a second sequence of an adapter. Similarly, a second sequence of the adapter may have a higher guanine and/or cytosine content (e.g., a higher % G and/or % C) than a first sequence of the adapter. In some cases, a sequence of the adapter may comprise one or more bases selected from the group consisting of adenine, thymine, uridine, inosine, and derivatives or modified versions thereof. In certain cases, a sequence may comprise only bases selected from the group consisting of adenine, thymine, uridine, and inosine. In one example, the adapter includes a first sequence and a second sequence that flank a third sequence, where the third sequence comprises only bases selected from the group consisting of adenine, thymine, uridine, and inosine and the flanking first and second sequences comprise bases selected from the group consisting of adenine, thymine, uridine, inosine, and other bases (e.g., cytosine, guanine, and/or non-natural bases). The first and second sequences may be the same or substantially similar or different and may have the same or substantially similar or different content and number of bases.

The adapter may have one or more melting points. For example, the adapter may comprise a single melting point. In another example, the adapter may comprise regions having different melting points. Alternatively, some regions may have the same or substantially the same melting points. A melting point of a region of the adapter may be at least about 10° C., 11° C., 12° C., 13° C., 14° C., 15° C., 16° C., 17° C., 18° C., 19° C., 20° C., 25° C., 30° C., 35° C., 40° C., 45° C., 50° C., 55° C., 60° C., 65° C., 70° C., 75° C., 80° C., 85° C., 90° C., 95° C., or higher. For example, a melting point of a region of the adapter may be at least about 10° C. A melting point of a region of the adapter may be between about 35° C. and 55° C., such as between about 40° C. and 45° C. A melting point of a region of the adapter may be between about 55° C. and 75° C., such as between about 60° C. and 70° C. In some cases, the adapter may include at least one region having a melting point between about 35° C. and 55° C. and at least one region having a melting point between about 55° C. and 75° C. For example, the adapter may include at least one region having a melting point between about 40° C. and 45° C. and at least one region having a melting point between about 60° C. and 70° C. The melting point of a region of the adapter may depend upon the base composition and/or sequence of the region.

For the adapter including two or more regions having two or more different melting points, the difference between the melting points of a first region of the adapter and a second region of the adapter may be at least about 1° C., 2° C., 3° C., 4° C., 5° C., 6° C., 7° C., 8° C., 9° C., 10° C., 11° C., 12° C., 13° C., 14° C., 15° C., or higher. For example, a first melting point for a first region of the adapter may be at least 1° C., 2° C., 3° C., 4° C., 5° C., 6° C., 7° C., 8° C., 9° C., 10° C., 11° C., 12° C., 13° C., 14° C., or 15° C. lower than a second melting point for a second region (e.g., a second region adjacent to the first region) of the adapter. In one example, the first melting point may be at least 1° C. lower than the second melting point. For example, the first melting point may be at least 5° C. lower than the second melting point. For the adapter including first and second regions having the same characteristics that flank a third region having different characteristics, the first and second regions may have first and second melting points and the third region may have a third melting point that differs from the first and second melting points. In some cases, the first and second melting points may be the same or approximately the same. In some cases, the third melting point may be higher than the first and second melting points, while in other cases the third melting point may be lower than the first and second melting points.

A nucleic acid molecule may comprise one or more adapters that are the same, substantially similar, or different. For example, a nucleic acid molecule may comprise a first adapter at a first end of the molecule and a second adapter at a second end of the molecule. The second adapter may be, in whole or in part, the reverse (e.g., the reverse sequence) of the first adapter. In one example, an adapter may be capable of ligating or hybridizing to two ends of a nucleic acid molecule, resulting in the circularization of the nucleic acid molecule.

In some cases, paired adapter oligonucleotide sequences may comprise regions of high and low melting temperatures. The paired adapters include a central low melting temperature domain with Poly (A) sequences on one strand and Poly (T) sequences on the opposite strand. High melting temperature domains flank the low melting temperature domain. The high melting temperature domains comprise sequences having higher G and C ratios. An additional small A-T rich region is present for additional functionality.

Localized partial denaturation (e.g., bubble formation) in a double-stranded nucleic acid molecule may form a site for hybridization of a primer to one or more of the resultant single-stranded regions, as described elsewhere herein. In some cases, a chemical denaturant such as a salt, urea, guanidine hydrochloride, or an organic solvent may be used to partially denature sequences in a defined region of a nucleic acid molecule. In some cases, the partial denaturation in a defined region of a nucleic acid molecule may occur without denaturing reagents or high temperatures, as described herein. A region of a double-stranded nucleic acid molecule may dynamically dissociate at a reaction temperature (e.g., a temperature higher than the melting point of a low melting point region and lower than the melting points of adjacent higher melting point regions) by allowing local opening of base pairs to create a single-stranded denaturation region. Melting is driven by entropy overruling the attraction of hydrogen bonds between the nucleic acid bases. The spontaneous and induced localized melting behavior may be determined by statistical models such as the Poland and Sheraga model and by thermodynamic nearest-neighbor model. The Mesoscopic Peyrard-Bishop-Dauxious model may also reflect bubble formation and stability seen experimentally. The rate of bubble formation may be affected by, for example, the A-T base sequence content and the temperature. It has been demonstrated that A-T rich regions of at least 12-20 bp of double-stranded nucleic acid molecules may form stable bubbles.

In addition to regions of low and high melting temperature, an adapter may comprise one or more additional sequences having different functionalities. For example, an adapter may comprise a priming sequence or a barcode sequence. An adapter may also comprise a region to facilitate immobilization of an adapter to a support (e.g., as described herein).

A target nucleic acid molecule of a biological sample may undergo one or more processing steps prior to undergoing analysis according to the methods provided herein. For example, a target nucleic acid molecule may be functionalized with one or more adapters (e.g., as described herein). The target nucleic acid molecule may be a double-stranded nucleic acid molecule that is denatured to provide a first strand and a second strand, which first and second strands may both be coupled to one or more adapters (e.g., a first adapter at a first end of the strand and a second adapter at a second end of the strand). Alternatively, the target nucleic acid molecule may be coupled to one or more adapters (e.g., at first and second ends of the molecule) prior to undergoing denaturation. The functionalized target nucleic acid molecule may then be denatured to provide first and second strands, which strands may be processed according to the methods provided herein. In other cases, a target nucleic acid molecule may be a single-stranded nucleic acid molecule, which single-stranded nucleic acid molecule is functionalized at one or more both ends with an adapter. An adapter may be coupled to a nucleic acid molecule or strand thereof by, for example, hybridization or ligation methods. A target nucleic acid molecule may optionally undergo additional processing prior to being coupled to an adapter. For example, a target nucleic acid molecule may be processed to add or remove one or more sequences prior to being coupled to one or more adapters. Adapters coupled to a target nucleic acid molecule or strand thereof may facilitate interaction with additional moieties such as other nucleic acid molecules and adapters, which moieties may include sequences (e.g., capture or primer sequences) complementary to sequences of the adapters.

In some cases, a sample may include a double-stranded nucleic acid molecule of interest (e.g., target or template nucleic acid molecule), and one or both strands of the nucleic acid molecule may be processed and/or analyzed. In other cases, a sample may include a single-stranded nucleic acid molecule of interest. Localized partial denaturation in a nucleic acid molecule depends upon the nucleic acid molecule comprising two strands. Accordingly, two complementary strands are prepared for processing and analysis. In some cases, a double-stranded adapter may be attached to a double-stranded nucleic acid molecule. For example, a double-stranded adapter may be ligated to an end of a double-stranded nucleic acid molecule using an enzyme such as DNA ligase that may facilitate the formation of a covalent bond between nucleotides of adjacent nucleotides to join adjacent strands of DNA. The double-stranded adapter may include a first strand comprising first and second sequences and a second strand comprising third and fourth sequences, where the first sequence is hybridized to the third sequence and the second sequence is hybridized to the fourth sequence. The first sequence hybridized to the third sequence may have a first melting point that is lower than the melting point of the second sequence hybridized to the fourth sequence.

In some cases, rather than attaching a double-stranded adapter to a double-stranded template nucleic acid molecule, two single-stranded adapters, each corresponding to a strand of a double-stranded nucleic acid molecule (e.g., a 3' adapter and a 5' adapter), may be ligated to the double-stranded nucleic acid molecule simultaneously or sequentially. For example, a first single-stranded adapter may be attached to a first strand of the double-stranded nucleic acid molecule and then a second single-stranded adapter may be attached to the second strand of the double-stranded nucleic acid molecule. Attachment of the second single-stranded adapter may involve partial degradation of the first single-stranded adapter and annealing of the second single-stranded adapter to the second strand. The first adapter may include first and second sequences and the second adapter may include third and fourth sequences, where the first sequence is hybridized to the third sequence and has a melting point that is lower than the melting point of the second sequence hybridized to the fourth sequence. In some cases, an adapter may be associated with or bound to a protein or other factor to increase its ability to interpolate and/or hybridize to a nucleic acid template. For example, an adapter may comprise a RecA protein that facilitates entrance into a double-stranded nucleic acid molecule and hybridization to a complementary sequence without denaturation of the double-stranded nucleic acid molecule by other agents.

In some cases, a single-stranded adapter may be hybridized to a strand of a nucleic acid molecule (e.g., a single-stranded target nucleic acid molecule). For example, an adapter comprising a first sequence and a second sequence may hybridize to a single-stranded nucleic acid molecule. The nucleic acid molecule may then undergo an extension reaction to generate a nucleic acid sequence that is complementary to the initial strand and includes the adapter. The newly formed strand including the complementary sequence and the adapter may then be denatured from the initial strand. Hybridization of a primer sequence to an end of the newly formed strand and subsequent extension may generate a double-stranded nucleic acid molecule in which the first strand includes the adapter and the sequence complementary to the template nucleic acid molecule, and the second strand is complementary to the first strand and includes a third sequence that is complementary to the first sequence of the adapter and a fourth sequence that is complementary to the second sequence of the adapter. The first sequence hybridized to the third sequence may have a melting point lower than the second sequence hybridized to the fourth sequence.

A nucleic acid molecule (e.g., target nucleic acid molecule) may comprise multiple adapters (e.g., attached thereto). For example, a single-stranded nucleic acid molecule may comprise a first adapter attached to a first end of the molecule and a second adapter attached to a second end of the molecule. The first and second adapters may be the same or different. For example, both the first adapter and the second adapter may comprise at least first and second sequences, where the first and second sequences have different melting points. Alternatively, the first adapter may comprise at least first and second sequences, where the first and second sequences have different melting points, and the second adapter may not include specified regions of low or high melting points. Adapters may be attached to ends of a nucleic acid molecule in different ways. For example, a first adapter may be ligated to an end of a nucleic acid molecule and a second adapter may be hybridized to an end of a nucleic acid molecule. In some cases, a strand comprising an adapter may be generated via an extension reaction (e.g., as described herein).

An adapter attached to a nucleic acid molecule may be included in a solution or may immobilized to a substrate (e.g., as described herein). A substrate may comprise a plurality of adapters immobilized thereto. Adapters may be uniformly or non-uniformly distributed on a substrate. In some cases, adapters may be uniformly distributed on all exposed areas of a substrate. Adapters may be immobilized to a substrate in a predetermined pattern. In some cases, one or more exposed areas of a substrate may not include adapters immobilized thereto. Adapters may be immobilized to a support at a density of at least 1,000 molecules per $mm^2$, such as at least 10,000 molecules per $mm^2$, 50,000 molecules per $mm^2$, 100,000 molecules per $mm^2$, 500,000 molecules per $mm^2$, 1,000,000 molecules per $mm^2$, 5,000,000 molecules per $mm^2$, 10,000,000 molecules per $mm^2$, or more molecules per $mm^2$. For example, adapters may be immobilized to a support at a density of least 10,000 molecules per $mm^2$. The support can be, for example, a bead or a surface, such as a flow cell surface. The surface may be a well of a well plate or flow cell surface.

An adapter immobilized to a substrate may be inactivated. For example, adapters immobilized to a given area of a substrate may be inactivated. An adapter may be removable from the substrate, e.g., upon application of sufficient conditions to detach an adapter from the substrate. For example, a chemical reagent, temperature condition, pH condition, and/or other condition may be applied to remove an adapter from a substrate. In some cases, a substrate may comprise a plurality of first adapters and a plurality of second adapters. The plurality of first adapters and the plurality of second adapters may be dispersed on the substrate such that a given exposed area of the substrate includes both first adapters and second adapters immobilized thereto. Alternatively, different subsets or types of adapters may be immobilized to different areas of the substrate. An adapter may be immobilized to a substrate at an end of the adapter. For example, an end (e.g., 5' end) of an adapter may comprise approaches to immobilize the end of the adapter onto a substrate. An adapter may be immobilized to a substrate via a covalent bond formed directly or indirectly between the adapter and the substrate or by interaction between molecules such as avidin and biotin. In some cases, an end of an adapter may comprise a thiol, hydroxyl, dimethoxyl-trityl (DMT), amino, or phosphate group to facilitate attachment of the adapter to a substrate. In certain cases, an end of an adapter may comprise a carboxylic or aldehyde moiety and a "click" chemistry reaction may be used to immobilize an adapter to a substrate. Like adapters, primers may also be immobilized to a substrate, as described above.

A capture sequence of a nucleic acid molecule (e.g., adapter) may be used to capture a template nucleic acid molecule. Where the nucleic acid molecule is immobilized to a support, the capture sequence may be used to immobilize a template nucleic acid molecule to the support (e.g., a substrate). The capture sequence may be an adaptor or a primer (e.g., as described herein). Immobilization, as used herein, may generally refer to substantially stable attachment of a first object (e.g., the nucleic acid molecule) to a second object (e.g., the support) under defined conditions, either directly or through a linking moiety. The attachment may occur via a chemical group. The attachment can be by any mechanism, including, but not limited to, non-covalent bonding, ionic interactions, and covalent linkage. The attachment may be releasable from surface or may not be releasable from a surface. If a first nucleic acid molecule (e.g., a first nucleic acid strand derived from a template nucleic acid molecule) is hybridized to a second nucleic acid molecule immobilized on a support, then the first nucleic acid molecule may also be considered to be immobilized to the support during amplification and/or sequencing, if amplification and sequencing conditions are such that substantial amounts of the first and second nucleic acid molecules are associated or connected with each other at any or all times during amplification and/or sequencing. For example, first and second nucleic acid molecules may be associated together by hybridization involving Watson-Crick base pairing or hydrogen bonding. In an example, amplification and/or sequencing conditions may allow at least 50%, 80%, 90%, 95% or 99% of a first nucleic acid molecule to remain hybridized with a second nucleic acid molecule, or vice versa, during amplification and/or sequencing. A nucleic acid molecule may be considered un-immobilized or non-immobilized if it is not directly or indirectly attached to or associated with a support.

The adapter may also comprise, in any region, one or more replication blocks, such as one or more chemical groups that can block replication and prevent extension of a nucleic acid strand with a polymerase. Examples of replication blocks include hexa ethylene glycol, bases that cannot be read by polymerases (e.g., uridine), abasic sites, and internal structures.

FIG. 16 illustrates example chemical structures of replication blocks. The replication block on the left is an abasic site 1600, which is a location in the immobilized nucleic acid 100 that contains neither a purine nor a pyrimidine base. The replication block on the right is an 18-atom hexaethylene glycol spacer 1600, which is an internal spacer introduced between the capture sequence and the first binding sequence. When DNA polymerase encounters either replication blocks, DNA replication is blocked, resulting in a break in the replicated nucleic acid strand.

Figure 15:
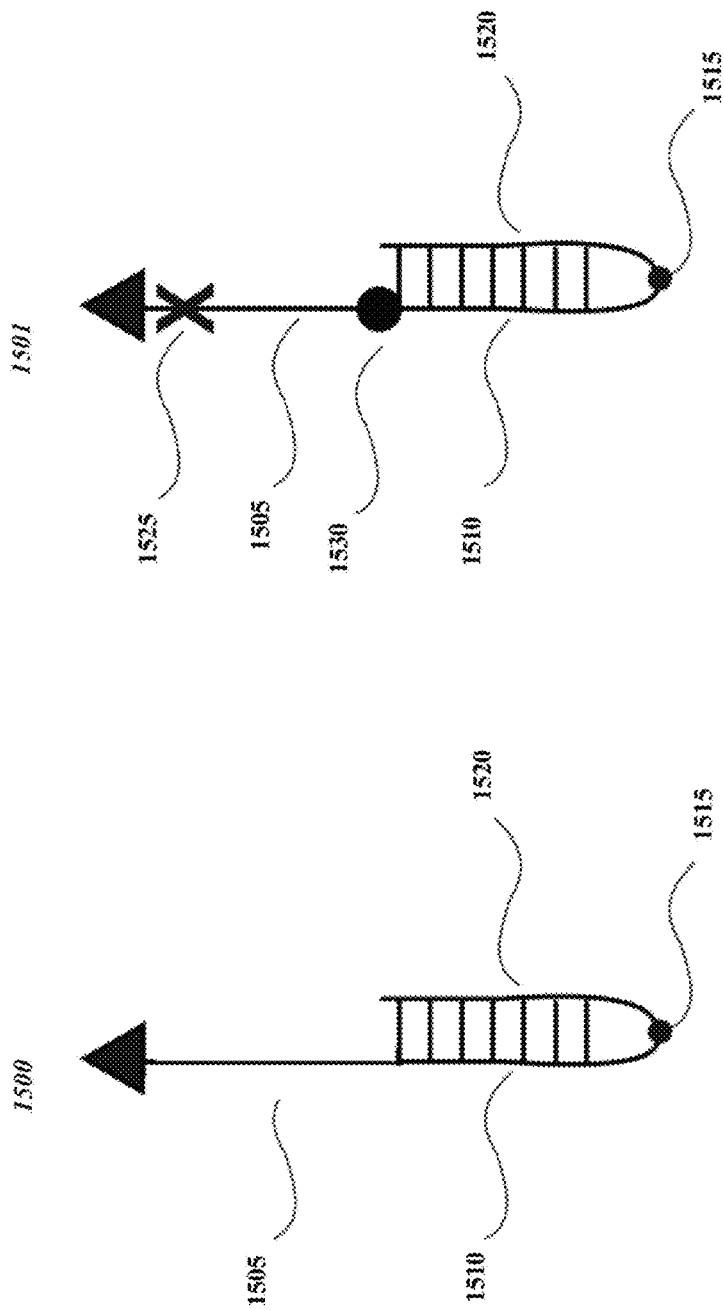
FIG. 15A-15B show schematics illustrating two J-shaped adapter configurations.

FIG. 15A-B show schematics illustrating two J-shaped adapter configurations. FIG. 15A shows a schematic illustrating a J-shaped adapter 1500 including a capture sequence 1505, a first binding sequence 1510, a region 1515 that facilitates attachment to a substrate, and a second binding sequence 1520 complementary to the first binding sequence 1510. In some cases, the capture sequence 1505 may be positioned closest to the terminus of 3' region of the J-shaped adapter. Capture sequence 1505 may hybridize to a complementary capture sequence present in a template nucleic acid strand. The first binding sequence 1510 can hybridize to the second binding sequence 1520, thereby forming a stable double-stranded region. The second binding sequence region 1520 may contain a blocking moiety to prevent degradation by a polymerase. Region 1515 contains chemical groups that bind the J-shaped adapter 1500 to the substrate. The sequence of the J-shaped adapter 1500 allows it to spontaneously form into a J-shaped structure.

FIG. 15B shows a schematic illustrating a second J-shaped adapter configuration 1501 further comprising a cleavage group 1525 closest to the terminus of 3' region and a replication block 1530 that blocks replication with a polymerase.

Amplification and Sequencing

The methods described herein may use one or more nucleic acid molecules (e.g., adapters as described herein) to amplify and/or sequence one or more nucleic acid templates. The methods described herein may be useful for processing a nucleic acid molecule (e.g., a target or template nucleic acid molecule). For example, the methods described herein may be used to amplify one or more nucleic acid molecules of a nucleic acid sample before or during sequencing. The methods of the present disclosure may be useful for, for example, for sequencing to identify genetic aberrations for, e.g., cancer detection.

In an aspect, the present disclosure provides a method for sequencing a template nucleic acid molecule comprising bringing a nucleic acid molecule (e.g., a J-shaped adapter) in contact with a first nucleic acid strand derived from the template nucleic acid molecule to hybridize a first capture sequence of the nucleic acid molecule to a second capture sequence of the first nucleic acid strand. The nucleic acid molecule may be immobilized to a substrate (e.g., as described herein). The second capture sequence may have sequence complementarity to the first capture sequence. The nucleic acid molecule may comprise the first capture sequence, a first binding sequence, and a second binding sequence hybridized to the first binding sequence. The first nucleic acid strand can comprise the second capture sequence that is complementary to the first capture sequence, a first template sequence, and a third capture sequence. In some cases, the first nucleic acid strand may be prepared by attaching (e.g., via a hybridization or ligation process) the second and third capture sequences to the template nucleic acid molecule. The first capture sequence of the nucleic acid molecule may be used as a primer to subject the first nucleic acid strand to a reaction under conditions sufficient to generate a second nucleic acid strand complementary to the first nucleic acid strand (e.g., via a primer extension reaction). The second nucleic acid strand may comprise a second template sequence complementary to the first template sequence and a fourth capture sequence complementary to the third capture sequence. The first nucleic acid strand may be removed from the nucleic acid molecule (e.g., J-shaped adapter) to provide the second nucleic acid strand attached to the nucleic acid molecule. Where the nucleic acid molecule is immobilized to a support, removal of the first nucleic acid strand may provide the second nucleic acid strand immobilized to the support via the immobilized nucleic acid molecule (e.g., immobilized J-shaped adapter). The immobilized nucleic acid molecule may be attached to the support via a chemical group (e.g., an amine). The template nucleic acid molecule may be a DNA or RNA molecule.

The second nucleic acid strand may be used as a template for a subsequent amplification and/or sequencing process. For example, the second nucleic acid strand may be subjected to a reaction under conditions sufficient to generate a third nucleic acid strand, complementary to the second nucleic acid strand (e.g., via primer hybridization and subsequent extension). Generation of the third nucleic acid strand may comprise generation of a sequencing read corresponding to the second nucleic acid strand. The second nucleic acid strand may be subjected to sequencing to yield a first sequencing read in a first direction away from the first end, which sequencing generates a third nucleic acid strand. The third nucleic acid strand may comprise (i) a third template sequence complementary to the second template sequence and (ii) a fifth capture sequence complementary to the fourth capture sequence. The sequencing read may be used to identify the first template sequence of the first nucleic acid strand, thereby sequencing the template nucleic acid molecule.

A capture sequence of the nucleic acid molecule (e.g., J-shaped adapter) may attach to a nucleic acid molecule via hybridization or ligation (e.g., as described herein). For example, a capture sequence (e.g., a capture sequence immobilized to a substrate) may hybridize to a complementary sequence of a single-stranded nucleic acid molecule (e.g., template nucleic acid molecule). The complementary sequence of the nucleic acid molecule may be introduced into the nucleic acid molecule via ligation of another capture sequence comprising the complementary sequence. Sequences of a capture sequence may be selected for maximal hybridization with a target sequence and very low hybridization to any other sequence. For an adapter immobilized to a substrate, the first region comprising the first sequence may be disposed closer to the substrate than the second region comprising the second sequence, or vice versa (e.g., the second region comprising the second sequence may be disposed closer to the substrate than the first region comprising the first sequence). A first capture sequence attached to a first end of a nucleic acid molecule may be the same or different adapter from a second capture sequence attached to a second end (opposite the first end) of the nucleic acid molecule.

A first nucleic acid strand (e.g., template nucleic acid strand) hybridized to a first capture sequence may be subjected to conditions sufficient to hybridize the first capture sequence to the first nucleic acid strand and to promote extension of the first capture sequence to generate a second nucleic acid strand complementary to the first nucleic acid strand, thereby providing a double-stranded nucleic acid molecule. The first capture sequence may be subjected to a primer extension reaction. The primer extension reaction can comprise the use of a polymerizing enzyme such as a DNA polymerase or an RNA polymerase. The polymerase may be a non-processive DNA-dependent DNA polymerase. Alternatively, the polymerase may be a processive DNA-dependent DNA polymerase, such as Bst, Bst2, Bst3, or Phi29. The polymerase may also be an RNA-dependent DNA polymerase or an RNA-dependent RNA polymerase. Extension may take place in the presence of nucleoside triphosphate molecules (e.g., natural or non-natural nucleotides, and/or nucleotides labeled with a detectable moiety) or other nucleotide precursors such as modified nucleoside triphosphate molecules.

Upon generating or otherwise providing a double-stranded nucleic acid molecule (e.g., a double-stranded nucleic acid molecule coupled to a J-shaped adapter, such as a double-stranded nucleic acid molecule comprising a first strand derived from a template nucleic acid molecule and a second strand including sequences complementary to those of the first strand), the double-stranded nucleic acid molecule may be subjected to conditions sufficient to denature the double-stranded nucleic acid molecule. Denaturing the double-stranded nucleic acid molecule may comprise exposing the molecule or a portion thereof to a chemical denaturant, such as a salt, formamide, urea, guanidine hydrochloride, or an organic solvent. Alternatively or in addition, denaturation may be achieved by lowering a salt concentration and/or increasing a pH of a solution including the double-stranded nucleic acid molecule. Alternatively or in addition, partially denaturing the double-stranded nucleic acid molecule may comprise subjecting the double-stranded nucleic acid molecule to heating. Heating the double-stranded nucleic acid molecule may include optical heating, resistive heating, convective heating, inductive heating, and/or microwave heating. Denaturation may result in the first nucleic acid strand separating from the nucleic acid molecule (e.g., J-shaped adapter, such as an immobilized J-shaped adapter) to provide the second nucleic acid strand coupled to the nucleic acid molecule (e.g., J-shaped adapter). Where the nucleic acid molecule is immobilized on a support, the second nucleic acid strand may be considered to be immobilized on the support via the immobilized nucleic acid molecule (e.g., immobilized J-shaped adapter).

A primer molecule (e.g., sequencing primer) having sequence complementarity with the fourth capture sequence of the second nucleic acid strand may be brought into contact with the second nucleic acid strand under conditions sufficient to permit the primer molecule to hybridize to the fourth capture sequence. Sequencing may be performed by, for example, single molecule sequencing, sequencing by synthesis, sequencing by hybridization, or sequencing by ligation. Following generating the sequencing read corresponding to the second nucleic acid strand, the third nucleic acid strand may be ligated to the second binding sequence of the nucleic acid molecule. In some cases, the second nucleic acid strand may be removed from the nucleic acid molecule by cleavage and denaturation. For example, the first capture sequence may reside in a region of the nucleic acid molecule that comprises a cleavable base (e.g., uridine base or an 8-oxoguanine base) that facilitates release of second nucleic acid strand from the support.

The first capture sequence of the nucleic acid molecule may be used as a primer to subject the third nucleic acid strand to a reaction under conditions sufficient to generate a second sequencing read corresponding to the third nucleic acid strand. In some cases, the sequencing read and the second sequencing read do not overlap. In other cases, the sequencing read and the second sequencing read overlap. The overlap between the first sequencing read and the second sequencing read may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, or more bases. In some cases, the overlap between the first sequencing read and the second sequencing read may comprise at most about 70, 60, 50, 40, 30, 20, 19, 18, 17, 16, 15, 14, 13, 12, 11, 10, 9, 8, 7, 6, 5, or less bases. In other cases, the first sequencing read and the second sequencing read may completely overlap.

In another aspect, the present disclosure provides a method for sequencing a template nucleic acid molecule comprising providing (i) the template nucleic acid molecule comprising a first nucleic acid strand comprising a first template nucleic acid sequence and (ii) a nucleic acid molecule (e.g., a J-shaped adapter) comprising a first capture sequence, a first binding sequence, and a second binding sequence hybridized to the first binding sequence. The nucleic acid molecule may be immobilized to a support (e.g., as described herein). The first capture sequence of the nucleic acid molecule may be used as a primer to generate a second nucleic acid strand attached to the nucleic acid molecule (e.g., via a primer extension reaction). The second nucleic acid strand may comprise a second template nucleic acid sequence complementary to the first template nucleic acid sequence. Generation of the second nucleic acid strand may comprise generation of a first sequencing read corresponding to the first template nucleic acid sequence. The first capture sequence of the nucleic acid molecule may be used as a sequencing primer to generate a first sequencing read corresponding to the first template nucleic acid sequence. The sequencing process may generate the second nucleic acid strand comprising a second template sequence complementary to the first template nucleic acid sequence. The second nucleic acid strand attached to the nucleic acid molecule may be sequenced, thereby generating a second sequencing read corresponding to the second template nucleic acid sequence.

In some cases, generating the first sequencing read and/or the second sequencing read (e.g., sequencing) comprises sequencing by synthesis. In some cases, the generating the first sequencing read and/or the second sequencing read (e.g., sequencing) comprises sequencing by hybridization. In some cases, the generating the first sequencing read and/or the second sequencing read (e.g., sequencing) comprises sequencing by ligation. In some cases, generating the second nucleic acid strand attached to the nucleic acid molecule comprises subjecting the first nucleic acid strand to conditions sufficient to hybridize the first capture sequence of the nucleic acid molecule to the first nucleic acid strand (e.g., complementary sequence of a single-stranded first nucleic acid molecule).

The complementary sequence of the single-stranded first nucleic acid molecule may be introduced into the nucleic acid molecule via ligation of another capture sequence comprising the complementary sequence. Sequences of a capture sequence may be selected for maximal hybridization with a target sequence and very low hybridization to any other sequence. For an adapter immobilized to a substrate, the first region comprising the first sequence may be disposed closer to the substrate than the second region comprising the second sequence, or vice versa (e.g., the second region comprising the second sequence may be disposed closer to the substrate than the first region comprising the first sequence). A first capture sequence attached to a first end of a nucleic acid molecule may be the same or different adapter from a second capture sequence attached to a second end (opposite the first end) of the nucleic acid molecule.

Generation of the second nucleic acid strand attached to the nucleic acid molecule may comprise subjecting the first capture sequence to a primer extension reaction. The primer extension reaction may comprise the use of a polymerizing enzyme such as a DNA polymerase or an RNA polymerase. The polymerase may be a non-processive DNA-dependent DNA polymerase. Alternatively, the polymerase may be a processive DNA-dependent DNA polymerase, such as Bst, Bst2, Bst3, or Phi29. The polymerase may also be an RNA-dependent DNA polymerase or an RNA-dependent RNA polymerase. Extension may take place in the presence of nucleoside triphosphate molecules (e.g., natural or non-natural nucleotides, and/or nucleotides labeled with a detectable moiety) or other nucleotide precursors such as modified nucleoside triphosphate molecules.

Prior to sequencing the second nucleic acid strand, the first nucleic acid strand may be removed (e.g., under conditions sufficient to denature) from the nucleic acid molecule (e.g., J-shaped adapter) to provide the second nucleic acid strand attached to the nucleic acid molecule. Denaturation may comprise exposing the molecule or a portion thereof to a chemical denaturant, such as a salt, formamide, urea, guanidine hydrochloride, or an organic solvent. Alternatively or in addition, denaturation may be achieved by lowering a salt concentration and/or increasing a pH of a solution including the double-stranded nucleic acid molecule. Alternatively or in addition, partially denaturation may comprise subjecting the double-stranded nucleic acid molecule (e.g., a double-stranded nucleic acid molecule comprising a first strand derived from a template nucleic acid molecule and a second strand including sequences complementary to those of the first strand) to heating. Heating the double-stranded nucleic acid molecule may include optical heating, resistive heating, convective heating, inductive heating, and/or microwave heating. Denaturation may result in the first nucleic acid strand separating from the nucleic acid molecule (e.g., J-shaped adapter, such as an immobilized J-shaped adapter) to provide the second nucleic acid strand coupled to the nucleic acid molecule (e.g., J-shaped adapter).

Where the nucleic acid molecule is immobilized to a support, removal of the first nucleic acid strand may provide the second nucleic acid strand immobilized to the support via the immobilized nucleic acid molecule (e.g., immobilized J-shaped adapter). In some cases, the immobilized nucleic acid molecule is attached to the support via a chemical group (e.g., an amine).

The second nucleic acid strand may be used as a template for a subsequent amplification process. For example, sequencing may comprise bringing the second nucleic acid strand in contact with a sequencing primer, hybridizing the sequencing primer to the second nucleic acid strand, and subjecting the sequencing primer to a primer extension reaction. Sequencing of the second nucleic acid strand may comprise generation of a third nucleic acid strand comprising a third template nucleic acid sequence complementary to the second template nucleic acid sequence.

In some cases, the first sequencing read and the second sequencing read do not overlap. In some cases, the first sequencing read and the second sequencing read overlap. The overlap between the first sequencing read and the second sequencing read may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, or more bases. In some cases, the overlap between the first sequencing read and the second sequencing read may comprise at most about 70, 60, 50, 40, 30, 20, 19, 18, 17, 16, 15, 14, 13, 12, 11, 10, 9, 8, 7, 6, 5, or less bases. In other cases, the first sequencing read and the second sequencing read may completely overlap.

In some cases, the template nucleic acid molecule is a deoxyribonucleic acid (DNA) molecule or a ribonucleic acid (RNA) molecule. The support may comprise a bead or a planar surface. In some cases, the first capture sequence resides in a region of the nucleic acid molecule (e.g., J-shaped adapter) that comprises a cleavable base. The cleavable base may be selected from a uridine base and/or an 8-oxoguanine base. The nucleic acid molecule may comprise a replication block. In some cases, the second binding sequence of the nucleic acid molecule may comprise the replication block.

In another aspect, the present disclosure provides a method for paired-end sequencing, comprising bringing a first end of a first nucleic acid strand comprising a first template sequence in contact with a sequencing primer and subjecting the first nucleic acid strand to sequencing to (i) generate a first sequencing read in a first direction away from the first end and (ii) generate a second nucleic acid strand comprising a second template sequence complementary to the first template sequence and a first capture sequence. The first nucleic acid strand may be attached to a nucleic acid molecule (e.g., J-shaped adapter) comprising a second capture sequence complementary to the first capture sequence, a first binding sequence, and a second binding sequence hybridized to the first binding sequence. The nucleic acid molecule may be immobilized to a support (e.g., as described herein). The second capture sequence of the nucleic acid molecule may be adjacent to a second end of the first nucleic acid strand opposite the first end and hybridized to the first capture sequence of the second nucleic acid strand. The first nucleic acid strand from the nucleic acid molecule may be removed to provide the second nucleic acid strand attached the immobilized nucleic acid molecule. Where the nucleic acid molecule is immobilized to a support, removal of the first nucleic acid strand may provide the second nucleic acid strand immobilized to the support via the immobilized nucleic acid molecule (e.g., immobilized J-shaped adapter). The immobilized nucleic acid molecule may be attached to the support via a chemical group (e.g., an amine).

The second capture sequence of the nucleic acid molecule (e.g., J-shaped adapter) may be used as a sequencing primer to subject the second nucleic acid strand to a reaction under conditions sufficient to generate a second sequencing read in a second direction opposite the first direction. The second capture sequence of the nucleic acid molecule (e.g., J-shaped adapter) may be used as a sequencing primer to subject the second nucleic acid strand to sequencing to generate a second sequencing read in a second direction opposite the first direction.

In some cases, the first sequencing read and/or the second sequencing read may be further processed to identify the first template sequence or the second template sequence. The first sequencing read may be processed. The second sequencing read may be processed.

In some cases, generation of the first sequencing read or the second sequencing read (e.g., sequencing) comprises sequencing by synthesis, sequencing by hybridization, and/or sequencing by ligation.

In some cases, bringing a first end of a first nucleic acid strand comprising a first template sequence in contact with a sequencing primer comprises subjecting a complementary sequence of the first nucleic acid strand to conditions sufficient to hybridize the sequencing primer to the first nucleic acid strand. The complementary sequence of the first nucleic acid strand may be introduced into the first nucleic acid strand via ligation of another capture sequence comprising the complementary sequence. Sequences of a capture sequence may be selected for maximal hybridization with a target sequence and very low hybridization to any other sequence. For an adapter immobilized to a substrate, the first region comprising the first sequence may be disposed closer to the substrate than the second region comprising the second sequence, or vice versa (e.g., the second region comprising the second sequence may be disposed closer to the substrate than the first region comprising the first sequence). A first capture sequence attached to a first end of a nucleic acid molecule may be the same or different adapter from a second capture sequence attached to a second end (opposite the first end) of the nucleic acid molecule.

The sequencing primer may be subjected to a primer extension reaction. The first capture sequence may be subjected to a primer extension reaction. The primer extension reaction can comprise the use of a polymerizing enzyme such as a DNA polymerase or an RNA polymerase. The polymerase may be a non-processive DNA-dependent DNA polymerase. Alternatively, the polymerase may be a processive DNA-dependent DNA polymerase, such as Bst, Bst2, Bst3, or Phi29. The polymerase may also be an RNA-dependent DNA polymerase or an RNA-dependent RNA polymerase. Extension may take place in the presence of nucleoside triphosphate molecules (e.g., natural or non-natural nucleotides, and/or nucleotides labeled with a detectable moiety) or other nucleotide precursors such as modified nucleoside triphosphate molecules.

In some cases, subsequent to generation of the second nucleic acid strand, the second nucleic acid strand is ligated to the second binding sequence of the nucleic acid molecule (e.g., J-shaped adapter). In some cases, generation of the second sequencing read (e.g., sequencing) comprises generation of a third nucleic acid strand comprising a third template sequence complementary to the second template sequence. The second nucleic acid strand may be removed from the nucleic acid molecule. For example, the second nucleic acid strand may be subjected to conditions sufficient to denature the double-stranded nucleic acid molecule (e.g., a double-stranded nucleic acid molecule coupled to a J-shaped adapter, such as a double-stranded nucleic acid molecule comprising the second nucleic acid strand and the third nucleic acid strand including sequences complementary to those of the second strand). Denaturing the double-stranded nucleic acid molecule may comprise exposing the molecule or a portion thereof to a chemical denaturant, such as a salt, formamide, urea, guanidine hydrochloride, or an organic solvent. Alternatively or in addition, denaturation may be achieved by lowering a salt concentration and/or increasing a pH of a solution including the double-stranded nucleic acid molecule. Alternatively or in addition, partially denaturing the double-stranded nucleic acid molecule may comprise subjecting the double-stranded nucleic acid molecule to heating. Heating the double-stranded nucleic acid molecule may include optical heating, resistive heating, convective heating, inductive heating, and/or microwave heating. Denaturation may result in the first or second nucleic acid strand separating from the nucleic acid molecule (e.g., J-shaped adapter, such as an immobilized J-shaped adapter) to provide the second or third nucleic acid strand coupled to the nucleic acid molecule (e.g., J-shaped adapter). Where the nucleic acid molecule is immobilized on a support, the nucleic acid strand may be considered to be immobilized on the support via the immobilized nucleic acid molecule (e.g., immobilized J-shaped adapter).

In some cases, the third nucleic acid strand may be brought in contact with an additional sequencing primer and subjecting the third nucleic acid strand to a reaction under conditions sufficient to generate a third sequencing read. In other words, the third nucleic acid strand may be sequenced to provide a third sequencing read.

In some cases, prior to bringing the first end of the first nucleic acid strand comprising the first template sequence in contact with the sequencing primer, the nucleic acid molecule (e.g., J-shaped adapter) and a template nucleic acid molecule comprising a template sequence complementary to the first template sequence, a first end comprising a third capture sequence complementary to the second capture sequence of the nucleic acid molecule, and a second end may be provided. The template nucleic acid molecule may be subjected to conditions sufficient to hybridize the third capture sequence of the template nucleic acid molecule to the second capture sequence. Next, the nucleic acid molecule may be subjected to conditions sufficient to extend the second capture sequence to the second end of the template nucleic acid molecule, thereby generating the first nucleic acid strand attached to the nucleic acid molecule. In some cases, the nucleic acid molecule may be immobilized to a substrate (e.g., as described herein). Generation of the first nucleic acid strand attached to the nucleic acid molecule may comprise generating a third sequencing read. For example, the nucleic acid molecule may be subjected to sequencing to generate a third sequencing read, which sequencing comprises generation of a first nucleic acid strand attached to the nucleic acid molecule. Sequencing may comprise sequencing by synthesis, sequencing by hybridization, and/or sequencing by ligation. In some cases, the template nucleic acid molecule attached to nucleic acid molecule may be subjected to conditions sufficient (e.g., as described herein) to remove the template nucleic acid molecule.

In some cases, extension of the second capture sequence may comprise subjecting the second capture sequence of the immobilized nucleic acid molecule to an extension reaction. The extension reaction may comprise the use of a polymerase.

The template nucleic acid molecule may be a deoxyribonucleic acid (DNA) molecule or a (RNA) molecule. The support may comprise a bead or a planar surface. In some cases, the second capture sequence resides in a region of the nucleic acid molecule (e.g., J-shaped adapter) that comprises a cleavable base. Separation of the first sequence of the first strand from the third sequence of the second strand may comprise cleaving the cleavable base using a cleaving enzyme. The cleavable base may be selected from a uridine base and/or an 8-oxoguanine base. The nucleic acid molecule may comprise a replication block. In some cases, the second binding sequence of the nucleic acid molecule may comprise the replication block.

In some cases, the first sequencing read and the second sequencing read do not overlap. In other cases, the first sequencing read and the second sequencing read overlap. The overlap between the first sequencing read and the second sequencing read may comprise at least about 1, 2, 3, 4, 5, 6, 7, 8, 9, 10, 11, 12, 13, 14, 15, 16, 17, 18, 19, 20, 25, 30, 35, 40, 45, 50, 55, 60, or more bases. In some cases, the overlap between the first sequencing read and the second sequencing read may comprise at most about 70, 60, 50, 40, 30, 20, 19, 18, 17, 16, 15, 14, 13, 12, 11, 10, 9, 8, 7, 6, 5, or less bases. In other cases, the first sequencing read and the second sequencing read may completely overlap.

Figure 17A:
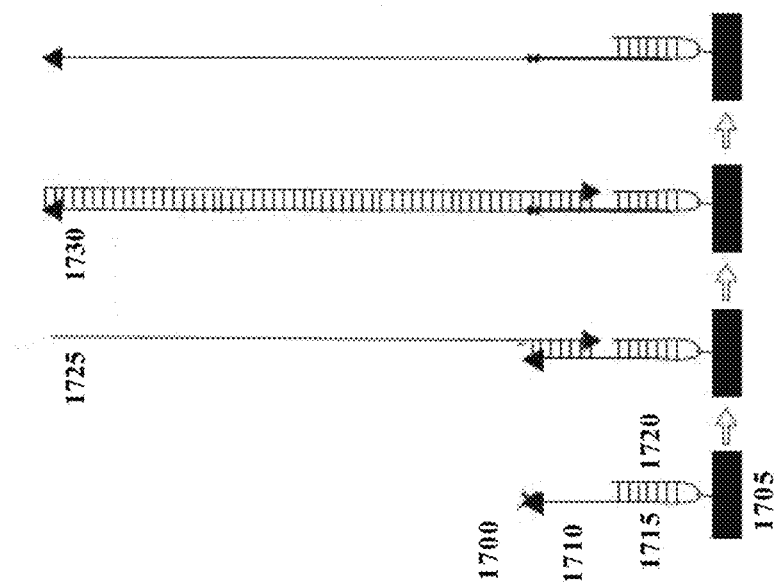
FIG. 17A-17B schematically illustrates a method of amplifying and sequencing a template nucleic acid molecule.

FIG. 17A-3B schematically illustrates a method of amplifying and sequencing a template nucleic acid molecule. FIG. 17A schematically illustrates a method of amplifying a template nucleic acid molecule. In the first panel, a nucleic acid molecule (e.g., a J-shaped adapter) 1700 is immobilized to a support 1705. The nucleic acid molecule 1700 comprises a first capture sequence 1710, a first binding sequence 1715, and a second binding sequence 1720. A first nucleic acid strand 1725 (from a template nucleic acid molecule) having a sequence complementary to the first capture sequence 1710 may hybridize to the nucleic acid molecule 1700. A polymerase (e.g., a DNA polymerase) may then attach to the 3' terminus of the nucleic acid molecule 1700 (indicated with an arrow head) and extend the first capture sequence 1710 to the end of the first nucleic acid strand 1725, thereby generating a complementary second nucleic acid strand 1730. Together, strands 1725 and 1730 form a double-stranded nucleic acid molecule. The first nucleic acid strand 1725 may then be removed by denaturation leaving the second nucleic acid strand 1730 immobilized on support 1705 via the nucleic acid molecule 1700.

Figure 17B:
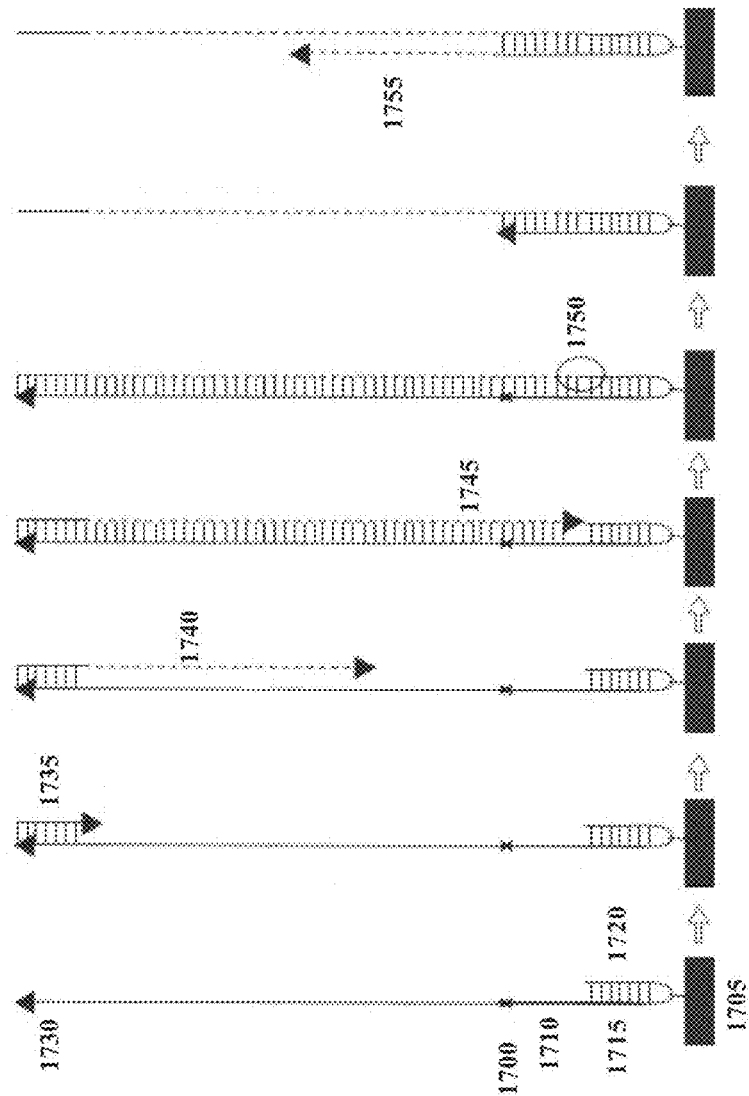

FIG. 17B schematically illustrates a method of amplifying and sequencing a template nucleic acid molecule. The second nucleic acid strand 1730 immobilized on support 1705 comprises a fourth capture sequence at the top end. A sequencing primer 1735 is hybridized to the fourth capture sequence at the top end of the second nucleic acid strand 1730 and sequencing commences 1740 to generate a third nucleic acid strand 1745 and a sequencing read corresponding to the second nucleic acid strand 1730. The sequencing strand (e.g., third nucleic acid strand 1745) may be extended by the polymerase until it reaches the top end of the second binding sequence 1720 of the nucleic acid molecule 1700. Alternatively, the sequencing strand (e.g., third nucleic acid strand 1745) may be removed by denaturation, and a new primer may be added to the fourth capture sequence at the top end of the second nucleic acid strand 1730 and extended to the top end of the second binding sequence 1720 with a polymerase (e.g., an exonuclease deficient non-strand displacing polymerase). The gap 1750 between the extended third nucleic acid strand 1745 and the top end of the second binding sequence 1720 may be ligated chemically or enzymatically (e.g., ligase enzymes). The first capture sequence 1710 comprises a cleavable group (e.g., a cleavable base). The second nucleic acid strand 1730 may be removed by excision of the cleavable base leaving the first capture sequence 1710 of the nucleic acid molecule 1700 as a sequencing primer. Next, sequencing is initiated with the first capture sequence 1710 (e.g., a sequencing primer) and performed on the third nucleic acid strand 1745, thereby obtaining a sequencing read corresponding to the third nucleic acid strand 1745. Based on the length of template nucleic acid molecule, sequencing of the second nucleic acid strand 1730 and the third nucleic acid strand 1745 may overlap partially, completely, or may contain an un-sequenced gap between the two end sequences.

In another aspect, the present disclosure provides a method for sequencing, comprising providing a support comprising a first nucleic acid strand comprising a first template sequence and a first capture sequence at a first end. The first nucleic acid strand may be immobilized to the support via a first nucleic acid molecule (e.g., first J-shaped adapter) that comprises a first binding sequence, a second binding sequence hybridized to the first binding sequence, and a second capture sequence.

The second capture sequence of the first nucleic acid molecule may be adjacent to a second end of the first nucleic acid strand opposite the first end. The support may also comprise a second nucleic acid molecule. The second nucleic acid molecule (e.g., second J-shaped adapter) may comprise a third binding sequence, a fourth binding sequence hybridized to the third binding sequence, and a third capture sequence. In some cases, the first and second nucleic acid molecules are attached to the support via one or more chemical groups (e.g., amines).

The first nucleic acid strand may be subjected to a reaction under conditions sufficient to (i) hybridize the first capture sequence of the first nucleic acid strand to the third capture sequence of the second nucleic acid molecule, (ii) generate a sequencing read in a first direction away from the first end, and (iii) generate a second nucleic acid strand comprising a second template sequence complementary to the first template sequence. In other words, the first nucleic acid strand may be subjected to sequencing, which sequencing comprises (i) hybridization the first capture sequence of the first nucleic acid strand to the third capture sequence of the second nucleic acid molecule, (ii) generation of a sequencing read in a first direction away from the first end, and (iii) generation a second nucleic acid strand comprising a second template sequence complementary to the first template sequence.

The complementary sequence of the nucleic acid strand may be introduced into the nucleic acid molecule via ligation of another capture sequence comprising the complementary sequence. Sequences of a capture sequence may be selected for maximal hybridization with a target sequence and very low hybridization to any other sequence. For an adapter immobilized to a substrate, the first region comprising the first sequence may be disposed closer to the substrate than the second region comprising the second sequence, or vice versa (e.g., the second region comprising the second sequence may be disposed closer to the substrate than the first region comprising the first sequence). A first capture sequence attached to a first end of a nucleic acid molecule may be the same or different adapter from a second capture sequence attached to a second end (opposite the first end) of the nucleic acid molecule.

The first nucleic acid strand and the second nucleic acid strand (e.g., a double-stranded nucleic acid molecule coupled to a J-shaped adapter, such as a double-stranded nucleic acid molecule comprising a first strand derived from a template nucleic acid molecule and a second strand including sequences complementary to those of the first strand) may be subjected to conditions sufficient to separate the first nucleic acid strand and the second nucleic acid strand, thereby providing the first nucleic acid strand attached to the support via the first nucleic acid molecule and the second nucleic acid strand attached to the support via the second nucleic acid molecule. Denaturing the double-stranded nucleic acid molecule may comprise exposing the molecule or a portion thereof to a chemical denaturant, such as a salt, formamide, urea, guanidine hydrochloride, or an organic solvent. Alternatively or in addition, denaturation may be achieved by lowering a salt concentration and/or increasing a pH of a solution including the double-stranded nucleic acid molecule. Alternatively or in addition, partially denaturing the double-stranded nucleic acid molecule may comprise subjecting the double-stranded nucleic acid molecule to heating. Heating the double-stranded nucleic acid molecule may include optical heating, resistive heating, convective heating, inductive heating, and/or microwave heating. Where the first nucleic acid molecule and second nucleic acid molecule are immobilized on a support, the first nucleic acid strand and the second nucleic acid strand may be considered to be immobilized on the support via the immobilized nucleic acid molecules (e.g., immobilized J-shaped adapters).

In some cases, the third binding sequence and the first binding sequence are the same. The fourth binding sequence and the second binding sequence may be the same. In some cases, the second capture sequence of the first immobilized nucleic acid molecule is the same as the third capture sequence of the second immobilized nucleic acid molecule. In some cases, the first capture sequence of the first nucleic acid strand is complementary to the third capture sequence of the second immobilized nucleic acid molecule.

In some cases, the sequencing process is repeated with a third immobilized nucleic acid molecule to generate another sequencing read, an amplified nucleic acid strand, and/or denaturation of the double stranded molecule. The third immobilized nucleic acid molecule may comprise a fifth binding sequence, a sixth binding sequence hybridized to the fifth binding sequence, and a fourth capture sequence. The sequencing read may be processed to identify the first template sequence. Sequencing may comprise sequencing by synthesis, sequencing by hybridization, and/or sequencing by ligation.

In some cases, sequencing and/or amplification may comprise the use of a polymerase. The capture sequence may be subjected to a primer extension reaction. The primer extension reaction can comprise the use of a polymerizing enzyme such as a DNA polymerase or an RNA polymerase. The polymerase may be a non-processive DNA-dependent DNA polymerase. Alternatively, the polymerase may be a processive DNA-dependent DNA polymerase, such as Bst, Bst2, Bst3, or Phi29. The polymerase may also be an RNA-dependent DNA polymerase or an RNA-dependent RNA polymerase. Extension may take place in the presence of nucleoside triphosphate molecules (e.g., natural or non-natural nucleotides, and/or nucleotides labeled with a detectable moiety) or other nucleotide precursors such as modified nucleoside triphosphate molecules.

In some cases, prior to providing the support, the first nucleic acid molecule (e.g., a J-shaped adapter) and a template nucleic acid molecule comprising a template sequence complementary to the first template sequence, a first end comprising a fourth capture sequence complementary to the second capture sequence of the first nucleic acid molecule, and a second end may be provided. The template nucleic acid molecule may be subjected to conditions sufficient to hybridize the fourth capture sequence of the template nucleic acid molecule to the second capture sequence. The first nucleic acid molecule may be subjected to conditions sufficient to extend the second capture sequence to the second end of the template nucleic acid molecule, thereby generating the first nucleic acid strand attached to the support and/or generating a second sequencing read. Extension of the second capture sequence may comprise subjecting the second capture sequence of the first immobilized nucleic acid molecule to an extension reaction. The extension reaction may comprise the use of a polymerase.

Sequencing may comprise sequencing by synthesis, sequencing by hybridization, and/or sequencing by ligation. The template nucleic acid molecule attached to the first nucleic acid molecule may be subjected to conditions sufficient to remove the template nucleic acid molecule.

In some cases, the template nucleic acid molecule is a deoxyribonucleic acid (DNA) molecule or a ribonucleic acid (RNA) molecule. The support may comprise a bead or a planar surface. In some cases, the second capture sequence resides in a region of the first nucleic acid molecule (e.g., J-shaped adapter) that comprises a cleavable base. The cleavable base may be selected from a uridine base and/or an 8-oxoguanine base. The nucleic acid molecule may comprise a replication block. In some cases, the second binding sequence of the nucleic acid molecule may comprise the replication block.

Figure 18:
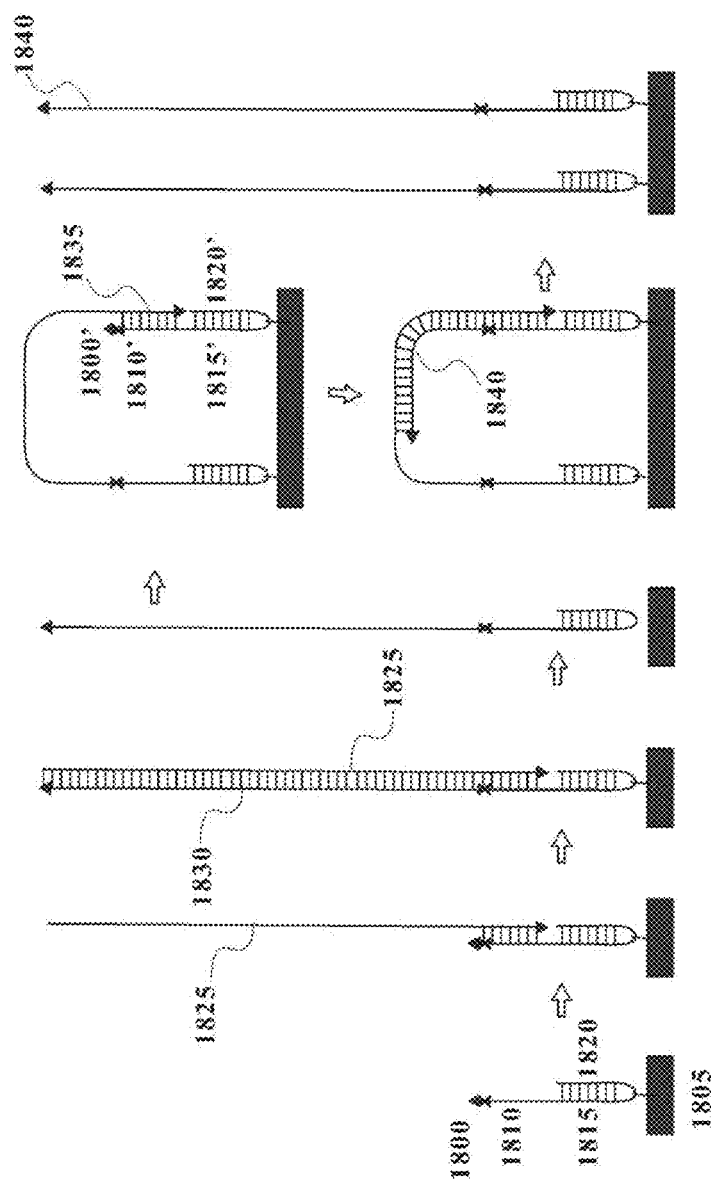
FIG. 18 schematically illustrates a method of bridged amplification and sequencing of a template nucleic acid molecule.

FIG. 18 schematically illustrates a method of amplifying and sequencing a template nucleic acid molecule. In the first panel, a nucleic acid molecule 1800 is immobilized to a support 1805. The nucleic acid molecule 1800 (e.g., a first J-shaped adapter) comprises a second capture sequence 1810, a first binding sequence 1815, and a second binding sequence 1820. A template nucleic acid strand 1825 (from a template nucleic acid molecule) having a sequence complementary to the second capture sequence 1810 may hybridize to the first nucleic acid molecule 1800. A polymerase (e.g., a DNA polymerase) may then attach to the 3' terminus of the first nucleic acid molecule 1800 (indicated with an arrow head) and extend the second capture sequence 1810 to the end of the template nucleic acid strand 1825, thereby generating a complementary first nucleic acid strand 1830. Together, strands 1825 and 1830 form a double-stranded nucleic acid molecule. The template nucleic acid strand 1825 may then be removed by denaturation leaving the first nucleic acid strand 1830 immobilized on support 1805 via the nucleic acid molecule 1800. The first nucleic acid strand 1830 comprises a first capture sequence at the first end (e.g., the top end) of strand 1830. The first nucleic acid strand 1830 bridges over towards a second nucleic acid molecule (e.g., a second J-shaped adapter) 1800' immobilized to the support 1805. The second nucleic acid molecule 1800' comprises a third capture sequence 1810', a third binding sequence 1815', and a fourth binding sequence 1820' hybridized to the third binding sequence 1815'. The first nucleic acid strand 1830 bridges over and the first capture sequence 1835 hybridizes to the third capture sequence 1810'. Next, the third capture sequence 1810' is extended in a direction away from the first end to generate a sequencing read and a second nucleic acid strand 1840 complementary to the first nucleic acid strand 1830. Strands 1830 and 1840 remain in a bridge configuration until they are denatured by heat and/or chemical approaches, thereby forming two single stranded strands 1830 and 1840. The newly formed single stranded molecules may bridge over again and bind to adjacent un-occupied nucleic acid molecules and the aforementioned process may continue until a cluster of nucleic acid strands are formed.

In another aspect, the present disclosure provides a method for sequencing a template nucleic acid molecule, comprising providing a support comprising (i) a first nucleic acid molecule (e.g., a first J-shaped adapter) that comprises a first binding sequence, a second binding sequence hybridized (e.g., as described herein) to the first binding sequence, and a first capture sequence; and (ii) a second nucleic acid molecule (e.g., a second J-shaped adapter) that comprises a third binding sequence, a fourth binding sequence hybridized to the third binding sequence, and a second capture sequence. Next, the first nucleic acid molecule may be brought in contact with a first nucleic acid strand derived from the template nucleic acid molecule to hybridize the first capture sequence of the first nucleic acid molecule to a third capture sequence of the first nucleic acid strand. The first nucleic acid strand comprises the third capture sequence that is complementary to the first capture sequence and a first template sequence. The first capture sequence of the first nucleic acid molecule may be used as a primer to subject the first nucleic acid strand to a reaction under conditions sufficient to generate a second nucleic acid strand complementary to the first nucleic acid strand. The second nucleic acid strand may comprise a second template sequence complementary to the first template sequence. The first nucleic acid strand may be immobilized to the support via the first nucleic acid molecule to conditions sufficient to (i) separate (e.g., as described herein) the third capture sequence from the first capture sequence of the first nucleic acid molecule and (ii) hybridize the third capture sequence to the second capture sequence of the second immobilized nucleic acid molecule. In some cases, the first nucleic acid molecule and the second nucleic acid molecule are attached to the support via one or more chemical groups (e.g., amines).

In some cases, the third capture sequence of the first nucleic acid strand may be hybridized to the second capture sequence of the second immobilized nucleic acid molecule to conditions sufficient to sequence the first nucleic acid read, thereby generating (i) a sequencing read corresponding to the first nucleic acid strand and (ii) a third nucleic acid strand comprising a second template sequence complementary to the first template sequence.

In some cases, the first nucleic acid strand comprises a fourth capture sequence and the second nucleic acid strand may comprise a fifth capture sequence complementary to the fourth capture sequence. The fifth capture sequence of the second nucleic acid strand may be brought in contact with a sequencing primer and the second nucleic acid strand may be subjected to sequencing to generate (i) a second sequencing read corresponding to the second nucleic acid strand and (ii) a fourth nucleic acid strand comprising a third template sequence complementary to the second template sequence of the second nucleic acid strand. Sequencing may comprise sequencing by synthesis, sequencing by hybridization, and/or sequencing by ligation.

In some cases, sequencing the first nucleic acid strand and generating the second nucleic acid strand may comprise subjecting the first capture sequence to a primer extension reaction (e.g., as described herein). The primer extension reaction may comprise the use of a polymerase (e.g., as described herein). Generation of a sequencing read corresponding to the second nucleic acid strand and/or generation of a fourth nucleic acid strand (e.g., sequencing the second nucleic acid strand) may comprise subjecting the second capture sequence to a primer extension reaction (e.g., as described herein). The primer extension reaction may comprise the use of a polymerase (e.g., as described herein).

In some cases, the template nucleic acid molecule is a deoxyribonucleic acid (DNA) molecule or a ribonucleic acid (RNA) molecule. The support may comprise a bead or a planar surface. In some cases, the first capture sequence resides in a region of the first nucleic acid molecule (e.g., J-shaped adapter) that comprises a cleavable base. The cleavable base may be selected from a uridine base and/or an 8-oxoguanine base. The nucleic acid molecule may comprise a replication block. In some cases, the second binding sequence of the nucleic acid molecule may comprise the replication block.

Figure 19:
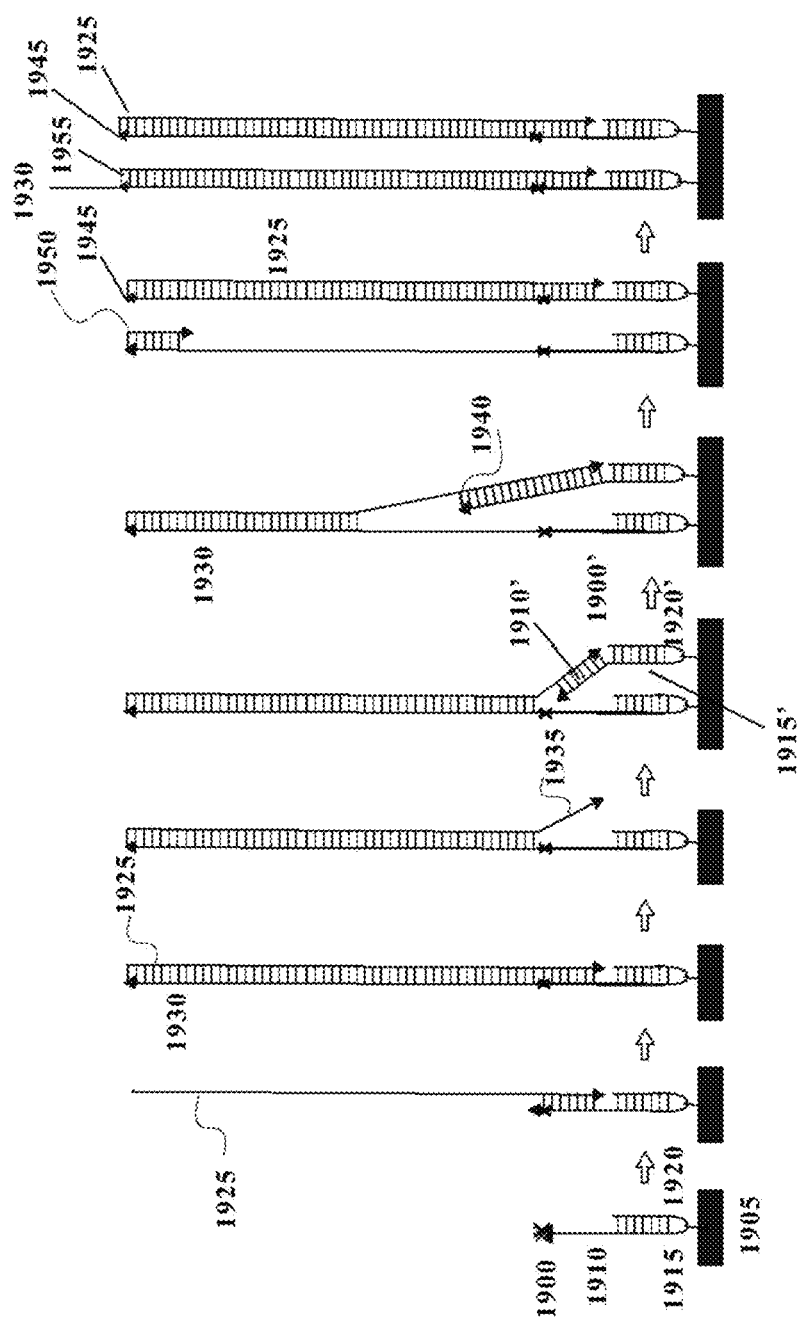
FIG. 19 schematically illustrates a method of wild-fire amplifying and sequencing of a template nucleic acid molecule.

FIG. 19 schematically illustrates a method of amplifying and sequencing a template nucleic acid molecule. In the first panel, a first nucleic acid molecule (e.g., a first J-shaped adapter) 1900 is immobilized to a support 1905. The first nucleic acid molecule 1900 comprises a first capture sequence 1910, a first binding sequence 1915, and a second binding sequence 1920 complementary to the first binding sequence 1915. A first nucleic acid strand 1925 (comprising a first template sequence) having a third capture sequence complementary to the first capture sequence 1910 may hybridize to the first nucleic acid molecule 1900. The first nucleic acid strand 1925 may also comprise a fourth capture sequence at the top end. A polymerase (e.g., a DNA polymerase) may then attach to the 3' terminus of the first nucleic acid molecule 1900 (indicated with an arrow head) and extend the first capture sequence 1910 to the top end of the first nucleic acid strand 1925, thereby generating a complementary second nucleic acid strand 1930. Together, strands 1925 and 1930 form a double-stranded nucleic acid molecule. The second nucleic acid strand 1930 comprises a fifth capture sequence at the top end that hybridizes to the fourth capture sequence of the first nucleic acid strand 1925. The first capture sequence 1910 may comprise sequences that melt and denature at lower temperatures. For example, at a lower temperature (e.g., 60° C.), region 1935 of the double-stranded nucleic acid molecule will denature and hybridize to an adjacent second capture sequence 1910' of a second nucleic acid 1900'. The second nucleic acid molecule (e.g., a second J-shaped adapter) 1900' may be immobilized to the support 1905. The second nucleic acid molecule 1900' may comprise a third binding sequence 1915' that hybridizes to a fourth binding sequence 1920'. The second capture sequence 1910' is then extended 1940 by a strand displacing polymerase to generate a sequencing read corresponding to the first nucleic acid strand 1925 and/or generate a third nucleic acid strand 1945 comprising a second template sequence complementary to the first template sequence. In parallel, an oligonucleotide (e.g. sequencing primer) 1950 in solution hybridizes to the fifth capture sequence of the second nucleic acid strand 1930 and is extended towards the support 1905. As a result, a second sequencing read corresponding to the second nucleic acid strand 1930 and/or a fourth nucleic acid strand 1955 comprising a third template sequence complementary to the second template sequence of the second nucleic acid strand 1930 may be generated.

In another aspect, the present disclosure provides a method for sequencing a template nucleic acid molecule, comprising providing a support comprising (i) a first nucleic acid molecule (e.g., a first J-shaped adapter) that comprises a first binding sequence, a second binding sequence hybridized to the first binding sequence, and a first capture sequence; and (ii) a second nucleic acid molecule (e.g., a second J-shaped adapter) that comprises a third binding sequence, a fourth binding sequence hybridized to the third binding sequence, and a second capture sequence. The first nucleic acid molecule may be brought in contact with a first nucleic acid strand derived from the template nucleic acid molecule to hybridize the first capture sequence of the first nucleic acid molecule to a third capture sequence of the first nucleic acid strand. The first nucleic acid strand may comprise the third capture sequence that is complementary to the first capture sequence and a first template sequence. The first capture sequence of the first nucleic acid molecule may be used as a primer to subject the first nucleic acid strand to a reaction under conditions sufficient to generate a second nucleic acid strand complementary to the first nucleic acid strand. The first capture sequence of the first nucleic acid molecule may be used as a sequencing primer to sequence the first nucleic acid strand, thereby generating a sequencing read and a second nucleic acid strand complementary to the first nucleic acid strand. The second nucleic acid strand may comprise a second template sequence complementary to the first template sequence. The second nucleic acid may be hybridized to a first portion of the first nucleic acid strand comprising the third capture sequence and a second portion of the first nucleic acid strand that does not comprise the third capture sequence. The first capture sequence of the first nucleic acid molecule hybridized to the third capture sequence of the first nucleic acid strand may be subjected to conditions sufficient to at least partially separate the first capture sequence from the third capture sequence. In some cases, the first nucleic acid molecule and the second nucleic acid molecule are attached to the support via one or more chemical groups (e.g., amines).

An adapter may attach to a nucleic acid molecule via hybridization or ligation (e.g., as described herein). For example, a nucleic acid molecule (e.g., an adapter, such as a J-shaped adapter immobilized to a substrate) may hybridize to a complementary sequence of a single-stranded nucleic acid molecule. The complementary sequence of the nucleic acid molecule may be introduced into the nucleic acid molecule via ligation of another adapter comprising the complementary sequence. As described elsewhere herein, an adapter may include two or more regions having different characteristics. For example, an adapter may include a first region comprising a first sequence and a second region comprising a second sequence. In some cases, the first region may comprise at least 5 bases, such as 10, 15, 20, 25, 30, 35, 40, 45 or more bases. The first region may comprise one or more adenine, thymine, uridine, and inosine bases, and may in some cases comprise only adenine, thymine, uridine, and inosine bases. The second region may comprise the same or a different number of bases. Sequences of an adapter may be selected for maximal hybridization with a target sequence and very low hybridization to any other sequence. For an adapter immobilized to a substrate, the first region comprising the first sequence may be disposed closer to the substrate than the second region comprising the second sequence, or vice versa (e.g., the second region comprising the second sequence may be disposed closer to the substrate than the first region comprising the first sequence). A first adapter attached to a first end of a nucleic acid molecule may be the same or different adapter from a second adapter attached to a second end (opposite the first end) of the nucleic acid molecule.

In some cases, all or a portion of the first capture sequence hybridized to the third capture sequence has a first melting point and the second nucleic acid strand hybridized to the second portion of the first nucleic acid strand has a second melting point that is higher than the first melting point. At least partially separating the first capture sequence from the third capture sequence may comprise exposing the first capture sequence hybridized to the third capture sequence to a chemical denaturant. The chemical denaturant may be selected from the group consisting of a salt, formamide, urea, guanidine hydrochloride, and an organic solvent. At least partially separating the first capture sequence from the third capture sequence may be performed under isothermal conditions. The first melting point may be at least about 0.5° C., 1° C., 2° C., 3° C., 4° C., 5° C., 6° C., 7° C., 8° C., 9° C., 10° C., 15° C., 20° C., 25° C., 30° C., or more lower than the second melting point. In some cases, the first melting point may be at most about 40° C., 30° C., 20° C., 15° C., 10° C., 9° C., 8° C., 7° C., 6° C., 5° C., 4° C., 3° C., 2° C., 1° C., 0.5° C. or less lower than the second melting point.

Alternatively or in addition, partial denaturation may be achieved by lowering a salt concentration and/or increasing a pH of a solution including the double-stranded nucleic acid molecule. Alternatively or in addition, partially denaturing the double-stranded nucleic acid molecule may comprise heating the molecule. For example, at least partially separating the first capture sequence from the third capture sequence may comprise heating the double-stranded nucleic acid molecule to a temperature higher than the first melting point and lower than the second melting point. In some cases, at least partially separating the first capture sequence from the third capture sequence may comprise heating the double-stranded nucleic acid molecule to partially denature the double-stranded nucleic acid molecule. Heating the double-stranded nucleic acid molecule may include optical heating, resistive heating, convective heating, inductive heating, and/or microwave heating. Partial denaturation may result in at most a portion of the first strand of the double-stranded nucleic acid molecule separating from the second strand of the double-stranded nucleic acid molecule. At the end of partial denaturation of the double-stranded nucleic acid molecule, at least a portion of the double-stranded nucleic acid molecule may remain double-stranded. For example, partial denaturation may result in the formation of a bubble in the double-stranded nucleic acid molecule. Partial denaturation may result in the separation of the first capture sequence of the first nucleic acid molecule from the third capture sequence of the first nucleic acid strand. In some cases, a bubble formed as a result of partial denaturation may expand to an end of the double-stranded nucleic acid molecule.

In some cases, the first capture sequence, or a portion thereof, may be brought in contact with a primer molecule such that the first capture sequence, or a portion thereof, hybridizes (e.g., as described herein) to the primer molecule. The primer molecule hybridized to the first capture sequence, or a portion thereof, may be subjected to a primer extension reaction (e.g., as described herein). A polymerase (e.g., as described herein) may then bind to and extend the primer molecule (e.g., as described herein), further separating the first and second strands and resulting in an increase in the size of the bubble.

Extension of the primer molecule may result in separation of two ends of the double-stranded nucleic acid molecule, such that the molecule is open ("unzipped") at an end. The further separation of the first and second strands may facilitate hybridization of a primer molecule to, for example, the first capture sequence of the first strand. In some cases, the primer extension reaction separates (e.g., as described herein) the first capture sequence and the third capture sequence of the first nucleic acid strand. The first capture sequence and the third capture sequence may also be separated. In some cases, this primer molecule may be immobilized to a substrate.

Subsequent to at least partially separating the first capture sequence from the third capture sequence, the third capture sequence of the first nucleic acid strand hybridizes to the second capture sequence of the second nucleic acid molecule. The second capture sequence may be subjected to conditions sufficient to (i) generate a sequencing read corresponding to the first nucleic acid strand and (ii) generate a third nucleic acid strand comprising a third template sequence, which third template sequence is complementary to the first template sequence of the first nucleic acid strand. In other words, the second capture sequence may be used as a sequencing primer and the first nucleic acid strand may be sequenced. Sequencing the first nucleic acid strand may comprise generation of (i) a sequencing read corresponding to the first nucleic acid strand and (ii) a third nucleic acid strand comprising a third template sequence, which third template sequence is complementary to the first template sequence of the first nucleic acid strand. Generation of the sequencing read and the third nucleic acid strand may comprise a primer extension reaction (e.g., as described herein). The primer extension reaction may comprise the use of a polymerase. Sequencing may comprise sequencing by synthesis, sequencing by hybridization, sequencing by ligation.

A polymerase may bind to and extend the primer molecule toward another end of the double-stranded nucleic acid molecule (e.g., as described herein). In some cases, an additional primer molecule (e.g., a primer molecule in solution that is not immobilized to a substrate) may hybridize to an end of the second strand (e.g., an end that is not attached to a substrate), and a polymerase molecule may bind to and extend the additional primer molecule (e.g., as described herein) to generate a fourth strand that is complementary to the second strand. In some cases, the additional primer molecule may be immobilized to a support. By repeating the processes described herein, multiple copies of the initial single-stranded nucleic acid molecule (e.g., the first nucleic acid strand), as well as its complement, may be generated. In some cases, 1 or more copies of an initial single-stranded nucleic acid molecule, and/or a complement thereof, may be generated. For example, 2, 3, 4, 5, 6, 7, 8, 9, 10, 20, 30, 40 50, 60, 70, 80, 90, 100, 150, 200, 250, 500, 750, 1,000, 1,500, 2,000, 2,500, 5,000, 7,500, 10,000, 15,000, 20,000, 50,000, 75,000, 100,000, 500,000, 1,000,000 or more copies may be generated.

In some cases, the first nucleic acid strand may comprise a fourth capture sequence and the second nucleic acid strand may comprise a fifth capture sequence complementary to the fourth capture sequence. The fifth capture sequence of the second nucleic acid strand may be brought in contact with a sequencing primer and the second nucleic acid strand may be sequenced to (i) generate a second sequencing read corresponding to the second nucleic acid strand and (ii) generate a fourth nucleic acid strand comprising a third template sequence complementary to the second template sequence of the second nucleic acid strand. The sequencing read may be used to identify the first template sequence of the first nucleic acid strand, thereby sequencing the template nucleic acid molecule.

In some cases, a partially denatured region may also form near another end of the double-stranded nucleic acid molecule. For example, the double-stranded nucleic acid molecule may include a fourth capture sequence at a second end of the first strand of the double-stranded nucleic acid molecule and a fifth capture sequence having sequence complementarity to the first region at a second end of the second strand of the double-stranded nucleic acid molecule. The fourth capture sequence may not include specified portions of low or high melting points. Alternatively, the fourth capture sequence hybridized to the fifth capture sequence may include one or more low melting point regions and one or more high melting point regions. The one or more low melting point regions may be susceptible to partial denaturation (e.g., as described herein). In some cases, the fourth capture sequence may be the same as, or similar to, the first capture sequence. For example, both the first capture sequence and the fourth capture sequence may include a single low melting point region that may be flanked by two high melting point regions.

In cases, where the fourth capture sequence hybridized to the fifth capture sequence is susceptible to partial denaturation, a bubble region formed upon partial separation of the first and second strands in the fourth and fifth capture sequences may be expanded to the second end of the double-stranded nucleic acid molecule. In some cases, expanding the bubble may comprise hybridizing a primer molecule to a sequence of the single-stranded region of the bubble and extending the primer molecule to the end of the double-stranded nucleic acid molecule. Upon expansion of the bubble and separation of the ends of the double-stranded nucleic acid molecule, a primer molecule may hybridize to the fourth and fifth capture sequence and then be extended to generate a strand having sequence complementarity to the first or second strand of the double-stranded nucleic acid molecule. The primer molecule may be free in solution or immobilized to a support. This process may also be repeated to facilitate the generation of multiple copies of first and second strands of the double-stranded nucleic acid molecule.

In some cases, the template nucleic acid molecule is a deoxyribonucleic acid (DNA) molecule or a ribonucleic acid (RNA) molecule. The support may comprise a bead or a planar surface. In some cases, the first capture sequence resides in a region of the first nucleic acid molecule (e.g., J-shaped adapter) that comprises a cleavable base. The cleavable base may be selected from a uridine base and/or an 8-oxoguanine base. The nucleic acid molecule may comprise a replication block.

Accordingly, the methods described herein may be used to amplify and/or sequence a template nucleic acid molecule without the need for high temperatures or complex reaction schemes. The amplification and/or sequencing processes may be repeated one or more times to generate additional copies of a template nucleic acid molecule and/or its complement. The template nucleic acid molecule and copies thereof, and/or its complement and copies thereof, may subsequently undergo additional processing and/or analysis including sequencing (e.g., as described herein).

Figure 20:
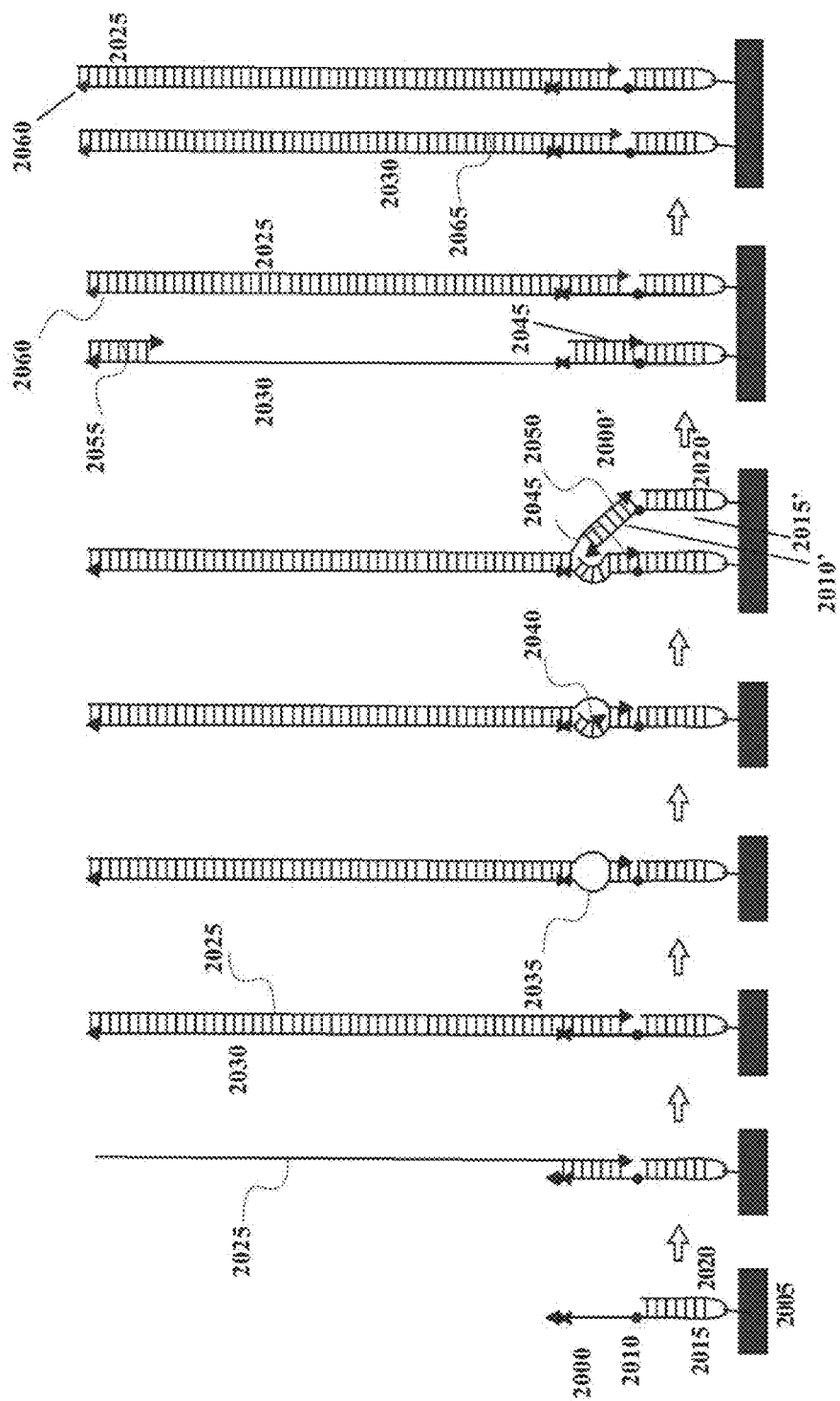
FIG. 20 schematically illustrates a method of a bubble expansion amplification and sequencing of a template nucleic acid molecule.

FIG. 20 schematically illustrates a method of amplifying and sequencing a template nucleic acid molecule. In the first panel, a first nucleic acid molecule (e.g., a first J-shaped adapter) 2000 is immobilized to a support 2005. The nucleic acid molecule 2000 comprises a first capture sequence 2010, a first binding sequence 2015, and a second binding sequence 2020 complementary to the first binding sequence 2015. A first nucleic acid strand 2025 (comprising a first template sequence) having a third capture sequence complementary to the first capture sequence 2010 may hybridize to the first nucleic acid molecule 2000. A polymerase (e.g., a DNA polymerase) may then attach to the 3' terminus of the first nucleic acid molecule 2000 (indicated with an arrow head) and extend the first capture sequence 2010 (as a primer) to the top end of the first nucleic acid strand 2025, thereby generating a complementary second nucleic acid strand 2030. Together, strands 2025 and 2030 form a double-stranded nucleic acid molecule. The first capture sequence 2010 may be configured to create a bubble (region of separation between the double-stranded nucleic acid molecule) at a specified temperature. At least a portion of the first capture sequence 2010 hybridized to the third capture sequence has a lower melting point than that of the second nucleic acid strand 2030 hybridized to the second portion of the first nucleic acid strand 2025 that does not comprise the third capture sequence. The temperature is raised to create a "bubble" 2035 between the double-stranded nucleic acid molecule. The "bubble" 2035 may extend such that the first capture sequence 2010 is partially separated from the third capture sequence of strand 2025. As described herein, the temperature may be elevated to increase the likelihood of localized denaturation or bubble formation in the double-stranded nucleic acid molecule. The regions of denaturation may be controlled by placing sequences in the nucleic acid template that are likely to denature at lower temperatures (e.g., as described herein). For example, the double-stranded nucleic acid molecule may comprise a region including a sequence of first capture sequence 2010 hybridized to a complementary sequence of second nucleic acid strand 2030 that has a low melting point. The low melting point region may be localized close to an end of double-stranded nucleic acid molecule.

Primer molecule 2040 may then hybridize to the single-stranded region of second nucleic acid strand 2030 in "bubble" 2035. A polymerase may be used to extend primer molecule 2040 to an end of strand 2030 (e.g., towards the support 2005) to accelerate generation of a partial complementary strand 2045, forcing the "bubble" 2035 to expand, and separate the end of strand 2030 from an end of strand 2025. The end of strand 2025 may then hybridize 2050 to a second capture sequence 2010' of second nucleic acid molecule (e.g., a second J-shaped adapter) 2000' that may be immobilized to substrate 2005. The second nucleic acid molecule 2000' may also comprise a third binding sequence 2015', and a fourth binding sequence 2020' complementary to the third binding sequence 2015'. A polymerase may then be used to extend the second capture sequence 2010' and generate a strand 2060 that is complementary to strand 2025. A primer molecule 2055 may then hybridize to strand 2030. A polymerase may then be used to sequence strand 2030 and generate a sequencing read and a strand that is complementary to strand 2030. The net effect of this process is the formation of two double-stranded nucleic acid molecules from an original single-stranded template nucleic acid molecule. The process may be repeated to further amplify the template nucleic acid molecule and its complement using the surface-bound nucleic acid molecules and other oligonucleotides (e.g., primers) in solution.

In some cases, a nucleic acid molecule may be amplified and/or sequenced from both ends of a double-stranded nucleic acid molecule. A single-stranded nucleic acid molecule may comprise a first adapter at a first end of the molecule and a second adapter at a second end (opposite the first end) of the molecule. Each adapter may include two or more different sequences. For example, the first adapter may include a first sequence and a second sequence, and the second adapter may include a third sequence and a fourth sequence. The first end of the single-stranded nucleic acid molecule may hybridize to an adapter that may be attached to a substrate, and a polymerase may be used to extend the adapter to the second end of the single-stranded nucleic acid molecule, thereby generating a second strand that is complementary to the template single-stranded nucleic acid molecule. The first sequence and the third sequence may, upon hybridization to complementary sequences in the second strand, form regions having low melting points, while the second and fourth sequence may form regions having high melting points. The double-stranded nucleic acid molecule comprising the first and second nucleic acid strands may then be partially denatured (e.g., as described herein). In some cases, a bubble may form at the site of the first sequence, and no bubble may form at the site of the third sequence. In some cases, a bubble may form at the site of the third sequence, and no bubble may form at the site of the first sequence. In certain cases, a first bubble may form at the site of the first sequence and a second bubble may form at the site of the third sequence. A first primer molecule may attach to a single strand in the first bubble, and a second primer molecule may attach to a single strand in the second bubble. Polymerases may be used to extend the first and second primers to, for example, (different) ends of the double-stranded nucleic acid molecule. Third and fourth primer molecules may then hybridize to single-stranded portions of the double-stranded nucleic acid molecule and be extended using polymerases to generate two double-stranded nucleic acid molecules.

In another aspect, the present disclosure provides a method for sequencing a template nucleic acid molecule, comprising providing a nucleic acid strand corresponding to the template nucleic acid molecule. The nucleic acid strand may be immobilized to a support. The nucleic acid strand comprises (i) a first nucleic acid strand derived from the template nucleic acid molecule, the first nucleic acid strand comprising a first capture sequence and a first template sequence, and (ii) a second capture sequence hybridized to the first capture sequence of the first nucleic acid strand. The first capture sequence and the second capture sequence may be separated by a single-stranded region. The nucleic acid strand may be subjected to sequencing to generate (i) a sequencing read corresponding to the first nucleic acid strand of the nucleic acid strand, and (ii) a second nucleic acid strand complementary to first nucleic acid strand, which second nucleic acid strand comprises a second template sequence complementary to the first template sequence. The single-stranded region of the immobilized nucleic acid strand may be brought into contact with a primer molecule and the nucleic acid strand may be subjected to conditions sufficient to extend the primer molecule, thereby separating the first nucleic acid strand and the second nucleic acid strand. The sequencing read may be used to identify the first template sequence of the first nucleic acid strand, thereby sequencing the template nucleic acid molecule. The nucleic acid molecule may be attached to the support via a chemical group (e.g., an amine).

In some cases, prior to providing the nucleic acid strand, the first nucleic acid strand may be immobilized to the support in contact with a capture nucleic acid molecule to hybridize the second capture sequence of the capture nucleic acid molecule to the first capture sequence of the first nucleic acid strand. The capture nucleic acid molecules may comprise the second capture sequence, a first binding sequence, and a second binding sequence hybridized to the first binding sequence. The second capture sequence of the capture nucleic acid molecule may be used as a primer to subject the first nucleic acid strand to sequencing to generate (i) a second sequencing read corresponding to the first nucleic acid strand and (ii) a third nucleic acid strand complementary to the first nucleic acid strand. The third nucleic acid strand may comprise a third template sequence complementary to the first template sequence. The third nucleic acid strand may be removed from the first nucleic acid strand and the first capture sequence hybridized to the second capture sequence may be removed (e.g., as described herein), thereby providing the nucleic acid strand (e.g., an immobilized nucleic acid strand).

Sequencing may comprise sequencing by synthesis, sequencing by hybridization, and/or sequencing by ligation. Generation of the sequencing read and/or the second sequencing read and the second nucleic acid strand and/or the third nucleic acid strand may comprise subjecting the nucleic acid strand to a primer extension reaction (e.g., as described herein). The primer extension reaction may comprise the use of a polymerase (e.g., as described herein).

In some cases, the template nucleic acid molecule is a deoxyribonucleic acid (DNA) molecule or a ribonucleic acid (RNA) molecule. The support may comprise a bead or a planar surface. In some cases, the second capture sequence resides in a region of the capture nucleic acid molecule (e.g., J-shaped adapter) that comprises a cleavable base. The cleavable base may be selected from a uridine base and/or an 8-oxoguanine base. The capture nucleic acid molecule may comprise a replication block.

In some cases, a sequencing primer may be brought in contact with the second nucleic acid strand and the second nucleic acid strand may be subjected to conditions sufficient to (i) generate a third sequencing read corresponding to the second nucleic acid strand and (ii) generate a fourth nucleic acid strand. The fourth nucleic acid strand may comprise a fourth template sequence that is complementary to the second template sequence of the second nucleic acid strand. In some cases, generation of the sequencing read and the second nucleic acid strand and extension of the primer molecule may occur simultaneously. In some cases, generation of the sequencing read and the second nucleic acid strand may occur before the extension of the primer molecule.

Figure 21:
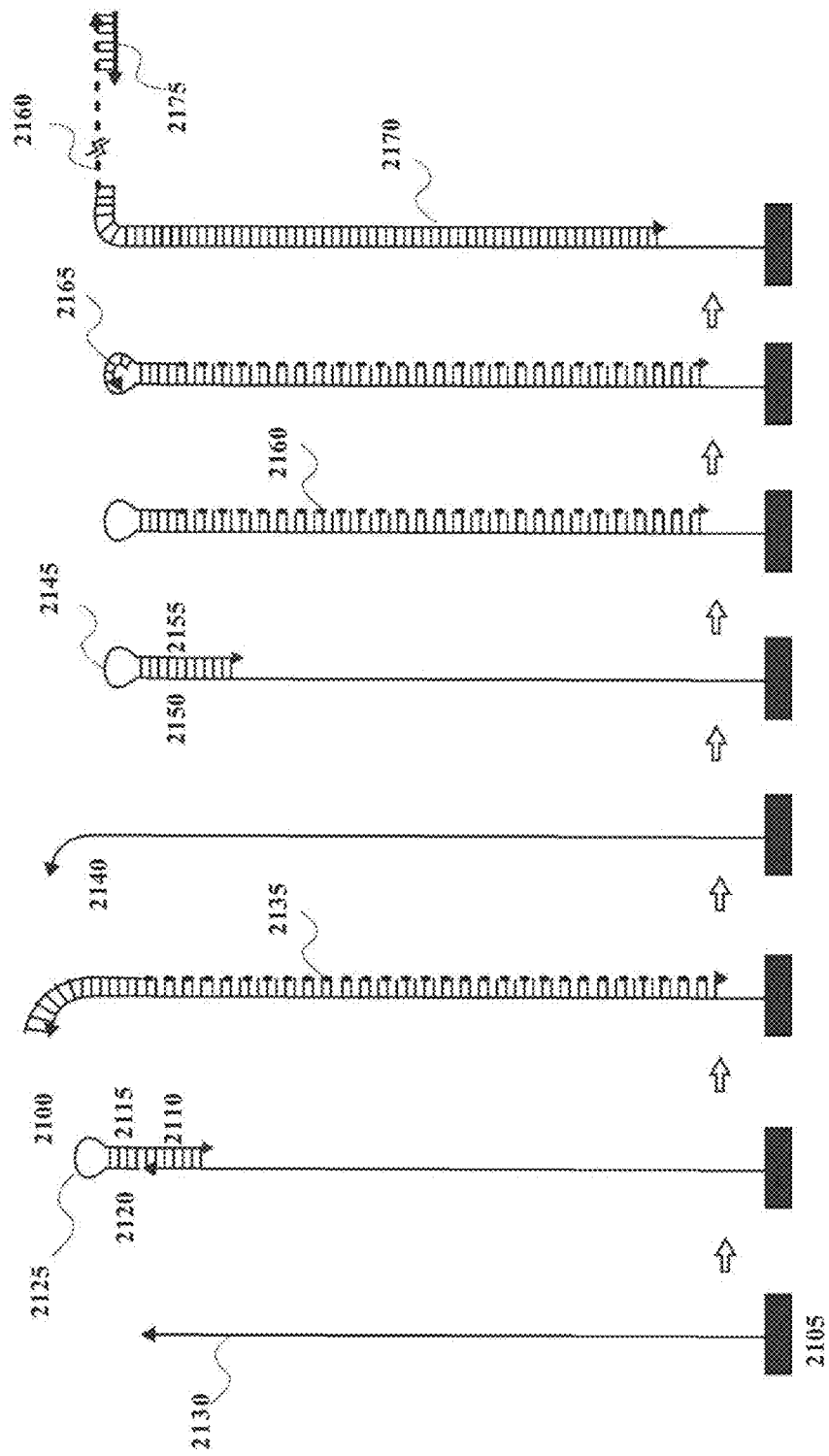
FIG. 21 schematically illustrates a method of amplifying and sequencing a template nucleic acid molecule using adapters attached to the free end of the template nucleic acid molecule.

FIG. 21 schematically illustrates a method of amplifying and sequencing a template nucleic acid molecule. In the first panel, a first nucleic acid strand 2130 (comprising a first template sequence) is immobilized to a support 2105. The first nucleic acid strand 2130 may comprise a first capture sequence. The first capture sequence of strand 2130 may hybridize to a second capture sequence 2110 of a capture nucleic acid molecule 2100. The capture nucleic acid molecule 2100 may also comprise a first binding sequence 2115, a second binding sequence 2120 complementary to the first binding sequence 2115, and a single stranded region 2125. A polymerase (e.g., a DNA polymerase) may attach to a terminus (e.g., 3' terminus) of the capture nucleic acid molecule 2100 (indicated with an arrow head) and extend the second capture sequence 2110 (as a primer) to the end of the first nucleic acid strand 2130 that is coupled to support 2105, thereby generating a first sequencing read corresponding to the first nucleic acid strand 2130 and a third nucleic acid strand 2135 complementary to the first nucleic acid strand 2130. The extension may occur using any polymerase, such as a polymerase with strand displacing activity for opening the capture nucleic acid molecule and/or polymerase with 3' to 5' exonuclease activity to chew back overhangs. During generation of third nucleic acid strand 2135, nucleic acid strand 2130 may also be extended to an end of binding sequence 2115 of capture nucleic acid molecule 2100. The third nucleic acid strand 2135 may be removed from the first nucleic acid strand 2130 by denaturation, thereby forming an immobilized nucleic acid 2140, which immobilized nucleic acid 2140 comprises a sequence complementary to binding sequence 2120, linking sequence 2125, and binding sequence 2115. By varying the reaction conditions, the first nucleic acid strand 2130 may fold back creating a new "J-structure". The immobilized nucleic acid molecules 2130 and 2140 may be attached to the support 2105 via a chemical group. The immobilized nucleic acid strand 2140 may comprise a first binding sequence 2150, a second binding sequence 2155 complementary to the first binding sequence 2150, and a single-stranded region 2145. Binding sequences 2150 and 2155 of strand 2140 may be the same as or complementary to binding sequences 2120 and 2115 of capture nucleic acid molecule 2100 and may be complementary to one another. The second binding sequence 2155 may be extended through a second extension reaction to generate a sequencing read corresponding to the first nucleic acid strand 2130 and a second nucleic acid strand 2160 complementary to the first nucleic acid strand 2130. The single-stranded region 2145 may be brought in contact with a primer molecule 2165. The primer molecule 2165 may be extended using a strand-displacing polymerase, thereby separating the first nucleic acid strand 2130 and the second nucleic acid strand 2160. A sequencing primer 2175 may then contact the second nucleic acid strand 2160 to generate a third sequencing read corresponding to the second nucleic acid strand and a fourth nucleic acid strand 2170 comprising a fourth template sequence that is complementary to the second template sequence of the second nucleic acid strand 2160.

Figure 22:
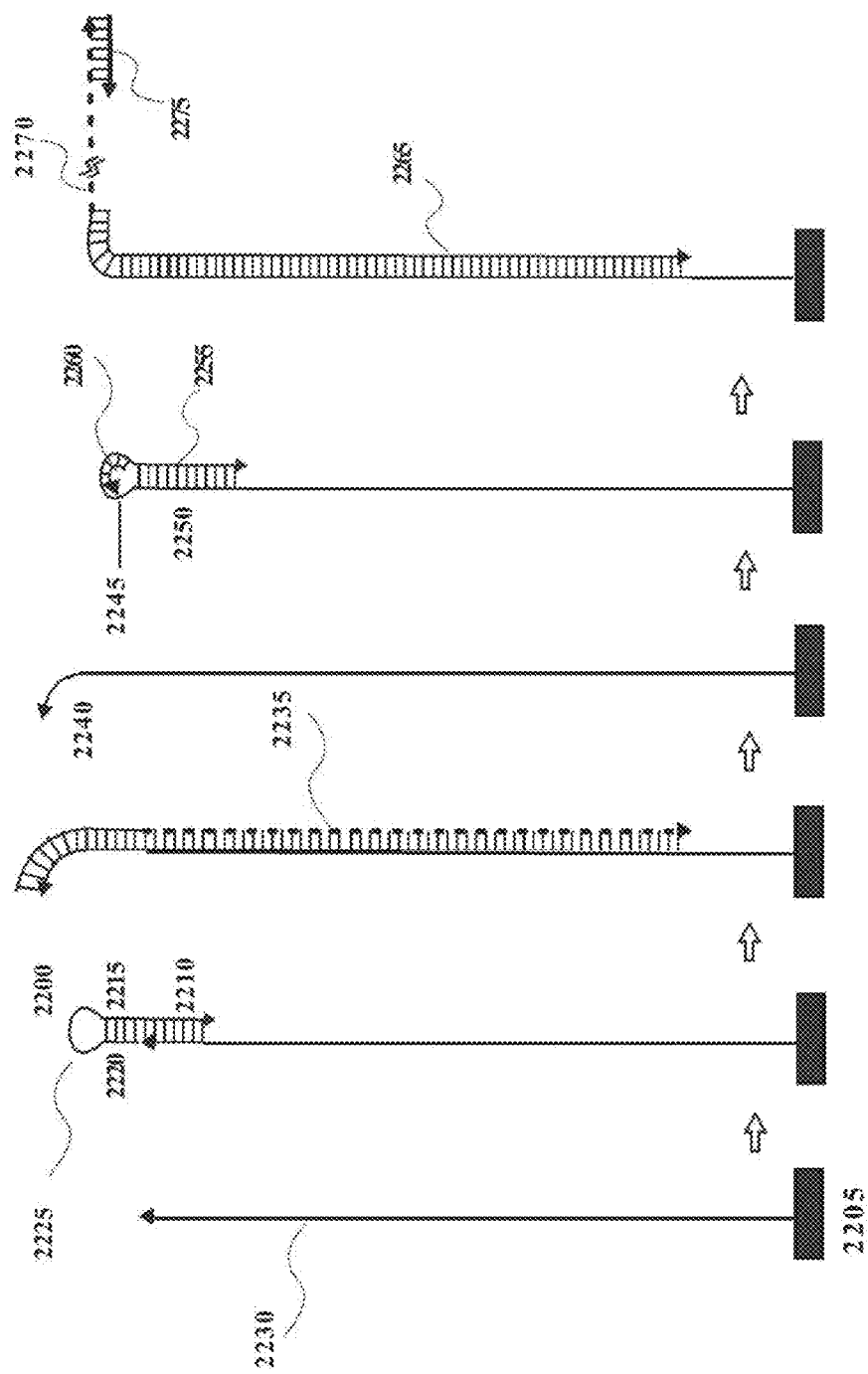
FIG. 22 schematically illustrates another method of amplifying and sequencing a template nucleic acid molecule using adapters attached to the free end of the template nucleic acid molecule.

FIG. 22 schematically illustrates a method of amplifying and sequencing a template nucleic acid molecule. In the first panel, a first nucleic acid strand 2230 (comprising a first template sequence) is immobilized to a support 2205. The first nucleic acid strand 2230 may comprise a first capture sequence. The first capture sequence of strand 2230 may hybridize to a second capture sequence 2210 of a capture nucleic acid molecule 2200. The capture nucleic acid molecule 2200 may also comprise a first binding sequence 2215, a second binding sequence 2220 complementary to the first binding sequence 2215, and a single stranded region 2225. A polymerase (e.g., a DNA polymerase) may attach to a terminus (e.g., 3' terminus) of the capture nucleic acid molecule 2200 (indicated with an arrow head) and extend the second capture sequence 2210 (as a primer) to the end of the first nucleic acid strand 2230 that is coupled to support 2205, thereby generating a first sequencing read corresponding to the first nucleic acid strand 2230 and a third nucleic acid strand 2235 complementary to the first nucleic acid strand 2230. The extension may occur using any polymerase, such as a polymerase with strand displacing activity for opening the capture nucleic acid molecule and/or polymerase with 3' to 5' exonuclease activity to chew back overhangs. During generation of third nucleic acid strand 2235, nucleic acid strand 2230 may also be extended to an end of binding sequence 2215 of capture nucleic acid molecule 2200. The third nucleic acid strand 2235 may be removed from the first nucleic acid strand 2230 by denaturation, thereby forming an immobilized nucleic acid 2240, which immobilized nucleic acid 2240 comprises a sequence complementary to binding sequence 2220, linking sequence 2225, and binding sequence 2215. By varying the reaction conditions, the first nucleic acid strand 2230 may fold back creating a new "J-structure". The immobilized nucleic acid molecules 2230 and 2240 may be attached to the support 2205 via a chemical group. The immobilized nucleic acid strand 2240 may comprise a first binding sequence 2250, a second binding sequence 2255 complementary to the first binding sequence 2250, and a single-stranded region 2245. Binding sequences 2250 and 2255 of strand 2240 may be the same as or complementary to binding sequences 2220 and 2215 of capture nucleic acid molecule 2200 and may be complementary to one another. The second binding sequence 2255 may be extended through a second extension reaction to generate a sequencing read corresponding to the first nucleic acid strand 2230 and a second nucleic acid strand 2270 complementary to the first nucleic acid strand 2230. Simultaneously, the single-stranded region 2245 may be brought in contact with a primer molecule 2260. The primer molecule 2260 may be extended using a strand-displacing polymerase, thereby separating the first nucleic acid strand 2230 and the second nucleic acid strand 2270 to generate fourth nucleic acid strand 2265 comprising a fourth template sequence that is complementary to the first template sequence of the first nucleic acid strand 2230. A sequencing primer 2275 may then contact the second nucleic acid strand 2270 to generate a third sequencing read corresponding to the second nucleic acid strand 2270 and an additional nucleic acid strand.

One or more processes of the methods described herein may be performed within a droplet (e.g., emulsion PCR). Beads coated with nucleic acid molecules (e.g., J-shaped adapters) may be added to a mixture comprising template nucleic acid molecules (e.g., first nucleic acid strand). The nucleic acid molecules may comprise a first capture sequence, a first binding sequence, and a second binding sequence hybridized to the first binding sequence. The first nucleic acid strand may comprise a second capture sequence (e.g., a 3'-terminal sequence) that is complementary to the first capture sequence. The mixture may also comprise one or more primers that can hybridize to 5' termini of the template nucleic acid strands, buffers, deoxyribonucleotide triphosphates, and a polymerase (e.g., a non-standing displacing polymerase). An emulsion comprising one or more aqueous droplets in an oil base may be generated and subjected to amplification (e.g., PCR) and/or a sequencing reaction. Each of the one or more aqueous droplets may form a microreactor containing template and adapter coated beads. Amplification and/or sequencing can result in the formation of copies of the template nucleic acid molecules attached to the beads through extension of the capture sequence of the nucleic acid molecules (e.g., J-shaped adapters). The binding sequence of the nucleic acid molecules may not be extended in the presence of a replication blocker, non-strand displacing activity of the polymerase, and/or the lack of 5' to 3' exonuclease activity in the polymerase.

One or more processes of the methods described herein may be performed isothermally. For example, hybridization of an adapter or primer to a nucleic acid molecule, as well as binding of a polymerase and extension of an adapter or primer, may occur isothermally. Partial denaturation may also occur at a constant temperature (e.g., if partial denaturation is initiated by adjustment of pH or a salt concentration or by exposure to a chemical denaturant). Where multiple processes of the present methods are performed isothermally, amplification and/or sequencing may be considered continuous. In some cases, partial denaturation may be initiated by heating a nucleic acid molecule to a given temperature (e.g., as described herein), and the temperature may remain elevated throughout multiple amplification cycles. In some cases, partial denaturation may not be performed isothermally but hybridization, polymerase binding, and extension processes may be performed isothermally. For example, thermal cycling may be used to promote multiple amplification cycles. A temperature (e.g., of a solution, substrate, or container) may be elevated to promote partial denaturation of a low melting point region of a double-stranded nucleic acid molecule and then lowered while hybridization, polymerase binding, and extension processes occur. In this manner, the amount of amplification and/or sequenced products produced by the methods described herein may be controlled. A temperature may be elevated for any useful amount of time. In some cases, a temperature may be elevated for at least 1 second, such as for at least about 2 seconds, 3 seconds, 4 seconds, 5 seconds, 6 seconds, 7 seconds, 8 seconds, 9 seconds, 10 seconds, 15 seconds, 30 seconds, 45 seconds, 60 seconds, 90 seconds, 120 seconds, or more. Alternatively or in addition, the temperature may be elevated for at most 120 seconds, such as for at most about 90 seconds, 60 seconds, 45 seconds, 30 seconds, 15 seconds, 10 seconds, 9 seconds, 8 seconds, 7 seconds, 6 seconds, 5 seconds, 4 seconds, 3 seconds, 2 seconds, 1 second or less. A temperature may be elevated by transferring thermal energy via, for example, inductive heating, convective heating, microwave heating, optical heating, or resistive heating. A temperature for performing one or more processes of the methods described herein (e.g., a binding and extension process) may be a temperature at or near a temperature in which a selected polymerase exhibits optimal activity. For example, the temperature may be between about 55° C. and 85° C., such as between 60° C. and 70° C. The temperature at which a polymerase exhibits optimal activity may also be a temperature at which partial denaturation of one or more regions of a nucleic acid molecule may occur (e.g., as described herein). Non-specific primer-template hybridization events may also be reduced at such a temperature.

The methods described herein may be used to amplify and/or sequence one or more nucleic acid templates. For example, different nucleic acid templates having the same capture sequences attached thereto may be amplified and/or sequenced simultaneously. Alternatively, different nucleic acid templates may have different capture sequences attached thereto and may be amplified and/or sequenced simultaneously or sequentially. Different nucleic acid molecules (e.g., J-shaped adaptors) may be immobilized to a substrate to facilitate amplification and/or sequencing of different nucleic templates having different capture sequences attached thereto. The different capture sequences attached to different nucleic acid templates may comprise one or more common sequences. For example, a first capture sequence attached to a first nucleic acid template may comprise first and second sequences, and a second capture sequence attached to a second nucleic acid template that is different from the first nucleic acid template may comprise third and fourth sequences, where the third and first sequences are the same. This may simplify the amplification and/or sequencing scheme, as the same or similar conditions (e.g., common melting temperatures for the regions having the third and first sequences) may be used to partially denature nucleic acid molecules including the different nucleic acid templates, and the same primers may hybridize to single-stranded regions of nucleic acid molecules including the different nucleic acid templates. In some cases, a plurality of different nucleic acid molecules comprising more than 103 molecules, 105 molecules, 107 molecules, 109 molecules, 1011 molecules, 1014 molecules, 1020 molecules, or more molecules may be amplified simultaneously or sequentially.

In some cases, the concentration of a nucleic acid template subjected to amplification using the methods described herein may be in the sub-nanomolar range. A template nucleic acid molecule may undergo one or more amplification processes prior to instigation of the methods described herein to, for example, increase a starting concentration of a template nucleic acid molecule to facilitate amplification by present methods. For example, a template nucleic acid may be inserted into an expression vector and amplified in a suitable biological host, or a polymerase chain reaction (PCR) may be performed.

In some cases, the concentration of primers (e.g., substrate-immobilized primers) in a reaction vessel may be at least 50 times greater than the concentration of a nucleic acid template (e.g., in a solution, flow cell, or container in which the present methods are performed). For example, the concentration of primers may be at least 60, 70 80, 90, 100, 200, 300, 400, 500, 1,000, 5,000, 10,000, 50,000, or 100,000 times greater than the concentration of a nucleic acid template.

In some cases, a double-stranded nucleic acid template that is not attached to a substrate-immobilized primer may partially denature (e.g., form a bubble) upon being subjected to, for example, a sufficient temperature, pH, salt, or other chemical condition. A partially denatured region may expand, e.g., to separate ends of the double-stranded nucleic acid template. A separated end may then hybridize to a substrate-immobilized primer and undergo additional hybridization and extension processes, as described herein. In some cases, a single-stranded region of a partially denatured region of such a molecule may hybridize to a primer that hybridizes to such a region and may subsequently displace a strand of the molecule. The displaced strand may then hybridize to a substrate-immobilized primer and undergo additional hybridization and extension processes, as described herein.

In some cases, while performing the methods described herein, additional sequences may be introduced into nucleic acid molecules, such as additional sequences for restriction enzyme sites, nucleic acid tags enabling the identification and/isolation of amplification products (e.g., barcode sequences or unique molecular identifiers), DNA sequences that form hairpin loops or other secondary structures when rendered single-stranded, 'control' DNA sequences which direct protein/DNA interactions, such as a promoter, an enhancer, a replication origin, or an operator DNA sequence which are recognized by specific DNA-binding proteins. In some cases, non-natural nucleotides (e.g., nucleotide analogs) may be used while performing the methods described herein. For example, non-natural nucleotides may be incorporated into nucleic acid strands during extension reactions. A non-natural nucleotide incorporated into a nucleic acid molecule may include, for example, an affinity moiety or a detectable label (e.g., as described herein). The presently described methods may be performed over short timescales. For example, the present methods may be performed in less than an hour, such as less than 50 minutes, 45 minutes, 40 minutes, 35 minutes, 30 minutes, 25 minutes, 20 minutes, or 15 minutes.

Systems for Processing and/or Sequencing a Nucleic Acid Molecule Utilizing J-Shaped Molecules In addition to the methods described herein, the present disclosure provides systems for performing amplification and/or sequencing reactions. A system may comprise a support configured to retain one or more nucleic acid molecules each comprising a first strand and a second strand having at least partial sequence complementarity to the first strand. A nucleic acid molecule may be a J-shaped adapter that comprises a first capture sequence, a first binding sequence, and a second binding sequence, where the first and second binding sequences are hybridized to one another (e.g., as described herein). The nucleic acid molecule may be configured to capture a target nucleic acid molecule (or a molecule derived from a target nucleic acid molecule) comprising a second capture sequence that is complementary to the first capture sequence of the nucleic acid molecule. The target nucleic acid molecule may also comprise a template sequence. The support may comprise a plurality of nucleic acid molecules coupled thereto (e.g., as described herein). The support may be a surface of a flow cell, such as a well of a flow cell, and/or may be configured for placement within a flow cell. The support may be a single bead or a plurality of beads, which bead or beads may be disposed on a surface of a flow cell.

The system may further comprise a controller operatively coupled to the container, where the controller is programmed to subject the nucleic acid molecule to conditions sufficient to hybridize a second capture sequence of a template nucleic acid molecule to a first capture sequence of a nucleic acid molecule coupled to a support. The controller may further be programmed to implement any of the methods provided herein. For example, the controller may be programmed to sequence the template nucleic acid molecule to generate a first sequencing read and a second nucleic acid strand, which second nucleic acid strand comprises a sequence complementary to the template sequence of the template nucleic acid molecule. The controller may further be programmed to separate the second nucleic acid strand and the template nucleic acid molecule (e.g., via denaturing) and to sequence the second nucleic acid strand to generate a second sequencing read and a third nucleic acid strand, which third nucleic acid strand comprises the template sequence. This process may be repeated one or more times. The controller may be programmed to implement any of the other methods provided herein, including a method comprising bridge amplification, strand displacement amplification, and/or amplification comprising bubble formation.

The present disclosure also provides a system for implementing a method utilizing nucleic acid molecules (e.g., J-shaped adapter, as described herein) that are included in solution rather than immobilized to a support. Such a system may comprise a controller programmed to hybridize such a solution-phase nucleic acid molecule to a template nucleic acid molecule coupled to a support and sequence the template nucleic acid molecule to generate a first sequencing read corresponding to the template nucleic acid molecule and a second nucleic acid strand comprising a sequence complementary to a template sequence of the template nucleic acid molecule. The controller may further be programmed to separate the second nucleic acid strand and the template nucleic acid molecule (e.g., via denaturing) and to sequence the second nucleic acid strand to generate a second sequencing read and a third nucleic acid strand, which third nucleic acid strand comprises the template sequence. This process may be repeated one or more times.

A system may be useful for processing a single-stranded nucleic acid molecule or a double-stranded nucleic acid molecule. For example, a system may include a support having immobilized thereto an adapter capable of hybridizing to a sequence of a region of a single-stranded nucleic acid molecule. The system may be configured to provide a polymerase capable of binding to and extending the adapter to generate a strand that is complementary to all or a portion of the template nucleic acid molecule. The resultant double-stranded nucleic acid molecule may then be processed using the controller (e.g., as described herein).

A controller of a system for processing a nucleic acid sample may be programmed to denature at most a portion of a double-stranded nucleic acid molecule such that at most a portion of a first strand of the double-stranded nucleic acid molecule separates from a second strand of the double-stranded nucleic acid molecule (e.g., as described herein).

A nucleic acid molecule (e.g., J-shaped adapter) may be immobilized to a support (e.g., as described herein). The support may comprise a plurality of such nucleic acid molecules (e.g., J-shaped adapters) immobilized thereto. The nucleic acid molecules may be immobilized to the support in a predetermined pattern, and may be immobilized at a density of at least 10,000 primer molecules per $mm^2$ (e.g., as described herein).

A support (e.g., as described herein) of a system may be included within or as a component of a container. For example, a support may be an element of a flow cell in which one or more processes such as partial denaturation, hybridization, binding of a polymerase, or extension of a primer or adapter may be performed (e.g., as described herein). A container may have any useful size and geometry and may comprise any useful material. The support may be, for example, a planar array. In other cases, a support may be a bead. In some cases, a system may include a plurality of beads. A support may a component of a sequencing instrument.

A controller of a system for processing a nucleic acid sample may be a component of a computer or processing system (e.g., as described herein). A controller may be operable by a user. A controller may include or be coupled to a display device and/or a user interface (e.g., as described herein). In some cases, a controller may be a component of a sequencing instrument. A controller may be used to initiate, increase the rate of, pause, suspend, and/or cancel one or more processes. For example, a controller may be used to control at least a partial denaturation (e.g., bubble formation) process, hybridization of a primer to a template nucleic acid, extension of a primer to a template nucleic acid, and/or another process. A controller may control one or more processes by regulating a temperature. For example, a controller may initiate, increase the rate of, pause, suspend, and/or terminate heating by, for example, interfacing with a device capable of providing thermal energy by resistive, convective, inductive, optical, or microwave heating. The controller may therefore be programmed to provide thermal energy to a double-stranded nucleic acid molecule to at least partially denature the double-stranded nucleic acid molecule. In some cases, the controller may be programmed to heat a double-stranded nucleic acid molecule to a temperature higher than a first melting point of a first region of the molecule and lower than a second melting point of a second region of the molecule (e.g., as described herein). The first melting point may be at least 1° C. lower than the second melting point. For example, the first melting point may be at least 5° C. lower than the second melting point.

A system for processing a nucleic acid sample may be configured to control exposure of a double-stranded nucleic acid molecule or a portion thereof to a chemical denaturant. For example, a controller of a system may be programmed to expose a double-stranded nucleic acid molecule or a portion thereof to a chemical denaturant selected from the group consisting of a salt, formamide, urea, guanidine hydrochloride, and an organic solvent. The controller may be configured to release a chemical denaturant or a solution including a chemical denaturant from a reservoir by, for example, opening a valve or removing a cap, lid, or stopper retaining the denaturant in the reservoir.

A system or component thereof may be configured for viewing and/or interrogation by a detector. For example, a component of a system may include an open area or a transparent region such as a window that may be viewable directly by a user, using a camera, or using an optical detector. A viewable or optically interrogable region may provide visual and/or optical access to a support. In some cases, fluorescence spectroscopy or imaging may be performed to monitor the progress of an amplification process being performed using the system.

Sequencing methods may be performed using a variety of commercially available sequencers. A sequencing platform can collect information from many millions of reaction centers simultaneously, thus sequencing many millions of nucleic acid molecules in parallel. Sequencing methods can be performed on a massively parallel array sequencer (e.g., Illumina sequencer), which may be performed using template nucleic acid molecules immobilized on a support, such as a flow cell or beads. Sequencer platforms may include, but are not limited, to high-throughput sequencer, next-generation sequencer, sequencing-by-synthesis sequencer, flow sequencer, massively-parallel sequencer, shotgun sequencer, single-molecule sequencer, nanopore sequencer, pyrosequencer, semiconductor sequencer, sequencing-by-ligation sequencer, sequencing-by-hybridization sequencer, RNA-Seq sequencer (Illumina), Digital Gene Expression sequencer (Helicos), Single Molecule Sequencing by Synthesis (SMSS) sequencer (Helicos), Clonal Single Molecule Array sequencer (Solexa), and Maxim-Gilbert sequencer. Some examples of sequencing providers include, SOLID®, Complete Genomics®, Illumina®, Qiagen®, Roche 454®, Ion Torrent®, Pacific Biosciences®, Oxford Nanopore Technologies®, and 10× Genomics®.

A system may include one or more elements capable of monitoring and/or controlling conditions such as temperature, pressure, air quality, air flow, fluid flow, pH, and concentrations of various reagents. For example, a system may include a temperature monitoring device.

A system described herein may facilitate amplification and/or sequencing of a nucleic acid template without requiring multiple reagent exchanges. Accordingly, a system may not require extensive automated and fluidic systems. In some cases, fluidic systems may be useful for providing one or more reagents (e.g., polymerases, primers, nucleotides, chemical denaturants, etc.) to a nucleic acid molecule for analysis. Automation may be employed to control the transfer of fluids and other materials between components of a system.

Kits for Processing Nucleic Acid Molecules Utilizing J-Shaped Molecules

In addition to the methods and systems described herein, the present disclosure provides kits for processing nucleic acid molecules. A kit may comprise one or more reagents and materials. For example, a kit may comprise instructions for implementing the methods of the present disclosure.

A kit may comprise one or more adapters (e.g., J-shaped adapters, as described herein). For example, a kit may comprise at least 1, 10, 100, 1,000, 10,000, 50,000, 100,000, 500,000, 1,000,000, or more adapters. Adapters included in a kit may be the same or different. For example, a kit may include a first adapter type and a second adapter type. Different adapters may be included in the same or different numbers. For example, approximately the same number of first adapters and second adapters may be included in a kit. Alternatively, a greater number of first adapters and a smaller number of second adapters may be included in the kit. One or more adapters of a kit may be provided immobilized to a substrate (e.g., as described herein). In some cases, a kit may comprise a plurality of J-shaped adapters immobilized to a substrate as well as a plurality of adapters configured for coupling to target nucleic acid molecules (e.g., comprising sequences complementary to sequences of the J-shaped adapters).

An adapter (e.g., J-shaped adapter) of a kit may comprise at least a first capture sequence, a first binding sequence, and a second binding sequence, where the first and second binding sequence may be hybridized to one another. The various sequences of the adapter may have any useful length, base composition, and/or other characteristics (e.g., as described herein). In some cases, an adapter of a kit may comprise two nucleic acid strands, where the first strand comprises a first sequence and a second sequence adjacent to the first sequence that are respectively hybridized to a third sequence and a fourth sequence of the second strand. The first sequence hybridized to the third sequence may have a first melting point and the second sequence hybridized to the fourth sequence may have a second melting point that is higher than the first melting point. A sequence of an adapter may be of any useful length or base composition. In some cases, a sequence of an adapter may comprise one or more thymine, adenine, uridine, and/or inosine bases. An adapter sequence may include only thymine, adenine, uridine, and/or inosine bases. Such a sequence may be, for example, at least 5 nucleotides in length, such as at least 10 nucleotides in length. In some cases, an adapter may include a first sequence and a second sequence adjacent to the first sequence, where the first sequence comprises only thymine, adenine, uridine, and/or inosine bases and the second sequence comprises one or more bases other than thymine, adenine, uridine, and inosine bases. Such an adapter may be a single-stranded adapter or a double-stranded adapter. Adapters may also comprise sequences to facilitate attachment to a substrate and/or a nucleic acid molecule, such as a template nucleic acid molecule.

A kit may comprise one or more primers, such as one or more sequencing primers (e.g., as described herein). For example, a kit may comprise at least 1, 10, 100, 1,000, 10,000, 50,000, 100,000, 500,000, 1,000,000, or more primers. The one or more primers may be complementary to a capture sequence of an adapter (e.g., an adapter for coupling to a target nucleic acid molecule or a J-shaped adapter). Primers included in a kit may be the same or different. For example, a kit may include a first primer type and a second primer type. Different primers may be included in the same or different numbers. For example, approximately the same number of first primers and second primers may be included in a kit. Alternatively, a greater number of first primers and a smaller number of second primers may be included in the kit. One or more primers of a kit may be provided immobilized to a substrate (e.g., as described herein).

A primer of a kit may comprise a nucleic acid sequence that is capable of attaching (e.g., hybridizing) to a sequence of an adapter. For example, a primer may comprise a nucleic acid sequence that is complementary to all or a portion of a sequence of an adapter (e.g., an adapter included in a kit). A kit may include a primer that is capable of hybridizing to a sequence comprising only thymine, adenine, uridine, and/or inosine bases. A primer may be of any useful length and base composition. In some cases, the length of a primer may be the same as or shorter than the length of a sequence of an adapter. A kit may further comprise one or more polymerases capable of extending a primer molecule attached to a nucleic acid molecule. For example, a kit may comprise a first polymerase capable of extending a first primer or primer type and a second polymerase capable of extending a second primer or primer type. Different polymerases may, for example, be capable of extending nucleic acid molecule in different directions (e.g., 5' to 3' or 3' to 5) or interacting with particular types of nucleic acid molecules.

A kit may further comprise one or more reagents for immobilizing one or more adapters to a substrate, attaching adapters to nucleic acid molecules, extending primer molecules attached to nucleic acid molecules, amplifying, and/or sequencing nucleic acid molecules. For example, a kit may further comprise one or more enzymes, nucleotides, nucleotide analogs, biotins, avidins, reagents for "click" chemistry, labels, or other reagents useful for implementing methods of the present disclosure.

In an example, a kit may comprise a plurality of adapters, where each adapter is a double-stranded adapter comprising a first strand and a second strand. The first strand may comprise a first sequence and a second sequence adjacent to the first sequence, where the first sequence and the second sequence are respectively hybridized to a third sequence and a fourth sequence of the second strand. The first sequence hybridized to the third sequence may have a first melting point and the second sequence hybridized to the fourth sequence may have a second melting point higher than the first melting point. In some cases, the kit may further comprise a plurality of second adapters that may be the same or different from the plurality of adapters. The kit may further comprise one or more reagents for attaching adapters to nucleic acid molecules.

In another example, a kit may comprise a plurality of adapters, a plurality of first primers, and a plurality of second primers. The plurality of adapters may be single-stranded adapters, where each adapter includes at least a first sequence and a second sequence adjacent to the first sequence. The first sequence may comprise only thymine, adenine, uridine, and/or inosine bases and may be at least 5 nucleotides in length. Alternatively, the plurality of adapters may be double-stranded adapters, where each adapter comprises a first strand and a second strand. The first strand may comprise a first sequence and a second sequence adjacent to the first sequence, where the first sequence and the second sequence are respectively hybridized to a third sequence and a fourth sequence of the second strand. The first sequence hybridized to the third sequence may have a first melting point and the second sequence hybridized to the fourth sequence may have a second melting point higher than the first melting point. The plurality of first primers may each comprise a sequence that is complementary to a sequence of the plurality of adapters, such as the first sequence of the plurality of adapters. The plurality of second primers may each comprise a sequence that is complementary to a sequence of the plurality of adapters or a complement thereof. For example, the plurality of second primers may each comprise a sequence that is complementary to a sequence of a fourth sequence of the second strand of a double-stranded adapter. Alternatively, the plurality of second primers may each comprise a sequence that is complementary to a complement of a sequence of a single-stranded adapter. A kit may further comprise one or more reagents for attaching adapters of the plurality of adapters to nucleic acid molecules, attaching primers to adapter sequences, amplifying, and/or sequencing nucleic acid molecules (e.g., as described herein).

EXAMPLES

Example 1. Amplification in Solution

An artificial DNA template was designed to include three regions: a low melting point region with a melting temperature $T_m$ of 42.5° C., and two higher melting point regions with melting temperatures Tm of 69.1° C. and 68.0° C., respectively, that flank the low melting point region. Oligonucleotides for the forward and reverse strand (see Table 1) were synthesized by Integrated DNA Technologies (Iowa, USA) and suspended in Tris-EDTA buffer at a concentration of 100 μM.

Figure 9:
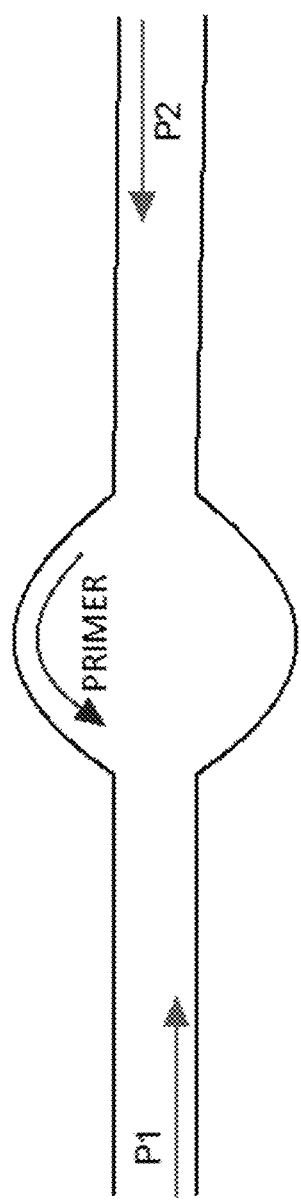
FIG. 9 schematically illustrates the construction of oligonucleotides for solution-based amplification.

FIG. 9 shows a schematic of the design of the template and primers for the in-solution amplification assay. A first primer configured to hybridize to the bubble region was also designed and synthesized with the HEX-fluorescent dye labeling 5' base. An additional oligonucleotide, complementary to the single-stranded end, created by the extension of the single-stranded primer, is synthesized with a FAM labeled end-nucleotide (P1 in FIG. 9). A primer that is configured to extend from the opposite end was also synthesized with a FAM fluorescent dye (P2 in FIG. 9). The oligonucleotide sequences for in-solution bubble amplification are shown in Table 1.

TABLE 1

Sequence of oligonucleotides for amplification in solution

| Oligonucleotide name | SEQ ID NO: | Oligonucleotide sequence | Label | Length | $T_m$* |
|---|---|---|---|---|---|
| Forward template | 1 | 5'-CCA TCT CAT CCC TGC GTG TCT CCG ACT CAG AAA AAA AAA AAA AAA AAA AAA AAC TGA GAC TGC CAA GGC ACA CAG GGG ATA GG-3' | Not labeled | 83 | 70.6° C. |
| Reverse template | 2 | 5'-CCT ATC CCC TGT GTG CCT TGG CAG TCT CAG TTT TTT TTT TTT TTT TTT TTT TTC TGA GTC GTC GGA GAC ACG CAG GGA TGA GAT GG-3' | Not labeled | 83 | 70.6° C. |
| First Primer | 3 | 5'-/5HEX/TTT TTT TTT TTT TTT TT-3' | HEX dye | 17 | 32.5° C. |
| P1 - Amplification primer 1 | 4 | 5'-/56-FAM/CCA TCT CAT CCC TGC GTG TCT-3' | FAM dye | 21 | 59.1° C. |
| P2 - Amplification primer 2 | 5 | 5'-/56-FAM/CCT ATC CCC TGT GTG CCT TGG -3' | FAM dye | 21 | 60.0° C. |

*$T_m$ at 50 millimolar (mM) NaCl

The calculated melting temperatures of the three regions for the template were calculated with the Poland software (http://www.biophys.uni-duesseldorf.de/html/local/POLAND/poland_help.html) and by the MELTING software, and are shown in Table 2.

TABLE 2

Localized $T_m$ for sub-regions in the bubble amplification template

| Sub-region | SEQ ID NO: | Oligonucleotide sub-region sequence | $T_m$ | Length |
|---|---|---|---|---|
| High $T_m$ region | 6 | 5'-CCATCTCATCCCTGCGTGTCTCCGACTCAG-3' | 69.1° C. | 30 |
|  | 7 | 5'-GGTAGAGTAGGGACGCACAGAGGCTGAGTC-3' |  |  |
| Low $T_m$ region | 8 | 5'-AAAAAAAAAAAAAAAAAAAAAAAAAAAAA-3' | 42.5° C. | 29 |
|  | 9 | 5'-TTTTTTTTTTTTTTTTTTTTTTTTTTTTT-3' |  |  |
| High $T_m$ region | 10 | 5'-CTGAGACTGCCAAGGCACACAGGGGATAGG-3' | 68.0° C. | 30 |
|  | 11 | 5'-GACTCTGACGGTTCCGTGTGTCCCCTATCC-3' |  |  |

To 98 microliters (µL) of Tris-EDTA buffer, 1 µL of the diluted forward template and 1 µL of the diluted reverse template were added. The mixture was mixed and heated to 95° C. and cooled slowly to room temperature to allow annealing of the template into a double-stranded molecule. The P1 and P2 primers at 100 micromolar (µM) concentrations were diluted 100× in Tris-EDTA buffer. The primer (100 µM) was diluted to 10 µM in Tris-EDTA buffer.

The double-stranded template was prepared by mixing 1 µL of Forward template with 1 µL of Reverse template and diluting to 100 µL with Tris-EDTA buffer. The mixture was heated to 95° C. and slow cooled to room temperature (~ 25° C.). The test and control reactions were set up as summarized below.

The following reagents in Table 3 were added to seven 0.2 milliliters (mL) PCR tubes: 2.5 µL of ultra-pure water, 2.5 µL of DMSO (VWR), and 2.5 µL of 10× Thermopol II buffer from New England Biolabs.

TABLE 3

Reagents added to samples for bubble amplification

| Tube | Label | Reagents |
| --- | --- | --- |
| 1 | No template control | Water, DMSO, Thermopol buffer; additional 6 µL water was added followed by 1.5 µL of 100 mM MgSO$_4$, 2.5 µL of 1 µM primer P1, 2.5 µL of 1 µM primer P2, and 0.5 µL of 10 µM First Primer |
| 2 | 1 pm template | Water, DMSO, Thermopol buffer; additional 5 µL water was added followed by 1 µL of Template (25 pM), 1.5 µL of 100 mM MgSO$_4$, 2.5 µL of 1 µM primer P1, 2.5 µL of 1 µM primer P2, and 0.5 µL of 10 µM First Primer |
| 3 | 10 pm template | Water, DMSO, Thermopol buffer; additional 6.25 µL water was added followed by 0.25 µL of Template (1 µM), 1.5 µL of 100 mM MgSO$_4$, 2.5 µL of 1 µM primer P1, 2.5 µL of 1 µM primer P2, and 0.5 µL of 10 µM First Primer |
| 4 | 100 pm template with premelt | Water, DMSO, Thermopol buffer; additional 3.5 µL water was added followed by 2.5 µL of Template (1 µM), 1.5 µL of 100 mM MgSO$_4$, 2.5 µL of 1 µM primer P1, 2.5 µL of 1 µM primer P2, and 0.5 µL of 10 µM First Primer |
| 5 | 100 pm template without premelt | Water, DMSO, Thermopol buffer; additional 3.5 µL water was added followed by 0.25 µL of Template (1 µM), 1.5 µL of 100 mM MgSO$_4$, 2.5 µL of 1 µM primer P1, 2.5 µL of 1 µM primer P2, and 0.5 µL of 10 µM First Primer |
| 6 | Just primers | Water, DMSO, Thermopol buffer; additional 6 µL water was added followed by 1.5 µL of 100 mM MgSO$_4$, 2.5 µL of 1 µM primer P1, 2.5 µL of 1 µM primer P2, and 0.5 µL of 10 µM First Primer |
| 7 | No P1 or P2 | Water, DMSO, Thermopol buffer; additional 8.5 µL water was added followed by 2.5 µL of Template (1 µM), 1.5 µL of 100 mM MgSO$_4$, and 0.5 µL of 10 µM First Primer |

Tube 4, labeled as "100 picomolar (pM) Template with premelt" was heated to 95° C. for 3 minutes and then slow cooled to 37° C. to allow the primers to anneal to the templates.

To all seven tubes, 3.5 µL of 10 mM dNTP and 1 µl of 8000 U/mL of Bst 2 DNA polymerase (from New England Biolabs) were added. The seven tubes were mixed and incubated at 37° C. for 10 minutes followed by incubation at 60° C. for 90 minutes. Reactions were stopped by the addition of 50 µL of formamide containing 0.1 mM EDTA.

Formation of products by bubble amplification was investigated by polyacrylamide gel electrophoresis. Oligonucleotide size standards and the seven samples were loaded on an acrylamide gel (BioRad) and run at 200 V for 3 hrs. The gel was imaged on a custom LED-illuminated gel imager with blue and red LED illumination. The FAM labeled primers (primer P1 and P2) fluoresce brightly under blue illumination. Extension products produced by the extension of P1 and P2 also fluoresce under the blue illumination.

Figure 10:
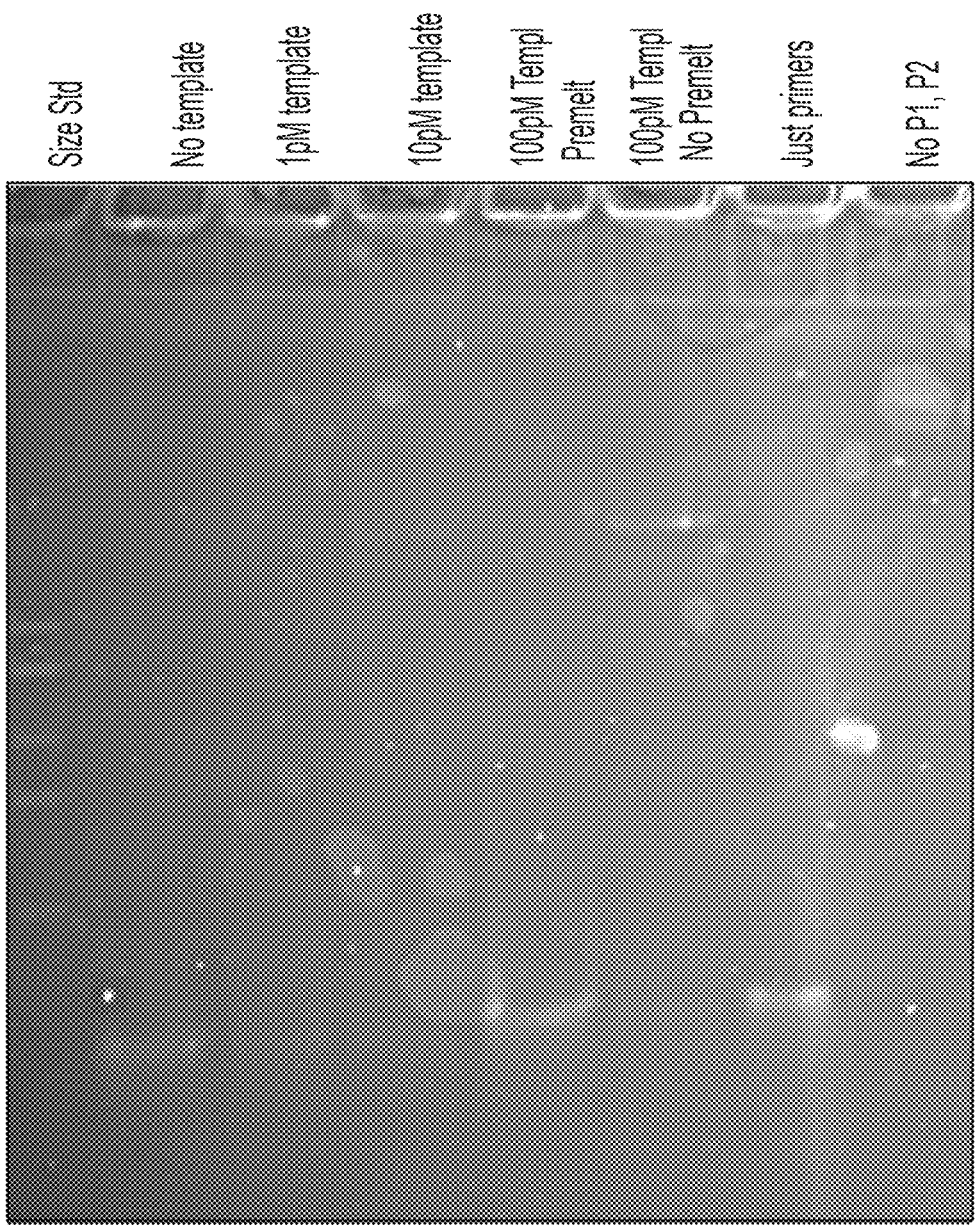
FIG. 10 shows a gel demonstrating the results of a clonal amplification method.

FIG. 10 shows the results of gel electrophoresis of solution-based bubble amplification. Lane 0 shows the size standard with molecular weights of 31, 57, 79, 99, 127. Lane 1 with "No template control" shows the P1 and P2 primers migrating at 21 nt but no product formation at ~ 160 bp. Lane 2 with 1 pM template also shows no product formation but at 10 pM template concentration, the expected amplified product is seen at 166 bp. Lane 3 with "100 pM Template with Premelt," in which the template and primers were preheated to 95° C. and slow cooled, no product was seen. In Lane 4 with "100 pM Template without Premelt," the expected product was seen. In additional controls labeled "Just primers" and "No P1, P2," the amplified product was not seen.

Figure 11:
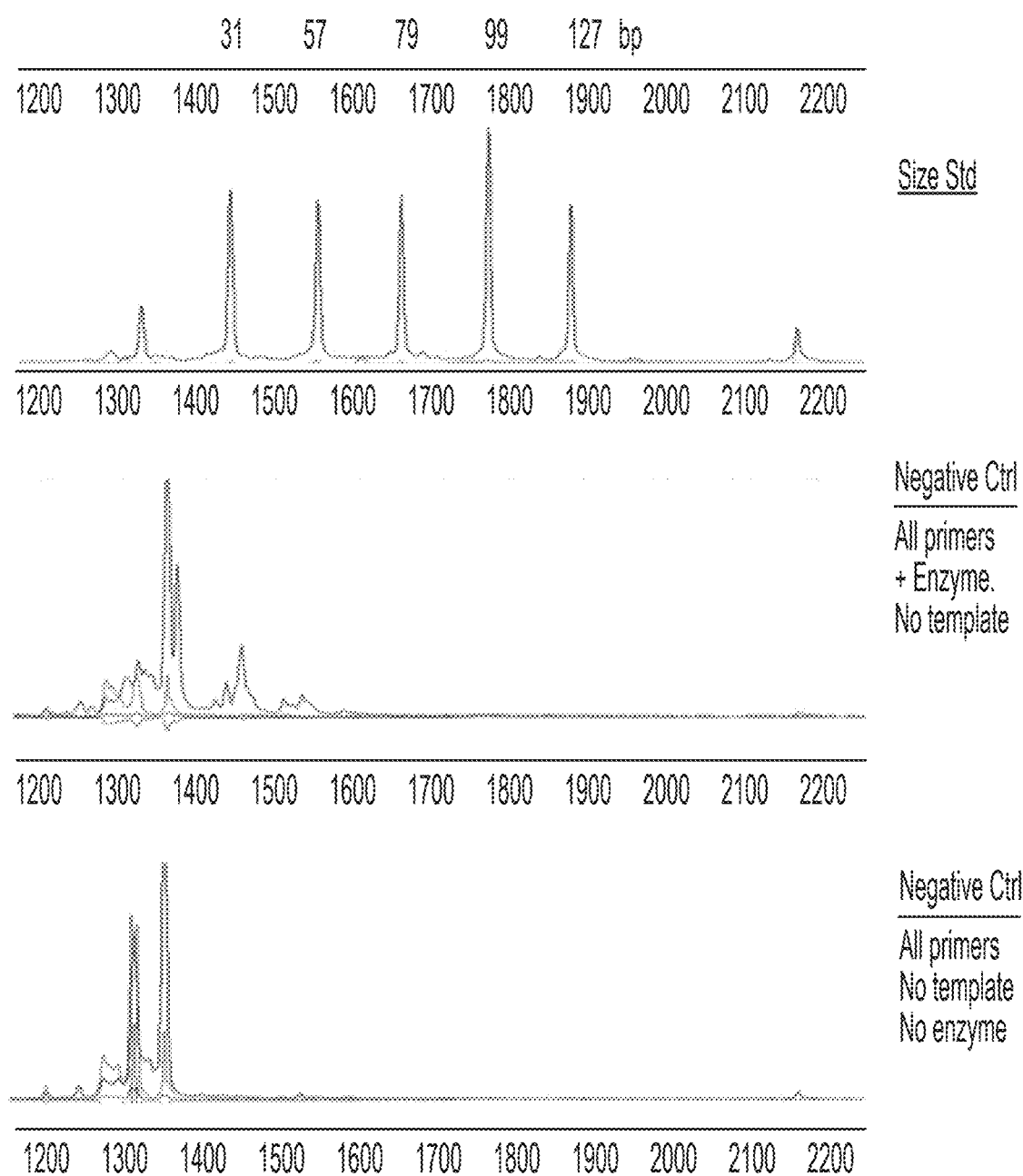
FIG. 11 shows an electropherogram demonstrating the results of a clonal amplification method.
Figure 11:
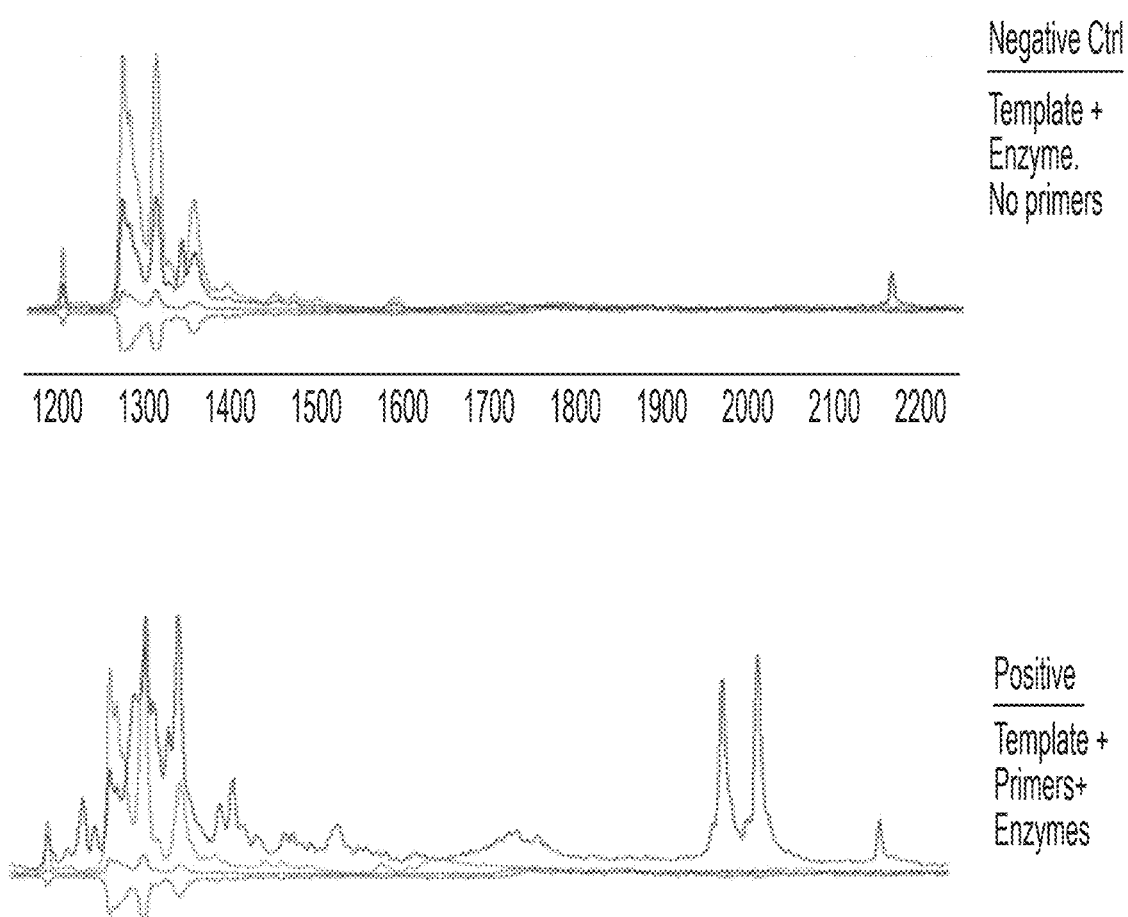

FIG. 11 shows results from higher resolution analysis of bubble by capillary electrophoresis on a Thermo Fisher Scientific Capillary electrophoresis system. The expected product is produced in the positive control reaction (template plus all constituents). In all controls where the template is absent, no amplification product is seen. In controls without the P1 and P2 primers, expected product is also not seen. Extension products from the inversion primer are seen and vary in range from 20-50 bp. Thermocycling between denaturing temperature and non-denaturing temperature may increase yield.

The experiment demonstrates that a specific product is amplified from the template under isothermal conditions.

Example 2: Bubble Amplification on Slides

Schott Nexterion H microscope slides (Cat. No. 1070936, supplied by Applied Microarrays, AZ, USA) are placed in a 5-slot polypropylene microscope slide holder to which a solution of 120 milligrams (mg) of azido-PEG4-amine (molecular weight 262; Broadpharm) and 200 µL tributylamine in 16 mL of dry N-Methylpyrrolidone (NMP) are added. The slide holder is tightly sealed and allowed to stand in the dark for 48 hours (hr). The functionalization solution is removed, and the slides are rinsed once with NMP, and then several times with water to remove residual NMP. The modified slides are stored in the dark at −20° C.

Immobilization of dibenzocyclooctyl (DBCO) modified oligonucleotides to the Azide modified substrate is achieved by loading into the flow cell, 20 µL of 20 µM of DBCO modified substrate oligonucleotide prepared in a mixture of 1 M NaCl and 20 mM Tris-HCl, pH 8.0. The incubation time for efficient covalent attachment of oligonucleotides to the glass substrate is about 24 hours at room temperature. After immobilization, the substrate is washed twice with 200 µL of high salt buffer containing 20 mM Tris-HCl and pH 8.0, 1 M NaCl.

The slide is assembled into a holder to create a flow cell chamber for the amplification reaction to happen at controlled temperatures.

A single-stranded DNA template is diluted to concentrations ranging from 1 pM to 100 pM. To the lanes created in the slide flow cell, 20 µL of different template concentrations are added and incubated at 50° C. for hybridization. The slide flow cell substrate is washed to remove free templates (e.g., templates that are not immobilized). 20 µL of primer extension reaction mix containing 1 mM dNTPs and 0.4 unit/µL of BST is added and incubated for 10 minutes (min) at 37° C. temperature. The slide is washed twice with 1 × Thermopol reaction buffer and flow master mix for the amplification reaction as per the following formulation. For 25 µL final volume, 9 µL of water, 2.5 µL of Thermopol 10× buffer, 3.5 µL of 10 mM dNTP, 1.5 µL of 100 mM MgSO4, 5 µL of 1 µM Primer P2, 2.5 µL of 10 µM First primer, and 1 µL of Bst 2 (8 k Units/mL) are mixed together. Thermocycling between denaturing temperature and non-denaturing temperature may increase yield.

Figure 12:
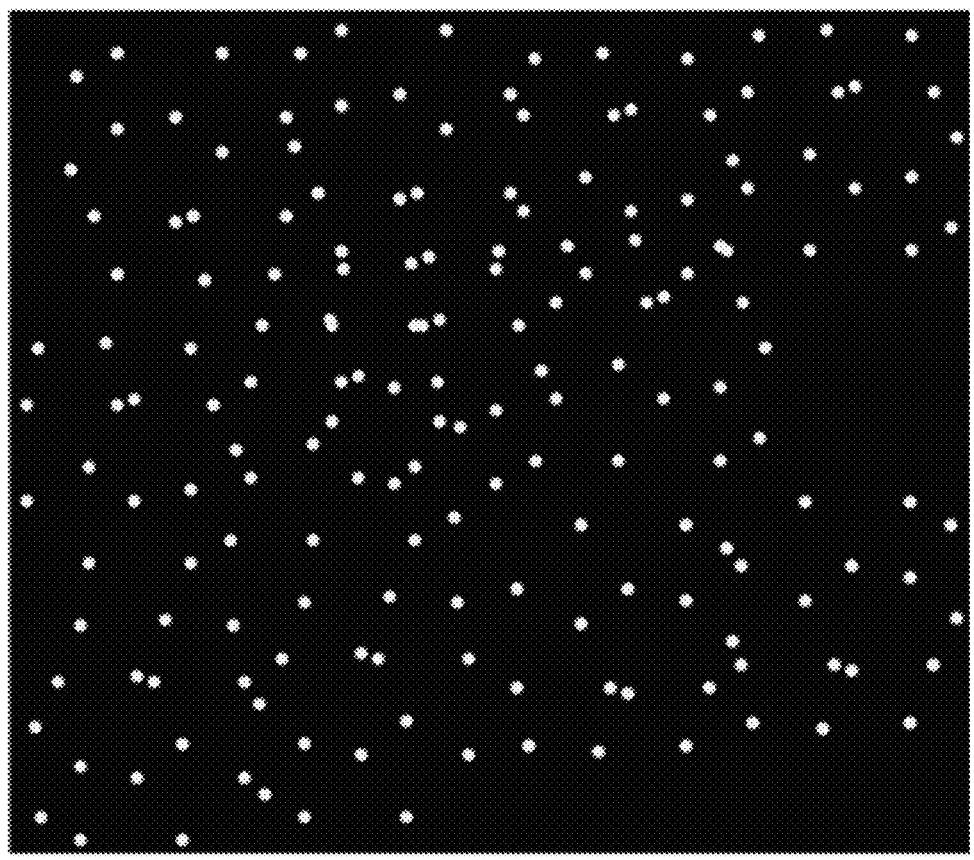
FIG. 12 shows a putative image of nucleic acid colonies amplified by a clonal amplification method on a solid substrate and imaged by hybridization of fluorescein amidite (FAM)-labeled oligonucleotides to nucleic acid molecules.

FIG. 12 shows a putative image of nucleic acid colonies generated by the amplification method described in the embodiments. Analyses can be performed on the nucleic acid strands in a colony that are covalently immobilized to the substrate or can be performed on nucleic acid strands that are not covalently immobilized to the substrate. A non-comprehensive list of such methods comprises the hybridization with labeled oligonucleotides, the incorporation of labeled nucleotides, the re-amplification using specific probes, the use of DNA binding dyes, digestion with sequence- or structure-specific nucleases, and the use of other DNA modifying enzymes (such as ligases, methylases, exonucleases) and other DNA binding proteins.

Example 3. Bubble Amplification on Slides

Microscopy slides are prepared as in Example 2 with the modification of immobilizing primers with the sequence UP1 and UP2. A single-stranded DNA template UT1 is diluted to concentrations ranging from 1 pM to 100 pM with an annealing buffer comprising 20 mM Tris-HCl, and 120 mM KCl, 0.05% Trition X-100, which has pH 8 at 25° C. 20 µL of different template concentrations are added to lanes created in the slide flow cell immobilized with equimolar UP1 and UP2 primers and incubated at 50° C. for hybridization. The slide flow cell substrate is washed to remove free templates (e.g. templates that are not immobilized) using a wash buffer comprising 20 mM Tris-HCl, 20 mM KCl, and 0.05% Trition X-100, which has pH 8 at 25° C. 20 µL of amplification mix consisting of an amplification buffer comprising 20 mM Tris-HCl, 20 mM KCl, 2 mM MgSO4, 0.05% Trition X-100, and 20% DMSO, which has pH 8.8 at 25° C.; 1 mM dNTPs; and 0.4 unit/µL of BST 2.0 (NEB) is added to the flow cell and incubated for 60 minutes at 70° C. Amplification is assessed by adding a fluorescent intercalating dye and imaged using fluorescence microscopy.
Sequences:
Template UTI Sequence:

```
                                        (SEQ ID NO: 12)
5'CAAGCAGAAGACGGCATACGAGATATATATATATATATATATGTGAC

TGGAGTTCAGACGTGTGCTCTTCCGATCTCAGTACGAGCGTGTAGACGT

GTCGTACGTGCGACGTAGTGAGTATACATGCTCTGACACTATGTACGct gtaggcatACGAGATCGGAAGAGCGTCGTGTAGGGAAAGAGTGTATATA

TATATATATATATATATATATGTGTAGATCTCGGTGGTCGCCGTATC

ATT 3'
```
Primer Sequences:

```
UP1:
                                        (SEQ ID NO: 13)
5'CAAGCAGAAGACGGCATACGAG 3';

UP2:
                                        (SEQ ID NO: 14)
5'AATGATACGGCGACCACCGAGATCTACACA
```

Figure 14:
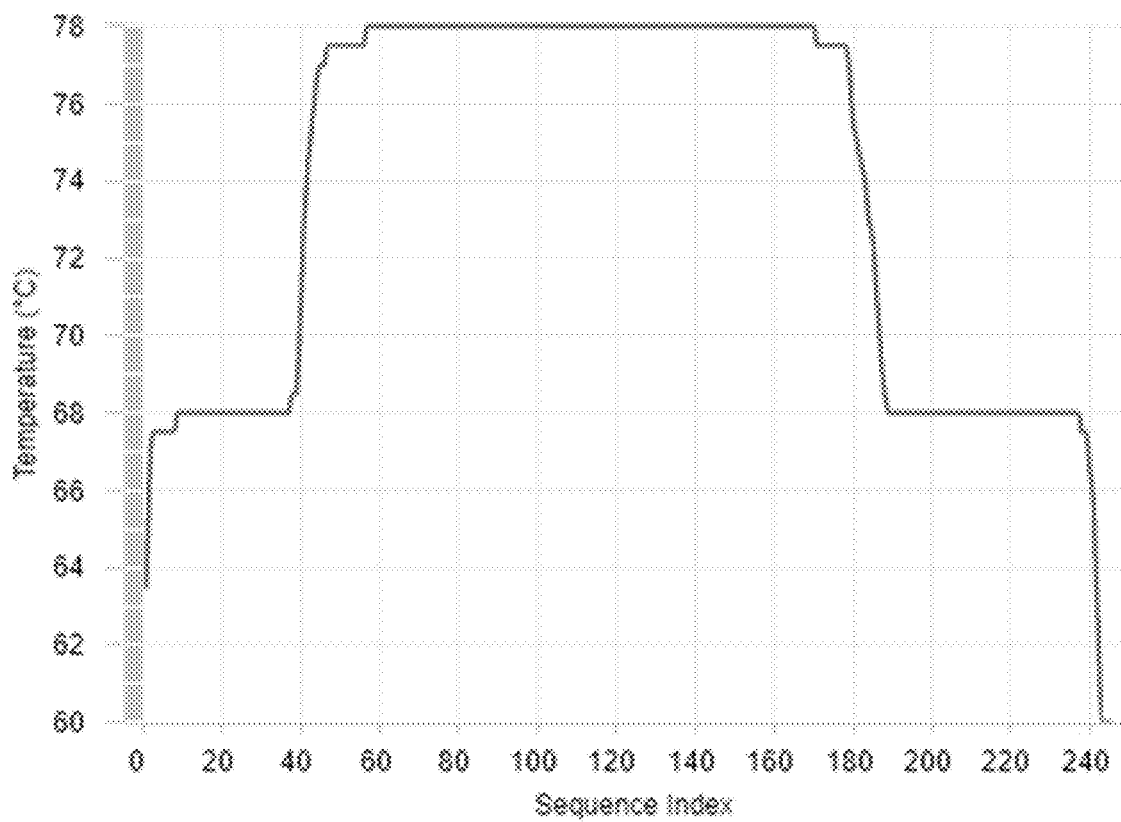
FIG. 14 shows a simulation of a melting profile.

A 3' UMelt (www.dna.utah.edu) simulation of a melting profile of the above sequences is prepared at 20 mM Na+, 2 mM Mg2+, and 20% DMSO, as shown in FIG. 14. Thermocycling between denaturing temperature and non-denaturing temperature may increase yield.

Several aspects are described with reference to example applications for illustration. Unless otherwise indicated, any embodiment may be combined with any other embodiment. It should be understood that numerous specific details, relationships, and methods are set forth to provide a full understanding of the features described herein. A skilled artisan, however, will readily recognize that the features described herein may be practiced without one or more of the specific details or with other methods. The features described herein are not limited by the illustrated ordering of acts or events, as some acts may occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, or within 2-fold, of a value. Where particular values are described in the application and claims, unless otherwise stated the term "about" meaning within an acceptable error range for the particular value may be assumed.

Example 4. Amplification in Solution

J-shaped adapter oligonucleotides may be loaded into a flow cell of a microscope slide to generate a lawn of J-shaped adapter oligonucleotides immobilized onto the microscope slide. The incubation time for efficient covalent attachment of oligonucleotides to the glass substrate may be about 24 hours at room temperature. After immobilization, the substrate may be washed twice with a high salt buffer solution. The slide may be assembled into a holder to create a flow cell chamber for the amplification reaction to happen at controlled temperatures.

A library of single-stranded DNA templates may be diluted to concentrations ranging from 1 pM to 100 pM. To the lanes created in the slide flow cell, varying template concentrations may be added and incubated at 50° C. for hybridization to generate a lawn of templates complementary to the J-shaped adapters. The flow cell substrate may then be washed to remove free templates (e.g., templates that are not immobilized). A primer extension reaction mix may be added and incubated for 10 minutes (min) at 37° C. temperature. The slide may be washed twice with reaction buffer and a flow master mix for the amplification reaction. Thermocycling between denaturing temperature and non-denaturing temperature may increase yield. Amplification may be assessed by adding a fluorescent intercalating dye and imaged using fluorescence microscopy.

Example 5. Sequencing in Solution

A plurality of J-shaped adapters comprising DNA template strands and strands complementary to DNA template strands may be prepared as provided in Example 1. The resulting double-stranded nucleic acid molecule on the substrate may be heated to denature the double-stranded molecule and separate the DNA template strands from the J-shaped adapters. The flow cell substrate may be washed to remove the unbound DNA templates. Sequencing primers and nucleotides chemically modified with a dye (e.g., a fluorescent nucleotides) or other label may be flowed into the cell. The sequencing primers may hybridized to free ends of the remaining strands and then be extended using the nucleotides and a polymerizing enzyme in a sequencing process. During each sequencing cycle, a single labeled deoxynucleoside triphosphate (dNTP) may be added to the nucleic acid chain. After electromagnetic excitation, an image may be captured to identify the base that is incorporated. The nucleotide label can serve as a terminator for polymerization, so after each dNTP incorporation, the fluorescent dye may be imaged to identify the base and then enzymatically cleaved to allow incorporation of the next nucleotide. The slide may be washed to remove the fluorophore after color recordation. Base calls may be generated directly from signal intensity measurements during each cycle.

Several aspects are described with reference to example applications for illustration. Unless otherwise indicated, any embodiment may be combined with any other embodiment. It should be understood that numerous specific details, relationships, and methods are set forth to provide a full understanding of the features described herein. A skilled artisan, however, will readily recognize that the features described herein may be practiced without one or more of the specific details or with other methods. The features described herein are not limited by the illustrated ordering of acts or events, as some acts may occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, or within 2-fold, of a value. Where particular values are described in the application and claims, unless otherwise stated the term "about" meaning within an acceptable error range for the particular value may be assumed.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a nucleic acid sample, comprising:
   (a) providing said nucleic acid sample comprising a double-stranded nucleic acid molecule comprising a first strand and a second strand attached to a surface at a 5' end of said second strand, wherein said second strand has having-sequence complementarity with said first strand, wherein said first strand comprises a template region that is attached at a 3' end of said template region to an adapter comprising, in a 5' to 3' direction, a first sequence and a second sequence adjacent to said first sequence, wherein said first sequence and said second sequence are respectively hybridized to a third sequence and a fourth sequence of an additional adapter located at a 5' end of said second strand, wherein said first sequence hybridized to said third sequence has a first melting point and said second sequence hybridized to said fourth sequence has a second melting point higher than said first melting point;
   (b) subjecting said double-stranded nucleic acid molecule to conditions sufficient to partially denature said double-stranded nucleic acid molecule, thereby separating said first sequence of said first strand from said third sequence of said second strand and retaining hybridization between said second sequence and said fourth sequence;
   (c) bringing a primer molecule having sequence complementarity with said third sequence of said second strand in contact with said second strand under conditions sufficient to permit said primer molecule to hybridize to said third sequence of said second strand; and
   (d) subjecting said second strand comprising said primer molecule hybridized to said third sequence of said second strand to a primer extension reaction under conditions sufficient to generate a third strand hybridized to at least a portion of said additional adapter of said second strand, wherein said third strand is complementary to at least a portion of said third sequence and said fourth sequence, and wherein said primer extension separates said second sequence from said fourth sequence.

2. The method of claim 1, further comprising (e) bringing an additional primer molecule having sequence complementarity with said first strand in contact with said first strand under conditions sufficient to permit said additional primer molecule to hybridize to said first strand, wherein said additional primer molecule hybridizes to said second sequence.

3. The method of claim 2, further comprising (f) subjecting said first strand comprising said additional primer molecule hybridized thereto to a primer extension reaction under conditions sufficient to generate a fourth strand hybridized to at least a portion of said first strand, thereby generating a double-stranded nucleic acid molecule comprising said first strand and said fourth strand.

4. The method of claim 1, wherein said additional adapter is immobilized to a support.

5. The method of claim 1, wherein said first strand, at a 5' end, further comprises a third adapter comprising, in a 3' to 5' direction an additional third sequence and an additional fourth sequence adjacent to said additional third sequence, wherein said additional third sequence and said additional fourth sequence are respectively hybridized to an additional first sequence and an additional second sequence at a 3' end of said second strand, wherein said additional first sequence hybridized to said additional third sequence has said first melting point and said additional second sequence hybridized to said additional fourth sequence has said second melting point.

6. The method of claim 1, wherein said nucleic acid sample comprises a plurality of double-stranded nucleic acid molecules, wherein each double-stranded nucleic acid molecule of said plurality of double-stranded nucleic acid molecules comprises another first strand and another second strand attached to said surface at a 5' end of said another second strand having sequence complementarity with said another first strand, wherein said another first strand comprises another template region that is attached at a 3' end of said another template region to another adapter comprising said first sequence and said second sequence adjacent to said first sequence, wherein said first sequence and said second sequence are respectively hybridized to said third sequence and said fourth sequence of said another second strand, wherein said plurality of double-stranded nucleic acid molecules comprises at least 100 double-stranded nucleic acid molecules, and wherein said plurality of double-stranded nucleic acid molecules comprise one or more different template regions; and further comprising:
  (e) repeating (b)-(d) for each double-stranded nucleic acid molecule of said plurality of double-stranded nucleic acid molecules of said nucleic acid sample; and
  (f) wherein (e) is performed simultaneously with (b)-(d).

7. The method of claim 1, wherein said adapter further comprises a fifth sequence, wherein said second sequence and said fifth sequence are disposed 3' of said first sequence, wherein said second strand of said double-stranded nucleic acid molecule further comprise a sixth sequence hybridized to said fifth sequence, and wherein said fourth sequence and said sixth sequence are disposed 5' of said third sequence.

8. A method for processing a nucleic acid sample, comprising:
  (a) providing said nucleic acid sample comprising a first nucleic acid molecule comprising a single strand;
  (b) attaching an adapter to a 3' end of said first nucleic acid molecule, wherein said adapter, in a 5' to 3' direction, comprises a first sequence and a second sequence; and
  (c) using said adapter to generate a double-stranded nucleic acid molecule comprising a second nucleic acid molecule that is complementary to said first nucleic acid molecule, wherein said double-stranded nucleic acid molecule comprises a third sequence hybridized to said first sequence and a fourth sequence hybridized to said second sequence, wherein said first sequence hybridized to said third sequence has a first melting point and said second sequence hybridized to said fourth sequence has a second melting point higher than said first melting point.

9. The method of claim 8, further comprising attaching an additional adapter to a 5' end of said first nucleic acid molecule.

10. The method of claim 8, wherein (b) comprises ligating said adapter to said first nucleic acid molecule, and wherein (c) comprises hybridizing a primer to said adapter and using said primer to perform a primer extension reaction to yield said second nucleic acid molecule hybridized to said first nucleic acid molecule.

11. The method of claim 8, wherein (b) further comprises attaching an additional adapter to a 5' end of said first nucleic acid molecule comprising, in a 3' to 5' direction, an additional third sequence and an additional fourth sequence, and wherein in (c) said second nucleic acid molecule of said double-stranded nucleic acid molecule further comprises, in a 5' to 3' direction, an additional first sequence and an additional second sequence adjacent to said additional first sequence, wherein said additional first sequence and said additional second sequence are respectively hybridized to said additional third sequence and said additional fourth sequence, wherein said additional first sequence hybridized to said additional third sequence has said first melting point and said additional second sequence hybridized to said additional fourth sequence has said second melting point-using said adapter as a primer to conduct a primer extension reaction to yield said second nucleic acid molecule hybridized the said first nucleic acid molecule.

12. A method for processing a nucleic acid sample, comprising:
  (a) providing said nucleic acid sample comprising a double-stranded nucleic acid molecule immobilized to a support, wherein said double-stranded nucleic acid molecule comprises a first strand and a second strand having sequence complementarity with said first strand, wherein:
    (i) said first strand comprises a template region that is attached at a 3' end of said template region to a first adapter comprising, in a 5' to 3' direction, a first sequence and a second sequence adjacent to said first sequence, and
    (ii) said second strand comprises a sequence complementary to said template region that is attached at a 5' end of said sequence complementary to said template region to a second adapter comprising, in a 3' to 5' direction, a third sequence and a fourth sequence adjacent to said third sequence,
  wherein said first sequence and said second sequence are respectively hybridized to said third sequence and said fourth sequence,
  wherein said first sequence hybridized to said third sequence has a first melting point and said second sequence hybridized to said fourth sequence has a second melting point higher than said first melting point, and
  wherein said support comprises a plurality of primer molecules immobilized thereto; and
  (b) performing an amplification reaction using a primer molecule of said plurality of primer molecules by subjecting said nucleic acid sample to conditions sufficient to (i) partially denature said double-stranded nucleic acid molecule, thereby separating said first sequence of said first adapter of said first strand from said third sequence of said second adapter of said second strand and retaining hybridization between said second sequence and said fourth sequence; (ii) further denature said second sequence from said fourth sequence and hybridize said primer molecule to said second sequence of said first strand; and (iii) generate a copy of said second strand.

13. The method of claim 12, wherein said nucleic acid sample comprises a plurality of double-stranded nucleic acid molecules immobilized to said support, wherein each double-stranded nucleic acid molecule of said plurality of double-stranded nucleic acid molecules comprises another first strand and another second strand having sequence complementarity with said another first strand, wherein said another first strand comprises a template region that is attached to another first adapter comprising in a 5' to 3' direction, said first sequence and said second sequence adjacent to said first sequence, and said another second strand comprises a sequence complementary to said another template region that is attached to another second adapter comprising said third sequence and said fourth sequence adjacent to said third sequence, wherein said first sequence and said second sequence are respectively hybridized to said third sequence and said fourth sequence; and further comprising:

(c) repeating (b) for each double-stranded nucleic acid molecule of said plurality of double-stranded nucleic acid molecules of said nucleic acid sample.

14. The method of claim 12, wherein said nucleic acid sample comprises a plurality of double-stranded nucleic acid molecules immobilized to said support, wherein each double-stranded nucleic acid molecule of said plurality of double-stranded nucleic acid molecules comprises a first strand hybridized to a second strand, wherein said first strand comprises a first sequence and a second sequence hybridized to a respective third sequence and fourth sequence, and wherein said second sequence is disposed closer to said support than said first sequence; and further comprising:

(c) repeating (b) for each double-stranded nucleic acid molecule of said plurality of double-stranded nucleic acid molecules of said nucleic acid sample.

15. The method of claim 1, wherein conditions sufficient to partially denature comprise exposure of said double-stranded nucleic acid molecule or a portion thereof to a chemical denaturant.

16. The method of claim 1, wherein said first melting point is at least 1° C. lower than said second melting point.

17. The method of claim 1, wherein conditions sufficient to partially denature comprise heating said double-stranded nucleic acid molecule to a temperature higher than said first melting point and lower than said second melting point.

18. The method of claim 1, wherein conditions sufficient to partially denature comprise heating said double-stranded nucleic acid molecule to partially denature said double-stranded nucleic acid molecule.

19. The method of claim 1, wherein said adapter is immobilized to a support, and wherein said support comprises a bead.

20. The method of claim 1, wherein each of said first sequence and said third sequence comprises at least 5 nucleotides.

* * * * *